(12) United States Patent
Marsault et al.

(10) Patent No.: US 9,133,235 B2
(45) Date of Patent: Sep. 15, 2015

(54) MACROCYCLIC ANTAGONISTS OF THE MOTILIN RECEPTOR FOR TREATMENT OF GASTROINTESTINAL DYSMOTILITY DISORDERS

(75) Inventors: Eric Marsault, Québec (CA); Graeme L. Fraser, Rixensart (BE); Kamel Benakli, Blue Bell, PA (US); Carl St-Louis, Québec (CA); Alain Rouillard, Québec (CA); Helmut Thomas, Québec (CA)

(73) Assignee: Ocera Therapeutics, Inc., Palo Alto, CA (US)

( * ) Notice: Subject to any disclaimer, the term of this patent is extended or adjusted under 35 U.S.C. 154(b) by 979 days.

(21) Appl. No.: 12/440,802

(22) PCT Filed: Sep. 11, 2007

(86) PCT No.: PCT/US2007/019705
§ 371 (c)(1),
(2), (4) Date: Dec. 22, 2009

(87) PCT Pub. No.: WO2008/033328
PCT Pub. Date: Mar. 20, 2008

(65) Prior Publication Data
US 2010/0093720 A1    Apr. 15, 2010

Related U.S. Application Data

(60) Provisional application No. 60/825,237, filed on Sep. 11, 2006.

(51) Int. Cl.
| | |
|---|---|
| *C07K 5/087* | (2006.01) |
| *C07C 271/16* | (2006.01) |
| *C07D 273/00* | (2006.01) |
| *C07D 413/06* | (2006.01) |
| *C07D 417/12* | (2006.01) |
| *A61K 38/00* | (2006.01) |

(52) U.S. Cl.
CPC ............. *C07K 5/0812* (2013.01); *C07C 271/16* (2013.01); *C07D 273/00* (2013.01); *C07D 413/06* (2013.01); *C07D 417/12* (2013.01); *A61K 38/00* (2013.01)

(58) Field of Classification Search
CPC .. C07C 271/16; C07C 273/00; C07C 413/06; C07C 417/12; C07K 5/0812; A61K 38/00
See application file for complete search history.

(56) References Cited

FOREIGN PATENT DOCUMENTS

| WO | WO 2004/111077 A1 | 12/2004 |
|---|---|---|
| WO | WO 2005/012331 A1 | 2/2005 |
| WO | WO 2005/012332 A1 | 2/2005 |
| WO | WO 2006/009674 A1 | 1/2006 |
| WO | WO 2006/046977 A1 | 5/2006 |
| WO | WO 2006/137974 A1 | 12/2006 |

OTHER PUBLICATIONS

Vippagunta et. al., Advanced Drug Delivery Reviews, 2001, Elsevier, vol. 48, pp. 3-26.*
Nairn, Remington's Pharmaceutical Sciences, 1985, Mack Publishing Co., 17th edition, p. 1492.*
U.S. Appl. No. 11/149,731, filed Jun. 10, 2005, Hoveyda et al.
U.S. Appl. No. 12/263,179, filed Oct. 31, 2008, Marsault et al.
U.S. Appl. No. 12/351,395, filed Jan. 9, 2009, Marsault et al.
U.S. Appl. No. 12/636,048, filed Dec. 11, 2009, Hoveyda et al.
U.S. Appl. No. 11/577,922, filed Jul. 15, 2009, Fraser et al.
U.S. Appl. No. 09/679,331, filed Oct. 4, 2000, DeLongchamps et al.
U.S. Appl. No. 11/615,332, filed Dec. 22, 2006, DeLongchamps et al.
U.S. Appl. No. 13/218,784, filed Aug. 26, 2011, DeLongchamps et al.
U.S. Appl. No. 10/961,856, filed Oct. 7, 2004, DeLongchamps et al.
U.S. Appl. No. 10/872,142, filed Jun. 18, 2004, Fraser et al.
U.S. Appl. No. 12/273,638, filed Nov. 19, 2008, Marsault et al.
U.S. Appl. No. 12/273,648, filed Nov. 19, 2008, Marsault et al.
U.S. Appl. No. 13/411,959, filed Mar. 5, 2012, Marsault et al.
U.S. Appl. No. 13/411,979, filed Mar. 5, 2012, Marsault et al.
U.S. Appl. No. 13/412,009, filed Mar. 5, 2012, Marsault et al.

(Continued)

*Primary Examiner* — Sarah Pihonak
(74) *Attorney, Agent, or Firm* — Myers Bigel Sibley & Sajovec, P.A.

(57) ABSTRACT

The present invention provides conformationally-defined macrocyclic compounds that bind to and/or are functional modulators of the motilin receptor including subtypes, isoforms and/or variants thereof. These macrocyclic compounds, at a minimum, possess adequate pharmacological properties to be useful as therapeutics for a range of disease indications. In particular, these compounds are useful for treatment and prevention of disorders characterized by hypermotilinemia and/or gastrointestinal hypermotility, including, but not limited to, diarrhea, cancer treatment-related diarrhea, cancer-induced diarrhea, chemotherapy-induced diarrhea, radiation enteritis, radiation-induced diarrhea, stress-induced diarrhea, chronic diarrhea, AIDS-related diarrhea, C. difficile associated diarrhea, traveller's diarrhea, diarrhea induced by graph versus host disease, other types of diarrhea, dyspepsia, irritable bowel syndrome, chemotherapy-induced nausea and vomiting (emesis) and post-operative nausea and vomiting and functional gastrointestinal disorders. In addition, the compounds possess utility for the treatment of diseases and disorders characterized by poor stomach or intestinal absorption, such as short bowel syndrome, celiac disease and cachexia. The compounds also have use for the treatment of inflammatory diseases and disorders of the gastrointestinal tract, such as inflammatory bowel disease, ulcerative colitis, Crohn's disease and pancreatitis. Accordingly, methods of treating such disorders and pharmaceutical compositions including compounds of the present invention are also provided.

9 Claims, 24 Drawing Sheets

(56) References Cited

OTHER PUBLICATIONS

U.S. Appl. No. 13/412,148, filed Mar. 5, 2012, Marsault et al.
U.S. Appl. No. 13/036,484, filed Feb. 28, 2011, Marsault et al.
U.S. Appl. No. 10/911,219, filed Aug. 2, 2004, DeLongchamps et al.
U.S. Appl. No. 12/471,978, filed May 26, 2009, DeLongchamps et al.
U.S. Appl. No. 10/911,221, filed Aug. 2, 2004, DeLongchamps et al.
U.S. Appl. No. 12/197,610 filed Aug. 25, 2008, DeLongchamps et al.
U.S. Appl. No. 13/036,204, filed Feb. 28, 2011, Marsault et al.
U.S. Appl. No. 12/122,094, filed May 16, 2008, Fraser et al.
Marsault et al. "Discovery of a New Class of Macrocyclic Antagonists to the Human Motilin Receptor", *J. Med. Chem.* 49:7190-7197 (2006).
Marsault et al. "Potent macrocyclic antagonists to the motilin receptor presenting novel unnatural amino acids", *Bioorganic & Medicinal Chemistry Letters* 17:4187-4190 (2007).
Salimbeni et al. "Synthesis and Antiarrhythimic Activity of New 3-[2-(ω-Aminoalkoxy)phenoxy]-4-phenyl-3-buten-2-ones and Related Compounds", *J. Med. Chem.* 30:773-780 (1987).
Notification of Transmittal of the International Search Report and the Written Opinion of the International Searching Authority, or the Declaration corresponding to International Application No. PCT/US2007/019705 dated Jun. 4, 2008.
Office Action corresponding to Japanese Application No. 2009-527455 issued Mar. 25, 2014.

\* cited by examiner (a) NaNO$_2$, AcOH (b) pTSA, BnOH, Toluene (c) DIAD, PPh$_3$, THF (d) Boc-propargylamine, PdCl$_2$(PPh$_3$)$_2$, CuI, Et$_3$N, CH$_3$CN (e) PtO$_2$, H$_2$, EtOH (f) (CF$_3$SO$_2$)$_2$O, CH$_2$Cl$_2$ (g) 2,6-Lutidine, CH$_2$Cl$_2$ (a) NaNO2, AcOH (b) pTSA, BnOH, Toluene (c) DIAD, PPh3, THF (d) Boc-propargylamine, PdCl2(PPh3)2, CuI, Et3N, CH3CN (e) PtO2, H2, EtOH (f) (CF3SO2)2O, CH2Cl2 (g) 2,6-Lutidine, CH2Cl2

C)

a. SO$_2$Cl$_2$, AcOH (85%); b. BtsCl, C$_5$H$_5$N, Et$_3$N, DCM (100%); c. Boc-T38(R), DIAD, PPh$_3$ (95%);
d. HS(CH$_2$)$_2$OH, Na$_2$CO$_3$, DMF (72%); e. LiOH, H$_2$O, THF (87%); f. 10-7, HATU, DIPEA, THF/DMF (66%);
g. TFA, DCM, Et$_3$SiH; h. DEPBT, DIPEA, THF (68%, 2 steps)

A)

B)

A)

B)

a. (CF$_3$CO)$_2$O, TEA, DCM, 0°C; b. H$_2$, Pd/C, ethyl acetate, RT, O/N
c. H$_2$CO, NaBH$_3$CN, TMOF, CH$_3$CN, RT, 2 h, then. MeONa, MeOH, RT, 2 h.

A)

B)

C)

D)

F)

G)

One-way ANOVA (p<0.001). Dunnett's MCT  *p<0.05, **p<0.01 compared to vehicle.

One-way ANOVA (p<0.001). Dunnett's MCT  **p<0.01 compared to vehicle.

- Severity scale: 1- normal, 2- soft stool, 3- diarrhea, 4- severe, bloody diarrhea
- Irinotecan treatment for 5 days; compound 552 drug treatment begins day 4
- All animals alive on the day of scoring are included in the score

MACROCYCLIC ANTAGONISTS OF THE MOTILIN RECEPTOR FOR TREATMENT OF GASTROINTESTINAL DYSMOTILITY DISORDERS

RELATED APPLICATION INFORMATION

The present application is a 35 U.S.C. §371 national phase application of PCT International Application No. PCT/US2007/019705, having an international filing date of Sep. 11, 2007, claiming priority to U.S. Provisional Patent Application No. 60/825,237 filed Sep. 11, 2006. The disclosures of each application are incorporated herein by reference in their entireties. The above PCT international Application was published in the English language and has International Publication No. WO 2008/033328.

FIELD OF THE INVENTION

The present invention relates to novel conformationally-defined macrocyclic compounds that bind to and/or are functional modulators of the motilin receptor including subtypes, isoforms and/or variants thereof. These macrocyclic compounds possess appropriate pharmacological properties to be useful as therapeutics for a range of disease indications. In particular, these compounds are useful for treatment and prevention of disorders characterized by hypermotilenemia or gastrointestinal hypermotility, including; but not limited to diarrhea, cancer treatment-related diarrhea, cancer-induced diarrhea, chemotherapy-induced diarrhea, radiation enteritis, radiation-induced diarrhea, stress-induced diarrhea, chronic diarrhea, AIDS-related diarrhea, *C. difficile* associated diarrhea, traveller's diarrhea, diarrhea induced by graph versus host disease, other types of diarrhea, dyspepsia, irritable bowel syndrome, functional gastrointestinal disorders, chemotherapy-induced nausea and vomiting (emesis) and post-operative nausea and vomiting. In addition, the compounds possess utility for the treatment of diseases and disorders characterized by poor stomach or intestinal absorption, such as short bowel syndrome, celiac disease and cachexia. The compounds may also be used to treat inflammatory diseases and disorders of the gastrointestinal tract, such as inflammatory bowel disease, ulcerative colitis, Crohn's disease and pancreatitis.

BACKGROUND OF THE INVENTION

A number of peptide hormones are involved in the control of the different functions in the gastrointestinal (GI) tract, including absorption, secretion, blood flow and motility (Mulvihill, S. J.; et al. in *Basic and Clinical Endocrinology*, 4$^{th}$ edition, Greenspan, F. S.; Baxter, J. D., Eds., Appleton & Lange: Norwalk, Conn., 1994, pp 551-570). Since interactions between the brain and GI system are critical to the proper modulation of these functions, these peptides can be produced locally in the GI tract or distally in the CNS.

One of these peptide hormones, motilin, a linear 22-amino acid peptide, plays a critical regulatory role in the GI physiological system through governing of fasting gastrointestinal motor activity. As such, the peptide is periodically released from the duodenal mucosa during fasting in mammals, including humans. More precisely, motilin exerts a powerful effect on gastric motility through the contraction of gastrointestinal smooth muscle to stimulate gastric emptying, decrease intestinal transit time and initiate phase III of the migrating motor complex (MMC) in the small bowel. (Itoh, Z., Ed., *Motilin*, Academic Press: San Diego, Calif., 1990, ASIN: 0123757304; Itoh, Z. *Peptides* 1997, 18, 593-608; Nelson, D. K. *Dig. Dis. Sci.* 1996, 41, 2006-2015; Peeters, T. L.; Vantrappen, G.; Janssens, J. *Gastroenterology* 1980, 79, 716-719; Itoh, Z.; Sekiguchi, T. *Scand. J. Gastroenterol. Suppl.* 1983, 82, 121-134; Itoh, Z.; Aizawa, I.; Sekiguchi, T. *Clin. Gastroenterol.* 1982, 11, 497-521; Luiking, Y. C.; Peeters, T. L.; Stolk, M. F.; Nieuwenhuijs, V. B.; Portincasa, P.; Depoortere, I.; Van Berge Henegouwen, G. P.; Akkermans, L. M. A. *Gut* 1998, 42, 830-835.)

Motilin can exert these effects through receptors located predominantly on the human antrum and proximal duodenum, although its receptors are found to some degree along the entire GI tract. (Peeters, T. L.; Bormans, V.; Vantrappen, G. *Regul. Pept.* 1988, 23, 171-182; Poitras, P.; Miller, P.; Dickner, M.; Mao, Y. K.; Daniel, E. E.; St-Pierre, S.; Trudel, L. *Peptides* 1996, 17, 701-707; Miller, P.; Trudel, L.; St-Pierre, S.; Takanashi, H.; Poitras, P. *Peptides* 2000, 21, 283-287; Takeshita E, Matsuura B, Dong M, Miller L J, Matsui H, Onji M. *J. Gastroenterol.* 2006, 41, 223-230.) Therefore, motilin hormone is involved in motility of both the upper and lower parts of the GI system. In addition, motilin and its receptors have been found in the CNS and periphery, suggesting a physiological role in the nervous system that has not yet been definitively elucidated. (Peeters, T. L.; Tang, M. *Peptides* 2007, 28, 625-631; Liu, M.; Dong, L.; Duan, Z.; Zhu, W.-y.; Cui, Y.; Lei, L. *J. Med. Colleges PLA* 2005, 20, 321-326; Thielemans, L.; Depoortere, I.; Van Assche, G.; Bender, E.; Peeters, T. L. *Brain Res.* 2001, 895, 119-128; Depoortere, I.; Peeters, T. L. *Am. J. Physiol.* 1997, 272, G994-G999 and O'Donohue, T. L.; et al. *Peptides* 1981, 2, 467-477.) Recently, motilin receptors were found to be expressed in Purkinje cells of both human and rat cerebellum. (Chen, H.; Chen, L.; Wang, J. J.; Wei, H. J.; Yung, W. H. *NeuroReport* 2007, 18, 1345-1349.) Motilin receptors in the brain have been suggested to play a regulatory role in a number of CNS functions, including feeding and drinking behavior, micturition reflex, central and brain stem neuronal modulation, and pituitary hormone secretion (Itoh, Z. *Peptides* 1997, 18, 593-608; Asakawa, A.; Inui, A.; Momose, K. M.; et al. *Peptides* 1998, 19, 987-990 and Rosenfeld, D. J.; Garthwaite, T. L. *Physiol. Behav.* 1987, 39, 753-756). Studies in infants have also indicated a role for motilin in the long-term regulation of energy balance. (Savino, R.; Grassino, E. C.; Fissore, M. F.; et al. *Clin. Endocrinol.* 2006, 65, 158-162.)

The recent identification and cloning of the human motilin receptor (Intl. Pat. Appl. Publ. WO 99/64436; Feighner, S. D.; Tan, C. P.; McKee, K. K.; et al. *Science* 1999; 284, 2184-2188) has simplified and accelerated the search for agents which can modulate its activity for specific therapeutic purposes. Due to the involvement of motilin in control of gastric motility, agents that either diminish (in the case of hypermotility disorders) or enhance (in the case of hypomotility disorders) the activity at the motilin receptor are a particularly attractive area for further investigation in the search for new effective pharmaceuticals towards a number of GI indications. (Besterman, H. S. *J. Clin. Pathol. Suppl.* 1978, 8, 76-84; Tack, J. *Basic Pract. Res. Clin. Gastroenterol.* 2007, 21, 633-644.)

Two primary avenues have been pursued to discover and develop motilin agonists as therapeutic agents to enhance motility. (Peeters, T. L. *Neurogastroenterol. Motil.* 2006; 18, 1-5; Sandham, D. A.; Plannkuche, H.-J. *Ann. Rep. Med. Chem.* 2006, 41, 211-219.) The first of these, peptidic agonists of the motilin receptor, have clinical application for the treatment of hypomotility disorders, in particular gastroparesis, (Haramura, M.; Tsuzuki, K.; Okamachi, A.; et al. *Bioorg. Med. Chem.* 2002, 10, 1805-1811; U.S. Pat. Nos. 5,422,341;

5,432,261; 5,459,049; 5,695,952; 5,721,353; 5,734,012; 6,018,037; 6,380,158; 6,420,521, 6,838,438; U.S. Pat. Appl. Publ. 2001/041791; 2003/176640; 2004/254345; 2005/065156; 2005/080116, 2005/106146; 2005/208626; Intl. Pat. Appl. Publ. WO 98/42840; WO 01/00830; WO 02/059141). Structure-activity studies have determined the key residues in the native peptide (Peeters, T. L.; Macielag, M. J.; Depoortere, I.; et al. *Peptides* 1992, 13, 1103-1107; Haramura, M.; Tsuzuki, K.; Okamachi, A.; et al. *Chem. Pharm. Bull.* 1999, 47, 1555-1559) and NMR studies have defined its solution structure (Massad, T.; Jarvet, J.; Taner, R.; et al. *J. Biomol. NMR* 2007, 38, 107-123). In addition, studies on the motilin receptor and on the interaction of peptide and non-peptide agonists with the motilin receptor have delineated differential contributions of the receptor extracellular domains to binding. (Matsuura, B.; Dong, M.; Miller, L. J. *J. Biol. Chem.* 2002, 277, 9834-9839; Matsuura, B.; Dong, M.; Naik, S.; Miller, L. J.; Onji, M. *J. Biol. Chem.* 2006, 281, 12390-12396.) Atilmotin, a peptide analogue derived from the C-terminal 14 residues of motilin, has shown promising results in early human studies. (Park, M. I.; Ferber, I.; Camilleri, M.; et al. *Neurogastroenterol. Motil.* 2006, 18, 28-36; Intl. Pat. Appl. Publ. WO 2006/138023; WO 2006/138026; U.S. Pat. Appl. Publ. 2006/287243; 2006/293243.)

The macrolide antibiotic erythromycin has long been known to have stimulation of GI motility as a side effect and, hence, has been utilized as a treatment for gastroparesis. This effect has subsequently been shown to be mediated through interaction at the motilin receptor. (Hasler, W. L.; Heldsinger, A.; Chungal, O. Y. *Am. J. Physiol.* 1992, 262, G50-G55; Peeters, T. L. *Gastroenterology* 1993, 105, 1886-1899; Weber, F. H., Jr.; Richards, R. D.; McCallum, R. W. *Am. J. Gastroenterol.* 1993, 88, 485-490.) However, use of erythromycin therapy can be associated with nausea, diarrhea, cramping and abdominal pain and, further, must be limited in duration to avoid development of bacterial resistance. Therefore, as the second major strategy aimed at motilin agonist therapeutics, the development of derivatives of erythromycin (commonly referred to as motilides) which have little or no antibiotic activity, yet maintain the GI stimulatory effects, has been the subject of a considerable number of research efforts. (Faghih, R.; Nellans, H. N.; Plattner, J. J. *Drugs of the Future* 1998, 23, 861-872; Salat, P.; Parikh, V. *Ind. J. Pharmacol.* 1999, 31, 333-339; Wu, Y. J. *Curr. Pharm. Des.* 2000, 6, 181-223; Inatomi, N.; Sato, F.; Itoh, Z.; Omura, S. Mode of action of macrolides with motilin agonistic activity-motilides. *Macrolide Antibiotics*, $2^{nd}$ edition, Omura, S., ed., Academic Press: San Diego, Calif., 2002, pp 501-531; U.S. Pat. Nos. 4,677,097; 4,920,102; 5,008,249; 5,175,150; 5,418,224; 5,470,961; 5,523,401; 5,523,418; 5,538,961; 5,554,605; 5,578,579; 5,658,888; 5,712,253; 5,854,407; 5,912,235; 5,922,849; 6,077,943; 6,084,079; 6,100,239; 6,165,985; 6,403,775; 6,562,795; 6,750,205; 6,939,861; 6,946,482; 7,211,568; U.S. Pat. Appl. Publ. 2002/025936; 2002/094962; 2003/220271; 2004/138150; 2004/147461; 2005/119515; 2006/270616; Intl. Pat. Appl. Publ. WO 01/60833; WO 02/051855; WO 2004/19879; WO 2005/18576; WO 2006/070937; WO 2006/127252.) Generally disappointing results in clinical trials have been observed for such motilides as EM-574 (Satoh, M.; Sakai, T.; Sano, I.; et al. *J. Pharmacol. Exp. Ther.* 1994, 271, 574-579; Choi, M. G.; Camilleri, M.; Burton, D. D.; Johnson, S.; Edmonds, A. *J. Pharmacol. Exp. Ther.* 1998, 285, 37-40), ABT-229 (alemcinal, Talley, N. J.; Verlinden, M.; Snape, W.; et al. *Aliment. Pharmacol. Ther.* 2000, 14, 1653-1661; Talley, N. J.; Verlinden, M.; Geenan, D. J.; et al. *Gut* 2001, 49, 395-401; Chen, C. L.; Orr, W. C.; Verlinden, M. H.; et al. *Aliment. Pharmacol. Ther.* 2002, 16, 749-757; Netzer, P.; Schmitt, B.; Inauen, W. *Aliment. Pharmacol. Ther.* 2002, 16, 1481-1490) and GM-611 (mitemcinal, Peeters, T. L. *Curr. Opin. Investig. Drugs.* 2001, 2, 555-557; Koga, H.; Takanashi, H.; Itoh, Z.; Omura, S. *Drugs of the Future* 2002, 27, 255-272; Takanashi, H.; Yogo, K.; Ozaki, K.; Koga, H.; Itoh, Z.; Omura, S. *Pharmacology* 2007, 79, 137-148; Ozaki, K. I.; Yogo, K.; Sudo, H.; Onoma, M.; Kamei, K.; Akima, M.; Koga, H.; Itoh, Z.; Omura, S.; Takanashi, H. *Pharmacology* 2007, 79, 223-235; Ozaki, K.; Sudo, H.; Muramatsu, H.; Yogo, K.; Kamei, K.; Koga, H.; Itoh, Z.; Omura, S.; Takanashi, H. *Inflammopharmacology* 2007, 15, 36-42; McCallum, R. W.; Cynshi, O. *Aliment. Pharmacol. Ther.* 2007, 26, 107-116), primarily due to issues such as poor bioavailability, chemical instability and tachyphylaxis. (Thielemans, L.; Depoortere, I.; Perret, J.; et al. *J. Pharmacol. Exp. Ther.* 2005, 313, 1397-1405; Mitselos, A.; Depoortere, I.; Peeters, T. L. *Biochem. Pharmacol.* 2007, 73, 115-124.) Nonetheless, due to the therapeutic potential of such agents, the search for motilin agonists in this class has continued and, recently, KOS-2187 (Carreras, C. W.; Liu, Y.; Chen, Y.; et al. *Gastroenterology* 2005, 128, A464; Carreras, C. W.; Burlingame, M.; Carney, J.; et al. *Can. J. Gastroenterol.* 2005, 19, 15) has been described and appears to circumvent many of these problems. A method useful for analyzing the therapeutic efficiency of these types of molecules has also been formulated (U.S. Pat. No. 6,875,576; U.S. Pat. Appl. Publ. 2002/192709; Intl. Pat. Appl. Publ. WO 02/64092).

Similarly, non-peptide, non-motilide motilin agonists have been reported (U.S. Pat. No. 7,262,195; U.S. Pat. Appl. Publ. No. 2004/152732; 2005/065156; Intl. Pat. Appl. Publ. WO 02/137127; WO 02/92592; WO 2005/027908; WO 2005/027637; Jap. Pat. Abstr. Publ. No. 09249620). Of these, BMS-591348 has been described as possessing a pharmacological profile that avoids the tachyphylaxis issues that plagued many of the previous motilin agonist efforts. (Li, J. J.; Chao, H. G.; Wang, H.; et al. *J. Med. Chem.* 2004, 47, 1704-1708; Lamian, V.; Rich, A.; Ma, Z.; Li, J. Seethala, R.; Gordon, D.; Dubaquie, Y. *Mol. Pharmacol.* 2006, 69, 109-118.)

On the other hand, antagonists of the motilin receptor are potentially useful as therapeutic treatments for diseases associated with hypermotilinemia and/or gastrointestinal hypermotility, including diarrhea, cancer treatment-related diarrhea, cancer-induced diarrhea, chemotherapy-induced diarrhea, radiation enteritis, radiation-induced diarrhea, stress-induced diarrhea, chronic diarrhea, AIDS-related diarrhea, *C. difficile* associated diarrhea, traveller's diarrhea, diarrhea induced by graph versus host disease, other types of diarrhea, dyspepsia, irritable bowel syndrome, functional gastrointestinal disorders, chemotherapy-induced nausea and vomiting (emesis) and post-operative nausea and vomiting. Current treatments for these conditions are ineffective in many cases. Loperamide, an opioid agonist, is useful for milder diarrhea and generally does not work in a high percentage of patients. Octreotide, a somatostatin agonist, is used off-label as a diarrheal treatment, but is relatively expensive, given by injection, and also not effective in many instances. Further, motilin levels have been observed to be elevated in patients with acute diarrhea (Besterman, H. S.; Christofides, N. D.; Welsby, P. D.; et al. *Gut* 1983, 24, 665-671) and traveler's diarrhea (Besterman, H. S.; Cook, G. C.; Sarson, D. L.; et al. *Br. Med. J.* 1979, 17, 1252-1255).

Diarrhea is a common and serious side-effect experienced by cancer patients resulting from surgery, bone marrow transplantation, chemotherapy and radiation treatment. (Stern, J.; Ippoliti, C. *Sem. Oncol. Nurs.* 2003, 19, 11-16; Benson, A. B., III; Ajani, J. A.; Catalano, R. B.; et al. *J. Clin. Oncol.* 2004, 22, 2918-2926; O'Brien, B. E.; Kaklamani, V. G.; Benson, A. B.

III *Clin. Colorectal Canc.* 2005, 4, 375-381.) Certain chemotherapeutic regimens, particularly those including fluoropyrimidines and irinotecan, result in chemotherapy-induced diarrhea (CID) rates as high as 50-80%. (Arbuckle, R. B.; Huber, S. L.; Zacker, C. *The Oncologist* 2000, 5, 250-259; Saltz, L. B. *J. Support. Oncol.* 2003, 1, 35-46; Goldberg-Arnold, R. J.; Gabrail, N.; Raut, M.; Kim, R.; Sung, J. C. Y.; Zhou, Y. *J. Support. Oncol.* 2005, 3, 227-232; Sharma, R.; Tobin, P.; Clarke, S. J. *Lancet Oncol.* 2005, 6, 93-102; Gibson, R. J.; Keefe, D. M. K. *Support. Care Cancer* 2006, 14, 890-900.) The implications of CID include increased morbidity and mortality. This presents a significant problem as, in 2001, over 1.4 million individuals in the U.S. were undergoing cancer chemotherapy. A large heterogeneous study of cancer patients at all stages of treatment placed the prevalence of diarrhea at 14%. (M. D. Anderson Symptom Inventory, *Cancer* 2000, 89(7), 1634-1646). However, for certain types of cancer, the occurrence is higher. In colorectal cancer, for example, more than half of patients experienced diarrhea rated serious (grade 3) or higher. Resulting from tissue damage in the intestine caused by drugs designed to thwart the rapid growth of tumor cells, it also affects the cells lining the intestinal wall. No effective therapy exists for this damage nor for the associated diarrhea.

In general, from 10-20% of patients experience CID, although for some chemotherapeutic agents the incidence can be as high as 90%. In approximately 20% of patients, the adverse effects are so severe, it requires a halt to or reduction of the treatment regimen and, often, hospitalization. In addition, parenteral nutrition often must be taken due to the inability of patients to take nourishment normally. Hence, this has an effect on the efficacy of the chemotherapy. Indeed, a review of clinical trials in colorectal cancer revealed higher death rates primarily due to gastrointestinal toxicity. (Rothenberg, M. L.; Meropol, N. J.; Poplin, E. A.; VanCutsem, E.; Wadler, S. J. *Clin. Oncol.* 2001, 19, 3801-3807.) Current pharmacological treatments only work in some patients and are much less effective against the more serious grades of diarrhea. (MacNaughton, W. K. *Aliment. Pharmacol. Ther.* 2000, 14, 523-528).

Acute radiation enteritis (ARE) or radiation induced intestinal dysfunction occurs in 75% of patients undergoing radiation therapy, typically occurring in the second or third week of therapy. Characterized by abdominal cramping and diarrhea, this is a serious and feared side effect that results in increased overall treatment time as well as reduced quality of life and can even result in death. In 5-15% of patients, the condition becomes chronic. In addition to discomfort, this side effect decreases the therapeutic benefit from radiation treatment by increasing the overall treatment time. (MacNaughton, W. K. *Aliment. Pharmacol. Ther.* 2000, 14, 523-528; Nguyen, N. P.; Antoine, J. E.; Dutta, S.; Karlsson, U.; Sallah, S. *Cancer* 2002, 95, 1151-1163; Gwede, C. K. *Sem. Nursing Oncol.* 2003, 19, 6-10.)

Indeed, chronic diarrhea can arise as a result of numerous medical conditions. (Schiller, L. R. *Curr. Treat. Options Gastroenterol.* 2005, 8, 259-266; Spiller, R. *Neurogastroenterol. Motil.* 2006, 18, 1045-1055.) For example, chronic diarrhea is a common problem for patients with human immunodeficiency virus infection, especially those with advanced disease. This is a debilitating side effect that occurs in 60-90% of AIDS patients. (Cohen, J.; West, A. B.; Bini, E. J. *Gastroenterol. Clin. North Am.* 2001, 30, 637-664; Oldfield, E. C., III *Rev. Gastroenterol. Disord.* 2002, 2, 176-88; Sestak, K.; *Curr. HIV Res.* 2005, 3, 199-205; Thom, K.; Forrest, G. *Curr. Opin. Gastroenterol.* 2006, 22, 18-23.) Additionally, psychological factors, such as stress, are known to play a role in adversely affecting the proper functioning of the GI tract. (North, C. S.; Alpers, D. H.; Thompson, S. J.; Spitznagel, E. L. *Dig. Dis. Sci.* 1996, 41, 633-640; Kamm, M. A. *Eur. J. Surg. Suppl.* 1998, 583, 37-40; Botha, C.; Libby, G. *Br. J. Hosp. Med. (Lond.)* 2006, 67, 344-349.)

Traveller's diarrhea affects over 50% of travellers to some destinations, particularly tropical ones, and is estimated to afflict over 11 million individuals annually. Apart from the disruption to business, travel and vacation schedules, this condition is often accompanied by other clinical manifestations such as nausea, vomiting, abdominal pain, fecal urgency, bloody stools, and fever. (Lima, A. A. M. *Curr. Opin. Infect. Dis.* 2001, 14, 547-552; Al-Abri, S. S.; Beeching, N. J.; Nye, F. J. *Lancet Infect. Dis.* 2005, 5, 349-360; DuPont, H. L. *Gastroenterol. Clin. North Am.* 2006, 35, 337-353.)

*Clostridium difficile* is the etiological agent responsible for about one-third of cases of antibiotic-associated diarrhea and is estimated to cause a $1 billion annual cost in the U.S. Antibiotic-associated diarrhea is more common in the hospital setting with up to 29% of patients developing the condition, resulting in increased length of stay, increased cost of care, and increased mortality. (Bartlett, J. G. *N. Engl. J. Med.* 2002, 346, 334-339; Kelly, C. P.; Pothoulakis, C.; LaMont, J. T. *N. Engl. J. Med.* 1994, 330, 257-262; Kyne, L.; Farrell, R. J.; Kelly, C. P. *Gastroenterol. Clin. N. Am.* 2001, 30, 753-777; Malnick, S. D. H.; Zimhony, O. *Ann. Pharmacother.* 2002, 36, 1767-1775; Hull, M. W.; Beck, P. L. *Can. Fam. Phys.* 2004, 50, 1536-1540; Schroeder, M. S. *Am. Fam. Phys.* 2005, 71, 921-928; Voth, D. E.; Ballard, J. D. *Clin. Microbiol. Rev.* 2005, 18, 247-263.) It is a serious condition with a mortality rate as high as 25% in frail elderly patients. Recently, the incidence and severity of *C. difficile*-associated diarrhea (CADD) has begun to increase dramatically. (Frost. F.; Craun, G. F.; Calderon, R. L. *Emerg. Infect. Dis.* 1998, 4, 619-625; Olfield, E. C. *Rev. Gastroenterol. Disord.* 2006, 6, 79-96.)

Diarrhea is also induced in patients with graft versus host disease (GVHD). GVHD is a common, potentially life-threatening complication of allogenic hematopoietic stem cell transplantation. Gastrointestinal GVHD frequently involves the colon and complicates management of these seriously ill patients. (Flowers, M. E.; Kansu, E.; Sullivan, K. M. *Hematol Oncol Clin North Am.* 1999, 13, 1091-1112; Ross, W. A.; Couriel, D. *Curr. Opin. Gastroenterol.* 2005, 21, 64-69.) In addition, diarrhea is a common side effect after other types of transplantation with an incidence ranging from 10% to 43%. Diarrhea is also a frequent side effect of immunosuppressive medications. (Ginsburg, P. M.; Thuluvath, P. J. *Liver Transpl.* 2005, 11, 881-890.)

Irritable bowel syndrome (IBS) is the most common functional GI disorder with an estimated worldwide prevalence of 10-15%. (Saito, Y. A.; Schoenfeld, P.; Locke, G. R. *Am. J. Gastroenterol.* 2002, 97, 1910-1915; Gilkin, R. J., Jr. *Clin. Ther.* 2005, 27, 1696-1709; Lacy, B. E.; De Lee, R. *J. Clin. Gastroenterol.* 2005, 39, S230-S242; Talley, N. J. *Intern. Med. J.* 2006, 36, 724-728; Ohman, L.; Simren, M. *Dig. Liver Dis.* 2007, 39, 201-215.) The total annual cost attributable to IBS is estimated to be $30 billion, including $10 billion in direct costs from physician visits and prescription pharmaceuticals, as well as a significant cost from missed work days. (Talley, N. J.; Gabriel, S. E.; Harmsen, W. S.; et al. *Gastroenterology* 1995, 109, 1736-1741; Maxion-Bergemann, S.; Thielecke, F.; Abel, F.; Bergemann, R. *Pharmacoeconomics* 2006, 24, 21-37.) IBS patients are sub-classified into diarrhea-predominant (IBS-d), constipation-predominant (IBS-c) or those alternating between these two patterns (IBS-m). Treatments for these various subsets generally must be approached with separate and specific therapies. Antispasmodics, tricyclic antidepressants, selective serotonin reuptake inhibitors, laxatives, antidiarrheals, and bulking agents have not proven to be widely effective and tend to treat symptoms, rather than underlying pathophysiology. (Schoenfeld, P. *Gastroenterol. Clin. North Am.* 2005, 34, 319-335; Cremonini, F.; Talley, N. J. *Nat. Clin. Pract. Gastroenterol. Hepatol.* 2005, 2, 82-88; Andersen, V.; Camilleri, M. *Drugs* 2006, 66, 1073-1088.) The plasma levels of motilin have been shown to be elevated in patients with IBS. (Simren, M.; Bjornsson, E. S.; Abrahamsson, H. *Neurogastroenterol. Motil.* 2005, 17, 51-57.) Motilin antagonists, hence, would be a useful treatment for patients with IBS. They would likely be more suited to IBS-d and to a lesser extent, IBS-m. IBS-d is manifested by fecal urgency and frequent loose bowel movements (>3 per day). Individuals suffering from IBS-d account, for approximately one-third of the entire IBS patient population.

Another extremely common GI disorder, dyspepsia, is characterized by chronic or recurrent upper GI distress with no obvious physical cause: (Tack, J.; Bisschops, R.; Sarnelli, G. *Gastroenterology* 2004, 127, 1239-1255; Kleibeuker, J. H.; Thijs, J. C. *Curr. Opin. Gastroenterol.* 2004, 20, 546-550; Talley, N. J.; Vakil, N.; et al. *Am. J. Gastroenterol.* 2005, 100, 2324-2337; Talley, N. J.; Vakil, N.; Moayyedi, P. *Gastroenterology* 2005, 129, 1756-1780; Smith, M. L. *Dig. Liver Dis.* 2005, 37, 547-558; Saad, R. J.; Chey, W. D. *Aliment. Pharmacol. Ther.* 2006, 24, 475-492; Suzuki, H.; Nishizawa, T.; Hibi, T. *J. Gastroenterol.* 2006, 41, 513-523.; Mahadeva, S.; Goh, K. L. *World J. Gastroenterol.* 2006, 12, 2661-2666; Monkemuller K, Malfertheiner P. *World J. Gastroenterol.* 2006, 12, 2694-2700; Mizuta, Y.; Shikuwa, S.; Isomoto, H.; Mishima, R.; Akazawa, Y.; Masuda, J.; Omagari, K.; Takeshima, F.; Kohno, S. *J. Gastroenterol.* 2006; 41, 1025-1040; Chua, A. S. *World J. Gastroenterol.* 2006, 12, 2656-2659.) Typical symptoms include gastric fullness, bloating, pain, nausea and vomiting. This disease has prevalence as high as 20% annually in Western countries. It accounts for up to 5% of all visits to primary care physicians and 30% of visits to GI specialists. As with IBS, the patient population can be categorized into various subsets based upon symptoms. (Choung, R. S.; Locke, G. R. III; Schleck, C. D.; Zinsmetister, A. R.; Talley, N. J. *Am. J. Gastroenterol.* 2007, 102, 1983-1989.) However, the largest patient subset (up to 60%) suffers from dyspepsia with no known organic cause, otherwise known as "functional dyspepsia (FD)." FD has a major impact on quality of life and health care resources. In analogy with IBS, no widely-accepted therapy for the treatment of FD currently exists. (Stanghellini, V.; De Ponti, F.; De Giorgio, R.; et al. *Drugs* 2003, 63, 869-892; Cremonini, F.; Delgado-Aros, S.; Talley, N. J. *Best Pract. Res. Clin. Gastroenterol.* 2004, 18, 717-733; McNally, M. A.; Talley, N. J. *Curr. Treatment Opt. Gastroenterol.* 2007, 10, 157-168.) Circulating plasma motilin levels are also seen to be raised in patients suffering from dyspepsia. (Kusano, M.; Sekiguchi, T.; Kawamura, O.; Kikuchi, K.; Miyazaki, M.; Tsunoda, T.; Horikoshi, T.; Mori, M. *Am. J. Gastroenterol.* 1997, 92, 481-484; Kamerling, I. M.; Van Haarst, A. D.; Burggraaf, J.; Schoemaker, R. C.; Biemond, I.; Heinzerling, H.; Jones, R.; Cohen, A. F.; Masclee, A. A. *Am. J. Physiol. Gastrointest. Liver Physiol.* 2003, 284, G776-G781.) As with IBS, motilin antagonists would mitigate the effects of motilin in such patients.

Chemotherapy-induced nausea and vomiting (CINV), or emesis, is one of the most severe adverse effects resulting from cancer treatment and is often cited as the side effect most feared by patients. From 70-80% of patients receiving cancer chemotherapy experience CINV. In addition to a significant deterioration in quality of life, this condition often requires modification or delay of chemotherapeutic regimens with concomitant negative impact on the effectiveness of treatment. Despite recent progress in the development and availability of new approaches to mitigating the effects of CINV, there remains a compelling need for alternative strategies for patients for whom current treatments are inadequate. (Lindley, C. M.; Hirsch, J. D.; O'Neill, C. V.; Transau, M. D.; Gilbert, C. S.; Osterhaus, J. T. *Qual. Life Res.* 1992, 1, 331-340; Martin, M. *Oncology* 1996, 53, 26-31; Kovac, A. L. *Drug Safety* 2003, 26, 227-259; Grunberg, S. M. *J. Support. Oncol.* 2004, 2, 1-12; Jordan, K.; Kasper, C.; Schmoll, H.-J. *Eur. J. Canc.* 2005, 41, 199-205; Herrstedt, J.; Dombernowsky, P. *Basic Clin. Pharmacol. Toxicol.* 2007, 101, 143-150.)

Post-operative nausea and vomiting (PONV) is a common complication from surgery, occurring in 30-50% of patients. PONV can lead to unintended or extended hospitalization, electrolyte abnormalities and strain on surgical sutures, plus a substantial negative effect on quality of life. As such, it increases health care costs and decreases patient satisfaction. The importance of dealing with PONV has become well-recognized in the medical community and there is a need for effective treatments. (Osoba, D.; Zee, B.; Warr, D.; et al. *Support. Care Cancer* 1997, 5, 303-313; Kovac, A. L. *Drugs* 2000, 59, 213-243; Gan, T. J. *J. Am. Med. Assoc.* 2002, 287, 1233-1236; Tramèr, M. R. *Best Pract. Res. Clin. Anaesthesiol.* 2004, 18, 693-701; Habib, A. S.; Gan, T. J. *Can. J. Anesth.* 2004, 51, 326-341; Golembiewski, J.; Chernin, E.; Chopra, T. *Am. J. Health-Syst. Pharm.* 2005, 62, 1247-1260.)

In addition to its actions on motility, motilin is involved in inducing secretion within the gastrointestinal tract. Motilin plays a role in gastric and pancreatic secretion in dogs. (Konturek, S. J.; Dembinski, A.; Krol, R.; Wunsch, E. *Scand. J. Gastroenterol.* 1976, 11, 57-61; Magee, D. F.; Naruse, S. *J. Physiol.* 1984, 355, 441-447; Lee, K. L.; Shiratori, K.; Chen, Y. F.; Chang, T.-M.; Chey, W. Y. *Am. J. Physiol.* 1986, 14, G759-764.) Similarly, intestinal secretagogue activity in humans has been described for [Nle$^{13}$]-motilin. (Kachel, G. W.; Frase, L. L.; Domschke, W.; Chey, W. Y.; Krejs, G. J. *Gastroenterology* 1984, 87, 550-556.) Hence, an antagonist of the motilin receptor may show anti-secretory effects and play a role as an anti-diarrheal agent. Anti-secretory agents have proven to be effective anti-diarrheal therapeutics. (Farthing, M. J. G. *Exp. Opin. Invest. Drugs* 2004, 13, 777-785; Farthing, M. J. G. *Dig. Dis.* 2006, 24, 47-58.) This dual role, as both an anti-motility and an anti-secretory agent would make motilin antagonists even more effective therapeutics for the treatment of diarrheal conditions.

In addition to treatment of disorders characterized by hypermotility, the use of motilin antagonists would also be useful in the treatment of diseases and disorders characterized by poor stomach or intestinal absorption. A motilin antagonist would slow gastrointestinal motility thereby permitting longer GI exposure time for absorption of necessary nutrients. Such diseases and disorders include celiac disease, a chronic disorder afflicting almost 1% of the population. Celiac disease is a GI disorder characterized by inflammation, leading to injury to the mucosal lining of the small intestine. The inflammation results when gliadin, a protein found in gluten-containing foods, is ingested by genetically susceptible individuals. The mucosal damage and subsequent malabsorption of nutrients can lead to numerous complications. (Alaedini, A.; Green, P. H. R. *Ann. Intern. Med.* 2005, 142, 289-298; Koning, F. *Gastroenterology* 2005, 129, 1294-1301; Chand, N.; Mihas, A. A. *J. Clin. Gastroenterol.* 2006, 40, 3-14; Westerberg, D. P.; Gill, J. M.; Dave, B.; et al. *J. Am.*

Osteopath. Assn. 2006, 106, 145-151; Jones, R. B.; Robins, G. G.; Howdle, P. D. Curr. Opin. Gastroenterol. 2006, 22, 117-123; Green, P. H. R.; Jabri, B. Ann. Rev. Med. 2006, 57, 207-221; Hill, I. D. Curr. Treat. Options Gastroenterol. 2006, 9, 399-408.) The only current treatment is modification to a gluten-free diet.

Short bowel syndrome is a medical condition that occurs after resection of a substantial portion of small intestine and is characterized by malnutrition. (Misiakos, E. P.; Macheras, A.; Kapetanakis, T.; Liakakos, T. J. Clin. Gastroenterol. 2007, 41, 5-18.; Buchman, A. L. Gastroenterology. 2006, 130 (Suppl. 1), S5-S15; Jackson, C.; Buchman, A. L. Curr. Gastroenterol. Rep. 2005, 7, 373-378; Scolapio, J. S. Curr. Opin. Gastroenterol. 2004, 20, 143-145; Buchman, A. L.; Scolapio, J.; Fryer, J. Gastroenterology 2003, 124, 1111-1134; Westergaard, H. Sem. Gastrointest. Dis. 2002, 13, 210-220.) The syndrome is particularly distressing in children, where mortality and morbidity are very high. (Vanderhoof, J. A.; Young, R. J.; Thompson, J. S. Pediatric Drugs 2003, 5, 625-631; Vanderhoof, J. A. J. Ped. Gastroenterol. Nutri. 2004, 39, 5768-5771; Sukhotnik, I.; Coran, A. G.; et al. Pediatr. Surg. Int. 2005, 21, 947-953.) No current pharmacological agents are currently approved for SBS, which is typically treated through intestinal adaptation or rehabilitation in order to improve nutritional status of SBS patients. (DiBaise, J. K.; Young, R. J.; Vanderhoof, J. A. Am. J. Gastroenterol. 2004, 99, 1823-1832.)

Additionally, the potential for improving nutrient absorption through the use of motilin antagonists could be useful in the treatment of cachexia, a wasting disorder common in serious illnesses such as cancer, AIDS, chronic heart failure and other cardiovascular diseases, and renal disease, as well as in the aged. Cancer cachexia is a therapeutic condition characterized by weight loss and muscle wasting and afflicts approximately 50% of all cancer patients and is the main cause of death in more than 20% of patients. Additionally, this condition has been shown to be a strong independent risk factor for mortality. (Kern, K. A.; Norton, J. A. JPEN 1980, 12, 286-298; Tisdale, M. J. J. Natl. Cancer Inst. 1997, 89, 1763-1773; Gagnon, B.; Bruera, E. Drugs 1998, 55, 675-688; Inui, A. CA Cancer J. Clin. 2002, 52, 72-91.) Likewise, patients suffering from chronic heart failure are at serious risk from a similar wasting syndrome. (Springer, J.; Filippatos, G.; Akashi, Y. J.; Anker, S. D. Curr. Opin. Cardiol. 2006, 21, 229-233; Akashi, Y. J.; Springer, J.; Anker, S. D. Curr. Heart Fail. Rep. 2005, 2, 198-203; Anker, S. D.; Steinborn, W.; Strassburg, S. Ann. Med. 2004, 36, 518-529.) This condition also affects an increasing proportion of the elderly. (Morley, J. E. J. Gerontology, Ser. A: Biol. Sci. Med. Sci. 2003, 58A, 131-137.)

Additionally, the association between intestinal inflammation and altered intestinal motility is well-established. Further, motilin has been implicated in inflammatory disorders of the GI system. Elevated motilin levels have been observed in patients with inflammatory bowel disease (Besterman, H. S.; Mallinson, C. N.; et al. Scand. J. Gastroenterol. 1983, 18, 845-852), ulcerative colitis (Greenberg, G. R.; Buchan, A. M.; McLeod, R. S.; Preston, P.; Cohen, Z. Gut 1989, 30, 1721-1730) and chronic pancreatitis (Besterman, H. S.; Adrian, T. E.; Bloom, S. R. et al. Digestion 1982, 24, 195-208). In addition, increased motilin and mRNA expression have been found in a rabbit colitis model (Depoortere, I.; Van Assche, G.; Peeters, T. L. Neurogastroenterol. Motil. 2001, 13, 55-63.) Increased plasma motilin concentrations were also obtained in patients after intestinal resection (Besterman, H. S.; Adrian, T. E.; Mallinson, C. N. Gut 1982, 23, 854-861) and ileostomy (Kennedy, H. J.; Sarson, D. L.; Bloom, S. R.; et al. Digestion 1982, 24, 133-136). It has further been shown that non-steriodal anti-inflammatory drugs can induce hypermolitinemia, disturb the interdigestive migrating motor complex, and contribute to the formation of gastric ulcers. (Narita, T.; Okabe, N.; Hane, M.; et al. J. Vet. Pharmacol. Ther. 2006, 29, 569-577.) Therefore, motilin antagonists may be used as anti-inflammatory agents, in particular for use in the GI tract, with beneficial properties relative to existing treatments.

Despite the potential offered by motilin antagonists as a novel approach to treat hypermotility and malabsorption disorders, efforts have lagged those directed at agonists. A variety of peptidic compounds have been described as antagonists of the motilin receptor [(ANQ-11125: Peeters, T. L.; Depoortere, I.; Macielag, M. J.; Marvin, M. S.; Florance, J. R.; Galdes, A. Biochem. Biophys. Res. Comm. 1994, 198, 411-416); (OHM-11526: Farrugia, G.; Macielag, M. J.; Peeters, T. L.; San, M. G.; Galdes, A.; Szurszewski, J. H. Am. J. Physiol. 1997, 273, G404-G412; Depoortere, I.; Macielag, M. J.; Galdes, A.; Peeters, T. L. Eur. J. Pharmacol. 1995, 286, 241-247); (MA-2029: Mitselos, A.; Depoortere, I.; Peeters, T. L. Biochem. Pharmacol. 2007, 73, 115-124); Poitras, P.; Miller, P.; Gagnon, D.; St-Pierre, S. Biochem. Biophys. Res. Comm. 1994, 205, 449-454; U.S. Pat. Nos. 5,470,830; 6,255, 285; 6,586,630; 6,720,433; U.S. Pat. Appl. Publ. 2003/176643; Intl. Pat. Appl. Publ. WO 99/09053; WO 00/17231; WO 00/44770; WO 02/64623). These peptidic antagonists suffer from the known limitations of peptides as drug molecules, in particular poor oral bioavailability and degradative metabolism.

Cyclization of peptidic derivatives is a method that can be employed to improve the properties of a linear peptide both with respect to metabolic stability and conformational freedom. Cyclic molecules tend to be more resistant to metabolic enzymes. Such cyclic peptide motilin antagonists have been reported, highlighted by GM-109. (Takanashi, H.; Yogo, K.; Ozaki, M.; Akima, M.; Koga, H.; Nabata, H. J. Pharm. Exp. Ther. 1995, 273, 624-628; Haramura, M.; Okamachi, A.; Tsuzuki, K.; Yogo, K.; Ikuta, M.; Kozono, T.; Takanashi, H.; Murayama, E. Chem. Pharm. Bull. 2001, 49, 40-43; Haramura, M.; Okamachi, A.; Tsuzuki, K.; Yogo, K.; Ikuta, M.; Kozono, T.; Takanashi, H.; Murayama, E. J. Med. Chem. 2002, 45, 670-675; U.S. Pat. No. 7,018,981; U.S. Pat. Appl. Publ. 2003/191053; Intl. Pat. Appl. Publ. WO 02/16404; Jap. Pat. Abstr. Publ. No. 07138284)

Macrocyclic peptidomimetics have been previously described as antagonists of the motilin receptor and their uses for the treatment of a variety of GI disorders and to modulate the migrating motor complex summarized. (Intl. Pat. Appl. Publ. WO 2004/111077; U.S. Pat. Appl. Publ. 2005/054562; U.S. Prov. Pat. Appl. Ser. No. 60/938,655; U.S. Prov. Pat. Appl. Ser. No. 60/939,280; Marsault, E.; Hoveyda, H. R.; Peterson, M. L.; Saint-Louis, C.; Landry, A.; Vézina, M.; Ouellet, L.; Wang, Z.; Ramaseshan, M.; Beaubien, S.; Benakli, K.; Beauchemin, S.; Déziel, R.; Peeters, T.; Fraser, G. L. J. Med. Chem. 2006, 49, 7190-7197; Marsault, E.; Benakli, K.; Beaubein, S.; Saint-Louis, C.; Déziel, R.; Fraser, G. Bioorg Med. Chem. Lett. 2007, 17, 4187-4190.) These peptidomimetic macrocyclic motilin antagonists are distinguished from the aforementioned cyclic peptide motilin antagonists in that it was found that such peptidic derivatives containing D-amino acids were devoid of activity. In contrast, for the tripeptidomimetic compounds of the present invention, the D-stereochemistry is beneficial for two of the three building elements. Further, the tether portion of the molecule provides a non-peptidic component and, hence, distinct structures.

The peptidomimetic macrocycles of the present invention are demonstrated to have binding and functional activity at the motilin receptor. Although binding potency and target affinity are factors in drug discovery and development, also important for development of viable pharmaceutical agents are optimization of pharmacokinetic (PK) and pharmacodynamic (PD) parameters. A focus area for research in the pharmaceutical industry has been to better understand the underlying factors which determine the suitability of molecules in this manner, often colloquially termed its "druglikeness." (Lipinski, C. A.; Lombardo, F.; Dominy, B. W.; Feeney, P. J. *Adv. Drug Delivery Rev.* 1997, 23, 3-25; Muegge, I. *Med. Res. Rev.* 2003, 23, 302-321; Veber, D. F.; Johnson, S. R.; Cheng, H.-Y.; Smith, B. R.; Ward, K. W.; Kopple, K. D. *J. Med. Chem.* 2002, 45, 2615-2623.) For example, molecular weight, log P, membrane permeability, the number of hydrogen bond donors and acceptors, total polar surface area (TPSA), and the number of rotatable bonds have all been correlated with compounds that have been successful in drug development. Additionally, experimental measurements of plasma protein binding, interaction with cytochrome P450 enzymes, and pharmacokinetic parameters are employed in the pharmaceutical industry to select and advance new drug candidates.

However, these parameters have not been widely explored or reported within the macrocyclic structural class. This creates tremendous challenges in drug development for such molecules. The macrocyclic compounds of the present invention have been found to possess desirable pharmacological characteristics, while maintaining sufficient binding affinity and selectivity for the motilin receptor, as illustrated in the Examples. These combined characteristics make them more suitable for development as pharmaceutical agents.

Other motilin antagonists, which are non-peptidic and non-macrocyclic in nature have also been reported. [(RWJ-68023: Beavers, M. P.; Gunnet, J. W.; Hageman, W.; Miller, W.; Moore, J. B.; Zhou, L.; Chen, R. H. K.; Xiang, A.; Urbanski, M.; Combs, D. W.; Mayo, K. H.; Demarest, K. T. *Drug Design Disc.* 2001, 17, 243-251); Johnson, S. G.; Gunnet, J. W.; Moore, J. B.; et al. *Bioorg. Med. Chem. Lett.* 2006, 16, 3362-3366; U.S. Pat. Nos. 5,972,939; 6,384,031; 6,392,040; 6,423,714; 6,511,980; 6,624,165; 6,667,309; 6,967,199; U.S. Pat. Appl. Publ. 2001/041701; 2001/056106, 2002/002192; 2002/013352; 2002/103238; 2002/111484; 2003/203906; 2005/148584; 2007/054888; Intl. Pat. Appl. Publ. WO 99/21846; WO 01/68620; WO 01/68621; WO 01/68622; WO 01/85694) Of these, RWJ-68023 has been examined in humans, but with a poor outcome, likely due to the level of potency of this molecule. (Kamerling, I. M. C.; van Haarst, A. D.; Burggraaf, J.; et al. *Br. J. Clin. Pharmacol.* 2003, 57, 393-401.)

Indeed, neither of the previously well-studied motilin antagonists, RWJ-68023 and GM-109, possessed the preferred full profile for a potential pharmaceutical product targeting this receptor including high binding affinity and functional activity at the motilin receptor, good Caco-2 membrane permeability, appropriate pharmacokinetic profile [reasonable plasma half-life ($t_{1/2}$) and clearance values ($Cl_T$)], oral bioavailability, sufficient solubility to facilitate formulation and in vivo efficacy. In contrast, the macrocyclic motilin antagonists of the present invention have been found to possess at least some, if not all, of these favorable characteristics.

SUMMARY OF THE INVENTION

The present invention provides novel conformationally-defined macrocyclic compounds with improved pharmacological properties. These compounds can function as antagonists of the motilin receptor.

According to aspects of the present invention, the present invention is directed to compounds of formula I:

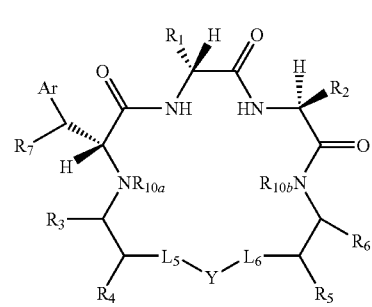

(I)

and pharmaceutically acceptable salts, hydrates or solvates thereof wherein:

Y is

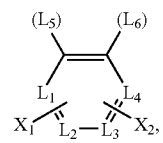

wherein ($L_5$) and ($L_6$) indicates the bonds to $L_5$ and $L_6$ of formula I, respectively;

Ar is selected from the group consisting of

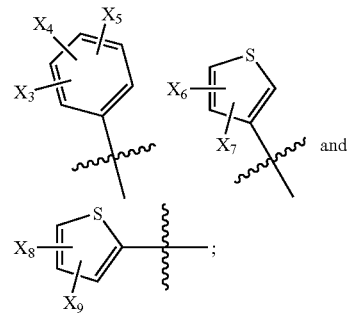

$R_1$ is selected from the group consisting of lower alkyl and cycloalkyl;

$R_2$ is selected from the group consisting of lower alkyl, substituted lower alkyl, cycloalkyl and substituted cycloalkyl;

$R_3$, $R_4$, $R_5$, and $R_6$ are independently selected from the group consisting of hydrogen, lower alkyl and substituted lower alkyl;

$R_7$ is selected from the group consisting of hydrogen, lower alkyl, hydroxy and amino;

$R_{10a}$ and $R_{10b}$ are independently selected from the group consisting of hydrogen, lower alkyl and substituted lower alkyl;

$X_1$, $X_2$, $X_6$, $X_7$, $X_8$ and $X_9$ are independently selected from the group consisting of hydrogen, halogen, trifluoromethyl and lower alkyl;

$X_3$, $X_4$ and $X_5$ are independently selected from the group consisting of hydrogen, hydroxyl, alkoxy, halogen, trifluoromethyl and lower alkyl;

$L_1$, $L_2$, $L_3$ and $L_4$ are independently selected from the group consisting of CH and N; with the proviso that the total number of nitrogens in the ring must be 0, 1, 2 or 3;

$L_5$ and $L_6$ are independently selected from the group consisting of O, $CR_{8a}R_{8b}$ and $NR_9$; wherein $R_{8a}$ and $R_{8b}$ are independently selected from the group consisting of hydrogen and lower alkyl; and $R_9$ is selected from the group consisting of hydrogen, lower alkyl, formyl, acyl and sulfonyl.

In particular aspects of the invention, Ar of formula I is selected from:

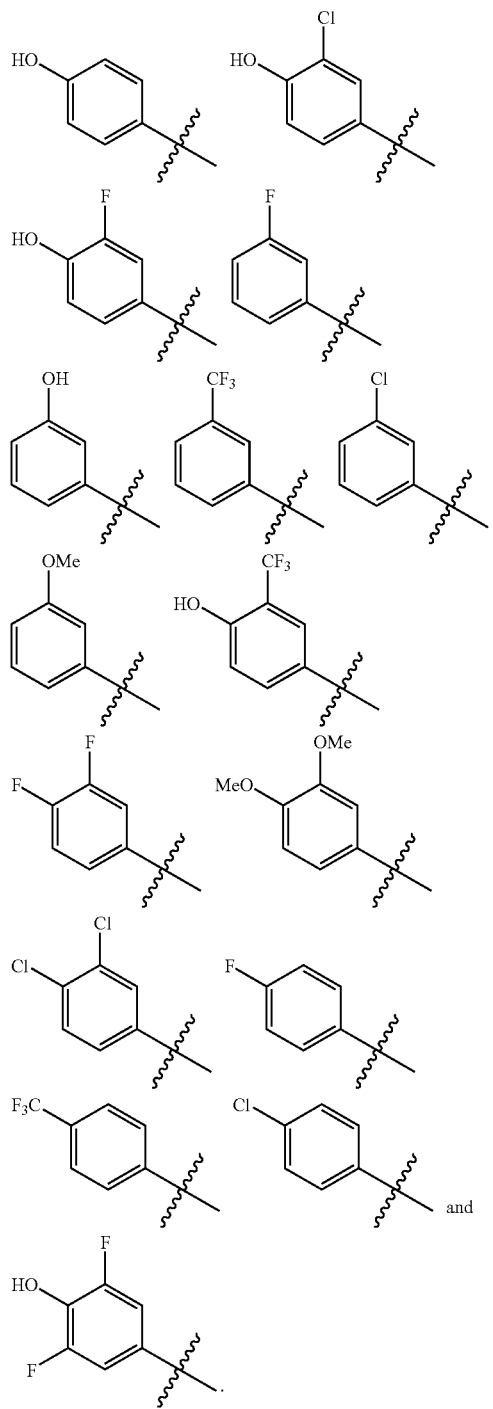

In another aspect of the invention, $R_1$ of formula I is selected from methyl, ethyl, isopropyl and cyclopropyl.

In other aspects of the invention, $R_2$ of formula I is selected from $(CH_2)_m CH_3$, $(CH_2)_{n1} R_{11}$, $CH_2 N_3$, $(CH_2)_{n2} NR_{12} R_{13}$, $(CH_2)_{n3} C(=NR_{14}) NR_{15} R_{16}$, $(CH_2)_{n4} NR_{17} C(=NR_{18}) NR_{19} R_{20}$, and $(CH_2)_{n5} NHC(=O) NR_{21} R_{22}$ wherein m is 0, 1, 2, or 3; n1, n2, n3, n4 and n5 are independently 1, 2, 3 or 4; $R_{11}$, $R_{13}$, $R_{16}$, $R_{17}$, $R_{20}$, $R_{21}$ and $R_{22}$ are independently selected from hydrogen and lower alkyl; $R_{12}$, $R_{15}$ and $R_{19}$ are independently selected from hydrogen, lower alkyl, carboxyalkyl, carboxyaryl and sulfonyl; $R_{14}$ and $R_{18}$ are independently selected from hydrogen, lower alkyl, carboxyalkyl, carboxyaryl sulfonyl and cyano.

In additional aspects of the invention, $R_2$ of formula I is selected from:

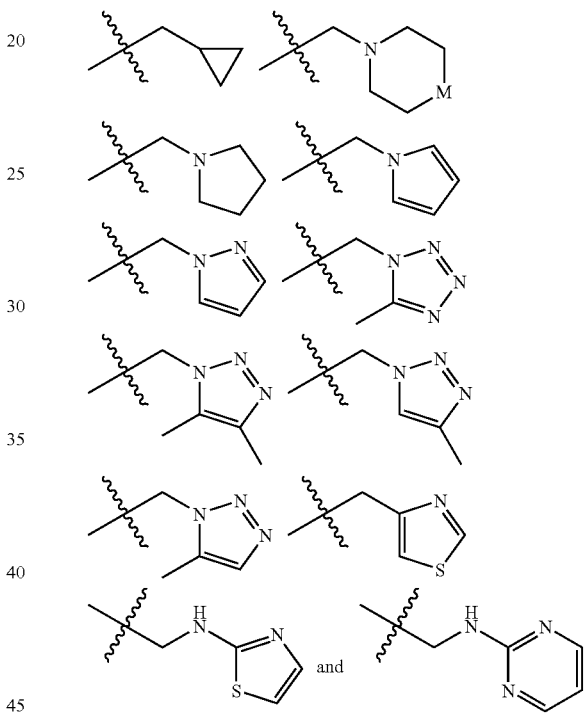

wherein M is selected from the group consisting of $CH_2$, O, NH, and $NCH_3$.

In another aspect of the invention, $L_1$, $L_2$, $L_3$ and $L_4$ in formula I are each CH, $L_5$ is O and $L_6$ is $CH_2$.

In other aspects of the invention, $R_3$, $R_4$, $R_5$ and $R_6$ in formula I are each hydrogen; or $R_3$ is methyl and $R_4$, $R_5$ and $R_6$ are each hydrogen; or $R_3$ is hydroxymethyl and $R_4$, $R_5$ and $R_6$ are each hydrogen; or $R_3$, $R_4$ and $R_6$ are each hydrogen and $R_5$ is methyl; or $R_3$ and $R_5$ are each methyl and $R_4$ and $R_6$ are each hydrogen.

In yet another aspect, Y in formula I is selected from:

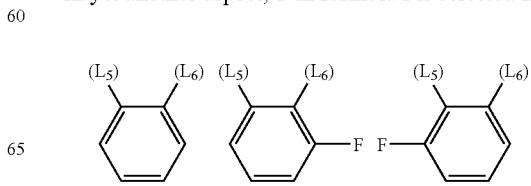

-continued

[structures: difluorobenzene with (L5) and (L6) substituents and pyridine with (L5) and (L6) substituents]

wherein (L5) and (L6) indicate the bond to $L_5$ and $L_6$, respectively.

In an additional aspect, the present invention relates to compounds of formula II:

(II)

[structure showing R26-N(R27)-CH(R28)-CO2R25]

wherein $R_{25}$ is selected from hydrogen, alkyl, aryl, cycloalkyl, heterocyclic and heteroaryl; $R_{26}$ is selected from hydrogen, alkyl, aryl, acyl, carboxyalkyl, carboxyaryl, sulfonyl and a standard protecting group used for amino acids; $R_{27}$ is selected from the group consisting of hydrogen and alkyl; and $R_{28}$ is selected from the group consisting of

[structures: cyclopropylmethyl, piperazinyl-M-methyl, pyrrolidinylmethyl, pyrrolylmethyl, pyrazolylmethyl, tetrazolylmethyl, triazolylmethyl, triazolylmethyl, triazolylmethyl, thiazolylmethyl, thiazol-2-ylaminomethyl, pyrimidin-2-ylaminomethyl]

and wherein M is selected from the group consisting of $CH_2$, O, NH, and $NCH_3$.

In other aspects, the present invention relates to compounds of formula III:

(III)

[structure of formula III showing R40, R41, R42, R43 substituents with OR46, NR44R45 groups, L11-L16 linkers and X10, X11]

wherein $X_{10}$ and $X_{11}$ are independently selected from the group consisting of hydrogen, halogen, trifluoromethyl and lower alkyl;

$R_{40}$, $R_{41}$, $R_{42}$, and $R_{43}$ are independently selected from the group consisting of hydrogen, lower alkyl and substituted lower alkyl;

$R_{44}$ is selected from the group consisting of hydrogen, alkyl, acyl, carboxyalkyl, carboxyaryl, sulfonyl and a protecting group for an amine functional group;

$R_{45}$ is selected from the group consisting of hydrogen and alkyl;

$R_{46}$ is selected from the group consisting of hydrogen, alkyl, acyl, sulfonyl and a protecting group for a hydroxy functional group;

$L_{11}$, $L_{12}$, $L_{13}$ and $L_{14}$ are independently selected from the group consisting of CH and N; with the proviso that the total number of nitrogens in the ring must be 0, 1, 2 or 3;

$L_{15}$ and $L_{16}$ are independently selected from the group consisting of O, $CR_{47}R_{48}$ and $NR_{49}$; wherein $R_{47}$ and $R_{48}$ are independently selected from the group consisting of hydrogen and lower alkyl; and $R_{49}$ is selected from the group consisting of hydrogen, lower alkyl, formyl, acyl and sulfonyl.

Compounds of formula III can be used in another aspect of the invention to provide compounds of formula I. Compounds of formula III can further be used to provide macrocyclic compounds including a building block structure, such as an amino acid building block structure, and the compounds of formula III.

In another aspect, the present invention also relates to methods of using the compounds as described herein and as used for the preparation of a medicament for prevention and/or treatment of the disorders described herein.

The foregoing and other aspects of the present invention are explained in greater detail in the specification set forth below.

DETAILED DESCRIPTION

Figure 1:
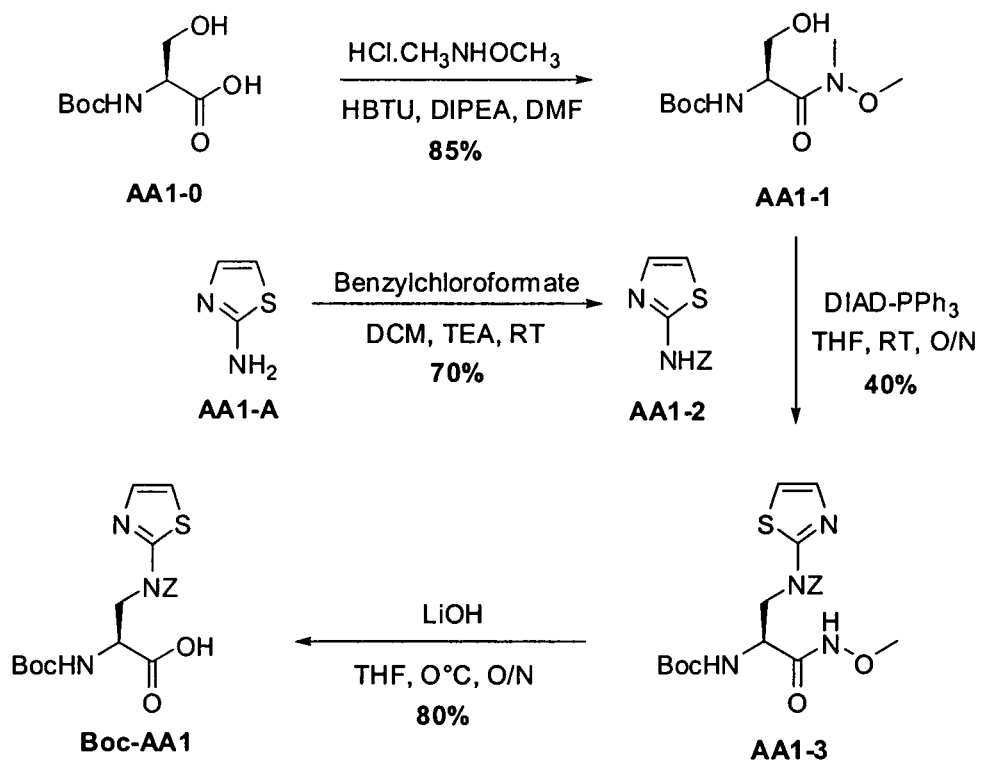
FIG. 1 shows a synthetic scheme for a representative amino acid building block of the invention.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Additionally, as used herein, the term "and/or" includes any and all combinations of one or more of the associated listed items and may be abbreviated as "/".

Unless otherwise defined, all technical and scientific terms used herein have the same meaning as commonly understood by one of ordinary skill in the art to which this invention belongs.

All publications, U.S. patent applications, U.S. patents and other references cited herein are incorporated by reference in their entireties.

The term "alkyl" refers to straight or branched chain saturated or partially unsaturated hydrocarbon groups having from 1 to 20 carbon atoms, in some instances 1 to 8 carbon atoms. The term "lower alkyl" refers to alkyl groups containing 1 to 6 carbon atoms. Examples of alkyl groups include, but are not limited to, methyl, ethyl, isopropyl, tert-butyl, 3-hexenyl, and 2-butynyl. By "unsaturated" is meant the presence of 1, 2 or 3 double or triple bonds, or a combination of the two. Such alkyl groups may also be optionally substituted as described below.

When a subscript is used with reference to an alkyl or other hydrocarbon group defined herein, the subscript refers to the number of carbon atoms that the group may contain. For example, $C_2$-$C_4$ alkyl indicates an alkyl group with 2, 3 or 4 carbon atoms.

The term "cycloalkyl" refers to saturated or partially unsaturated cyclic hydrocarbon groups having from 3 to 15 carbon atoms in the ring, in some instances 3 to 7, and to alkyl groups containing said cyclic hydrocarbon groups. Examples of cycloalkyl groups include, but are not limited to, cyclopropyl, cyclopropylmethyl, cyclopentyl, 2-(cyclohexyl)ethyl, cycloheptyl, and cyclohexenyl. Cycloalkyl as defined herein also includes groups with multiple carbon rings, each of which may be saturated or partially unsaturated, for example decalinyl, [2.2.1]-bicycloheptanyl or adamantanyl. All such cycloalkyl groups may also be optionally substituted as described below.

The term "aromatic" refers to an unsaturated cyclic hydrocarbon group having a conjugated pi electron system that contains 4n+2 electrons where n is an integer greater than or equal to 1. Aromatic molecules are typically stable and are depicted as a planar ring of atoms with resonance structures that consist of alternating double and single bonds, for example benzene or naphthalene.

The term "aryl" refers to an aromatic group in a single or fused carbocyclic ring system having from 6 to 15 ring atoms, in some instances 6 to 10, and to alkyl groups containing said aromatic groups. Examples of aryl groups include, but are not limited to, phenyl, 1-naphthyl, 2-naphthyl and benzyl. Aryl as defined herein also includes groups with multiple aryl rings which may be fused, as in naphthyl and anthracenyl, or unfused, as in biphenyl and terphenyl. Aryl also refers to bicyclic or tricyclic carbon rings, where one of the rings is aromatic and the others of which may be saturated, partially unsaturated or aromatic, for example, indanyl or tetrahydronaphthyl (tetralinyl). All such aryl groups may also be optionally substituted as described below.

The term "heterocycle" or "heterocyclic" refers to saturated or partially unsaturated monocyclic, bicyclic or tricyclic groups having from 3 to 15 atoms, in some instances 3 to 7, with at least one heteroatom in at least one of the rings, said heteroatom being selected from O, S or N. Each ring of the heterocyclic group can contain one or two O atoms, one or two S atoms, one to four N atoms, provided that the total number of heteroatoms in each ring is four or less and each ring contains at least one carbon atom. The fused rings completing the bicyclic or tricyclic heterocyclic groups may contain only carbon atoms and may be saturated or partially unsaturated. The N and S atoms may optionally be oxidized and the N atoms may optionally be quaternized. Heterocyclic also refers to alkyl groups containing said monocyclic, bicyclic or tricyclic heterocyclic groups. Examples of heterocyclic rings include, but are not limited to, 2- or 3-piperidinyl, 2- or 3-piperazinyl, 2- or 3-morpholinyl. All such heterocyclic groups may also be optionally substituted as described below The term "heteroaryl" refers to an aromatic group in a single or fused ring system having from 5 to 15 ring atoms, in some instances 5 to 10, which have at least one heteroatom in at least one of the rings, said heteroatom being selected from O, S or N. Each ring of the heteroaryl group can contain one or two O atoms, one or two S atoms, one to four N atoms, provided that the total number of heteroatoms in each ring is four or less and each ring contains at least one carbon atom. The fused rings completing the bicyclic or tricyclic groups may contain only carbon atoms and may be saturated, partially unsaturated or aromatic. In structures where the lone pair of electrons of a nitrogen atom is not involved in completing the aromatic pi electron system, the N atoms may optionally be quaternized or oxidized to the N-oxide. Heteroaryl also refers to alkyl groups containing said cyclic groups. Examples of monocyclic heteroaryl groups include, but are not limited to pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, benzopyranyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to carbazolyl, benzindolyl, phenanthrollinyl, acridinyl, phenanthridinyl, and xanthenyl. All such heteroaryl groups may also be optionally substituted as described below.

The term "hydroxy" refers to the group —OH.

The term "alkoxy" refers to the group —$OR_a$, wherein $R_a$ is alkyl, cycloalkyl or heterocyclic. Examples include, but are not limited to methoxy, ethoxy, tert-butoxy, cyclohexyloxy and tetrahydropyranyloxy.

The term "aryloxy" refers to the group —$OR_b$ wherein $R_b$ is aryl or heteroaryl. Examples include, but are not limited to phenoxy, benzyloxy and 2-naphthyloxy.

The term "acyl" refers to the group —C(=O)—$R_c$, wherein $R_c$ is alkyl, cycloalkyl, heterocyclic, aryl or heteroaryl. Examples include, but are not limited to, acetyl, benzoyl and furoyl.

The term "amino acyl" indicates an acyl group that is derived from an amino acid.

The term "amino" refers to an —$NR_dR_e$, group wherein $R_d$ and $R_e$ are independently selected from the group consisting of hydrogen, alkyl, cycloalkyl, heterocyclic, aryl and heteroaryl. Alternatively, $R_d$ and $R_e$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "amido" refers to the group —C(=O)—$NR_fR_g$ wherein $R_f$ and $R_g$ are independently selected from the group consisting of hydrogen, alkyl, cycloalkyl, heterocyclic, aryl and heteroaryl. Alternatively, $R_f$ and $R_g$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "amidino" refers to the group —C(=$NR_h$)$NR_iR_j$ wherein $R_h$ is selected from the group consisting of hydrogen, alkyl, cycloalkyl, heterocyclic, aryl and heteroaryl; and $R_i$ and $R_j$ are independently selected from the group consisting of hydrogen, alkyl, cycloalkyl, heterocyclic, aryl and heteroaryl. Alternatively, $R_i$ and $R_j$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "carboxy" refers to the group —$CO_2H$.

The term "carboxyalkyl" refers to the group —$CO_2R_k$, wherein $R_k$ is alkyl, cycloalkyl or heterocyclic.

The term "carboxyaryl" refers to the group —$CO_2R_m$, wherein $R_m$ is aryl or heteroaryl.

The term "cyano" refers to the group —CN.

The term "formyl" refers to the group —C(=O)H, also denoted —CHO.

The term "halo," "halogen" or "halide" refers to fluoro, fluorine or fluoride, chloro, chlorine or chloride, bromo, bromine or bromide, and iodo, iodine or iodide, respectively.

The term "hydroxymethyl" refers to the group —$CH_2OH$.

The term "mercapto" refers to the group —$SR_n$ wherein $R_n$ is hydrogen, alkyl, cycloalkyl, heterocyclic, aryl or heteroaryl.

The term "nitro" refers to the group —$NO_2$.

The term "oxo" refers to the bivalent group =O, which is substituted in place of two hydrogen atoms on the same carbon to form a carbonyl group.

The term "sulfinyl" refers to the group —S(=O)$R_p$ wherein $R_p$ is alkyl, cycloalkyl, heterocyclic, aryl or heteroaryl.

The term "sulfonyl" refers to the group —S(=O)$_2$—$R_{q1}$ wherein $R_{q1}$ is alkyl, cycloalkyl, heterocyclic, aryl or heteroaryl.

The term "trifluoromethyl" refers to the group —$CF_3$.

The term "aminosulfonyl" refers to the group —$NR_{q2}$—S(=O)$_2$—$R_{q3}$ wherein $R_{q2}$ is hydrogen, alkyl, cycloalkyl, heterocyclic, aryl or heteroaryl; and $R_{q3}$ is alkyl, cycloalkyl, heterocyclic, aryl or heteroaryl.

The term "sulfonamido" refers to the group —S(=O)$_2$—$NR_rR_s$ wherein $R_r$ and $R_s$ are independently selected from the group consisting of hydrogen, alkyl, cycloalkyl, heterocyclic, aryl or heteroaryl. Alternatively, $R_r$ and $R_s$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "carbamoyl" refers to a group of the formula —N($R_t$)—C(=O)—$OR_u$ wherein $R_t$ is selected from hydrogen, alkyl, cycloalkyl, heterocyclic, aryl or heteroaryl; and $R_u$ is selected from alkyl, cycloalkyl, heterocyclic, aryl or heteroaryl. The term "guanidino" refers to a group of the formula —N($R_v$)—C(=$NR_w$)—$NR_xR_y$, wherein $R_v$, $R_w$, $R_x$ and $R_y$ are independently selected from hydrogen, alkyl, cycloalkyl, heterocyclic, aryl or heteroaryl. Alternatively, $R_x$ and $R_y$ together form a heterocyclic ring or 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "ureido" refers to a group of the formula —N($R_z$)—C(=O)—$NR_{aa}R_{bb}$ wherein $R_z$, $R_{aa}$ and $R_{bb}$ are independently selected from hydrogen, alkyl, cycloalkyl, heterocyclic, aryl or heteroaryl. Alternatively, $R_{aa}$ and $R_{bb}$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

The term "substituted" when used with the terms alkyl, cycloalkyl, heterocyclic, aryl and heteroaryl refers to an alkyl, cycloalkyl, heterocyclic, aryl or heteroaryl group having one or more of the hydrogen atoms of the group replaced by substituents independently selected from unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, halo, oxo, mercapto, sulfinyl, sulfonyl, sulfonamido, amidino, carbamoyl, guanidino, ureido and groups of the formulas —$NR_{cc}C$(=O)$R_{dd}$, —$NR_{ee}C$(=$NR_{ff}$)$R_{gg}$, —OC(=O)$NR_{hh}R_{ii}$, —OC(=O)$R_{jj}$, —OC(=O)O$R_{kk}$, —$NR_{mm}SO_2R_{nn}$, or —$NR_{pp}SO_2NR_{qq}R_{rr}$ wherein $R_{cc}$, $R_{dd}$, $R_{ee}$, $R_{ff}$, $R_{gg}$, $R_{hh}$, $R_{ii}$, $R_{jj}$, $R_{mm}$, $R_{pp}$, $R_{qq}$ and $R_{rr}$ are independently selected from hydrogen, unsubstituted alkyl, unsubstituted cycloalkyl, unsubstituted heterocyclic, unsubstituted aryl or unsubstituted heteroaryl; and wherein $R_{kk}$ and $R_{nn}$ are independently selected from unsubstituted alkyl, unsubstituted cycloalkyl, unsubstituted heterocyclic, unsubstituted aryl or unsubstituted heteroaryl. Alternatively, $R_{gg}$ and $R_{hh}$, $R_{jj}$ and $R_{kk}$ or $R_{pp}$ and $R_{qq}$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N. In addition, the term "substituted" for aryl and heteroaryl groups includes as an option having one of the hydrogen atoms of the group replaced by cyano, nitro or trifluoromethyl.

A substitution is made provided that any atom's normal valency is not exceeded and that the substitution results in a stable compound. Generally, when a substituted form of a group is present, such substituted group is preferably not further substituted or, if substituted, the substituent comprises only a limited number of substituted groups, in some instances 1, 2, 3 or 4 such substituents.

When any variable occurs more than one time in any constituent or in any formula herein, its definition on each occurrence is independent of its definition at every other occurrence. Also, combinations of substituents and/or variables are permissible only if such combinations result in stable compounds.

A "stable compound" or "stable structure" refers to a compound that is sufficiently robust to survive isolation to a useful degree of purity and formulation into an efficacious therapeutic agent.

The term "amino acid" refers to the common natural (genetically encoded) or synthetic amino acids and common derivatives thereof, known to those skilled in the art. When applied to amino acids, "standard" or "proteinogenic" refers to the genetically encoded 20 amino acids in their natural configuration. Similarly, when applied to amino acids, "unnatural" or "unusual" refers to the wide selection of non-natural, rare or synthetic amino acids such as those described by Hunt, S. in *Chemistry and Biochemistry of the Amino Acids*, Barrett, G. C., Ed., Chapman and Hall: New York, 1985.

The term "residue" with reference to an amino acid or amino acid derivative refers to a group of the formula:

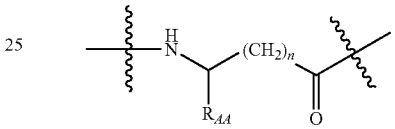

wherein $R_{AA}$ is an amino acid side chain, and n=0, 1 or 2 in this instance.

The term "fragment" with respect to a dipeptide, tripeptide or higher order peptide derivative indicates a group that contains two, three or more, respectively, amino acid residues.

The term "amino acid side chain" refers to any side chain from a standard or unnatural amino acid, and is denoted $R_{AA}$. For example, the side chain of alanine is methyl, the side chain of valine is isopropyl and the side chain of tryptophan is 3-indolylmethyl.

The term "agonist" refers to a compound that duplicates at least some of the effect of the endogenous ligand of a protein, receptor, enzyme or the like.

The term "antagonist" refers to a compound that inhibits at least some of the effect of the endogenous ligand of a protein, receptor, enzyme or the like.

The term "variant" when applied to a receptor is meant to include dimers, trimers, tetramers, pentamers and other biological complexes containing multiple components. These components can be the same or different.

The term "peptide" refers to a chemical compound comprised of two or more amino acids covalently bonded together.

The term "peptidomimetic" refers to a chemical compound designed to mimic a peptide, but which contains structural differences through the addition or replacement of one of more functional groups of the peptide in order to modulate its activity or other properties, such as solubility, metabolic stability, oral bioavailability, lipophilicity, permeability, etc. This can include replacement of the peptide bond, side chain modifications, truncations, additions of functional groups, etc. When the chemical structure is not derived from the peptide, but mimics its activity, it is often referred to as a "non-peptide peptidomimetic."

The term "peptide bond" refers to the amide [—C(=O)—NH—] functionality with which individual amino acids are typically covalently bonded to each other in a peptide.

The term "protecting group" refers to any chemical compound that may be used to prevent a potentially reactive functional group, such as an amine, a hydroxyl or a carboxyl, on a molecule from undergoing a chemical reaction while chemical change occurs elsewhere in the molecule. A number of such protecting groups are known to those skilled in the art and examples can be found in "Protective Groups in Organic Synthesis," Theodora W. Greene and Peter G. Wuts, editors, John Wiley & Sons, New York, 3$^{rd}$ edition, 1999 [ISBN 0471160199]. Examples of amino protecting groups include, but are not limited to, phthalimido, trichloroacetyl, benzyloxycarbonyl, tert-butoxycarbonyl, and adamantyloxycarbonyl. In some embodiments, amino protecting groups are carbamate amino protecting groups, which are defined as an amino protecting group that when bound to an amino group forms a carbamate. In other embodiments, amino carbamate protecting groups are allyloxycarbonyl (Alloc), benzyloxycarbonyl (Cbz), 9-fluorenylmethoxycarbonyl (Fmoc), tert-butoxycarbonyl (Boc) and α,α-dimethyl-3,5-dimethoxybenzyloxycarbonyl (Ddz). For a recent discussion of newer nitrogen protecting groups: Theodoridis, G. *Tetrahedron* 2000, 56, 2339-2358. Examples of hydroxyl protecting groups include, but are not limited to, acetyl, tert-butyldimethylsilyl (TBDMS), trityl (Trt), tert-butyl, and tetrahydropyranyl (THP). Examples of carboxyl protecting groups include, but are not limited to methyl ester, tert-butyl ester, benzyl ester, trimethylsilylethyl ester, and 2,2,2-trichloroethyl ester.

The term "solid phase chemistry" refers to the conduct of chemical reactions where one component of the reaction is covalently bonded to a polymeric material (solid support as defined below). Reaction methods for performing chemistry on solid phase have become more widely known and established outside the traditional fields of peptide and oligonucleotide chemistry.

The term "solid support," "solid phase" or "resin" refers to a mechanically and chemically stable polymeric matrix utilized to conduct solid phase chemistry. This is denoted by "Resin," "P-" or the following symbol:

Examples of appropriate polymer materials include, but are not limited to, polystyrene, polyethylene, polyethylene glycol, polyethylene glycol grafted or covalently bonded to polystyrene (also termed PEG-polystyrene, TentaGel™, Rapp, W.; Zhang, L.; Bayer, E. In *Innovations and Perspectives in Solid Phase Synthesis. Peptides, Polypeptides and Oligonucleotides*; Epton, R., Ed.; SPCC Ltd.: Birmingham, UK; p 205), polyacrylate (CLEAR™), polyacrylamide, polyurethane, PEGA [polyethyleneglycol poly(N,N-dimethylacrylamide) co-polymer, Meldal, M. *Tetrahedron Lett.* 1992, 33, 3077-3080], cellulose, etc. These materials can optionally contain additional chemical agents to form cross-linked bonds to mechanically stabilize the structure, for example polystyrene cross-linked with divinylbenzene (DVB, usually 0.1-5%, preferably 0.5-2%). This solid support can include as non-limiting examples aminomethyl polystyrene, hydroxymethyl polystyrene, benzhydrylamine polystyrene (BHA), methylbenzhydrylamine (MBHA) polystyrene, and other polymeric backbones containing free chemical functional groups, most typically, —NH$_2$ or —OH, for further derivatization or reaction. The term is also meant to include "Ultraresins" with a high proportion ("loading") of these functional groups such as those prepared from polyethyleneimines and cross-linking molecules (Barth, M.; Rademann, J. *J. Comb. Chem.* 2004, 6, 340-349). At the conclusion of the synthesis, resins are typically discarded, although they have been shown to be able to be reused such as in Frechet, J. M. J.; Hague, K. E. *Tetrahedron Lett.* 1975, 16, 3055.

In general, the materials used as resins are insoluble polymers, but certain polymers have differential solubility depending on solvent and can also be employed for solid phase chemistry. For example, polyethylene glycol can be utilized in this manner since it is soluble in many organic solvents in which chemical reactions can be conducted, but it is insoluble in others, such as diethyl ether. Hence, reactions can be conducted homogeneously in solution, then the product on the polymer precipitated through the addition of diethyl ether and processed as a solid. This has been termed "liquid-phase" chemistry.

The term "linker" when used in reference to solid phase chemistry refers to a chemical group that is bonded covalently to a solid support and is attached between the support and the substrate typically in order to permit the release (cleavage) of the substrate from the solid support. However, it can also be used to impart stability to the bond to the solid support or merely as a spacer element. Many solid supports are available commercially with linkers already attached.

Abbreviations used for amino acids and designation of peptides follow the rules of the IUPAC-IUB Commission of Biochemical Nomenclature in *J. Biol. Chem.* 1972, 247, 977-983. This document has been updated: *Biochem. J.,* 1984, 219, 345-373; *Eur. J. Biochem.,* 1984, 138, 9-37; 1985, 152, 1; *Internat. J. Pept. Prot. Res.,* 1984, 24, following p 84; *J. Biol. Chem.,* 1985, 260, 14-42; *Pure Appl. Chem.,* 1984, 56, 595-624; *Amino Acids and Peptides,* 1985, 16, 387-410; and in *Biochemical Nomenclature and Related Documents,* 2nd edition, Portland Press, 1992, pp 39-67. Extensions to the rules were published in the JCBN/NC-IUB Newsletter 1985, 1986, 1989; see *Biochemical Nomenclature and Related Documents,* 2nd edition, Portland Press, 1992, pp 68-69.

The term "effective amount" or "effective" is intended to designate a dose that causes a relief of symptoms of a disease or disorder as noted through clinical testing and evaluation, patient observation, and/or the like, and/or a dose that causes a detectable change in biological or chemical activity. The detectable changes may be detected and/or further quantified by one skilled in the art for the relevant mechanism or process. As is generally understood in the art, the dosage will vary depending on the administration routes, symptoms and body weight of the patient but also depending upon the compound being administered.

Administration of two or more compounds "in combination" means that the two compounds are administered closely enough in time that the presence of one alters the biological effects of the other. The two compounds can be administered simultaneously (concurrently) or sequentially. Simultaneous administration can be carried out by mixing the compounds prior to administration, or by administering the compounds at the same point in time but at different anatomic sites or using different routes of administration. The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

The term "pharmaceutically active metabolite" is intended to mean a pharmacologically active product produced through metabolism in the body of a specified compound.

The term "solvate" is intended to mean a pharmaceutically acceptable solvate form of a specified compound that retains the biological effectiveness of such compound. Examples of solvates, without limitation, include compounds of the invention in combination with water, isopropanol, ethanol, methanol, DMSO, ethyl acetate, acetic acid, or ethanolamine.

The term "simultaneously" or "concurrently" is intended to mean, when applied to a disease or disorder, that the diseases or disorders occur at the same point in time for at least some of the time the subject is suffering from the diseases or disorders, but not necessarily the entire time.

The term "sequentially" is intended to mean, when applied to a disease or disorder, that the diseases or disorders do not occur at the same point in time, but occur immediately after each other.

1. Compounds

Novel macrocyclic compounds of the present invention include macrocyclic compounds comprising a building block structure including a tether component that undergoes cyclization to form the macrocyclic compound. The building block structure can comprise amino acids (standard and unnatural) and a tether component as described herein. The tether component can be selected from compounds that result in the following structures:

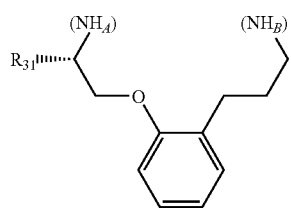

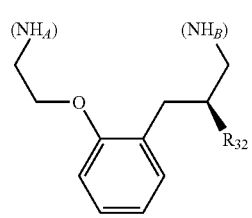

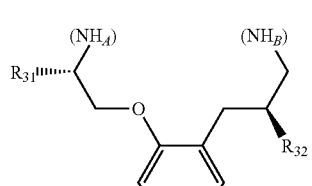

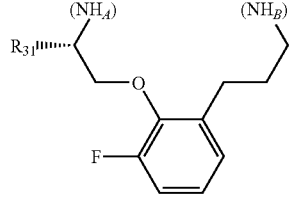

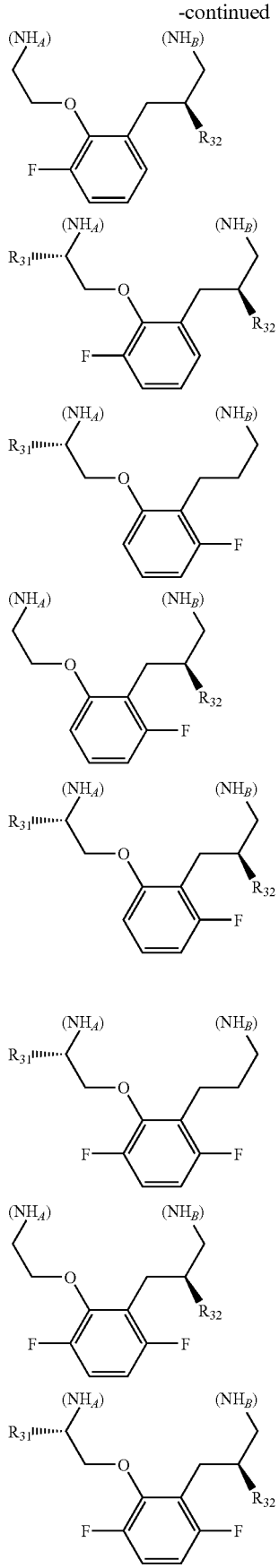

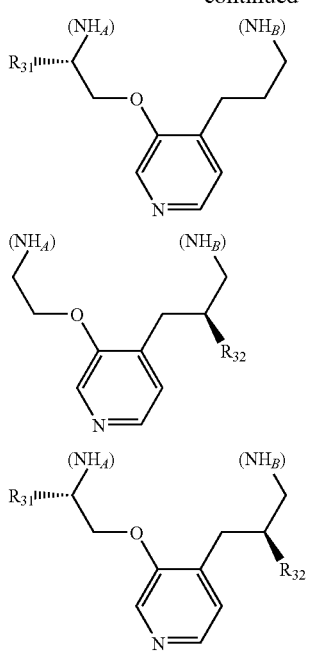

wherein $(NH_A)$ indicates the bond to the nitrogen atom in formula I to which $CH(CHR_7Ar)$ is bonded; $(NH_B)$ indicates the bond to the nitrogen atom in formula I to which a carbonyl (C=O) is bonded; $R_{31}$ is selected from hydrogen, methyl and hydroxymethyl; and $R_{32}$ is selected from hydrogen, methyl and hydroxyl.

Macrocyclic compounds of the present invention further include those of formula I:

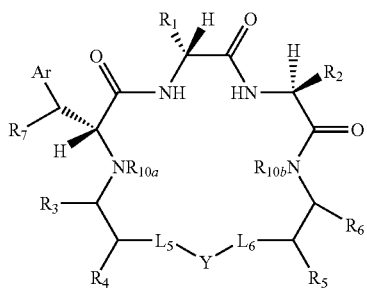

and pharmaceutically acceptable salts, hydrates or solvates thereof wherein:

Y is

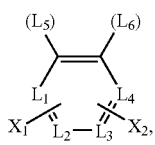

wherein $(L_5)$ and $(L_6)$ indicates the bonds to $L_5$ and $L_6$ of formula I, respectively;

Ar is selected from the group consisting of:

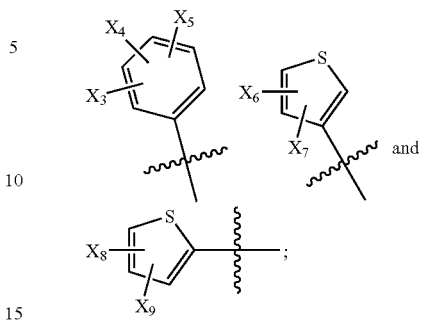

$R_1$ is selected from the group consisting of lower alkyl and cycloalkyl;

$R_2$ is selected from the group consisting of lower alkyl, substituted lower alkyl, cycloalkyl and substituted cycloalkyl;

$R_3$, $R_4$, $R_5$, and $R_6$ are independently selected from the group consisting of hydrogen, lower alkyl and substituted lower alkyl;

$R_7$ is selected from the group consisting of hydrogen, lower alkyl, hydroxy and amino;

$R_{10a}$ and $R_{10b}$ are independently selected from the group consisting of hydrogen, lower alkyl and substituted lower alkyl;

$X_1$, $X_2$, $X_6$, $X_7$, $X_8$ and $X_9$ are independently selected from the group consisting of hydrogen, halogen, trifluoromethyl and lower alkyl;

$X_3$, $X_4$ and $X_5$ are independently selected from the group consisting of hydrogen, hydroxyl, alkoxy, halogen, trifluoromethyl and lower alkyl;

$L_1$, $L_2$, $L_3$ and $L_4$ are independently selected from the group consisting of CH and N; with the proviso that the total number of nitrogens in the ring must be 0, 1, 2 or 3;

$L_5$ and $L_6$ are independently selected from the group consisting of O, $CR_{8a}R_{8b}$ and $NR_9$; wherein $R_{8a}$ and $R_{8b}$ are independently selected from the group consisting of hydrogen and lower alkyl; and $R_9$ is selected from the group consisting of hydrogen, lower alkyl, formyl, acyl and sulfonyl.

The present invention includes isolated compounds. An isolated compound refers to a compound that, in some embodiments, comprises at least 10%, at least 25%, at least 50% or at least 70% of the compounds of a mixture. In some embodiments, the compound, pharmaceutically acceptable salt thereof or pharmaceutical composition containing the compound exhibits a statistically significant binding and/or antagonist activity when tested in biological assays at the human motilin receptor.

In the case of compounds, salts, or solvates that are solids, it is understood by those skilled in the art that the inventive compounds, salts, and solvates may exist in different crystal or polymorphic forms, all of which are intended to be within the scope of the present invention and specified formulas.

The compounds of formula I disclosed herein have asymmetric centers. The inventive compounds may exist as single stereoisomers, racemates, and/or mixtures of enantiomers and/or diastereomers. All such single stereoisomers, racemates, and mixtures thereof are intended to be within the scope of the present invention. In particular embodiments, however, the inventive compounds are used in optically pure form. The terms "S" and "R" configuration as used herein are as defined by the IUPAC 1974 Recommendations for Section E, Fundamentals of Stereochemistry (*Pure Appl. Chem.* 1976, 45, 13-30.)

Unless otherwise depicted to be a specific orientation, the present invention accounts for all stereoisomeric forms. The compounds may be prepared as a single stereoisomer or a mixture of stereoisomers. The non-racemic forms may be obtained by either synthesis or resolution. The compounds may, for example, be resolved into the component enantiomers by standard techniques, for example formation of diastereomeric pairs via salt formation. The compounds also may be resolved by covalently bonding to a chiral moiety. The diastereomers can then be resolved by chromatographic separation and/or crystallographic separation. In the case of a chiral auxiliary moiety, it can then be removed. As an alternative, the compounds can be resolved through the use of chiral chromatography. Enzymatic methods of resolution could also be used in certain cases.

As generally understood by those skilled in the art, an "optically pure" compound is one that contains only a single enantiomer. As used herein, the term "optically active" is intended to mean a compound comprising at least a sufficient excess of one enantiomer over the other such that the mixture rotates plane polarized light. Optically active compounds have the ability to rotate the plane of polarized light. The excess of one enantiomer over another is typically expressed as enantiomeric excess (e.e.). In describing an optically active compound, the prefixes D and L or R and S are used to denote the absolute configuration of the molecule about its chiral center(s). The prefixes "d" and "l" or (+) and (−) are used to denote the optical rotation of the compound (I.e., the direction in which a plane of polarized light is rotated by the optically active compound). The "l" or (−) prefix indicates that the compound is levorotatory (i.e., rotates the plane of polarized light to the left or counterclockwise) while the "d" or (+) prefix means that the compound is dextrarotatory (i.e., rotates the plane of polarized light to the right or clockwise). The sign of optical rotation, (−) and (+), is not related to the absolute configuration of the molecule, R and S.

A compound of the invention having the desired pharmacological properties will be optically active and, can be comprised of at least 90% (80% e.e.), at least 95% (90% e.e.), at least 97.5% (95% e.e.) or at least 99% (98% e.e.) of a single isomer.

Likewise, many geometric isomers of double bonds and the like can also be present in the compounds disclosed herein, and all such stable isomers are included within the present invention unless otherwise specified. Also included in the invention are tautomers and rotamers of formula I, II and/or III.

The use of the following symbols refers to substitution of one or more hydrogen atoms of the indicated ring with the defined substituent R.

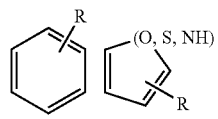

The use of the following symbol indicates a single bond or an optional double bond: ----.

2. Synthetic Methods

The compounds of formula I can be synthesized using traditional solution synthesis techniques or solid phase chemistry methods. Synthetic methods for this general type of macrocyclic structure are described in Intl. Pat. Appls. WO 01/25257, WO 2004/111077, WO 2005/012331, WO 2005/012332, WO 2006/009645 and WO 2006/009674, including purification procedures described in WO 2004/111077 and WO 2005/012331. Representative procedures for compounds of the invention are presented in the Examples.

A. General

Reagents and solvents were of reagent quality or better and were used as obtained from various commercial suppliers unless otherwise noted. DMF, DCM ($CH_2Cl_2$), DME, $CH_3CN$ and THF used are of DriSolv® (EMD Chemicals, Inc., part of Merck KGaA, Darmstadt, Germany) or synthesis grade quality except for (i) deprotection, (ii) resin capping reactions and (iii) washing. NMP used for the amino acid (AA) coupling reactions is of analytical grade. DMF was adequately degassed by placing under vacuum for a minimum of 30 min prior to use. Homogeneous catalysts were obtained from Strem Chemicals, Inc. (Newbury Port, Mass., USA). Cbz-, Boc- and Fmoc-protected amino acids and side chain protected derivatives, including those of N-methyl and unnatural amino acids, were obtained from commercial suppliers or synthesized through standard methodologies known to those in the art. Ddz-amino acids were either synthesized by standard methods, or obtained commercially from Orpegen (Heidelberg, Germany) or Advanced ChemTech (Louisville, Ky., USA). Bts-amino acids were synthesized by established procedures. Analytical TLC was performed on pre-coated plates of silica gel 60F254 (0.25 mm thickness) containing a fluorescent indicator and were visualized using the method(s) and reagent(s) indicated, for example using ultraviolet light (UV) and/or ceric-molybdic acid (CMA) solution (prepared by mixing 100 mL of sulfuric acid, 10 g ceric ammonium sulfate and 25 g ammonium molybdate).

The term "concentrated/evaporated/removed under reduced pressure" indicates removal of solvent and volatile components utilizing a rotary evaporator under either water aspirator pressure (typically 10-30 torr) or the stronger vacuum provided by a mechanical oil vacuum pump ("high vacuum," typically ≤1 torr) as appropriate for the solvent being removed. Drying of a compound "in vacuo" or under "high vacuum" refers to drying using an oil vacuum pump at low pressure (≤1 torr). "Flash chromatography" was performed using silica gel 60 (230-400 mesh, EMD Chemicals, Still, W. C.; Kahn, M.; Mitra, A. *J. Org. Chem.* 1978, 43, 2923-2925) and is a procedure well-known to those in the art. "Dry pack" indicates chromatography on silica gel that has not been pre-treated with solvent, generally applied on larger scales for purifications where a large difference in $R_f$ exists between the desired product and any impurities. For solid phase chemistry processes, "dried in the standard manner" is that the resin is dried first in air (1 h), and subsequently under vacuum (oil pump usually) until full dryness is attained (~30 min to O/N). Glassware used in air and water sensitive reactions were dried in an oven at least O/N and cooled in a desiccator prior to use.

B. Amino Acids

Amino acids, Boc- and Fmoc-protected amino acids and side chain protected derivatives, including those of N-methyl and unnatural amino acids, were obtained from commercial suppliers [for example: Advanced ChemTech (Louisville, Ky., USA), Bachem (Bubendorf, Switzerland), ChemImpex (Wood Dale, Ill., USA), Novabiochem (subsidiary of Merck KGaA, Darmstadt, Germany), PepTech (Burlington, Mass., USA), Synthetech (Albany, Oreg., USA), AstaTech (Bristol, Pa., USA)] or synthesized through standard methodologies known to those in the art. Ddz-amino acids were either obtained commercially from Orpegen (Heidelberg, Germany) or Advanced ChemTech (Louisville, Ky., USA) or synthesized using standard methods utilizing Ddz-OPh or Ddz-N$_3$. (Bin, C.; Lochinger, W.; Stahnke, G.; Lang, P. *Justus Liebigs Ann. Chem.* 1972, 763, 162-172.) Bts-amino acids were synthesized by known methods. (Vedejs, E.; Lin, S.; Klapara, A.; Wang, J. *J. Am. Chem. Soc.* 1996, 118, 9796-9797; Vedejs, E.; Kongkittingam, C. *J. Org. Chem.* 2000, 65, 2309-2318; also Intl. Pat. Appl. Nos. WO 01/25257, WO 2004/111077) N-Alkyl amino acids, in particular N-methyl amino acids, are commercially available from multiple vendors (Bachem, Novabiochem, Advanced ChemTech, ChemImpex, Peptech). In addition, N-alkyl amino acid derivatives were accessed via literature methods. (Hansen, D. W., Jr.; Pilipauskas, D. *J. Org. Chem.* 1985, 50, 945-950.) Aziridine-2-carboxylic acid was constructed using reported methods from the literature (Baldwin, J. E. et al. *Tetrahedron* 1993, 49, 6309-6330; Nakajima, K. et al. *Bull. Chem. Soc. Jpn.* 1978, 51, 1577-1578.) 3-Chlorotyrosine was synthesized using the literature method. (Yu, G.; Mason, H. J.; Galdi, K.; et al. *Synthesis* 2003, 403-407.)

Other amino acids have been constructed specifically for use in these macrocycles, such as those of formula II:

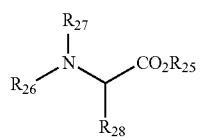

(II)

wherein R$_{25}$ is selected from hydrogen, alkyl, aryl, cycloalkyl, heterocyclic and heteroaryl; R$_{26}$ is selected from hydrogen, alkyl, aryl, acyl, carboxyalkyl, carboxyaryl, sulfonyl and a standard protecting group used for amino acids; R$_{27}$ is selected from the group consisting of hydrogen and alkyl; and R$_{28}$ is selected from the group consisting of

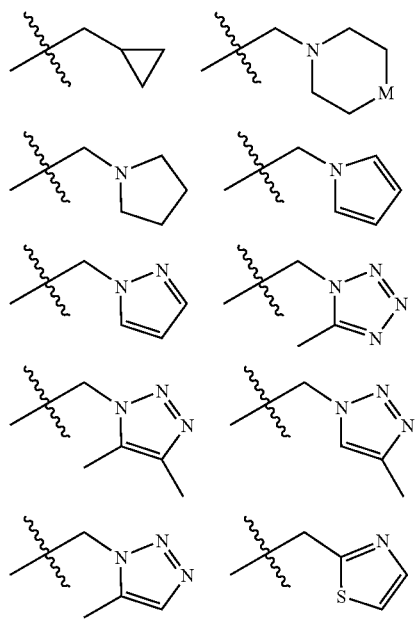

wherein M is selected from the group consisting of CH$_2$, O, NH, and NCH$_3$.

Methods for the construction of representative amino acids of this type are provided in the Examples. Some of these amino acids can be considered as mimics of arginine and/or its guanidine moiety (Peterlin-Masic, L.; Kikelj, D. *Tetrahedron* 2001, 57, 7073 and references cited therein).

C. Tethers

Tethers were obtained from the methods previously described in Intl. Pat. Appl. Nos. WO 01/25257, WO 2004/111077, WO 2005/012331, WO 2006/009645 and WO 2006/009674. Procedures for the synthesis of representative tethers as described herein are also presented in the Examples below. Tethers useful for the compounds of the present invention can include suitable tethers as described in the references cited above as well as known and/or novel tethers described herein. Exemplary tethers include, but are not limited to, the following:

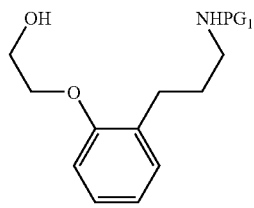
T9

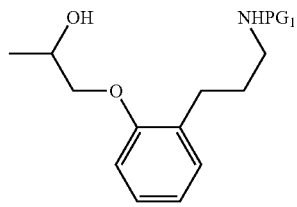
T38

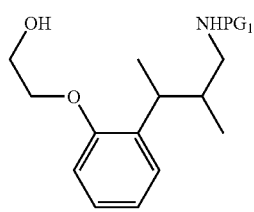
T39

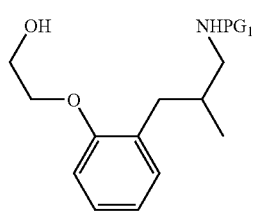
T40

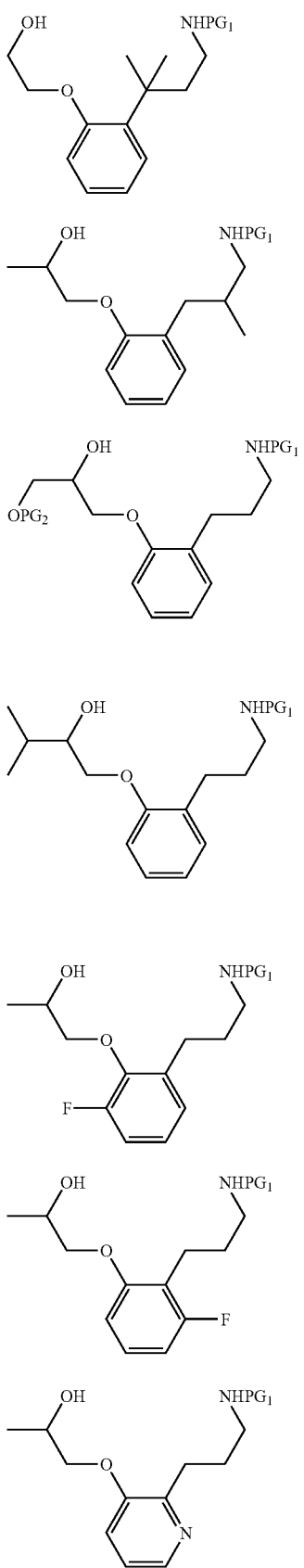
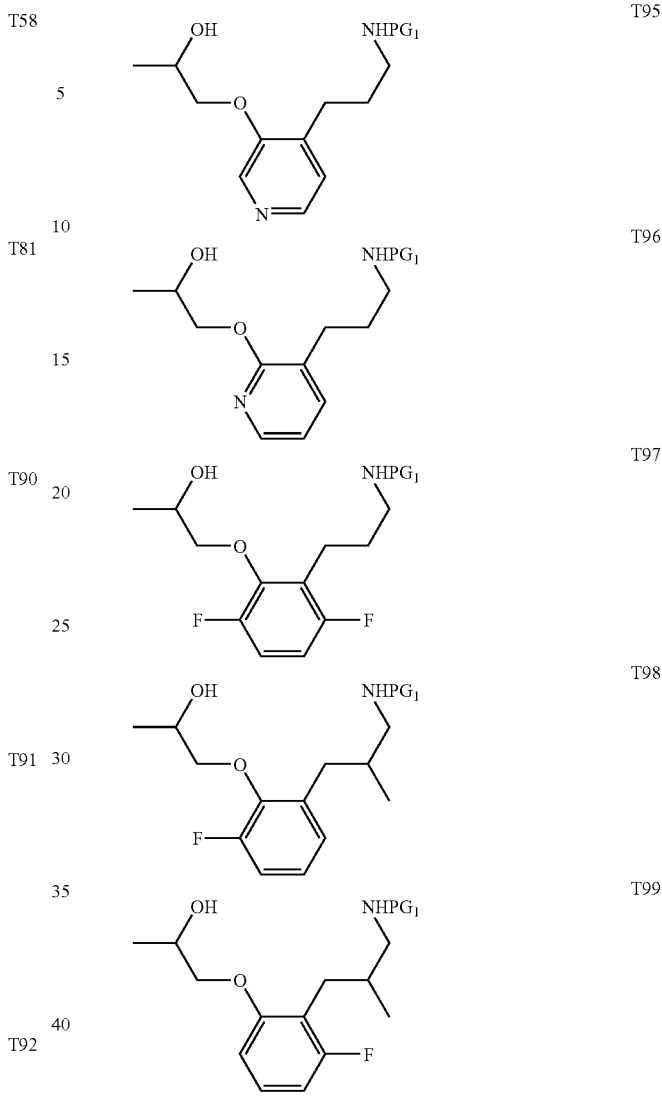

and intermediates in the manufacture thereof, wherein $PG_1$ is selected from hydrogen and a protecting group for an amine functional group and $PG_2$ is selected from hydrogen and a protecting group for a hydroxy functional group.

Specific procedures applicable for the synthesis of exemplary compounds of the invention using these tethers are provided in the Examples.

D. Macrocycle Synthesis

Figure 7:
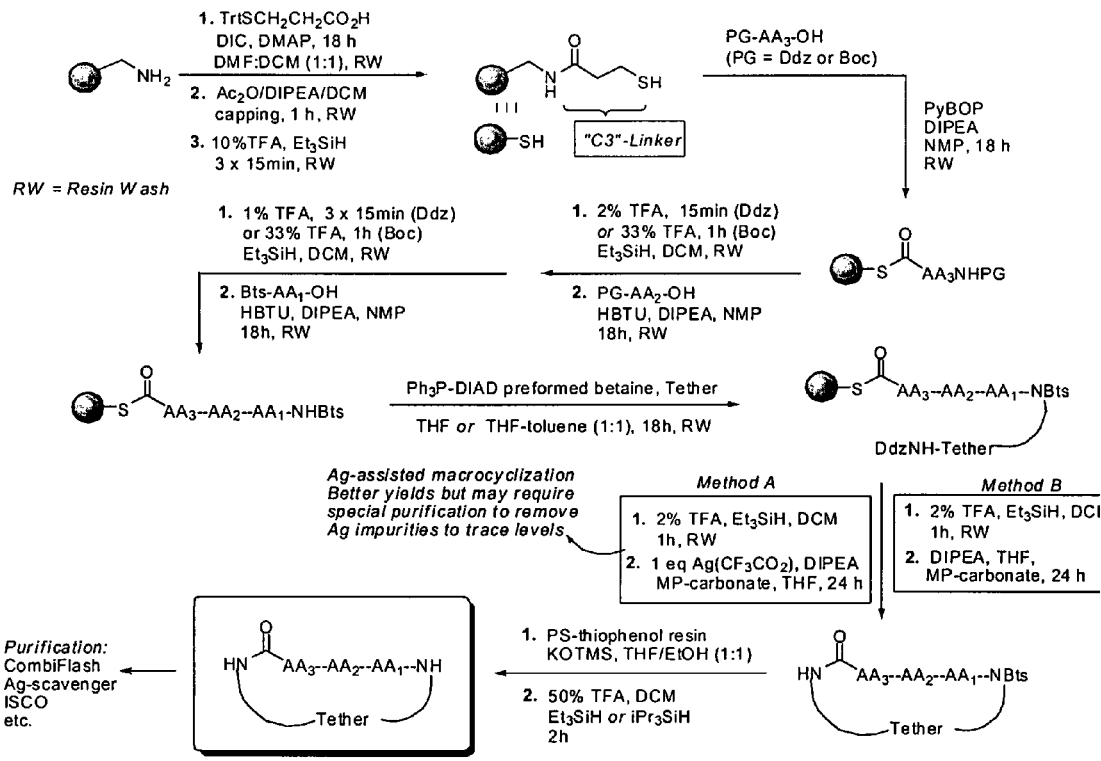
FIG. 7 shows a general scheme for the solid phase synthesis of macrocyclic compounds of the present invention.
Figure 8:
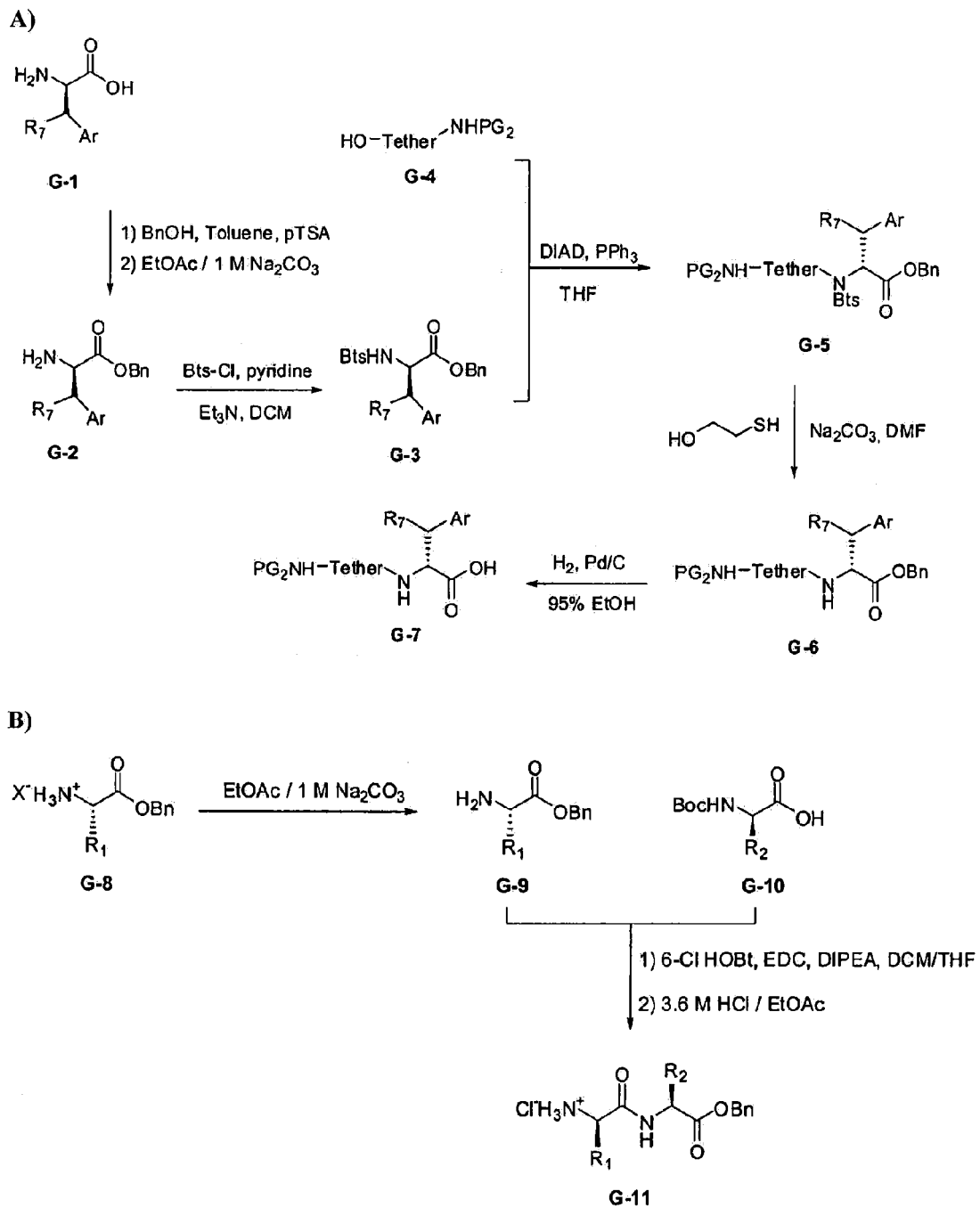
FIG. 8 shows a general scheme for the solution phase synthesis of macrocyclic compounds of the present invention of the invention.
Figure 8:
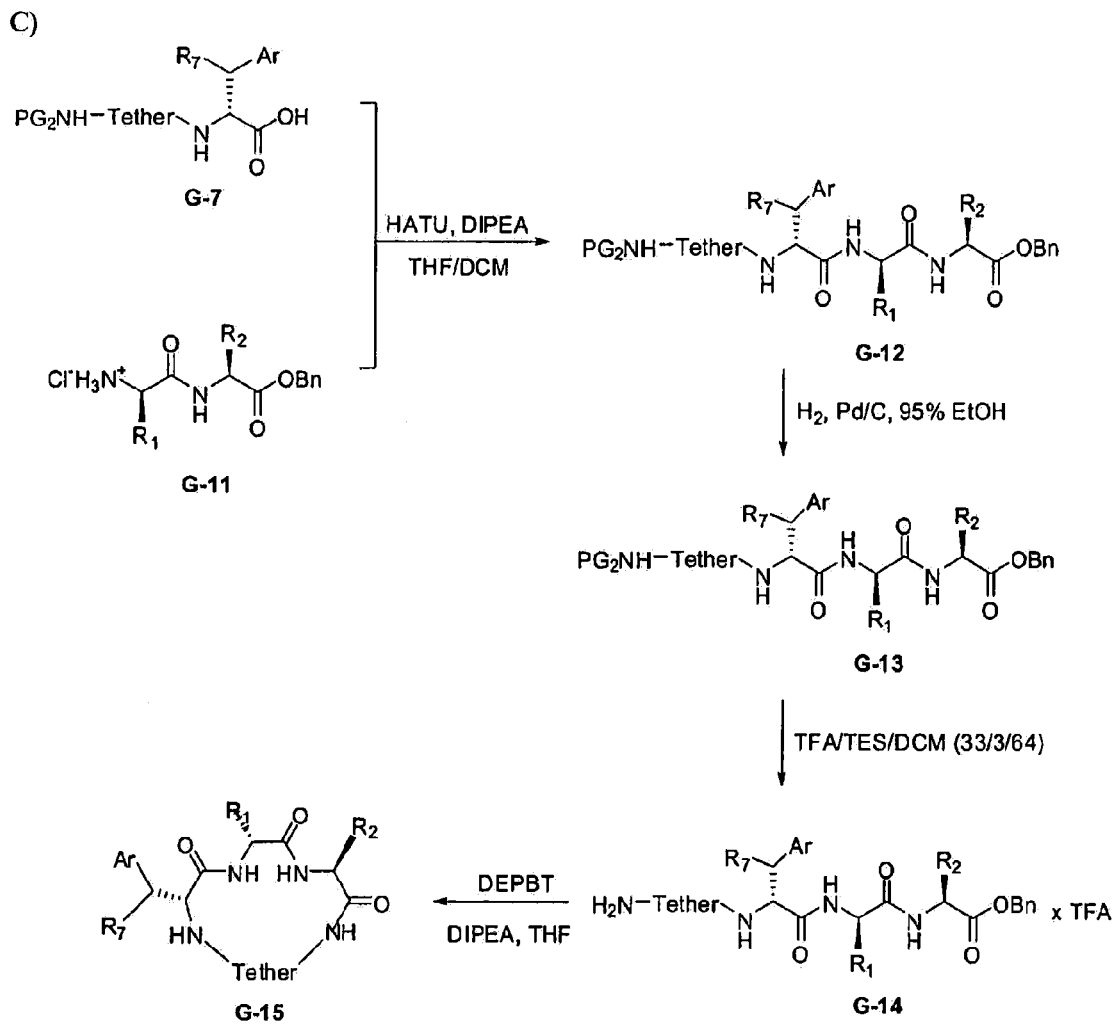

Specific solid phase techniques for the synthesis of the macrocyclic compounds of the invention have been described in Intl. Pat. Appl. Publ. Nos. WO 01/25257, WO 2004/111077, WO 2005/012331 and WO 2005/012332. Solution phase synthesis routes, including methods amenable to larger scale manufacture, were described in Intl. Pat. Appl. Publ. Nos. WO 2006/009645 and WO 2006/009674. These methods for representative compounds of the present invention are further described in the Examples. Table 1 presents a summary of the synthesis of 90 representative compounds of the present invention. The reaction methodology employed for the construction of the macrocyclic molecule is indicated in Column 2 and relates to the particular scheme of the synthetic strategy, for example, use of the solid phase strategy as shown in FIG. 7 or the solution phase approach as shown in FIG. 8 and described in Example 9. Columns 3-6 indicate the individual amino acid and tether building blocks employed for each compound, utilizing either standard nomenclature or referring to the building block designations presented elsewhere in this application. $AA_1$ refers to the building block that forms the —$NR_{10a}$—CH($CHR_7Ar$)—C(=O)— portion of the compounds of formula I; $AA_2$ refers to the building block that forms the —NH—$CHR_1$—C(=O)— portion of the compounds of formula I; $AA_1$ refers to the building block that forms the —NH—$CHR_2$—C(=O)— portion of the compounds of formula I; Tether refers to the building block that forms the remaining portion of the compound of formula I that between $NR_{10a}$ and $NR_{10b}$, typically including $NR_{10a}$ It should be noted that for 1-substituted tethers, for example T38, T90, T91, T92, T93, T94, T95, T96, T97, T98 and T99, the reaction chemistry for its introduction inverts the stereochemistry at that center. Hence, (R)-substituted tether building blocks result in compounds of formula I with an (S)-stereocenter. Likewise, (S)-substituted tether building blocks result in compounds of formula I with an (R)-stereocenter. Tethers T90 and T91 are introduced along with $AA_1$ as fragments F2 and F1 respectively as described in Examples 6 and 5. The relevant deprotection and coupling protocols required for the assembly of the cyclization precursors are performed utilizing standard procedures and those described in WO 2004/111077, WO 2006/009645 and WO 2006/009674 as appropriate for the nature of the building block. The final macrocycles are obtained after application of the appropriate deprotection sequences. If any reaction(s) was(were) required to be carried out post-cyclization, they are listed in Column 7. All of the macrocycles presented in Table 1 were purified and met internal acceptance criteria.

TABLE 1

Synthesis of Representative Compounds of the Invention

| Compound No.[1] | Strategy | $AA_1$ | $AA_2$ | $AA_3$ | Tether | Post-cyclization Reaction(s) |
|---|---|---|---|---|---|---|
| 501 | Solution phase | Bts-(D)Phe(3Cl)-OBn | Boc-(D)Val | Boc-AA5 | Boc-T9 | Example 17, then Example 28 |
| 502 | Solution phase | Bts-(D)Phe(3CF3)-OBn | Boc-(D)Val | Boc-AA5 | Boc-T9 | Example 17, then Example 28 |
| 503 | Solution phase | Bts-(D)Phe(3CF3)-OBn | Boc-(D)Val | Boc-AA5 | Boc-T9 | Example 17, then Example 13 |
| 504 | Solution phase | Bts-(D)Phe(3CF3)-OBn | Boc-(D)Val | Boc-AA5 | Boc-T40(R) | Example 17, then Example 13 |
| 505 | Solution phase | Bts-(D)Phe(3CF3)-OBn | Boc-(D)Val | Boc-AA5 | Boc-T40(S) | Example 17, then Example 13 |
| 506 | Solid phase | Bts-(D)Phe(3Cl) | Boc-(D)Val | Boc-Abu(CN) | Boc-T9 | Example 33 |
| 507 | Solid phase | Bts-(D)Phe(3Cl) | Ddz-(D)Val | Ddz-Dab(Boc) | Ddz-T9 | Example 17, then Example 13 |
| 508 | Solution phase | Bts-(D)Phe(3Cl)-OBn | Boc-(D)Val | Boc-AA5 | Boc-T9 | Example 17, then Example 28 |
| 509 | Solid phase | Bts-(D)Phe(3Cl) | Boc-(D)Val | Boc-AA1 | Boc-T9 | Example 29 |
| 510 | Solid phase | Bts-(D)Phe(3Cl) | Boc-(D)Val | Boc-AA2 | Boc-T9 | none |
| 511 | Solid phase | Bts-(D)Phe(3Cl) | Boc-(D)Val | Boc-AA3 | Boc-T9 | none |
| 512 | Solution phase | Bts-(D)Phe(3Cl)-OBn | Boc-(D)Val | Boc-AA5 | Boc-T9 | Example 17, then Example 25 |
| 513 | Solution phase | Bts-(D)Phe(3F)-OBn | Boc-(D)Val | H-Nva-OBn | Boc-T38(S) | none |
| 514 | Solution phase | Bts-(D)Phe(3F)-OBn | Boc-(D)Val | Boc-AA5 | Boc-T40(R) | Example 17, then Example 28 |
| 515 | Solution phase | Bts-(D)Phe(3F)-OBn | Boc-(D)Val | Boc-AA5 | Boc-T40(S) | Example 17, then Example 28 |
| 516 | Solution phase | Bts-(D)Phe(3Cl)-OBn | Boc-(D)Val | Boc-AA5 | Boc-T38(R) | Example 17, then Example 13 |
| 517 | Solution phase | Bts-(D)Phe(3Cl)-OBn | Boc-(D)Val | Boc-AA5 | Boc-T38(S) | Example 17, then Example 13 |
| 518 | Solid phase | Bts-(D)Phe(3Cl) | Boc-(D)Val | Boc-Ala(CN) | Boc-T9 | Example 33 |
| 519 | Solution phase | Bts-(D)Phe(3Cl)-OBn | Boc-(D)Val | Boc-AA5 | Boc-T9 | Example 17, then Example 12 |
| 520 | Solution phase | Bts-(D)Phe(3Cl)-OBn | Boc-(D)Val | H-Cpa-OBn | Boc-T39 | none |
| 521 | Solution phase | Bts-(D)Phe(3Cl)-OBn | Boc-(D)Val | Boc-AA5 | Boc-T9 | Example 17, then Example 12 |
| 522 | Solution phase | Bts-(D)Phe(3Cl)-OBn | Boc-(D)Val | Boc-AA5 | Boc-T9 | Example 17, then Example 14 |
| 523 | Solution phase | Bts-(D)Phe(3CF3)-OBn | Boc-(D)Val | Boc-AA5 | Boc-T9 | Example 24 |
| 524 | Solution phase | Bts-(D)Phe(3CF3)-OBn | Boc-(D)Val | Boc-AA5 | Boc-T9 | Example 17, then Example 26 |
| 525 | Solution phase | Bts-(D)Phe(3CF3)-OBn | Boc-(D)Val | Boc-AA5 | Boc-T9 | Example 17, then Example 18 |
| 526 | Solution phase | Bts-(D)Phe(3CF3)-OBn | Boc-(D)Val | Boc-AA5 | Boc-T9 | Example 21 |
| 527 | Solution phase | Bts-(D)Phe(3CF3)-OBn | Boc-(D)Val | Boc-AA5 | Boc-T9 | Example 23 |
| 528 | Solution phase | Bts-(D)Phe(3CF3)-OBn | Boc-(D)Val | Boc-AA5 | Boc-T9 | Example 22 |
| 529 | Solution phase | Bts-(D)Phe(3F)-OBn | Boc-(D)Val | Boc-AA5 | Boc-T38(R) | Example 17, then Example 28 |
| 530 | Solution phase | $F_1$ (with Tether) | Boc-(D)Val | H-Nva-OBn | $F_1$ (with $AA_1$) | none |
| 531 | Solution phase | Bts-(D)Phe(3F)-OBn | Boc-(D)Val | H-Cpa-OBn | Boc-T40 | none |
| 532 | Solution phase | Bts-(D)Phe(3CF3)-OBn | Boc-(D)Val | Boc-AA5 | Boc-T9 | Example 17, then Example 19, then Example 20 |
| 533 | Solution phase | Bts-(D)Phe(3F)-OBn | Boc-(D)Val | Boc-AA5 | Boc-T38(R) | Example 17, then Example 19, then Example 21 |
| 534 | Solution phase | Bts-(D)Phe(3F)-OBn | Boc-(D)Val | Boc-AA5 | Boc-T38(R) | Example 17, then Example 18 |
| 535 | Solution phase | Bts-(D)Phe(3F)-OBn | Boc-(D)Val | Boc-AA5 | Boc-T38(R) | Example 17, then Example 26 |
| 536 | Solution phase | Bts-(D)Phe(3F)-OBn | Boc-(D)Val | Boc-AA5 | Boc-T38(R) | Example 21 |
| 537 | Solution phase | Bts-(D)Phe(3CF3)-OBn | Boc-(D)Val | Boc-AA5 | Boc-T9 | none |
| 538 | Solution phase | Bts-(D)Phe(3F)-OBn | Boc-(D)Val | Boc-AA5 | Boc-T38(R) | none |
| 539 | Solution phase | Bts-(D)Phe(3CF3)-OBn | Boc-(D)Val | Boc-AA5 | Boc-T9 | Example 17, then Example 19 |
| 540 | Solution phase | Bts-(D)Phe(3F)-OBn | Boc-(D)Val | Boc-AA5 | Boc-T38(R) | Example 17, then Example 19 |
| 541 | Solution phase | $F_2$ (with Tether) | Boc-(D)Val | H-Nva-OBn | $F_2$ (with $AA_1$) | none |
| 542 | Solid phase | Bts-(D)Phe(3CF3) | Ddz-(D)Val | Ddz-Dap(Boc) | Ddz-T9 | none |
| 543 | Solid phase | Bts-(D)Phe(3F) | Ddz-(D)Val | Ddz-Dap(Boc) | Ddz-T38(R) | none |
| 544 | Solution phase | Bts-(D)Phe(3F)-OBn | Boc-(D)Val | Boc-AA5 | Boc-T81(1R,8S) | Example 17 |
| 545 | Solution phase | Bts-(D)Phe(3F)-OBn | Boc-(D)Val | Boc-AA5 | Boc-T81(1R,8S) | none |
| 546 | Solution phase | Bts-(D)Phe(3F)-OBn | Boc-(D)Val | Boc-AA5 | Boc-T81(1R,8S) | Example 17, then Example 25 |
| 547 | Solution phase | Bts-(D)Phe(3CF3)-OBn | Boc-(D)Val | Boc-AA5 | Boc-T9 | Example 17, then Example 25 |
| 548 | Solution phase | Bts-(D)Phe(3F)-OBn | Boc-(D)Val | Boc-AA5 | Boc-T38(R) | Example 17, then Example 25 |
| 549 | Solution phase | Bts-(D)Phe(3F)-OBn | Boc-(D)Val | Boc-AA5 | Boc-T38(R) | Example 17, then Example 28, then methylation under standard conditions |

TABLE 1-continued

Synthesis of Representative Compounds of the Invention

| Compound No.[1] | Strategy | AA₁ | AA₂ | AA₃ | Tether | Post-cyclization Reaction(s) |
|---|---|---|---|---|---|---|
| 550 | Solution phase | Bts-(D)Phe(3F)-OBn | Boc-(D)Val | Boc-AA5 | Boc-T81(1R,8S) | Example 17, then Example 26 |
| 551 | Solution phase | Bts-(D)Phe(3F)-OBn | Boc-(D)Val | H-Nva-OBn | Boc-T38(R) | none |
| 552 | Solution phase | Bts-(D)Tyr(3Cl)(Bts)-OMe | Boc-(D)Val | H-Nva-OBut | Boc-T38(R) | none |
| 553 | Solution phase | Bts-(D)Tyr(3tBu)-OBn | Boc-(D)Val | H-Nva-OBn | Boc-T9 | none |
| 554 | Solution phase | Bts-(D)Phe(3F)-OBn | Boc-(D)Val | H-Cpa-OBn | Boc-T38(R) | none |
| 555 | Solution phase | Bts-(D)Phe(3F)-OBn | Boc-(D)Cpg | H-Cpa-OBn | Boc-T38(R) | none |
| 556 | Solution phase | Bts-(D)Phe(3F)-OBn | Boc-(D)Val | H-Leu-OBn | Boc-T38(R) | none |
| 557 | Solution phase | Bts-(D)Phe(3F)-OBn | Boc-(D)Ala | H-Nva-OBn | Boc-T38(R) | none |
| 558 | Solution phase | Bts-(D)Phe(3F)-OBn | Boc-(D)Abu | H-Nva-OBn | Boc-T38(R) | none |
| 559 | Solution phase | Bts-(D)Phe(4F)-OBn | Boc-(D)Val | H-Cpa-OBn | Boc-T38(R) | none |
| 560 | Solution phase | Bts-(D)Phe(4F)-OBn | Boc-(D)Val | H-Nva-OBn | Boc-T38(R) | none |
| 561 | Solution phase | Bts-(D)Phe(3,4diF)-OBn | Boc-(D)Val | H-Nva-OBn | Boc-T38(R) | none |
| 562 | Solution phase | Bts-(D)Phe(3OMe)-OBn | Boc-(D)Val | H-Nva-OBn | Boc-T38(R) | none |
| 563 | Solution phase | Bts-(D)Phe(3F)-OBn | Boc-(D)Val | H-Nva-OBn | Boc-T92(R) | none |
| 564 | Solution phase | Bts-(D)Phe(3F)-OBn | Boc-(D)Val | H-Nva-OBn | Boc-T93(R) | none |
| 565 | Solution phase | Bts-(D)Phe(3F)-OBn | Boc-(D)Val | H-Nva-OBn | Boc-T95(R) | none |
| 566 | Solution phase | Bts-(D)Phe(3F)-OBn | Boc-(D)Cpg | H-Cpa-OBn | Boc-T40(S) | none |
| 567 | Solution phase | Bts-(D)Phe(4F)-OBn | Boc-(D)Val | H-Cpa-OBn | Boc-T40(S) | none |
| 568 | Solution phase | Bts-(D)Phe(3F)-OBn | Boc-(D)Val | H-Ser(But)-OBn | Boc-T38(R) | none |
| 569 | Solution phase | Bts-(D)Phe(3F)-OBn | Boc-(D)Val | H-Ser(OMe)-OBn | Boc-T38(R) | none |
| 570 | Solution phase | Bts-(D)Phe(3F)-OBn | Boc-(D)Val | H-Nva-OBn | Boc-T81(1R,8S) | none |
| 571 | Solution phase | Bts-(D)2Thi-OBn | Boc-(D)Val | H-Nva-OBn | Boc-T38(R) | none |
| 572 | Solution phase | Bts-(D)3Thi-OBn | Boc-(D)Val | H-Nva-OBn | Boc-T38(R) | none |
| 573 | Solution phase | Bts-(D)Phe(3F)-OBn | Boc-(D)Val | H-Nva-OBn | Boc-T94(R) | none |
| 574 | Solution phase | Bts-(D)Phe(3F)-OBn | Boc-(D)Val | H-Nva-OBn | Boc-T96(R) | none |
| 575 | Solution phase | Bts-(D)Phe(4CF3)-OBn | Boc-(D)Val | H-Nva-OBn | Boc-T9 | none |
| 576 | Solution phase | Bts-(D)Phe(4Cl)-OBn | Boc-(D)Val | Boc-AA5 | Boc-T9 | Example 17, then Example 30 |
| 577 | Solution phase | Bts-(D)Phe(4Cl)-OBn | Boc-(D)Val | Boc-AA5 | Boc-T9 | Example 17, then Example 31 |
| 578 | Solution phase | Bts-(D)Tyr(OBut)-OBn | Boc-(D)Val | Boc-AA5 | Boc-T9 | Example 17, then Example 33 |
| 579 | Solution phase | Bts-(D)Tyr(OBut)-OBn | Boc-(D)Val | Boc-AA5 | Boc-T9 | Example 17, then Example 32 |
| 580 | Solution phase | Bts-(D)Phe(4Cl)-OBn | Boc-(D)Val | Boc-AA5 | Boc-T9 | Example 17, then Example 28 |
| 581 | Solution phase | Bts-(D)Phe(4Cl)-OBn | Boc-(D)Val | Boc-AA5 | Boc-T9 | Example 17, then Example 32 |
| 582 | Solid phase | Bts-(D)Tyr(3,5diI)-OBn | Boc-(D)Val | Boc-Nva | Boc-T9 | none |
| 583 | Solution phase | Bts-(D)Tyr(OMe)-OBn | Boc-(D)Val | H-Hse-OBn | Boc-T9 | none |
| 584 | Solution phase | Bts-(D)Phe(3F)-OBn | Boc-(D)Val | H-Cpa-OBn | Boc-T9 | none |
| 585 | Solution phase | Bts-(D)Phe(3Cl)-OBn | Boc-(D)Val | H-Cpa-OBn | Boc-T40(S) | none |
| 586 | Solution phase | Bts-(D)Phe(3Cl)-OBn | Boc-(D)Val | H-Cpa-OBn | Boc-T40(R) | none |
| 587 | Solution phase | Bts-(D)Phe(3F)-OBn | Boc-(D)Val | H-Cpa-OBn | Boc-T40(R) | none |
| 588 | Solution phase | Bts-(D)Phe(3F)-OBn | Boc-(D)Val | H-Cpa-OBn | Boc-T40(S) | none |
| 589 | Solution phase | Bts-(D)Phe(3F)-OBn | Boc-(D)Val | H-Cpa-OBn | Boc-T38(S) | none |
| 590 | Solution phase | Bts-(D)Phe(3Cl)-OBn | Boc-(D)Val | H-Cpa-OBn | Boc-T58 | none |

[1] In instances where diastereomeric products were isolated after purification, the individual isomers are denoted with letters (a, b, c) after the compound identifier.

The table directly below presents analytical data obtained for compounds 501-589 (Table 2), as determined by LC-MS analysis of the purified products. These compounds were further examined for their ability to interact at the human motilin receptor utilizing the biological test methods described herein.

TABLE 2

Analytical Data for Representative Compounds of the Invention

| Compound No. | Molecular Formula | MW Calc (g/mol) | MS [(M + H)⁺] Found |
|---|---|---|---|
| 501 | C30H42N5O4Cl | 572.1 | 572 |
| 502 | C31H42N5O4F3 | 605.7 | 606 |
| 503 | C30H40N7O4F3 | 619.7 | 620 |
| 504 | C31H42N7O4F3 | 633.7 | 634 |
| 505 | C31H42N7O4F3 | 633.7 | 634 |
| 506 | C30H41N6O4Cl | 585.1 | 585 |
| 507 | C30H42N7O4Cl | 600.2 | 600 |
| 508 | C31H44N5O4Cl | 586.2 | 586 |
| 509 | C31H39N6O4SCl | 627.2 | 627 |
| 510 | C31H39N6O4Cl | 595.1 | 595 |
| 511 | C31H39N6O4Cl | 595.1 | 595 |
| 512 | C29H40N5O4Cl | 558.1 | 558 |
| 513 | C31H43N4O4F | 554.7 | 555 |
| 514 | C31H44N5O4F | 569.7 | 570 |
| 515 | C31H44N5O4F | 569.7 | 570 |
| 516 | C30H42N7O4Cl | 600.2 | 600 |
| 517 | C30H42N7O4Cl | 600.2 | 600 |
| 518 | C29H39N6O4Cl | 571.1 | 571 |
| 519 | C31H42N7O4Cl | 612.2 | 612 |
| 520 | C31H43N4O4Cl | 571.2 | 571 |
| 521 | C32H44N7O4Cl | 626.2 | 626 |
| 522 | C31H41N8O4Cl | 625.2 | 611 |
| 523 | C32H41N8O4F3 | 658.7 | 659 |
| 524 | C33H40N7O4F3 | 655.7 | 656 |
| 525 | C33H44N5O5F3 | 647.7 | 648 |
| 526 | C32H40N7O4F3 | 643.7 | 644 |
| 527 | C31H39N8O4F3 | 644.7 | 645 |
| 528 | C33H42N7O4F3 | 657.7 | 658 |
| 529 | C31H44N5O4F | 569.7 | 570 |
| 530 | C33H47N4O4F | 582.7 | 583 |
| 531 | C31H43N4O4F | 554.7 | 555 |
| 532 | C33H44N5O4F3 | 631.7 | 632 |
| 533 | C33H46N5O4F | 595.7 | 596 |
| 534 | C33H46N5O5F | 611.7 | 612 |
| 535 | C33H42N7O4F | 619.7 | 620 |
| 536 | C32H42N7O4F | 607.7 | 608 |

TABLE 2-continued

Analytical Data for Representative Compounds of the Invention

| Compound No. | Molecular Formula | MW Calc (g/mol) | MS [(M + H)$^+$] Found |
|---|---|---|---|
| 537 | C29H36N7O4F3 | 603.6 | 604 |
| 538 | C29H38N7O4F | 567.7 | 568 |
| 539 | C33H40N5O4F3 | 627.7 | 628 |
| 540 | C33H42N5O4F | 591.7 | 592 |
| 541 | C31H43N4O5F | 570.7 | 571 |
| 542 | C29H38N5O4F3 | 577.6 | 578 |
| 543 | C29H40N5O4F | 541.7 | 542 |
| 544 | C30H42N5O4F | 555.7 | 556 |
| 545 | C30H40N7O4F | 581.7 | 582 |
| 546 | C31H44N5O4F | 569.7 | 570 |
| 547 | C30H40N5O4F3 | 591.7 | 592 |
| 548 | C30H42N5O4F | 555.7 | 556 |
| 549 | C32H46N5O4F | 583.7 | 584 |
| 550 | C34H44N7O4F | 633.8 | 634 |
| 551 | C31H43N4O4F | 554.7 | 555 |
| 552 | C31H43N4O5Cl | 587.1 | 587 |
| 553 | C34H50N4O5 | 594.8 | 595 |
| 554 | C32H43N4O4F | 566.7 | 567 |
| 555 | C32H41N4O4F | 564.7 | 565 |
| 556 | C32H45N4O4F | 568.7 | 569 |
| 557 | C29H39N4O4F | 526.6 | 527 |
| 558 | C30H41N4O4F | 540.7 | 541 |
| 559 | C32H43N4O4F | 566.7 | 567 |
| 560 | C31H43N4O4F | 554.7 | 555 |
| 561 | C31H42N4O4F2 | 572.7 | 573 |
| 562 | C32H46N4O5 | 566.7 | 567 |
| 563 | C31H42N4O4F2 | 572.7 | 573 |
| 564 | C31H42N4O4F2 | 572.7 | 573 |
| 565 | C30H42N5O4F | 555.7 | 556 |
| 566 | C32H41N4O4F | 564.7 | 565 |
| 567 | C32H43N4O4F | 566.7 | 567 |
| 568 | C29H39N4O5F | 542.6 | 543 |
| 569 | C30H41N4O5F | 556.7 | 557 |
| 570 | C32H45N4O4F | 568.7 | 569 |
| 571 | C29H42N4O4S | 542.7 | 543 |
| 572 | C29H42N4O4S | 542.7 | 543 |
| 573 | C30H42N5O4F | 555.7 | 556 |
| 574 | C30H42N5O4F | 555.7 | 556 |
| 575 | C31H41N4O4F3 | 590.7 | 591 |
| 576 | C29H40N5O6SCl | 622.2 | 622 |
| 577 | C29H39N6O5Cl | 587.1 | 587 |
| 578 | C29H41N7O5 | 567.7 | 568 |
| 579 | C31H45N5O5 | 567.7 | 568 |
| 580 | C30H42N5O4Cl | 572.1 | 572 |
| 581 | C31H44N5O4Cl | 586.2 | 586 |
| 582 | C30H40N4O5I2 | 790.5 | 791 |
| 583 | C30H42N4O6 | 554.7 | 555 |
| 584 | C31H41N4O4F | 552.7 | 553 |
| 585 | C32H43N4O4Cl | 583.2 | 583 |
| 586 | C32H43N4O4Cl | 583.2 | 583 |
| 587 | C32H43N4O4F | 566.7 | 567 |
| 588 | C32H43N4O4F | 566.7 | 567 |
| 589 | C32H43N4O4F | 566.7 | 567 |
| 590 | C33H45N4O4Cl | 597.2 | 597 |

Notes
1. Molecular formulas and molecular weights are calculated automatically from the structure via ActivityBase software (ID Business Solutions, Ltd., Guildford, Surrey, UK).
2. [M + H]$^+$ obtained from LC-MS analysis using standard methods.
3. All analyses conducted on material after preparative purification.

E. Analytical Methods $^1$H and $^{13}$C NMR spectra were recorded on a Varian Mercury 300 MHz spectrometer (Varian, Inc., Palo Alto, Calif.) and are referenced internally with respect to the residual proton signals of the solvent unless otherwise noted. $^1$H NMR data are presented, using the standard abbreviations, as follows: chemical shift (δ) in ppm (multiplicity, integration, coupling constant(s)). The following abbreviations are used for denoting signal multiplicity: s=singlet, d=doublet, t=triplet, q=quartet, quint=quintet, b or br=broad, and m=multiplet. Information about the conformation of the molecules in solution can be determined utilizing appropriate two-dimensional NMR techniques known to those skilled in the art. (Martin, G. E.; Zektzer, A. S. *Two-Dimensional NMR Methods for Establishing Molecular Connectivity: A Chemist's Guide to Experiment Selection, Performance, and Interpretation*, John Wiley & Sons: New York, 1988, ISBN 0471187070.)

HPLC analyses were performed on a Waters Alliance® system 2695 running at 1 mL/min using an Xterra® MS C18 column (or comparable) 4.6×50 mm (3.5 μm) and the indicated gradient method. A Waters 996 PDA provided UV data for purity assessment (Waters Corporation, Milford, Mass.). An LCPackings (Dionex Corporation, Sunnyvale, Calif.) splitter (50:40:10) allowed the flow to be separated in three parts. The first part (50%) was diverted to a mass spectrometer (Micromass® Platform II MS equipped with an APCI probe) for identity confirmation. The second part (40%) went to an evaporative light scattering detector (ELSD, Polymer Laboratories, now part of Varian, Inc., Palo Alto, Calif., PL-ELS-1000™) for purity assessment and the last portion (10%) went to a chemiluminescence nitrogen detector (CLND, Antek® Model 8060, Antek Instruments, Houston, Tex., part of Roper Industries, Inc., Duluth, Ga.) for quantitation and purity assessment. Data was captured and processed utilizing the most recent version of the Waters Millennium® software package.

Enantiomeric and diastereomeric purity were assessed using appropriate chiral HPLC columns using a Waters Breeze system (or comparable). Although other packing materials can be utilized, particularly useful columns for these analyses are: Chiralpak AS-RH and Chiralcel OD-RH (Chiral Technologies, West Chester, Pa., USA).

Preparative HPLC purifications were performed on final deprotected macrocycles using the Waters FractionLynx® system, on an XTerra® MS C18 column (or comparable) 19×100 mm (5 μm). The injections were done using an At-Column-Dilution configuration with a Waters 2767 injector/collector and a Waters 515 pump running at 2 mL/min. The mass spectrometer, HPLC, and mass-directed fraction collection are controlled via MassLynx® software version 3.5 with FractionLynx®. Fractions (13×125 mm tubes) shown by MS analysis to contain the product were evaporated under reduced pressure, most typically on a centrifugal evaporator system (Genevac® HT-4 (Genevac Inc, Valley Cottage, N.Y.), ThermoSavant Discovery®, SpeedVac® or comparable (Thermo Electron Corporation, Waltham, Mass.) or, alternatively, lyophilized. Compounds were then thoroughly analyzed by LC-MS-UV-ELSD-CLND analysis for identity confirmation, purity and quantity assessment.

Automated medium pressure chromatographic purifications were performed on an Isco CombiFlash® 16× system with disposable silica or C18 cartridges that permitted up to sixteen (16) samples to be run simultaneously (Teledyne Isco, Inc., Lincoln, Nebr.). MS spectra were recorded on a Waters Micromass® Platform II or ZQ™ system. HRMS spectra were recorded with a VG Micromass ZAB-ZF spectrometer. Chemical and biological information were stored and analyzed utilizing the ActivityBase® database software (ID Business Solutions Ltd., Guildford, Surrey, UK).

F. Chiral Purity Determination

General methods for the HPLC determination of stereoisomeric purity were employed according to techniques known to those skilled in the art and further optimized for the compounds of the present invention.

Method Chiral A: Grad35A-05 (Column: Chiralcel AS-RH, 0.46 cm×15 cm):
1. Isocratic plateau of 40 min at 35% ACN, 65% of a 50 mM solution of $CH_3COONH_4$ in $H_2O$.

2. 5 min gradient to 70% ACN, 30% of a 50 mM solution of CH₃COONH₄ in H₂O:
3. Isocratic plateau of 10 min at 70% ACN, 30% of a 50 mM solution of CH₃COONH₄ in H₂O.
4. 5 min gradient to 35% ACN, 65% of a 50 mM solution of CH₃COONH₄ in H₂O.
5. Isocratic plateau of 10 min at 35% ACN, 65% of a 50 mM solution of CH₃COONH₄ in H₂O.
6. Flow: 0.5 mL/min
7. Column temperature: room temperature
8. Sample temperature: room temperature Method Chiral B: Grad40A-05 (Column: Chiralcel OD-RH, 0.46 cm×15 cm):
1. Isocratic plateau of 40 min at 40% ACN, 60% of a solution 50 mM of CH₃COONH₄ in H₂O.
2. 5 min gradient to 70% ACN, 30% of a solution 50 mM of CH₃COONH₄ in H₂O.
3. Isocratic plateau of 10 min at 70% ACN, 30% of a solution 50 mM of CH₃COONH₄ in H₂O.
4. 5 min gradient to 40% ACN, 60% of a solution 50 mM of CH₃COONH₄ in H₂O.
5. Isocratic plateau of 10 min at 40% ACN, 60% of a solution 50 mM of CH₃COONH₄ in H₂O.
6. Flow: 0.5 mL/min
7. Column temperature: room temperature
8. Sample temperature: room temperature Method Chiral C: Grad 55A-05 (Column: Chiralcel OD-RH, 0.46 cm×15 cm):
1. 40 min isocratic 55%/45% of ACN/50 mM CH₃COONH₄ in H₂O
2. 5 min gradient to 70%/30% of ACN/50 mM CH₃COONH₄ in H₂O
3. 10 min isocratic 70%/30% of ACN/50 mM CH₃COONH₄ in H₂O
4. 5 min gradient to 55%/44% of ACN/50 mM CH₃COONH₄ in H₂O
5. 10 min isocratic 55%/45% of ACN/50 mM CH₃COONH₄ in H₂O
6. Flow: 0.5 mL/min
7. Column temperature: room temperature
8. Sample temperature: room temperature Method Chiral D: Grad Iso100B_05 (Column: Chiralcel OD-RH, 0.46 cm×15 cm):
1. 40 min isocratic 27%/73% of ACN/50 mM CH₃COONH₄ in H₂O
2. 5 min gradient to 70%/30% of ACN/50 mM CH₃COONH₄ in H₂O
3. 10 min isocratic 70%/30% of ACN/50 mM CH₃COONH₄ in H₂O
4. 5 min gradient to 27%/73% of ACN/50 mM CH₃COONH₄ in H₂O
5. 10 min isocratic 27%/73% of ACN/50 mM CH₃COONH₄ in H₂O
6. Flow: 0.5 mL/min
7. Column temperature: room temperature
8. Sample temperature: room temperature 3. Biological Methods The compounds of the present invention were evaluated for their ability to interact at the human motilin receptor utilizing a competitive radioligand binding assay, fluorescence assay or Aequorin functional assay as described below. Such methods can be conducted in a high throughput manner to permit the simultaneous evaluation of many compounds.

Specific assay methods for the motilin receptor and their use in generally identifying agonists and antagonists thereof are known. (Peeters, T. L.; Depoortere, I.; Macielag, M. J.; Marvin, M. S.; Florance, J. R.; Galdes, A. *Biochem. Biophys. Res. Comm.* 1994, 198, 411-416; Farrugia, G.; Macielag, M. J.; Peeters, T. L.; San, M. G.; Galdes, A.; Szurszewski, J. H. *Am. J. Physiol.* 1997, 273, G404-G412; Depoortere, I.; Macielag, M. J.; Galdes, A.; Peeters, T. L. *Eur. J. Pharmacol.* 1995, 286, 241-247; Poitras, P.; Miller, P.; Gagnon, D.; St-Pierre, S. *Biochem. Biophys. Res. Comm.* 1994, 205, 449-454; Haramura, M.; Okamachi, A.; Tsuzuki, K.; Yogo, K.; Ikuta, M.; Kozono, T.; Takanashi, H.; Murayama, E. *J. Med. Chem.* 2002, 45, 670-675; Beavers, M. P.; Gunnet, J. W.; Hageman, W.; Miller, W.; Moore, J. B.; Zhou, L.; Chen, R. H. K.; Xiang, A.; Urbanski, M.; Combs, D. W.; Mayo, K. H.; Demarest, K. T. *Drug Des. Disc.* 2001, 17, 243-251.)

Appropriate methods for determining the functional activity, pharmacological profile and in vivo activity of compounds of the present invention that interact at the human motilin receptor are also described below.

A. Competitive Radioligand Binding Assay (Motilin Receptor)

The competitive binding assay at the human motilin receptor was carried out analogously to assays described in the literature.

Materials:
  Membranes were prepared from CHO cells stably transfected with the human motilin receptor and utilized at a quantity of 1.5 μg/assay point. [PerkinElmer™ SignalScreen Product #6110544]
  [¹²⁵I]-Motilin (PerkinElmer, #NEX-378); final concentration: 0.04-0.06 nM
  Motilin (Bachem™, #H-4385); final concentration: 1 μM
  Multiscreen Harvest plates-GF/B (Millipore™, #MAHFB1H60)
  Deep-well polypropylene titer plate (Beckman Coulter™, #267006)
  TopSeal-A (PerkinElmer, #6005185)
  Bottom seal (Millipore, #MATAH0P00)
  MicroScint-0 (PerkinElmer, #6013611)
  Binding Buffer: 50 mM Tris-HCl (pH 7.4), 10 mM MgCl₂, 1 mM EDTA, 0.1% BSA Assay Volumes:
  150 μL of membranes diluted in binding buffer
  10 μL of compound diluted in binding buffer
  10 μL of radioligand ([¹²⁵I]-Motilin) diluted in binding buffer Final Test Concentrations (N=11) for Compounds:
  10, 5.0, 2.0, 1.0, 0.50, 0.20, 0.10, 0.050, 0.020, 0.010, 0.0050 μM.

Compound Handling:
  Compounds were provided frozen on dry ice at a stock concentration of 10 mM diluted in 100% DMSO and stored at −20° C. until the day of testing. On the test day, compounds were allowed to thaw at room temperature and than diluted in assay buffer according to the desired test concentrations. Under these conditions, the maximum final DMSO concentration in the assay was 0.5%.

Assay Protocol:
  In deep-well plates, diluted cell membranes (1.5 μg/mL) are combined with 10 μL of either binding buffer (total binding, N=5), 1 μM motilin (non-specific binding, N=3) or the appropriate concentration of test compound. The reaction is initiated by addition of 10 μL of [¹²⁵I]-motilin (final conc. 0.04-0.06 nM) to each well. Plates are sealed with TopSeal-A, vortexed gently and incubated at room temperature for 2 hours. The reaction is arrested by filtering samples through pre-soaked (0.3% polyethyleneimine, 2 h) Multiscreen Harvest plates using a Tomtec Harvester, washed 9 times with 500 μL of cold 50 mM Tris-HCl (pH 7.4), and than plates are air-dried in a fumehood for 30 minutes. A bottom seal is applied to the plates prior to the addition of 25 μL of MicroScint-0 to each well. Plates are than sealed with TopSeal-A and counted for 30 sec per well on a TopCount Microplate Scintillation and Luminescence Counter (PerkinElmer) where results are expressed as counts per minute (cpm).

Data are analyzed by GraphPad™ Prism® (GraphPad Software, San Diego, Calif.) using a variable slope non-linear regression analysis. $K_i$ values were calculated using a $K_d$ value of 0.16 nM for [$^{125}$I]-motilin (previously determined during membrane characterization).

$$D_{max} = 1 - \frac{\text{test concentration with maximal displacement} - \text{non-specific binding}}{\text{total binding} - \text{non-specific binding}} \times 100$$

where total and non-specific binding represent the cpm obtained in the absence or presence of 1 μM motilin, respectively.

Binding activity at the motilin receptor for representative compounds of the present invention is shown in Table 3. Compound structures for Table 3 are presented with the various groups as defined for the general structure of formula I.

TABLE 3

Binding Activity at the Human Motilin Receptor for Representative Compounds of the Invention

| Compound No. | $K_i$ (nM) |
| --- | --- |
| 501a | B |
| 501b | B |
| 502a | A |
| 502b | B |
| 503a | A |
| 503b | B |
| 503c | A |
| 504 | B |
| 505 | A |
| 506a | B |
| 506b | B |
| 507 | B |
| 508 | B |
| 509 | B |
| 510 | B |
| 511a | B |
| 511b | C |
| 512a | B |
| 512b | C |
| 513 | B |
| 514 | C |
| 515a | A |
| 515b | B |
| 516a | A |
| 516b | B |
| 516c | C |
| 517a | C |
| 517b | C |
| 518 | B |
| 519a | B |
| 519b | B |
| 520 | B |
| 521 | B |
| 522 | B |
| 523 | B |
| 524 | B |
| 525 | B |
| 526 | B |
| 527 | B |
| 528 | B |
| 529 | A |
| 530 | B |
| 531 | B |
| 532 | A |

TABLE 3-continued

Binding Activity at the Human Motilin Receptor for Representative Compounds of the Invention

| Compound No. | $K_i$ (nM) |
| --- | --- |
| 533 | B |
| 534 | B |
| 535 | B |
| 536 | B |
| 537 | A |
| 538 | A |
| 539 | A |
| 540 | A |
| 541 | A |
| 542 | B |
| 543 | B |
| 544 | A |
| 545 | A |
| 546 | A |
| 547 | A |
| 548 | A |
| 549 | C |
| 550 | A |
| 551 | A |
| 552 | A |
| 553 | A |
| 554a | A |
| 554b | C |
| 554c | B |
| 555 | A |
| 556 | A |
| 557 | A |
| 558 | A |
| 559 | A |
| 560 | A |
| 561 | A |
| 562 | A |
| 563 | B |
| 564 | A |
| 565 | A |
| 566 | A |
| 567 | A |
| 568 | B |
| 569 | A |
| 570 | A |
| 571 | A |
| 572 | A |
| 573 | B |
| 574 | B |
| 575 | B |
| 576 | C |
| 577 | C |
| 578a | C |
| 578b | D |
| 579 | C |
| 580a | B |
| 580b | B |
| 581 | B |
| 582a | C |
| 582b | D |
| 583 | C |
| 584 | B |
| 585 | A |
| 586 | B |
| 587 | B |
| 588 | A |
| 589a | C |
| 589b | D |
| 590 | B |

[a] Binding activity determined using standard method, $K_i$ values are expressed as follows: A ≤ 10 nM, B ≤ 100 nM, C ≤ 1000 nM, D > 1000 nM B. Aequorin Functional Assay (Motilin Receptor)

The evaluation of compounds of the invention for functional activity can be conducted according to literature methods or as described below. (Carreras, C. W.; Siani, M. A.; Santi, D. V.; Dillon, S. B. *Anal. Biochem.* 2002, 300, 146-151.)

Materials:
Membranes were prepared using AequoScreen™ (EURO-SCREEN, Belgium) cell lines expressing the human motilin receptor (cell line ES-380-A; receptor accession #AF034632). This cell line is constructed by transfection of the human motilin receptor into CHO-K1 cells co-expressing $G_{\alpha16}$ and the mitochondrially targeted Aequorin (Ref. #ES-WT-A5).
Motilin (Bachem, #H-4385)
Assay buffer: DMEM-F12 (Dulbeccoe's Modified Eagles Medium) with 15 mM HEPES and 0.1% BSA (pH 7.0)
Coelenterazine (Molecular Probes™, Leiden, The Netherlands)
Final Test Concentrations (N=5) for Compounds:
10, 3.16, 1.0, 0.316, 0.10 µM.
Compound Handling:
Compounds were provided as dry films at a quantity of approximately 1.2 µmol in pre-formatted 96-well plates. Compounds were dissolved in 100% DMSO at a concentration of 10 mM and stored at −20° C. until further use. Daughter plates were prepared at a concentration of 500 µM in 30% DMSO with 0.1% BSA and stored at −20° C. until testing. On the test day, compounds were allowed to thaw at room temperature and than diluted in assay buffer according to the desired test concentrations. Under these conditions, the maximum final DMSO concentration in the assay was 0.6%.
Cell Preparation:
Cells are collected from culture plates with $Ca^{2+}$ and $Mg^{2+}$-free phosphate buffered saline (PBS) supplemented with 5 mM EDTA, pelleted for 2 minutes at 1000×g, resuspended in assay buffer (see above) at a density of $5\times10^6$ cells/mL and incubated overnight in the presence of 5 µM coelenterazine. After loading, cells were diluted with assay buffer to a concentration of $5\times10^5$ cells/mL.
Assay Protocol:
For agonist testing, 50 µL of the cell suspension was mixed with 50 µL of the appropriate concentration of test compound or motilin (reference agonist) in 96-well plates (duplicate samples). The emission of light resulting from receptor activation was recorded using the Functional Drug Screening System 6000 'FDSS 6000' (Hamamatsu Photonics K. K., Japan).
For antagonist testing, an approximate $EC_{80}$ concentration of motilin (i.e. 0.5 nM; 100 µL) was injected onto the cell suspension containing the test compounds (duplicate samples) 15-30 minutes after the end of agonist testing and the consequent emission of light resulting from receptor activation was measured as described in the paragraph above.
Results are expressed as Relative Light Units (RLU). Concentration response curves were analyzed using GraphPad™ Prism® (GraphPad Software, San Diego, Calif.) by non-linear regression analysis (sigmoidal dose-response) based on the equation $E=E_{max}/(1+EC_{50}/C)n$ where E is the measured RLU value at a given agonist concentration (C), $E_{max}$ is the maximal response, $EC_{50}$ is the concentration producing 50% stimulation and n is the slope index. For agonist testing, results for each concentration of test compound were expressed as percent activation relative to the signal induced by motilin at a concentration equal to the $EC_{80}$ (i.e. 0.5 nM). For antagonist testing, results for each concentration of test compound were expressed as percent inhibition relative to the signal induced by motilin at a concentration equal to the $EC_{80}$ (i.e. 0.5 nM).
A wider evaluation of receptor selectivity can be obtained through the use of "ExpresSProfile", a broad target screen offered commercially by CEREP (Poitiers, France). In this screen, a single-point (10 µM) binding assay is performed across 50 individual receptors from four distinct target classes: non-peptide G-Protein Coupled Receptors (GPCRs), peptide GPCRs, ion channels and amine transporters.

Binding activity at the motilin receptor for representative compounds of the present invention is shown in Table 4. Compound structures for Table 4 are presented in Table 3 with the various groups as defined for the general structure of formula I.

TABLE 4

Functional Activity at the Motilin Receptor for Representative Compounds of the Invention

| Compound No. | $IC_{50}$ (nM)[a] |
|---|---|
| 502 | B |
| 503 | C |
| 504 | C |
| 505 | B |
| 511 | C |
| 512 | C |
| 513 | C |
| 515 | B |
| 516 | C |
| 529 | B |
| 530 | C |
| 532 | C |
| 533 | B |
| 534 | B |
| 535 | B |
| 536 | C |
| 537 | A |
| 538 | A |
| 539 | A |
| 540 | A |
| 541 | B |
| 542 | B |
| 543 | C |
| 544 | A |
| 545 | A |
| 546 | A |
| 547 | B |
| 548 | B |
| 550 | A |
| 552 | A |
| 555 | A |
| 557 | B |
| 563 | B |
| 564 | A |
| 565 | B |
| 568 | B |
| 569 | B |
| 570 | A |
| 571 | B |
| 572 | A |
| 573 | B |
| 574 | D |
| 585 | B |
| 586 | C |

[a] Functional activity determined using standard method, $IC_{50}$ values are expressed as follows: A ≤ 1 nM, B ≤ 10 nM, C ≤ 100 nM, D ≤ 1000 nM C. FlashPlate Motilin [$^{35}$S]-GTPγS Functional Assay
Materials:
Membranes were prepared from CHO cells stably transfected with the human motilin receptor and utilized at a quantity of 1.5 µg/assay point.
[PerkinElmer SignalScreen Product #6110544]
GTPγS (Sigma, #G-8634)
[$^{35}$S]-GTPγS (PerkinElmer, #NEX-030H)
Motilin (Bachem, #H-4385)
96-well FlashPlate microplates (PerkinElmer, #SMP200)
Deep-well polypropylene titer plate (Beckman Coulter, #267006)
TopSeal-A (PerkinElmer, #6005185)
Assay Buffer: 50 mM Tris (pH 7.4), 100 mM NaCl, 10 mM $MgCl_2$, 1 mM EDTA, 1 µM GDP, 0.1% BSA Assay Volumes:
  25 µL of compound diluted in assay buffer
  25 µL of assay buffer (agonist assay) or 0.6 µM motilin (0.1 µM final concentration) diluted in assay buffer (antagonist assay)
  100 µL of [35S]-GTPγS diluted in assay buffer
Final Test Concentrations (N=12) for Compounds:
  50, 20, 10, 5.0, 2.0, 1.0, 0.50, 0.20, 0.10, 0.050, 0.020, 0.010 µM.

Compound Handling:

Compounds were provided frozen on dry ice at a stock concentration of 10 mM diluted in 100% DMSO and stored at −20° C. until the day of testing. On the test day, compounds were allowed to thaw at room temperature and than diluted in assay buffer according to the desired test concentrations. Under these conditions, the maximum final DMSO concentration in the assay was 0.5%.

Assay Protocol:

CHO membranes were immobilized into 96-well FlashPlate microplates. Test compound, GTPγS, motilin and [35S]-GTPγS were combined in each well according to the Assay Volumes described above.

For the assay to measure agonist activity, an additional 25 µL of buffer was added to each well in addition to 25 µL of either buffer (basal value, N=4), 1.0 µM (final conc.) motilin ($E_{max}$ value, N=3), 25 µM (final conc.) GTPγS (non-specific value, N=4), or the appropriate concentration of test compound (N=3).

For the assay to measure antagonist activity, an additional 25 µL of either buffer (unstimulated control) or motilin (0.10 µM final conc.) is added to each well, in addition to either 25 µL of buffer (basal value, N=3), 1.0 µM (final conc.) motilin ($E_{max}$ value, N=3), 25 µM (final conc.) GTPγS (non-specific value, N=4), or the appropriate concentration of test compound (N=3).

The reaction is initiated by addition of 100 mL of [35S]-GTPγS to each well. Each plate is sealed (TopSeal-A) and incubated in the dark at room temperature for 150 min. Then, plates are counted for 30 seconds per well on the TopCount NXT.

Data were analyzed by GraphPad™ Prism® 3.0 (GraphPad Software, San Diego, Calif.) using non-linear regression analysis (sigmoidal dose-response) for the calculation of $IC_{50}/EC_{50}$ values.

$$E_{max}(\text{agonist}) \text{ or } D_{max}(\text{antagonist}) = \frac{\text{Top} - \text{Bottom}}{\text{Bottom}} \times 100$$

Where Top and Bottom correspond to the top and bottom values of the dose-response curve calculated by GraphPad Prism.

D. Rabbit Duodenum Contractility Assay

Evaluation of compounds of the invention for ex vivo activity was conducted on strips of rabbit duodenum according to literature methods. (Van Assche, G.; Depoortere, I.; Thijs, T.; Janssens, J. J.; Peeters, T. L. Eur. J. Pharmacol. 1997, 337, 267-274; Matthijs, G.; Peeters, T. L.; Vantrappen, G. Naunyn-Schmiedeberg's Arch. Pharmacol. 1989, 339, 332-339.) Related methods can also be employed for this type of study. (Tomomasa, T.; Yagi, H.; Kimura, S.; Snape, W. J., Jr.; Hyman, P. E. Pediatric Res. 1989, 26, 458-461; Takanishi, H.; Yogo, K.; Ozaki, M.; Akima, M.; Koga, H.; Nabata, H. J. Pharm. Exp. Ther. 1995, 273, 624-628.)

Duodenal segments were vertically suspended in organ chambers of 10 mL filled with Krebs buffer and connected to an isotonic force transducer, with a preload of 1 g. After a stabilization period, the muscle strips were challenged with $10^{-4}$ M acetylcholine and washed. This was repeated until a stable maximal contraction was obtained (2-3 times), with an interval of at least 20 minutes.

After a stable base line was reached, test compounds were added to the bath. After a 15 minute incubation, a dose response to motilin was recorded by adding logarithmically increasing concentrations of motilin to the bath (final concentration $10^{-9}$ to $10^{-6}$ M). A blank experiment (no test compound present) was also performed. At the end of the dose response curve, a supramaximal dose of acetylcholine ($10^{-4}$ M) was given and this response was used as a reference (100% contraction).

The results of experiments at different concentrations of test compound were combined and analyzed to derive the $pA_2$ value from the Schild plot.

E. Animal Model of Chemotherapy-Induced Diarrhea

The in vivo efficacy of the compounds of the present invention can be evaluated utilizing appropriate animal models. Rat models have been utilized for evaluation of compounds in chemotherapy-induced diarrhea (CID). (Takasuna, K.; Kasai, Y.; Kitano, Y.; et al. Jpn. J. Cancer Res. 1995, 86, 978-984; Tavakkolizadeh, A.; Shen, R.; Abraham, P.; et al. J. Surg. Res. 2000, 91, 77-82; Horikawa, M.; Kato, Y.; Sugiyama. Pharm. Res. 2002, 19, 1345-1353.) Similarly, mouse models have been used to test agents for amelioration of gastrointestinal toxicity of chemotherapeutic agents. (Boushey R P, Yusta B, Drucker D J. Cancer Res 2001, 61, 687-93; Zhao, J.; Huang, L.; Belmar, N.; Buelow, R.; Fong, T. Clin. Canc. Res. 2004, 10, 2851-2859.) Additionally, dogs are known to suffer from diarrhea during treatment with common chemotherapeutic agents. (Kawato, Y.; Sekiguchi, M.; Akahane, K.; Tsutomi, Y.; Hirota, Y.; Kuga, H.; Suzuki, W.; Hakusui, H.; Sato, K. J. Pharm. Pharmacol. 1993, 45, 444-448; Kato, T.; Shimamoto, Y.; Uchida, J.; Ohshimo, H.; Abe, M.; Shirasaka, T.; Fukushima, M. Anticancer Res. 2001, 21, 1705-12.) However, rats and mice do not possess a functional motilin receptor and would not be appropriate animal models for a motilin antagonist, but could be used to differentiate effects at the motilin receptor from non-specific effects. The dog is an appropriate model species as it possesses a functional motilin receptor and has been used previously for studies involving motilin modulation. Other species appropriate for such an evaluation include hamster, pig, rabbit, shrew, guinea pig and opossum. In addition, methods analogous to those described for rats and mice could be adapted to canine or other models to test the compounds of the invention. Hence, the effect of treatment with compounds of the invention on the frequency and severity of incidences of diarrhea in a dog or other animal model can be used as a measure of the effectiveness of the compounds of the invention.

Dog Model

The objective of this study was to determine the efficacy of representative macrocyclic compounds of the present invention in chemotherapy-induced diarrhea (CID) following intravenous administration to the male beagle dog (Canis familiaris) for up to 32 days. Comparison with existing agents utilized for this condition, octreotide and loperamide, was an additional objective.

Experimental Design

Twenty-one (21) male naïve Beagle dogs were randomly assigned to 7 groups and treated as follows:

mg/mL formulation with 5% dextrose for injection, USP. The dosing formulation was stored refrigerated (2 to 8° C.), protected from light and used within 48 hours.

TABLE 5

Treatment Groups

| Group Number | Group Designation | Dose Level (mg/kg/day) TA1[a] | Dose Level (mg/kg/day) TA2/Comparator | Dose Concentration (mg/mL) TA1 | Dose Concentration (mg/mL) TA2/Comparator | Routes TA1 | Routes TA2/Comparator | Animal Numbers (male) |
|---|---|---|---|---|---|---|---|---|
| 1 | Positive Control (Irinotecan) | 4/8/6 | 0 | 0.5/4/2 | 0 | IF/IV/IV | NA | 3 |
| 2 | Compound 552 Low Dose | 6 | 5.0[b] | 2 | 0.33 | IV | IF | 3 |
| 3 | Compound 552 High Dose | 6 | 15.0[b] | 2 | 1.00 | IV | IF | 3 |
| 4 | Compound 552 Pre-Dose | 6 | 5.0[c] | 2 | 0.33 | IV | IF | 3 |
| 5 | Vehicle Control[d] | 0 | 0 | 0 | 0 | IV | IF | 3 |
| 6 | Octreotide | 6 | 0.021[e] | 2 | 0.1 | IV | SC | 3 |
| 7 | Loperamide | 6 | 0.18[f] | 2 | 0.1 | IV | PO | 3 |

Abbreviations:
IF, intravenous infusion;
IV, intravenous bolus injection;
NA, not applicable;
TA1, Irinotecan (ready-to-use solution for Group 1 and irinotecan hydrochloride for Groups 2 to 4, 6 and 7);
TA2, Compound 552.

Notes:
[a]TA1 (irinotecan solution or irinotecan hydrochloride) was used to induce diarrhea in the animals in Groups 1 to 4, 6 and 7. For the animals in Group 1, treatment with TA1 consisted of three (3) cycles: Cycle 1, irinotecan solution was administered at a dose level of 4 mg/kg/day by one hour infusion via implanted catheter for 5 consecutive days followed by a 9-day rest period. Cycle 2, irinotecan solution was administered by one hour infusion via implanted catheter for four consecutive days at a dose level of 4 mg/kg/day and by bolus injection (over approximately one minute) at a dose level of 8 mg/kg/day via implanted catheter for the fifth day followed by a 5-day rest period; for Cycle 3, one spare animal was added to Group 1. Irinotecan formulation was prepared with irinotecan hydrochloride powder and administered to the four animals by bolus injection via implanted catheter at a dose level of 4 mg/kg/day for five consecutive days. These four animals were observed for 9 days and subjected to necropsy following an overnight period without food.
For the animals in Groups 2 to 4, 6 and 7, irinotecan formulation was prepared with irinotecan hydrochloride powder and administered by bolus injection via implanted catheter up to two treatment cycles for a 28-day study period. In each treatment cycle, animals were treated with a single daily dose at 6 mg/kg for 5 consecutive days followed by a 9-day rest period without treatment. Before commencing treatment with irinotecan (Group 4) or upon onset of irinotecan-induced diarrhea (Groups 2, 3, 6 and 7), these animals were treated with TA2 (compound 552) (Group 2 to 4), octreotide (Group 6) or loperamide (Group 7) as detailed below. Upon completion of the treatment/observation periods and following an overnight period without food, all surviving animals were subjected to necropsy.
[b]TA2 (compound 552) was administered by infusion to all the animals in the group via an implanted catheter over 45 minutes. The treatment with compound 552 started on the day of onset of diarrhea, if diarrhea was observed in any of the three animals from the group in the morning or on the following day if diarrhea was observed in the afternoon. Treatment with compound 552 then continued throughout the remainder of the 28-day study period. The daily dosage (i.e. 5.0 and 15.0 mg/kg/day for Groups 2 and 3 respectively) was divided into two equal doses (ie 2.5 and 7.5 mg/kg/occasion for Groups 2 and 3 respectively) and infused at least 6 hours apart on each day. The animals received 0.9% Sodium Chloride for Injection USP at a rate of 2.5 mL/hour between each infusion of compound 552.
[c]TA2 (compound 552) was administered to all three animals in the group following the same procedures for Groups 2 and 3, starting four days before the start of TA1 (irinotecan) treatment and throughout the 28-day study period. The daily dose (5.0 mg/kg/day) was divided into two equal doses (2.5 mg/kg/occasion) and infused at least 6 hours apart on each day. The animals received 0.9% Sodium Chloride for Injection USP at a rate of 2.5 mL/hour between each infusion of compound 552.
[d]The animals in the Vehicle Control group (5% dextrose for injection, USP) were treated with the vehicles for irinotecan and compound 552. The vehicle for irinotecan was administered by a slow bolus injection (approximately over one minute) via infusion line for up to two treatment cycles. In each treatment cycle, animals were treated with single daily doses for 5 consecutive days followed by a 9-day rest period. The vehicle for compound 552 was administered by following the dosing procedures for compound 552 administration or 23 days (from Day 6 to Day 28.
[e]All the animals in the group were dosed with octreotide by subcutaneous injection on the day of onset of irinotecan-induced diarrhea, if diarrhea was observed in any of the three animals from the group in the morning or on the following day if diarrhea was observed in the afternoon. The treatment was maintained throughout the remainder of the 28-day study period. The daily dosage (0.021 mg/kg/day) was divided into three equal doses (0.007 mg/kg/occasion) and administered by subcutaneous injection early in the morning, noon and late in the afternoon, respectively. Each administration was separated by at least 4 hours (±30 minutes).
[f]All the animals in the group were dosed with loperamide by oral gavage on the day of onset of irinotecan-induced diarrhea, if diarrhea was observed in any of the three animals from the group in the morning or on the following day if diarrhea was observed in the afternoon. The treatment was maintained throughout the remainder of the 28-day study period. The daily dosage (0.18 mg/kg/day) was divided into three equal doses (0.06 mg/kg/occasion) and administered by oral gavage approximately early in the morning, noon and late in the afternoon, respectively. Each administration was separated by at least 4 hours (±30 minutes).

Dose levels for irinotecan (*Seminars in Oncology* 1996, 23, 11-20) as well as loperamide and octreotide (*The Oncologist* 1998, 3, 50-53) were selected based on the indicated literature data.

Preparation of Test Compounds and Controls

The test compounds, controls and comparators were prepared at appropriate intervals. All formulations intended for administration to the test animals were stored refrigerated at 2-8° C. Irinotecan was obtained as a sterile solution for intravenous injection containing irinotecan hydrochloride trihydrate at a concentration of 20 mg/mL, ready to use. The irinotecan formulation for dosing the animals (0.5 mg/mL) in Group 1 (Cycles 1 and 2 only) was achieved by dilution of 20

For the remaining treatment with irinotecan (i.e. Cycle 3 for Group 1; Groups 2 to 4; Groups 6 and 7), a stock irinotecan formulation was prepared from irinotecan solid (irinotecan hydrochloride) and used for preparation of a dose formulation as described below:

Preparation of Vehicle Article: 4.5% Sorbitol (w/v) and 0.09% Lactic Acid (w/v) in Sterile Water for Injection The following protocol was employed. The procedure is for preparation of 10 mL. This procedure may be scaled as necessary:

1. Accurately weigh/measure 450 mg sorbitol and 9 mg of lactic acid and place in an appropriate size container.
2. Gradually add sterile water for injection to the container to approximately 90% of the final volume. Mix well.

3. Measure pH. Adjust pH to 3.0-3.8 with sodium hydroxide and/or hydrochloric acid, if necessary.
4. Quality sufficient to the final volume. Mix well.

Preparation of Irinotecan Stock Formulation (10 mg/mL)

The following protocol was employed:
1. An appropriate amount of Irinotecan hydrochloride will be weighed accurately and placed in an appropriate size sterile container.
2. An appropriate volume of vehicle solution (approximately 90% of final volume) will be added to the test article powder. Mix on a stir plate until Irinotecan hydrochloride is completely dissolved. Water bath (i.e. 45-55° C.) or short term sonication may be used to facilitate dissolution.
3. Measure pH. Adjust pH to 3.0-3.8 with sodium hydroxide and/or hydrochloric acid, if necessary.
4. Quality sufficient to the final volume. Mix well.
5. The above solution will be sterile filtered with a 0.22 μm filter into a sterile container. Duplicate samples (1.0 mL each) will be obtained and stored frozen (approximately −80 C) pending shipment. The stock solution will be stored refrigerated (2-8° C.), if not used immediately after preparation, and used within one week of preparation.
6. The formulation for dosing the animals is achieved by dilution of the stock formulation with 5% dextrose for injection, USP. The dosing formulation is stored refrigerated (2 to 8° C.), protected from light and used within 48 hours.

Octreotide was provided as a sterile lyophilisate and reconstituted with sterile water for injection to yield a stock solution (10 mg/mL). The stock solution was stored refrigerated (2 to 8° C.). On each day of dosing, the stock solution is diluted with sterile water for injection to a final concentration of 0.1 mg/mL. Loperamide hydrochloride was dissolved in saline for injection to yield a final concentration of loperamide base of 0.1 mg/mL (Note: 1 g of loperamide hydrochloride=0.929 g of loperamide base. A correction factor of 1.076 was used for formulation preparation). Loperamide hydrochloride solution is prepared weekly. Compound 552 was formulated as a solution with 10% hydroxypropyl-β-cyclodextrin (97%) in water. In order to verify the concentration of the test articles in the formulations, representative samples (1.0 mL in duplicate, except for octreotide, where only 0.1 mL each will be collected) were collected at appropriate intervals during the study.

Test Animals

A total of 21 males and 2 spare males were obtained from a commercial supplier (for example Marshall BioResources, North Rose, N.Y.) with ages 5 to 7 months old at onset of treatment and weights 6-9 kg at onset of treatment. The animals were acclimated between receipt of the animals and the start of treatment to accustom the dogs to the laboratory environment prior to the start of the study approximately 3 weeks for Group 1, 5 weeks for Group 2 to 4, and 3 weeks for Group 5 to 7. Each dog was housed in a stainless steel cage equipped with an automatic watering system supplemented by water bottles as appropriate. Each cage was clearly labeled with a color-coded cage card indicating the study, group and animal numbers, sex and dose level. Each animal was uniquely identified by the supplier by means of a tattoo on the ventral aspect of one pinna. The animal room environment was controlled (targeted ranges: temperature 21±3° C., relative humidity 50±20%, 12 hours light, 12 hours dark, 10-15 air changes per hour) except during designated procedures. Temperature and relative humidity were monitored continuously and recorded 4 times daily.

A standard certified commercial dog chow (for example 400 g of Teklad Certified 25% Lab Dog Diet #8727C) was available to each dog once daily during a minimum two-hour feeding period but up to a maximum of 4 hours. During acclimation, the animals were slowly acclimated to the two-hour feeding regimen. Concentrations of the constituents of the diet and contaminants (e.g., heavy metals, aflatoxin, organophosphates, pesticides and chlorinated hydrocarbons) were controlled and routinely measured by the manufacturers. Municipal tap water (which has been purified by reverse osmosis, ultraviolet light and further filtered with a 0.2 μm filter) was provided to the animals ad libitum except during designated procedures.

Preparation of the Animals

During the pretreatment period, all the dogs were prepared for surgery approximately 2-3 weeks before starting treatment. These animals were food deprived overnight prior to the surgical procedure and water was removed on the morning of surgery to insert an intravenous catheter. The dogs were injected intramuscularly with a pre-anesthetic cocktail (e.g. butorphanol, acepromazine and glycopyrrolate) for preparation of the surgical sites. Before and during surgery, animals were anesthetized by isoflurane inhalation. The intravenous catheter consisted of a length of medical-grade tubing inserted into the femoral vein and advanced into the vena cava. The catheter was exteriorized at the nape of the neck using a trocar which created a subcutaneous tunnel from the inguinal area to the dorso-cervical area. During the recovery from anesthesia, each animal was dressed in a clean jacket. The catheter was attached to a swivel device, via a jacket and tether system, and connected to a syringe by another section of medical-grade tubing. The pumps and reservoirs were contained in a specially designed box positioned on the exterior of the cage.

Each dog received an intramuscular injection of antibiotic (for example benzanthine penicillin G and procaine penicillin G) prophylactically one day prior to surgery and 2 days post-surgery. A topical antiseptic was applied to the surgical site once daily, as needed. Throughout the study period, the catheter exit site, localized in the nape of the neck, was inspected daily. When necessary, the site was shaved, cleansed free of debris and painted with a topical antiseptic/antibiotic. The jacket was changed monthly or more frequently, if deemed necessary. Following recovery from surgery, animals received 0.9% Sodium Chloride for Injection, USP at a rate of 2.5 mL/h until the start of infusion of compound 552. The syringes/bags containing the saline solution were changed with appropriate frequency during the pretreatment period.

Administration of the Test, Control/Vehicle Articles and Comparators

For the animals in Group 1, treatment with test article No. 1 (irinotecan) consisted of three (3) cycles: Cycle 1, irinotecan was administered at a dose level of 4 mg/kg/day by one hour infusion via implanted catheter for 5 consecutive days followed by a 9-day rest period. Cycle 2, irinotecan was administered by one hour infusion via implanted catheter for four consecutive days at a dose level of 4 mg/kg/day and by bolus injection (approximately over one minute) at a dose level of 8 mg/kg/day via implanted catheter for the fifth day followed by a 5-day rest period; Cycle 3, one spare animal was added to Group 1. Irinotecan formulation was prepared with irinotecan hydrochloride powder and administered to the four animals by bolus injection via implanted catheter at a dose level of 4 mg/kg/day for five consecutive days. For the animals in Groups 2 to 4, 6 and 7, irinotecan formulation that was prepared with irinotecan hydrochloride powder was administered by bolus injection via implanted catheter up to two treatment cycles for a 28-day study period. In each treatment cycle, animals were treated with a single daily dose at 6 mg/kg for 5 consecutive days followed by a 9-day rest period without treatment. The control/vehicle article for irinotecan was administered to all dogs in Group 5 by following the same dosing procedures for irinotecan administration. The dose volume was 8 mL/kg for Cycle 1 and the first 4 days of Cycle 2 for Group 1, 2 mL/kg for the last day of Cycle 2 for Group 1, and 3 mL/kg for Groups 2 to 4, 6 and 7. The actual volume infused to each dog was calculated and adjusted based on the most recent practical body weight of each animal.

The test article No. 2 (compound 552) was intravenously infused via an implanted catheter over 45 minutes to all the animals in Group 4 four days before the start of TA1 (irinotecan) treatment and throughout the 28-day study period. By following the same dosing procedure, TA2 (compound 552) was administered to all the animals in Groups 2 and 3 on the same day of onset of irinotecan-induced diarrhea, if diarrhea was observed in any one of the three animals from the group in the morning, or on the following day of diarrhea onset if diarrhea was observed in anyone of the three animals in the group in the afternoon, and throughout the remainder of the 28-day study period. The daily dosage (i.e. 5.0, 15.0 and 5.0 mg/kg/day for Groups 2 to 4 respectively) was administered by two equal doses (i.e. 2.5, 7.5 and 2.5 mg/kg/occasion for Groups 2 to 4 respectively) which were separate by at least 6 h. Each dose was infused at a dose volume of 10 mL/kg/h. The vehicle for compound 552 was administered to all dogs in Group 5 by following the same dosing procedures and regimen for compound 552 administration for 23 days (from Day 6 to Day 28). The actual volume infused was calculated and adjusted based on the most recent practical body weight of each animal. The syringes/bags were changed at appropriate intervals as necessary and the weights recorded prior to the start and at the end of the infusion.

Octreotide was administered by subcutaneous injection to all animals in Group 6 starting on the same day of diarrhea onset, if diarrhea was observed in any one of the three animals from the group in the morning, or on the following day of diarrhea onset, if diarrhea was observed in any one of the three animals in the group in the afternoon. The treatment was maintained throughout the remainder of the 28-day study period. The daily dosage (0.021 mg/kg/day) was divided into three equal doses (0.007 mg/kg/occasion) and administered by subcutaneous injection approximately early in the morning, noon and late in the afternoon, respectively. Each administration was separated by at least 4 hours (±30 minutes). The dose volume for each administration was 0.07 mL/kg. The actual dose volume was calculated and adjusted based on the most recent practical body weight of each animal.

Loperamide was administered by oral gavage to all animals in Group 7 starting on the same day of diarrhea onset, if diarrhea was observed in any one of the three animals of the group in the morning, or on the following day of diarrhea onset, if diarrhea was observed in anyone of the three animals in the group in the afternoon. The treatment was maintained throughout the remainder of the 28-day study period. The daily dosage (0.18 mg/kg/day) was divided into three equal doses (0.06 mg/kg/occasion) and administered by oral gavage approximately early in the morning, noon and late in the afternoon, respectively. Each administration was separated at least 4 h (±30 min). The dose volume for each administration was 0.6 mL/kg. The actual dose volume was calculated and adjusted based on the most recent practical body weight of each animal.

During the treatment periods of the study, the infusion line in each animal was maintained by infusion of 0.9% Sodium Chloride for Injection USP at a rate of 2.5 mL/h between each treatment of irinotecan, compound 552 or vehicles.

Cage-side clinical signs (ill health, behavioral changes, stool changes etc.) were recorded once daily during the acclimation period except on detailed clinical examination days. Cage-side clinical signs were recorded twice a day (am and pm) during the treatment/observation period except on the days of a detailed clinical examination where they were recorded once (PM). A detailed clinical examination of each dog was performed once pretreatment, weekly during the treatment/observation periods and before necropsy. Particular attention was paid to the surgical sites.

Observations of stool consistency was recorded twice daily one week prior to first treatment of irinotecan and throughout the 28-day study period and graded as follows:

TABLE 6

Observations of Stool Consistency.

| Stool Observation | Grade |
| --- | --- |
| Normal | 1 |
| loose | 2 |
| Liquid | 3 |
| Liquid with mucous or blood etc | 4 |

Whenever possible, number of vomits and discharges per day, severity of diarrhea was recorded as well as stool consistency. Symptoms of diarrhea-induced dehydration are treated by infusion of Ringer solution at the discretion of a veterinarian.

Body weights were recorded for all animals once prior to group assignment, and approximately one week prior to initiation of treatment. Body weights were recorded for all animals up to 1 day prior to dosing and twice weekly thereafter during the treatment/observation periods, as well as terminally prior to necropsy (fasted). Food consumption was measured daily during the week prior to treatment and throughout the treatment/observation periods. A series of blood samples (approximately 2.0 mL each) were removed from each dog in Groups 2 and 3 after the first (am) infusion on the first day of treatment with compound 552 and after the second (pm) infusion on the last day of treatment with compound 552. (Note: the second (pm) infusion on the first day of treatment with compound 552 was performed after completion of the last blood sampling). For this purpose, each dog was bled by venipuncture and the samples collected into tubes containing the anticoagulant, $K_2$ EDTA. Tubes were placed on wet ice pending processing. On each occasion, samples were collected prior to the start of infusion, 5, 15, 30, 45, 50, 65, 95, 135 minutes, 3 and 6 hours after the start of infusion of compound 552. Following collection, the samples were centrifuged at approximately 1500×g, approximately 4° C., for at least 10 minutes and the resulting plasma recovered and dispensed into two aliquots and stored frozen (at approximately −80° C.) pending shipment.

Figure 19:
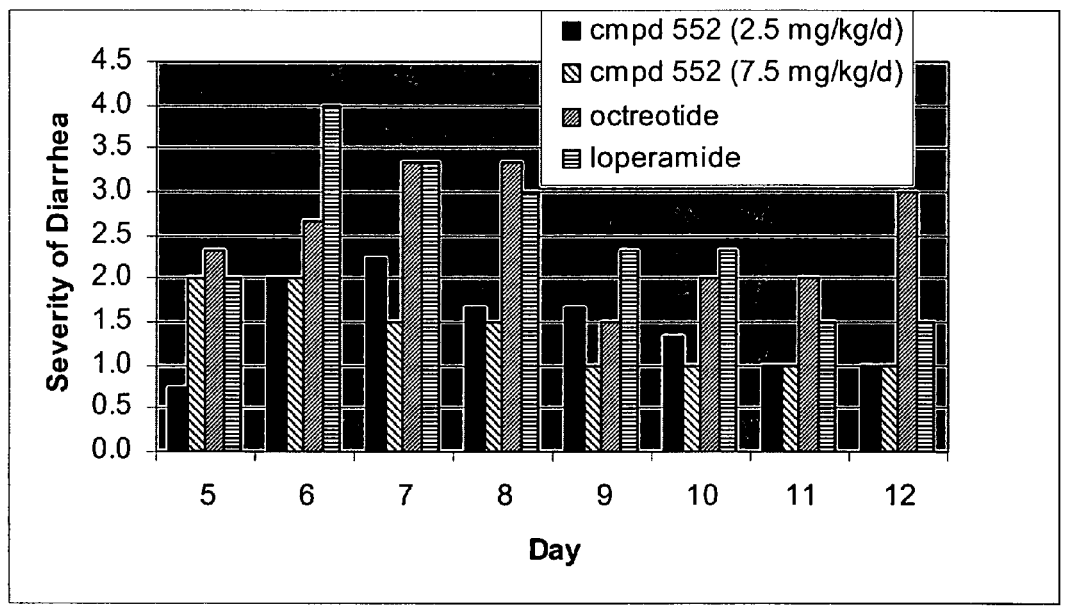
FIG. 19 presents a graph depicting the effect of a representative compound of the present invention in a dog model of chemotherapy-induced diarrhea.

Numerical data obtained during the conduct of the study was subjected to calculation of group means and standard deviations and will be reported along with all individual numerical and non numerical results. The data was analyzed for homogeneity of variance using Levene Median and for normality using Kolmogorov-Smirnov tests. Homogeneous data was analyzed using the Analysis of Variance and the significance of intergroup differences was analyzed using Dunnett's test. Heterogeneous data was analyzed using Kruskal-Wallis test and the significance of intergroup differences between the control and treated groups assessed using Dunn's test. A significance level of p≤0.05 was reported.
Results As shown in FIG. 19, compound 552, a potent and selective motilin antagonist, demonstrated superior efficacy in the treatment of irinotecan-induced CID in dogs versus the current standard of care. The compound proved to be more effective, with a quicker onset and longer duration of action as well.

Plasma concentrations of compound 552 in male beagle dogs receiving low and high intravenous doses of compound 552 as part of the above experiment were determined. Plasma samples were prepared for analysis by solid phase extraction and analyzed by LC-MS/MS. The average $C_{max}$ observed at 30 min after the start of the 45-min infusion was about 1.5 and 1.8 µg/mL on the first and last day of treatment with compound 552, respectively, for the animals receiving 2.5 mg/kg. The average $C_{max}$ observed for the high dose group administered with 7.5 mg/kg occurred between 15 and 45 min after the start of the 45-min infusion and was about 3.4 and 5.0 µg/mL on the first and last day of treatment with compound 552, respectively. The average $AUC_{0-t}$ was similar on the first (78,233 ng·min/mL) and last day (83,047 ng·min/mL) of dosing for the low dose group (2.5 mg/kg/occasion) and was proportionally higher on the first day (246,073 ng·min/mL) of dosing for the high dose group (7.5 mg/kg/occasion). The average $AUC_{0-t}$ was higher (380,758 ng·min/mL) on the last day of dosing for the high dose group, however the higher average value resulted from one animal exhibiting particularly high $AUC_{O-t}$. The plasma concentration data demonstrated dose-related exposure for compound 552 in beagle dogs during the CID efficacy study.

Alternative treatment regimens can also be employed to induce diarrhea in these model.

F. Assay for Cytochrome P450 Inhibition

Cytochrome P450 enzymes are implicated in the phase I metabolism of drugs. The majority of drug-drug interactions are metabolism-based and, moreover, these interactions typically involve inhibition of cytochrome P450s. Six CYP450 enzymes (CYP1A2, CYP2C8, CYP2C9, CYP2C19, CYP2D6 and CYP3A4) appear to be commonly responsible for the metabolism of most drugs and the associated drug-drug interactions. Assays to determine the binding of compounds of the invention to the various metabolically important isoforms of cytochrome P450 metabolizing enzymes are commercially available, for example NoAb BioDiscoveries (Mississaugua, ON, Canada) and Absorption Systems (Exton, Pa., USA). As well, a number of appropriate methods have been described or reviewed in the literature. (White, R. E. *Ann. Rev. Pharmacol. Toxicol.* 2000, 40, 133-157; Li, A. P. *Drug. Disc. Today* 2001, 6, 357-366; Turpeinen, M.; Korhonen, L. E. Tolonen, A.; et al. *Eur. J. Pharm. Sci.* 2006, 29, 130-138.)

The key aspects of the experimental method were as follows:
Assay was performed on microsomes (Supersomes®, BD Gentest, Becton-Dickinson) prepared from insect cells expressing individual human CYP-450 subtypes, specifically:
CYP subtypes: 1A2, 2A6, 2B6, 2C8, 2C9, 2C19, 2D6, 2E1, 3A4

Two substrates are typically tested for CYP-3A4 as this enzyme exhibits complex inhibition kinetics Assays monitored, via fluorescence detection, the formation of a fluorescent metabolite following incubation of the microsomes with a specific CYP substrate.

Compounds of the present invention were tested in duplicate samples at eight test concentrations using 3-fold serial dilutions (concentration range of 0.0457 to 100 µM).

For each CYP-450 enzyme, a specific inhibitor was tested in duplicate at eight concentrations as a positive control. The concentration of the inhibitor or test compound that inhibited metabolite formation by 50% ($IC_{50}$) was calculated by non-linear regression analysis of the % inhibition vs. log concentration (M) curve.

Results for representative compounds of the invention are summarized in Table 5.

TABLE 7

Rabbit Duodenum Contractile Assay Results for Representative Compounds of the Invention

| Compound | Contractile Potency (pA$_2$) | Binding $K_i$ (nM) |
|---|---|---|
| 502 | 7.92 | A |
| 551 | 8.29 | A |
| 553 | 8.71 | A |

$^a$Binding activity is expressed as follows: A ≤ 10 nM, B ≤ 100 nM, C ≤ 1000 nM, D > 1000 nM G. Plasma Protein Binding The pharmacokinetic and pharmacodynamic properties of drugs are largely a function of the reversible binding of drugs to plasma or serum proteins such as albumin and $\alpha_1$-acid glycoprotein. In general, only unbound drug is available for diffusion or transport across cell membranes, and for interaction at the pharmacological target. On the other hand, drugs with low plasma protein binding generally have large volumes of distribution and rapid clearance since only unbound drug is available for glomerular filtration and, in some cases, hepatic clearance. Thus, the extent of plasma protein binding can influence efficacy, distribution and elimination. The ideal range for plasma protein binding is in the range of 87-98% for most drug products.

Protein binding studies were performed using human plasma. Briefly, 96-well microplates were used to incubate various concentrations of the test article for 60 min at 37° C. Bound and unbound fractions are separated by equilibrium dialysis, where the concentration remaining in the unbound fraction is quantified by LC-MS or LC-MS-MS analysis. Drugs with known plasma protein binding values such as quinine (~35%), warfarin (~98%) and naproxen (~99.7%) were used as reference controls.

Results for representative compounds of the invention are summarized in Table 6.

TABLE 8

Inhibition of CYP P450 Isozymes by Representative Compounds of the Invention

| | | | $IC_{50}$ (μM)[a] | | | | | | | |
|---|---|---|---|---|---|---|---|---|---|---|
| Compound | 3A4 (BQ) | 3A4 (BFC) | 1A2 | 2A6 | 2B6 | 2C8 | 2C9 | 2C19 | 2D6 | 2E1 |
| 551 | 10.4 | 2.37 | n/a | n/a | n/a | n/a | 26.9 | 37.0 | 30.1 | >100 |
| 553 | 3.48 | 0.0192 | n/a | n/a | n/a | >100 | 44.5 | n/a | 80.8 | >100 |

[a] n/a indicates $IC_{50}$ value much above 100 μM

H. Determination of Caco-2 Permeability

The Caco-2 cell line, derived from a human colorectal carcinoma, has become an established in vitro model for the prediction of drug absorption across the human intestine. (Sun, D.; Yu, L. X.; Hussain, M. A.; Wall, D. A.; Smith, R. L.; Amidon, G. L. *Curr. Opin. Drug Discov. Devel.* 2004, 7, 75-85; Bergstrom, C. A. *Basic Clin. Pharmacol. Toxicol.* 2005, 96, 156-61; Balimane, P. V.; Han, Y. H.; Chong, S. *AAPS J* 2006, 8, E1-13; Shah, P.; Jogani, V.; Bagchi, T.; Misra, A. *Biotechnol. Prog.* 2006, 22, 186-198) When cultured on semi-permeable membranes, Caco-2 cells differentiate into a highly functionalized epithelial barrier with remarkable morphological and biochemical similarity to the small intestinal columnar epithelium. Fully differentiated cell monolayers can be used to assess the membrane transport properties of novel compounds. In addition, the apparent permeability coefficients ($P_{app}$) obtained from Caco-2 cell transport studies have been shown to reasonably correlate with human intestinal absorption.

Assays to determine the permeability of compounds of the invention utilizing Caco-2 cells are commercially available, for example NoAb BioDiscoveries (Mississaugua, ON, Canada) and Absorption Systems (Exton, Pa., USA).

Alternatively, parallel artificial membrane permeability assays (PAMPA) can be utilized to assess intestinal permeability. (Avdeef, A. *Expert Opin. Drug. Metab. Toxicol.* 2005, 1, 325-42.)

Method

Permeability across the Caco-2 cell layer was determined by growing the cells on a membrane placed between two (donor and acceptor) chambers. Drug candidates are typically added to the apical (A) side of the cell layer and their appearance in the basolateral (B) side is measured over incubation time. Permeability in this direction represents intestinal absorption. Permeability may also be determined from the basolateral to the apical side of the Caco-2 cell. A higher apical to basolateral $P_{app}$, compared to the basolateral to apical $P_{app}$, is indicative of carrier-mediated transport. P-gp mediated transport is suggested when a higher basolateral to apical $P_{app}$ is observed relative to the apical to basolateral $P_{app}$.

Permeability (10 μM) for compounds of the invention in the apical to basolateral and basolateral to apical direction were tested in duplicate. Samples will be collected from the donor and acceptor chambers at the beginning (0 min) and following 60 min of incubation at 37° C. and stored frozen at −70° C. until bioanalysis. Samples for each test compound generated from the Caco-2 permeability assay were further analyzed by LC-MS-MS. The permeability of [$^3$H]-mannitol and [$^3$H]-propranolol were determined in parallel as controls.

The permeability coefficient ($P_{app}$) of each compound and radiolabeled standard was determined using the following equation:

$$P_{app} = \frac{dQ}{dT} \times 1/C_i \times \frac{1}{A}$$

where $dQ/dT$ represents the permeability rate, $C_i$ denotes the initial concentration in the donor compartment, and A represents the surface area of the filter. $C_i$ is determined from the mean concentration of duplicate samples taken prior to addition to the donor compartment. Permeability rates were calculated by plotting the cumulative amount of compound measured in the acceptor compartment over time and determining the slope of the line by linear regression analysis. The duplicate and mean apical to basolateral and basolateral to apical $P_{app}$'s were reported for each compound and standard.

Results for representative compounds of the invention are summarized in Table 7.

TABLE 9

Caco-2 Permeability Assays for Representative Compounds of the Invention

| Compound | $P_{app}$ A to B cm/sec × $10^{-6}$ | $P_{app}$ B to A cm/sec × $10^{-6}$ | B to A/ A to B |
|---|---|---|---|
| 502 | 5 | 11 | 2 |
| 508 | 1 | 5 | 5 |
| 511 | 15 | 17 | 1 |
| 512 | 0.3 | 11 | 37 |
| 515 | 3 | 9 | 3 |
| 531 | 19 | 18 | 1 |
| 554 | 15 | 18 | 1 |
| 580 | 5 | 7 | 1 |
| 590 | 2 | 11 | 6 |

I. Pharmacokinetic Analysis of Representative Compounds of the Invention

The pharmacokinetic behavior of compound of the invention can be ascertained by methods well known to those skilled in the art. (Wilkinson, G. R. "Pharmacokinetics: The Dynamics of Drug Absorption, Distribution, and Elimination" in *Goodman & Gilman's The Pharmacological Basis of Therapeutics*, Tenth Edition, Hardman, J. G.; Limbird, L. E., Eds., McGraw Hill, Columbus, Ohio, 2001, Chapter 1.) The following method was used to investigate the pharmacokinetic parameters (elimination half-life, total plasma clearance, etc.) for intravenous, subcutaneous and oral administration of compounds of the present invention.

Collection of Plasma

Rats: male, Sprague-Dawley (~250 g)

Rats/Treatment Group: 6 (2 subsets of 3 rats each, alternate bleeds)

Each sample of test compound was sent in solution in a formulation (such as with cyclodextrin) appropriate for dosing. It will be appreciated by one skilled in the art that appropriate modifications to this protocol can be made as required to adequately test the properties of the compound under analysis.

Typical Dose
1. Intravenous (i.v.): 2 mg/kg
2. Subcutaneous(s.c): 2 mg/kg
3. Oral (p.o.): 8 mg/kg

TABLE 10

Representative Intravenous Blood Sampling Schedule.

| Subset ID | Pre-dose | 1 | 5 | 20 | 60 | 90 | 120 | 180 | 240 | 300 |
|---|---|---|---|---|---|---|---|---|---|---|
| Subset A | ✓ | | ✓ | | ✓ | | ✓ | ✓ | | ✓ |
| Subset B | | ✓ | | ✓ | | ✓ | | | ✓ | |

Time (min.) relative to Dose Administration

TABLE 11

Representative Subcutaneous & Oral Blood Sampling Schedule.

| Subset ID | Pre-dose | 5 | 15 | 30 | 60 | 90 | 120 | 180 | 270 | 360 |
|---|---|---|---|---|---|---|---|---|---|---|
| Subset A | ✓ | ✓ | | ✓ | | ✓ | ✓ | | ✓ | |
| Subset B | | | ✓ | | ✓ | | | ✓ | | ✓ |

Time (min.) relative to Dose Administration

Plasma Collection
1. Same protocol for all dosing groups
2. For each group, 2 subsets (A and B) of 3 rats/subset At the time intervals indicated above, 0.7 mL of blood were collected from each animal. It is expected that this volume of blood will yield a sample of at least 0.3 mL of plasma. EDTA was used as an anti-coagulant for whole blood collection. Whole blood samples were chilled and immediately processed by centrifugation to obtain plasma.

Plasma samples were stored frozen (−70° C.) until analysis. Analytical detection of parent compound in plasma samples performed by LC-MS after an appropriate preparation protocol: extraction using solid phase extraction (SPE) cartridges (Oasis MCX, Oasis HLB) or liquid-liquid extraction.

HPLC-MS Method
Column: Atlantis dC18 from Waters 2.1×30 mm
Mobile phases:
A: 95% MeOH, 5% water, 0.1% TFA
B: 95% water, 5% MeOH, 0.1% TFA
Flow: 0.5 mL/min
Gradient (Linear):

| Time (min) | A | B |
|---|---|---|
| 0 | 30% | 70% |
| 0.5 | 30% | 70% |
| 2.8 | 100% | 0% |
| 3.8 | 100% | 0% |
| 4.0 | 30% | 70% |
| 5.0 | 30% | 70% |

The analyte was quantitated based upon a standard curve and the method validated with internal standards.

TABLE 12

Pharmacokinetic Parameters for Representative Compounds of the Invention

| Compound | Mode of Administration[a] | Elimination ($t_{1/2}$, min) | Clearance (mL/min/kg) | Bio-availability (oral)[b] |
|---|---|---|---|---|
| 502 | i.v. | 102 | 57 | na |
| 502 | s.c. | 146 | 79 | na |
| 551 | i.v. | 139 | 33 | na |
| 551 | p.o.[d] | 70-125 | | 6% |
| 552 | i.v. | 24 | 45 | na |
| 552 | s.c. | 103 | 39 | na |
| 552 | p.o.[c] | 307 | | 10% |
| 563 | i.v. | 55 | 27 | na |
| 563 | p.o.[c] | 117 | | 21% |
| 568 | s.c. | 132 | 42 | na |
| 568 | i.v. | 25 | 65 | na |

[a] i.v. = intravenous (10 time points over 150 min); s.c. = subcutaneous (10 time points over 360 min), p.o. = oral (10 time points over 240 min)
[b] na = not applicable
[c] Done in the presence of 10% beta-cyclodextrin
[d] Done without cyclodextrin Results of the time courses for compounds 502, 552 and 563 are provided in FIGS. 13A-13G.

J. Evaluation of Contractile Activity of Isolated Muscle Strips from the Stomach, Duodenum and Colon of the Shrew.

Previous studies have demonstrated that motilin stimulates the contractile activity in smooth muscle strips isolated from the rabbit gastric antrum (Van Assche, G.; Depoortere, I.; Thijs, T.; Janssens, J. J.; Peeters, T. L. Concentration-dependent stimulation of cholinergic motor nerves or smooth muscle by [Nle$^{13}$]-motilin in the isolated rabbit gastric antrum. *Eur. J. Pharmacol.* 1997, 337, 267-274.) or from the circular muscle of the duodenum as described in Method 3-D above. Motilin (threshold concentration of 10$^{-8}$ M) enhances contractions induced by electrical field stimulation (4 Hz) by a post-ganglionic interaction with the cholinergic neurotransmission. At higher concentrations, motilin causes a tonic contraction interacting directly with the antral smooth muscle. Analogously, the effects of motilin and [Nle$^{13}$]-motilin (Calbiochem), as selective agonists of the motilin receptor, on smooth muscle strips isolated from the gastric antrum, the circular muscle of the duodenum and the colon of the shrew were investigated. Immunohistochemical studies have shown that endocrine cells in the GI tract of the musk shrew express motilin (Kanamori, Y.; Nakazawa, S.; Kitoh, J.; Hoshino, M. The distribution of endocrine cells in the mucosa of the gastrointestinal tract of the house musk shrew, *Suncus murinus* (Insectivora). *Cell. Tissue Res.* 1989, 258, 365-71; Kitamura, N.; Yamada, J.; Watanabe, T.; Yamashita, T. An immunohistochemical study on the distribution of endocrine cells in the gastrointestinal tract of the musk shrew, *Suncus murinus. Histol Histopathol.* 1990, 5, 83-88.) Shrews were fasted for 8-10 h, euthanized with $CO_2$ inhalation, and the stomach, the duodenum and colon isolated immediately and placed in Krebs buffer aerated with 95% $O_2$ and 5% $CO_2$. Specifically, mucosa-free circular muscle strips were isolated from the antral region, the duodenum and the colon using a dissecting microscope. Isometric contractions were recorded in organ baths following equilibration at optimal tension using the PowerLab data acquisition system. Electrical field stimulation (EFS: 0.5 ms pulse duration, 1-32 Hz pulse frequency) was used to induce neurally mediated contractions. In particular, four colonic segments (10-12 mm) were prepared from each animal. The segments were suspended at 1 g initial tension in 10-mL organ baths and equilibrated for 90 min. Experiments were performed to investigate the effect of motilin and [Nle$^{13}$]-motilin ($10^{-9}$-$10^{-7}$ M): a) on the basal tone and the development of spontaneous phasic contractions; b) on neurally mediated contractile responses induced by EFS. The contractile effects induced by motilin or [Nle$^{13}$]-motilin applied at a bath concentration of 0.3 μM reached a maximum within the first 4 min of treatment and diminished within 8-10 min. The results confirm that motilin receptors are involved in the regulation of GI muscle contractility in the shrew.

Figure 18:
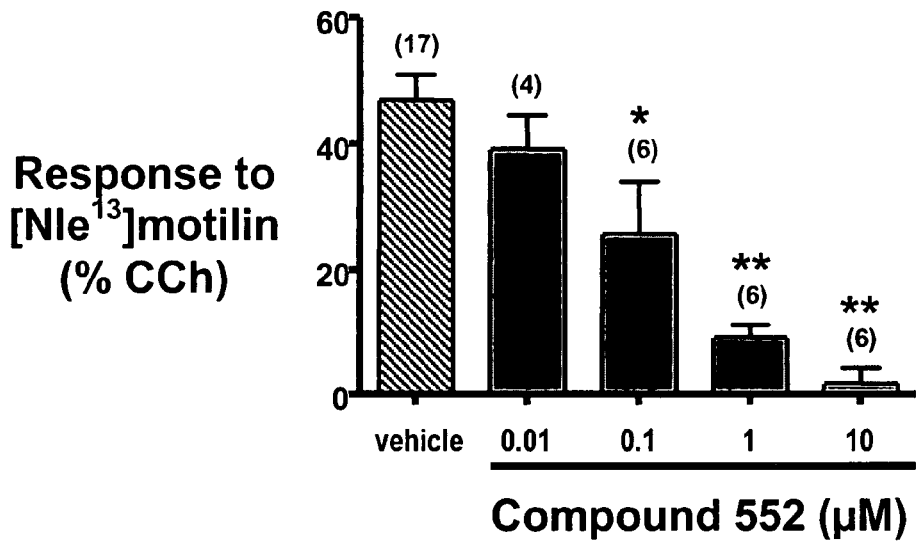
FIG. 18 presents graphs depicting the effect of a representative compound of the present invention on motilin-induced contractions in shrew colon (panel A) and [Nle$^{13}$]-motilin-induced contractions in shrew colon (panel B).
Figure 18:
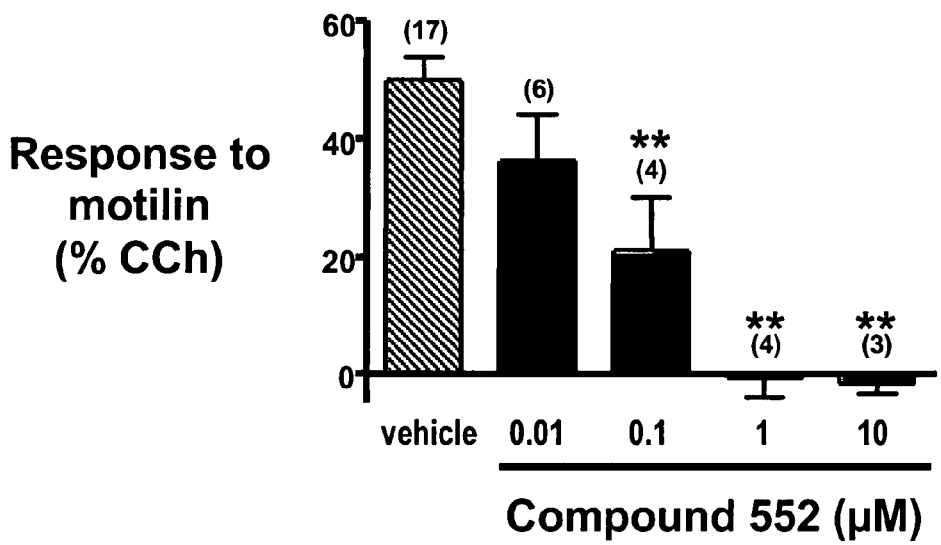

To define the effect of test compounds on different regions of the GI tract of the shrew (gastric antrum, ileum and colon) and to evaluate the antagonist affinity of test compounds in this model system, the ability of varying concentrations of test compound to antagonize the motilin or [Nle$^{13}$]-motilin-induced contractions was measured in organ baths as described above. Compound 552 dose-dependently inhibited the contractions induced in isolated colonic segments from the shrew by activation of the motilin receptor by motilin and [Nle$^{13}$] motilin as depicted in FIG. 18. Compound 552 (0.01 μM-10 μM) caused a dose-dependent inhibition of the contractile response to 0.3 μM motilin or to 0.3 μM [Nle$^{13}$]-motilin. For each experiment, data are mean±SEM and the number of animals was as indicated for each treatment. Compound 552 did not cause a significant change in basal contractile activity (data not shown).

K. Animal Model of Stress-Induced or PGE$_2$-Induced Diarrhea

Animal models can be used to investigate the effect of treatment with representative compounds of the present invention on amelioration of the symptoms or prevention of the development of diarrhea induced in different manners, in particular by stress or by PGE$_2$. Since rats and mice do not express motilin receptors, the musk shrew (*Suncus murinus*) is one appropriate animal model expressing the motilin receptor and suitable for this work. In addition, opossum, rabbit or the pig are also suitable animal models for this type of evaluation.

Animals

Laboratory musk shrews (*Suncus murinus*) were used in the study. Musk shrews do not live in social groups and have aggressive behavior when placed together, thus the animals were housed singly in Plexiglas cages with pine shavings and shredded paper for bedding (for appropriate handling procedures see Temple, J. L. The musk shrew (*Suncus murinus*): a model species for studies of nutritional regulation of reproduction. *ILAR J.* 2004, 45, 25-34). The temperature was kept at 70-72° F. and a 14:10 h light:dark cycle maintained throughout the study. Since the shrews are most active at dawn and dusk, the experiments were started within the first hour of the light-on phase. Food and water was provided ad libitum in accordance with the species requirements: Food: 3 part Purina Cat Chow and 1 part Mink Chow (for example Wisconsin "Mink Complete Pellets-Grow-Fur": crude protein<34%, crude fat>20%, crude fiber>4%). The food was placed in a small plastic dish within the cage. Water: Slightly acidic (pH 5.5) distilled water, to reduce contamination of tap water supply. The cages and water bottles were changed weekly. All animals were acclimated to the animal facility for at least 1 week prior to initiating the study.

Experimental Design and Methods

First, information regarding normal food intake and fecal pellet output in the shrew was obtained. Animals were acclimated to handling and daily food intake and fecal pellet output measured in a group of 12 shrews. The animals were brought to the laboratory in their home cages and left there for 3 h. During this period, each animal was taken out of the cage and covered with a folded towel. The skin on the top of the back was gently pressed and lifted to mimic the procedure used to administer a subcutaneous injection. Then the animal was returned in the home cage and the fecal pellet output followed for 2 h. The data served as a reference to naïve animals when establishing the model of PGE$_2$-induced defecation. When acclimated to handling, the shrews were randomly assigned in two groups (n=6 per group) and subjected to different procedures to induce fecal pellet output reminiscent of diarrhea. In the first group, the shrews were placed in individual restraint cages for 1 h at room temperature. Fecal output (number of pellets) was measured during 1 h of immobilization and within 1 h after the restraint stress. The consistency was evaluated using a 3 level scoring system: 0, normal; 1, soft; 2 unformed. (Saito, T.; Mizutani, F.; Iwanaga, Y.; Morikawa, K.; Kato, H. Laxative and anti-diarrheal activity of polycarbophil in mice and rats. *Jpn. J. Pharmacol.* 2002, 89, 133-141.) In the second group, an increase in fecal output was induced by administration of PGE$_2$ (0.3 mg/kg, i.p.) and changes in stool consistency monitored for 2 h. Stool consistency was evaluated using the 3 level scoring system. Based on the literature results obtained by Saito in mice, soft or unformed stool should be produced within 15-30 min. after PGE$_2$ dosing. The time measured from PGE$_2$ administration to the induction of diarrhea (first appearance of soft watery stool) was also recorded. In addition, wet weight/dry weight ratio of the fecal pellets was measured prior to and after administration of PGE$_2$ or restraint.

To investigate the effect of a test compound or its vehicle on accelerated defecation induced by restraint stress, as a model of stress-induced diarrhea, the animals (8 per dose level) were treated with test compound (0.1, 1 and 10 mg/kg s.c. or other appropriate doses and mode of administration) or vehicle. Animals were placed in individual restraint cages for 1 h at room temperature and fecal output was measured as described above. The animals had free access to food and water prior to the experiment.

To investigate the effect of a test compound or its vehicle on PGE$_2$-induced diarrhea, the animals were randomly assigned to groups of 8 and each group treated with test compound (0.1, 1 and 10 mg/kg s.c. or other appropriate doses and mode of administration) or vehicle. Diarrhea was induced by administration of PGE$_2$ (0.3 mg/kg, i.p.) and changes in stool consistency were evaluated as described above. The animals were acclimated with free access to food and water.

Statistical Analysis

All values are presented means±SE from 8 successful experiments for each treatment group. The statistical significance of values was determined by one-way ANOVA and Dunnett's multiple-comparison test (differences from the vehicle control). Probabilities of <5% (p<0.05) are considered significant.

L. Animal Models of Inflammation

A number of animal models of inflammation and, in particular, inflammatory diseases and disorders of the GI tract, are well-established in the art and can be used to evaluate the efficacy of representative compounds of the present invention on treating gastrointestinal inflammation. (Wirtz, S.; Neurath, M. F. *Int. J. Colorectal. Dis.* 2000, 15, 144-160; Powrie, F.; Uhlig, H. *Novartis Found. Symp.* 2004, 263, 164-178; Jurjus, A. R.; Khoury, N. N.; Reimund, J.-M. *J. Pharmacol. Toxicol. Methods* 2004, 50, 81-92; Eckmann, L. *Ann. NY Acad. Sci.* 2006, 1072, 28-38; Byrne, F. R.; Viney, J. L. *Curr. Opin. Drug Disc. Develop.* 2006, 9, 207-217.)

4. Pharmaceutical Compositions

The macrocyclic compounds of the present invention or pharmacologically acceptable salts thereof according to the invention may be formulated into pharmaceutical compositions of various dosage forms. To prepare the pharmaceutical compositions of the invention, one or more compounds, including optical isomers, enantiomers, diastereomers, racemates or stereochemical mixtures thereof, or pharmaceutically acceptable salts thereof as the active ingredient is intimately mixed with appropriate carriers and additives according to techniques known to those skilled in the art of pharmaceutical formulations.

A pharmaceutically acceptable salt refers to a salt form of the compounds of the present invention in order to permit their use or formulation as pharmaceuticals and which retains the biological effectiveness of the free acids and bases of the specified compound and that is not biologically or otherwise undesirable. Examples of such salts are described in *Handbook of Pharmaceutical Salts: Properties, Selection, and Use*, Wermuth, C. G. and Stahl, P. H. (eds.), Wiley-Verlag Helvetica Acta, Zürich, 2002 [ISBN 3-906390-26-8]. Examples of such salts include alkali metal salts and addition salts of free acids and bases Examples of pharmaceutically acceptable salts, without limitation, include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, xylenesulfonates, phenylacetates, phenylpropionates, phenylbutyrates, citrates, lactates, γ-hydroxybutyrates, glycollates, tartrates, methanesulfonates, ethane sulfonates, propanesulfonates, toluenesulfonates, naphthalene-1-sulfonates, naphthalene-2-sulfonates, and mandelates.

If an inventive compound is a base, a desired salt may be prepared by any suitable method known to those skilled in the art, including treatment of the free base with an inorganic acid, such as, without limitation, hydrochloric acid, hydrobromic acid, hydroiodic, carbonic acid, sulfuric acid, nitric acid, phosphoric acid, and the like, or with an organic acid, including, without limitation, formic acid, acetic acid, propionic acid, maleic acid, succinic acid, mandelic acid, fumaric acid, malonic acid, pyruvic acid, oxalic acid, stearic acid, ascorbic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid, 2-hydroxyethanesulfonic acid, benzenesulfonic acid, cyclohexyl-aminosulfonic acid or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine, lysine and arginine; ammonia; primary, secondary, and tertiary amines such as ethylenediamine, N,N'-dibenzylethylenediamine, diethanolamine, choline, and procaine, and cyclic amines, such as piperidine, morpholine, and piperazine; as well as inorganic salts derived from sodium, calcium, potassium, magnesium, manganese, iron, copper, zinc, aluminum, and lithium.

The carriers and additives used for such pharmaceutical compositions can take a variety of forms depending on the anticipated mode of administration. Thus, compositions for oral administration may be, for example, solid preparations such as tablets, sugar-coated tablets, hard capsules, soft capsules, granules, powders and the like, with suitable carriers and additives being starches, sugars, binders, diluents, granulating agents, lubricants, disintegrating agents and the like. Because of their ease of use and higher patient compliance, tablets and capsules represent the most advantageous oral dosage forms for many medical conditions.

Similarly, compositions for liquid preparations include solutions, emulsions, dispersions, suspensions, syrups, elixirs, and the like with suitable carriers and additives being water, alcohols, oils, glycols, preservatives, flavoring agents, coloring agents, suspending agents, and the like. Typical preparations for parenteral administration comprise the active ingredient with a carrier such as sterile water or parenterally acceptable oil including polyethylene glycol, polyvinyl pyrrolidone, lecithin, arachis oil or sesame oil, with other additives for aiding solubility or preservation may also be included. In the case of a solution, it can be lyophilized to a powder and then reconstituted immediately prior to use. For dispersions and suspensions, appropriate carriers and additives include aqueous gums, celluloses, silicates or oils.

The pharmaceutical compositions according to embodiments of the present invention include those suitable for oral, rectal, topical, inhalation (e.g., via an aerosol) buccal (e.g., sub-lingual), vaginal, topical (i.e., both skin and mucosal surfaces, including airway surfaces), transdermal administration and parenteral (e.g., subcutaneous, intramuscular, intradermal, intraarticular, intrapleural, intraperitoneal, intrathecal, intracerebral, intracranially, intraarterial, or intravenous), although the most suitable route in any given case will depend on the nature and severity of the condition being treated and on the nature of the particular active agent which is being used.

Compositions for injection will include the active ingredient together with suitable carriers including propylene glycol-alcohol-water, isotonic water, sterile water for injection (USP), emulPhor™-alcohol-water, cremophor-EL™ or other suitable carriers known to those skilled in the art. These carriers may be used alone or in combination with other conventional solubilizing agents such as ethanol, propylene glycol, or other agents known to those skilled in the art.

Where the macrocyclic compounds of the present invention are to be applied in the form of solutions or injections, the compounds may be used by dissolving or suspending in any conventional diluent. The diluents may include, for example, physiological saline, Ringer's solution, an aqueous glucose solution, an aqueous dextrose solution, an alcohol, a fatty acid ester, glycerol, a glycol, an oil derived from plant or animal sources, a paraffin and the like. These preparations may be prepared according to any conventional method known to those skilled in the art.

Compositions for nasal administration may be formulated as aerosols, drops; powders and gels. Aerosol formulations typically comprise a solution or fine suspension of the active ingredient in a physiologically acceptable aqueous or non-aqueous solvent. Such formulations are typically presented in single or multidose quantities in a sterile form in a sealed container. The sealed container can be a cartridge or refill for use with an atomizing device. Alternatively, the sealed container may be a unitary dispensing device such as a single use nasal inhaler, pump atomizer or an aerosol dispenser fitted with a metering valve set to deliver a therapeutically effective amount, which is intended for disposal once the contents have been completely used. When the dosage form comprises an aerosol dispenser, it will contain a propellant such as a compressed gas, air as an example, or an organic propellant including a fluorochlorohydrocarbon or fluorohydrocarbon.

Compositions suitable for buccal or sublingual administration include tablets, lozenges and pastilles, wherein the active ingredient is formulated with a carrier such as sugar and acacia, tragacanth or gelatin and glycerin.

Compositions for rectal administration include suppositories containing a conventional suppository base such as cocoa butter.

Compositions suitable for transdermal administration include ointments, gels and patches.

Other compositions known to those skilled in the art can also be applied for percutaneous or subcutaneous administration, such as plasters.

Further, in preparing such pharmaceutical compositions comprising the active ingredient or ingredients in admixture with components necessary for the formulation of the compositions, other conventional pharmacologically acceptable additives may be incorporated, for example, excipients, stabilizers, antiseptics, wetting agents, emulsifying agents, lubricants, sweetening agents, coloring agents, flavoring agents, isotonicity agents, buffering agents, antioxidants and the like. As the additives, there may be mentioned, for example, starch, sucrose, fructose, dextrose, lactose, glucose, mannitol, sorbitol, precipitated calcium carbonate, crystalline cellulose, carboxymethylcellulose, dextrin, gelatin, acacia, EDTA, magnesium stearate, talc, hydroxypropylmethylcellulose, sodium metabisulfite, and the like.

In some embodiments, the composition is provided in a unit dosage form such as a tablet or capsule.

In further embodiments, the present invention provides kits including one or more containers comprising pharmaceutical dosage units comprising an effective amount of one or more compounds of the present invention.

The present invention further provides prodrugs comprising the compounds described herein. The term "prodrug" is intended to mean a compound that is converted under physiological conditions or by solvolysis or metabolically to a specified compound that is pharmaceutically active. The "prodrug" can be a compound of the present invention that has been chemically derivatized such that, (i) it retains some, all or none of the bioactivity of its parent drug compound, and (ii) it is metabolized in a subject to yield the parent drug compound. The prodrug of the present invention may also be a "partial prodrug" in that the compound has been chemically derivatized such that, (i) it retains some, all or none of the bioactivity of its parent drug compound, and (ii) it is metabolized in a subject to yield a biologically active derivative of the compound. Known techniques for derivatizing compounds to provide prodrugs can be employed. Such methods may utilize formation of a hydrolyzable coupling to the compound.

The present invention further provides that the compounds of the present invention may be administered in combination with a therapeutic agent used to prevent and/or treat metabolic and/or endocrine disorders, gastrointestinal disorders, cardiovascular disorders, obesity and obesity-associated disorders, central nervous system disorders, genetic disorders, hyperproliferative disorders and inflammatory disorders. Exemplary agents include analgesics (including opioid analgesics), anesthetics, antifungals, antibiotics, anti-inflammatories (including nonsteroidal anti-inflammatory agents), anthelmintics, antiemetics, antihistamines, antihypertensives, antipsychotics, antiarthritics, antitussives, antivirals, cardioactive drugs, cathartics, chemotherapeutic agents (such as DNA-interactive agents, antimetabolites, tubulin-interactive agents, hormonal agents, and agents such as asparaginase or hydroxyurea), corticoids (steroids), antidepressants, depressants, diuretics, hypnotics, minerals, nutritional supplements, parasympathomimetics, hormones (such as corticotrophin releasing hormone, adrenocorticotropin, growth hormone releasing hormone, growth hormone, thyrptropin-releasing hormone and thyroid stimulating hormone), sedatives, sulfonamides, stimulants, sympathomimetics, tranquilizers, vasoconstrictors, vasodilators, vitamins and xanthine derivatives.

Subjects suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The present invention is primarily concerned with the treatment of human subjects, but the invention can also be carried out on animal subjects, particularly mammalian subjects such as mice, rats, dogs, cats, livestock and horses for veterinary purposes. The invention can be further carried out for drug screening and drug development purposes.

In therapeutic use for treatment of conditions in mammals (i.e. humans or animals) for which an antagonist of the motilin receptor is effective, the compounds of the present invention or an appropriate pharmaceutical composition thereof may be administered in an effective amount. Since the activity of the compounds and the degree of the therapeutic effect vary, the actual dosage administered will be determined based upon generally recognized factors such as age, condition of the subject, route of delivery and body weight of the subject. The dosage can be from about 0.1 to about 100 mg/kg, administered orally 1-4 times per day. In addition, compounds can be administered by injection at approximately 0.01-20 mg/kg per dose, with administration 1-4 times per day. Treatment could continue for weeks, months or longer. Determination of optimal dosages for a particular situation is within the capabilities of those skilled in the art.

5. Methods of Use

The compounds of formula I of the present invention can be used for the prevention and treatment of a range of gastrointestinal disorders characterized by hypermotility or hypermotilinemia.

In particular embodiments, the macrocyclic compounds of the present invention can be used to treat diarrhea, cancer treatment-related diarrhea, chemotherapy-induced diarrhea, radiation enteritis, radiation-induced diarrhea, stress-induced diarrhea, chronic diarrhea, AIDS-related diarrhea, *C. difficile* associated diarrhea, traveller's diarrhea, diarrhea induced by graph versus host disease and other types of diarrhea.

In other embodiments, the present invention is directed to a method of treating irritable bowel syndrome, inflammatory bowel disease, dyspepsia, functional gastrointestinal disorders, chemotherapy-induced nausea and vomiting (emesis), post-operative nausea and vomiting, Crohn's disease, gastroesophogeal reflux disorders, ulcerative colitis, pancreatitis, infantile hypertrophic pyloric stenosis, carcinoid syndrome, malabsorption syndrome, diabetes mellitus, obesity, postgastroenterectomy syndrome, atrophic colitis or gastritis, gastric stasis, gastrointestinal dumping syndrome, celiac disease, short bowel syndrome, cachexia and eating disorders leading to obesity in humans and other mammals comprising administering a therapeutically effective amount of a compound of formula I.

As used herein, "treatment" is not necessarily meant to imply cure or complete abolition of the disorder or symptoms associated therewith.

The compounds of the present invention can further be utilized for the preparation of a medicament for the treatment of a range of medical conditions involving gastrointestinal motility disorders.

Further embodiments of the present invention will now be described with reference to the following examples. It should be appreciated that these examples are for the purposes of illustrating embodiments of the present invention, and do not limit the scope of the invention.

Example 1

Standard Procedure for the Synthesis of Boc-Dap(thiazol-2-yl) (Boc-AA1, FIG. 1)

Step 1-1. [2-Hydroxy-1-(methoxy-methyl-carbamoyl)-ethyl]-carbamic acid tert-butyl ester (AA1-1)

To a solution of Boc-Ser-OH (AA1-0, 3.0 g, 0.015 mol) in DMF (40 mL) was added DIPEA (2.6 mL, 15.0 mmol) and HBTU (5.53 g, 15.0 mmol), then the mixture stirred at room temperature until a homogeneous solution was obtained. N,O-Dimethylhydroxylamine hydrochloride (1.60 g, 16.5 mmol) and DIPEA (2.85 mL, 16.0 mmol) were then added. The solution was stirred at room temperature O/N. The mixture was quenched addition of a saturated aqueous solution of NaHCO$_3$ at 0° C., then extracted with ethyl acetate. The organic phase was dried over Na$_2$SO$_4$ and concentrated under reduced pressure to dryness. Flash chromatography using ethyl acetate as eluent furnished AA1-1 in 85% yield.

TLC (100% ethyl acetate): R$_f$=0.40 (CMA).

Step 1-2. Thiazol-2-yl-carbamic acid benzyl ester (AA1-2)

To a stirred solution of 2-aminothiazole (AA1-A, 3.0 g, 30.0 mmol) and triethylamine (6.30 mL, 45.0 mmol) at 0° C. was added benzyl chloroformate (5 mL, 36 mmol). The reaction was stirred at RT O/N. The reaction mixture was washed with a saturated aqueous solution of NaHCO$_3$, then water and concentrated to dryness under reduced pressure. The resulting yellow solid was crystallized from ethanol to afford AA1-2 in 70% yield.

Step 1-3. Boc-Dap(Z-thiazol-2-yl) (Boc-AA1)

This procedure is based on that presented for other substrates in Gautam Panda et al. SynLett 2004, 4, 714-716. A mixture of Boc-Ser-Weinreb amide AA1-1 (3.0 g, 12.0 mmol) and triphenylphosphine (4.75 g, 18 mmol) in anhydrous THF (100 mL) was cooled in an ice bath. A solution of DIAD (3.63 g, 18 mmol) in THF (20 mL) was added to this mixture dropwise. After mixing of the solution for 5 min, AA1-2 (5.65 g, 24 mmol) in THF (50 mL) was slowly added. The mixture was allowed to warm to room temperature and stirred O/N. The solvent was removed under reduced pressure. The crude residue was purified by flash chromatography (petroleum ether:ethyl acetate, 8:2) to provide AA1-3 in 40% yield.

TLC (petroleum ether/ethyl acetate 8:2): R$_f$=0.30 (CMA)

The next reaction sequence was based on the procedure described in the literature (Evans, D. A. et al. *Tetrahedron Lett.* 1987, 28, 6141.) To a solution of AA1-3 (1.0 g, 2.15 mmol) in THF (50 mL) and H$_2$O (10 mL) was added LiOH (150 mg, 3.22 mmol) and the reaction stirred at 0° C. for 12 h. The reaction mixture was quenched with saturated aqueous NH$_4$Cl and extracted with ethyl acetate. Flash chromatography (ethyl acetate:methanol, 8:2) furnished an 80% yield of Boc-AA1.

TLC (ethyl acetate:methanol, 8:2): R$_f$=0.40 (CMA);

$^1$H NMR (CD$_3$OD): δ 1.28 (s, 9H), 4.48 (m, 2H), 4.63 (m, 1H), 5.30 (s, 2H), 7.09 (m, 1H), 7.34-7.39 (m, 4H), 7.47 (m, 1H);

LC-MS (Grad_A4): t$_R$=7.67 minutes; mass calculated for C$_{19}$H$_{23}$N$_3$O$_6$S: 421.4674. found: 421

Example 2

Standard Procedure for the Synthesis of Boc-Imidazol-1-yl-Ala (AA2)

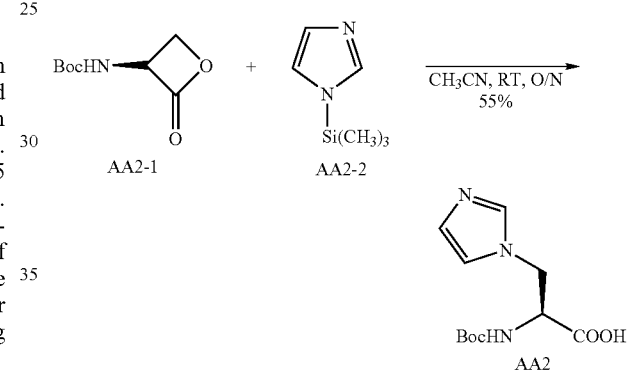

Step 2-1. Boc-Serine-β-lactone (AA2-1)

This procedure is based on that found in the literature (Vederas, J. C.; et al. *J. Am. Chem. Soc.* 1987, 109, 4649-4659). Into a dry 250 mL 3-neck flask equipped with a mechanical stirrer under a nitrogen atmosphere was added triphenylphosphine (4.5 g, 17.1 mmol, 1.1 eq), followed by 100 mL of an anhydrous THF:CH$_3$CN (1:9) mixture. The mixture was stirred until a solution was obtained, then cooled to −55° C. (bath temperature) and dimethylazodicarboxylate (DMAD, 1.9 mL, 17.1 mmol, 1.1 eq) added dropwise over 10 min. After the addition, the mixture was stirred for 20 min and a solution of Boc-Ser-OH (3.18 g, 15.5 mmol, 1.0 eq.) in 50 mL of anhydrous THF:CH$_3$CN (1:9) was added dropwise over 30 min. The mixture was stirred at −55° C. for 1.5 h, then the bath was removed and the solution allowed to warm slowly to room temperature. Once the mixture reached room temperature, the solvent was evaporated under reduced pressure. The resulting yellow oil was purified by flash chromatography [gradient, hexanes:EtOAc, (80:20) to (60:40)] to give 2.10 g of AA2-1 as a white solid in 72% yield. Purification of the crude material is best performed on the same day as the reaction to avoid decomposition. DCM can be added to help dissolve the crude residue.

TLC (Hex/EtOAc, 60/40): R$_f$=0.55 (CMA)

Step 2-2. 1-Trimethylsilylimidazole (AA2-2)

HMDS (11.46 mL, 0.055 mol, 1.5 eq) was added dropwise over 20 min to a solution of imidazole (5.0 g, 0.074 mol, 2 eq) in 150 ml of toluene under argon, then the reaction mixture heated to reflux for 3 h. The reaction mixture was then concentrated to dryness under reduced pressure. Distillation of the residue gave AA2-2 as a colorless oil in 85%. For best results, this product should be stored at 0° C. under argon.

Step 2-3. Boc-imidazol-1-yl-Ala (AA2)

Similar to the method described in Vederas, J. C.; et al. *J. Am. Chem. Soc.* 1985, 107, 7105-7109, trimethylsilylimidazole AA2-2 (0.488 g, 3.50 mmol, 1.3 eq) in dry $CH_3CN$ (10 mL) was treated dropwise over 5 min with AA2-1 (0.5 g, 2.67 mmol, 1 eq) in dry $CH_3CN$ (10 mL) under argon, then the mixture stirred for 28 h. The reaction was then cooled in an ice-water bath and 10 ml of a cold aqueous solution of ammonium chloride (0.1 M) added. The mixture was brought to room temperature and stirred for 5 min. The aqueous phase was extracted with DCM (3×50 mL) and submitted to chromatography on $C_{18}$ cartridges (10 g) [gradient, water:methanol, (100:00) to (90:10)] to give 0.48 g of AA2 as a white solid in 55% yield.

TLC (ethyl acetate:methanol:water, 8:2:1): $R_f$=0.30 (CMA);

$^1$H NMR ($D_2O$): δ 1.20 (s, 9H), 4.20 (m, 2H), 4.50 (M, 1H), 7.30 (s, 1H), 7.32 (s, 1H), 8.50 (s, 1H);

LC-MS (Grad_A4): $t_R$=3.02 min; mass calculated for $C_{11}H_{17}N_3O_4$: 255.2704; found: 255.

Example 3

Standard Procedure for the Synthesis of Boc-Pyrazol-1-yl-Ala (AA3)

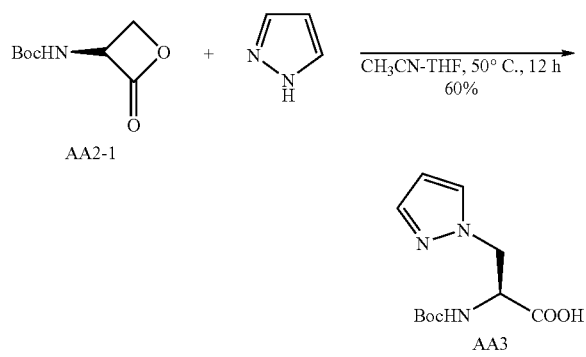

The procedure is based on that described in the literature (Vederas, J. C.; et al. *J. Am. Chem. Soc.* 1985, 107, 7105-7109). Pyrazole (0.80 g, 11.5 mmol, 1.5 eq) in dry $CH_3CN$ (10 mL) was treated dropwise over 5 min with lactone AA3-1 (synthesized as described previously, 0.50 g, 2.67 mmol, 1.0 eq) in dry $CH_3CN$ (10 mL) under argon and the resulting mixture stirred for 12 h at 50° C. The reaction was then concentrated to dryness under reduced pressure and the crude residue purified by flash chromatography (ethyl acetate:methanol, 8:2) to give 1.0 g (60% yield) of AA3 as a white solid.

TLC (ethyl acetate:methanol, 8:2): $R_f$=0.30 (CMA);
LC-MS (Grad_A4): $t_R$=5.14 min; mass calculated for $C_{11}H_{17}N_3O_4$: 255.2704, found: 255.

Example 4

Figure 2:
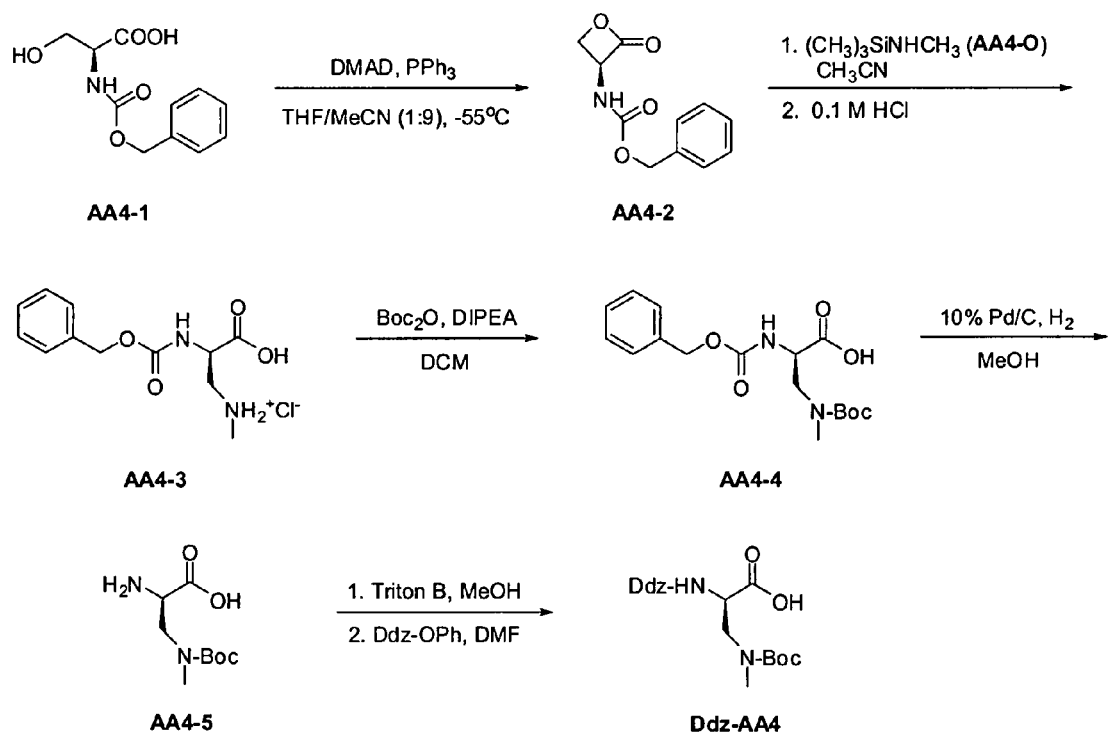
FIG. 2 shows a synthetic scheme for another representative amino acid building block of the invention.

Standard Procedure for the Synthesis of Ddz-Dap(Boc-Me)-OH (Ddz-AA4, FIG. 2)

Step 4-1. Z-Serine-β-lactone (AA4-2)

This intermediate was prepared in an analogous fashion to that described previously for the Boc derivative AA3-1. In a dry 250 mL 3-neck flask equipped with a mechanical stirrer under nitrogen atmosphere was added triphenylphosphine (4.5 g, 17.1 mmol, 1.1 eq.), followed by 100 mL of an anhydrous THF:$CH_3CN$ (1:9) solvent mixture. The mixture was stirred until a solution was obtained and then cooled to −55° C. (bath temperature) and dimethylazodicarboxylate (DMAD, 1.9 mL, 17.1 mmol, 1.1 eq) was added dropwise over 10 min. After completion of the addition, the mixture was stirred for 20 min, then a solution of Z-Ser-OH (AA4-1, 3.7 g, 15.5 mmol, 1.0 eq) in 50 mL of anhydrous THF:$CH_3CN$ (1:9) was added dropwise over 30 min. The reaction mixture was stirred at −55° C. for 1.5 h, then the cooling bath removed and the solution allowed to warm slowly to room temperature. Once the mixture reached room temperature, the solvent was evaporated under reduced pressure. The resulting yellow oil was purified by flash chromatography [gradient, hexanes/EtOAc, (80:20) to (60:40)] to give 2.5 g of AA4-2 as a white solid in 72% yield. Purification of the crude oil is preferentially performed the same day to avoid decomposition. DCM can be added to help solubilize the residue.

TLC (hexanes/EtOAc (60/40): $R_f$=0.55 (UV, CMA)

Step 4-2. Z-Dap(Me)-OH hydrochloride salt (AA4-3)

A dry 500 mL round bottom flask under nitrogen atmosphere was charged with 60 ml of anhydrous $CH_3CN$ followed by N-methyl trimethylsilylamine (AA4-0, synthesized as described in Step 4-6, 1.9 mL, 13.3 mmol, 1.5 eq.). A solution of AA4-2 (2.0 g, 8.9 mmol, 1.0 eq) in 40 mL of anhydrous MeCN was added to the flask and the mixture was stirred under nitrogen at room temperature until TLC indicates no trace of starting material [hexanes:EtOAc (60:40), UV, CMA]. The mixture was then cooled to 0° C. and 180 mL of cold 0.1 M HCl added. The mixture was allowed to warm to room temperature and stirred for 30 min. The solvent was evaporated under reduced pressure, the resulting residue azeotroped twice with toluene then dried under vacuum to give 3.1 g of crude AA4-3 as a light yellow foam. The crude material was used without any purification.

Step 4-3. Z-Dap(Boc-Me)-OH (AA4-4)

To a flask containing the crude AA4-3 (8.9 mmol, 1.0 eq based on theoretical yield) was added 90 mL of anhydrous DCM. The mixture was cooled to 0° C. and diisopropylethylamine (DIPEA, 7.8 mL, 44.5 mmol, 5.0 eq) added dropwise, which helps to solubilize the crude substrate. Di-tert-butyl dicarbonate (2.1 g, 9.8 mmol, 1.1 eq) was added in one portion, then the mixture warmed to room temperature and stirred O/N. Solvent was evaporated under reduced pressure and the resulting residue taken up in 50 mL of an $Et_2O$: NaOH (1 M, 1:1) mixture. The pH was confirmed to be between 9 and 10 and adjusted to this level if it was not. The separated aqueous phase was washed with Et$_2$O (2×25 mL), acidified to pH 2 with 1 M HCl and extracted with EtOAc (3×25 mL). The combined organic phases were washed with brine (2×25 mL), dried over MgSO$_4$, filtered, evaporated under reduced pressure and dried under vacuum to give 2.5 g (80% yield) of AA4-4 as a white foam.

Step 4-4. H-Dap(Boc-Me)-OH (AA4-5)

A solution of AA4-4 (2.5 g, 7.1 mmol, 1.0 eq.) in 75 mL of MeOH was added to 10% palladium on activated carbon (250 mg, 10% w/w) under a nitrogen atmosphere. Hydrogen was then bubbled into the mixture until completion of the reaction. [TLC BuOH:AcOH:H$_2$O (4:1:1), UV, ninhydrin]. The mixture was then purged with nitrogen, filtered on a Celite® (World Minerals Inc., Santa Barbara, Calif.) pad and rinsed well with MeOH (3×25 mL). The filtrate was evaporated under reduced pressure and dried under vacuum to give 1.5 g (93%) of AA5-5 as a pale yellow solid.

Step 4-5. Ddz-Dap(Boc-Me)-OH (Ddz-AA4)

To a solution of AA4-5 (1.9 g, 8.7 mmol, 1.0 eq) in 20 mL of MeOH was added Triton B (4.3 mL, 9.5 mmol, 1.1 eq). The mixture was stirred 30 min at room temperature, then concentrated under reduced pressure. The residue was azeotroped with toluene (2×) to remove excess H$_2$O and MeOH. The resulting slurry was dissolved in 20 mL of anhydrous DMF and Ddz-OPh (3.1 g, 9.5 mmol, 1.1 eq) added in one portion. The mixture was stirred 36-48 h at 50° C. under nitrogen. DMF was then removed under high vacuum and the residue diluted in H$_2$O (50 mL). The resulting aqueous phase (checked to ensure pH was 9 and adjusted if necessary) was washed with Et$_2$O until TLC indicates no phenol in the aqueous phase. The basic aqueous phase was cooled to 0° C., Et$_2$O (50 mL) added, and the aqueous phase acidified with citrate buffer (1.0 M, pH 3.5). The separated aqueous phase was extracted with Et$_2$O (2×50 mL). The combined organic phases were then washed sequentially with citrate buffer (2×50 mL), H$_2$O (2×50 mL) and brine (1×50 mL), dried with MgSO$_4$, filtered and concentrated under reduced pressure to afford 2.5 g (65%) of Ddz-AA4 as a pale brown solid.

$^1$H NMR (DMSO-d$_6$): δ 12.65 (s, 1H), 7.45-7.35 (dd, 1H), 6.50 (s, 2H), 6.35 (2, 1H), 4.10 (q, 1H), 3.70 (s, 6H), 3.65-3.55 (dd, 1H), 3.25-3.15 (dd, 1H), 2.75 (d, 3H), 1.60 (d, 6H), 1.35 (s, 9H).

Step 4-6. Synthesis of N-methyl trimethylsilylamine (AA4-0)

Methylamine (25.0 mL, 0.56 mol, 2.5 eq) was condensed at −20° C., then added to 250 mL of anhydrous Et$_2$O at −20° C. under a nitrogen atmosphere. Freshly distilled (from LAH) chlorotrimethylsilane (28.1 mL, 0.22 mol, 1.0 eq) was added dropwise to the solution at −20° C. A white precipitate was formed. After completion of the addition, the reaction was warmed to room temperature and stirred for 4 h. The mixture was then cooled to 0° C. and filtered cold. The filtered salts are washed with anhydrous Et$_2$O (2×50 mL), then the filtrate distilled through a 45 cm Vigreux column to remove Et$_2$O. The residue is then redistilled on a 15 cm Vigreux column to isolate 9.7 g (44%) of N-methyl trimethylsilylamine (bp 68-72° C.) as a colorless liquid.

Example 5

Figure 3:
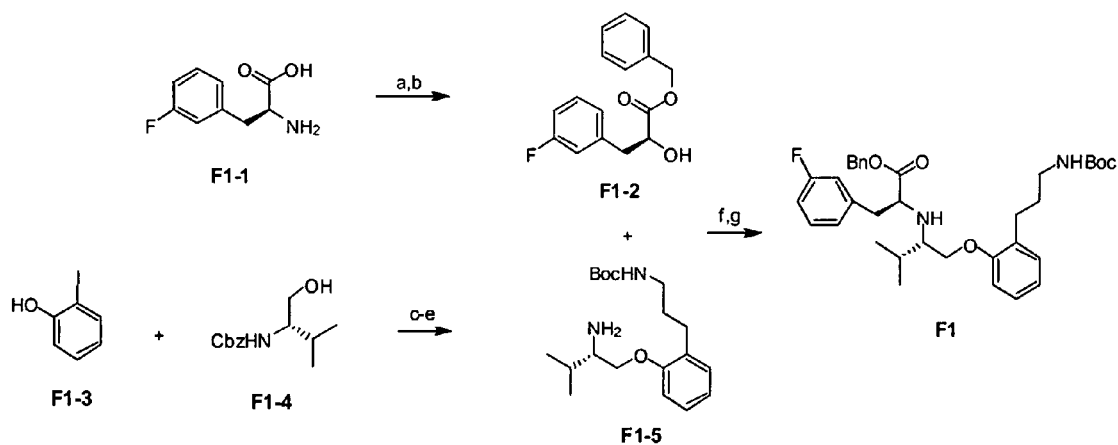
FIG. 3 shows a synthetic scheme for a representative building block of the invention.

Standard Procedure for the Synthesis of Fragment F1 (FIG. 3)

Step 5-1. 3-(3-Fluorophenyl)-2-hydroxy-propionic acid benzyl ester (F1-2)

Sodium nitrite (3.77 g, 54.6 mmol) was added in portions to a solution of L-3-fluorophenylalanine (F1-1, 5.0 g, 27.3 mmol) in acetic acid (82 mL) which is maintained at room temperature by immersion in an ice-water bath bearing a thermocouple. The solution is stirred at room temperature for 1 hr, then concentrated under reduced pressure. Water was then added to the residue and the product extracted with Et$_2$O, dried over MgSO$_4$, filtrated and concentrated under reduced pressure to yield 2.57 g (42%) of the corresponding acid. The crude product was dissolved in toluene (120 mL), then p-toluenesulfonic acid (pTSA, 216 mg, 1.14 mmol) and BnOH (5.62 mL, 56.9 mmol) added and the solution refluxed with a Dean-Stark apparatus O/N. The resulting solution was cooled to room temperature, concentrated under reduced pressure and purified by flash chromatography (gradient, 100% hexanes to hexanes/ethyl acetate, 4/1) to yield 1.63 g (52%) of benzyl ester F1-2 along with an impure fraction (3.14 g).

TLC: R$_f$=0.5 (4/1 hexanes/ethyl acetate);

$^1$H NMR (CDCl$_3$): δ2.77 (br s, 1H, OH); 2.95 (dd, J=4.39 and 13.67 Hz, 1H, CH$_2$CHOH); 3.11 (dd, J=6.45 and 13.78 Hz, 1H, CH$_2$CHOH); 4.48 (m, 1H, CH$_2$CHOH); 5.18 (s, 2H, PhCH$_2$O); 6.86 to 6.93 (m, 3H); 7.17 to 7.20 (m, 1H); 7.31 to 7.39 (m, 5H);

LC-MS (Grad_A4): t$_R$=7.16 min; (M+Na)$^+$297.

Step 5-2. {3-[2-(2-Amino-3-methyl-butoxy)-phenyl]-propyl}-carbamic acid tert-butyl ester (F1-5)

Diisopropyl azodicarboxylate (DIAD, 3.13 mL, 15.9 mmol) is added dropwise to a well-stirred solution of triphenylphosphine (4.17 g, 15.9 mmol) in THF (150 mL) at 0° C. under nitrogen. The mixture is stirred at 0° C. for 30 min, then warmed to room temperature. The PPh$_3$-DIAD adduct should precipitate as a white solid. Cbz-valinol (F1-4, 3.43 g, 14.5 mmol) in THF (150 mL) was added to this solution followed by iodophenol (F1-3, 3.18 g, 14.5 mmol) and the resulting solution was stirred O/N under nitrogen. The solution was then concentrated under reduced pressure, and the crude product purified by flash chromatography (gradient, 9/1 to 8/2 hexanes/ethyl acetate) to yield the corresponding adduct (2.98 g, 47%). This was dissolved in CH$_3$CN (70 mL) and Boc-propargylamine (1.31 g, 8.48 mmol) added to the solution. Argon was bubbled into this solution for 15 min, then Et$_3$N (23 mL) added. Argon was bubbled into the resulting solution for 5 min, then CuI (45 mg) and PdCl$_2$(PPh$_3$)$_2$ (145 mg) added and the resulting solution was stirred under argon O/N. The solution was concentrated under reduced pressure, dissolved with Et$_2$O, washed sequentially with aqueous citrate buffer (2×), saturated aqueous NaHCO$_3$ (2×), and brine (1×), dried over MgSO$_4$, filtered and concentrated under reduced pressure. The resulting oil was purified by flash chromatography (8/2 hexanes/ethyl acetate) to yield the corresponding alkyne (2.39 g, 76%). The crude product can also be used without further purification in the next reaction.

$^1$H NMR (CDCl$_3$): δ 1.01 (d, J=6.7 Hz, 3H, CH$_3$CH); 1.02 (d, J=6.7 Hz, 3H, CH$_3$CH); 1.22 to 1.28 (m, 1H); 1.43 (s, 9H, (CH$_3$)$_3$C); 2.01 to 2.16 (m, 1H, CHCH(CH$_3$)$_2$); 3.79 to 3.84 (m, 1H); 3.99 to 4.03 (m, 1H); 4.08 to 4.15 (m, 2H); 5.04 (br.

S, 1H); 5.12 (s, 2H, PhCH$_2$O); 5.28 (d, J=9.4 Hz, 1H); 6.83 (d, J=8.2 Hz, 1H); 6.90 (t, J=7.6 Hz, 1H); 7.21 to 7.37 (m, 7H);

LC-MS (Grad_A4): t$_R$=12.45 min, (M+H-Boc)$^+$367.

The alkyne (2.39 g, 5.13 mmol) was dissolved in 95% EtOH (50 mL). PtO$_2$ (116 mg) was added and the solution purged with H$_2$ (2×), then pressurized under H$_2$ (120 psi) and stirred O/N. The resulting solution was depressurized, filtered over Celite® (World Minerals Inc., Santa Barbara, Calif.), washed with ethyl acetate and concentrated under reduced pressure. The residue was dissolved in ethyl acetate (50 mL). 10% Pd/C (500 mg) was added and the solution purged with H$_2$ (2×), then pressurized under H$_2$ (120 psi) and stirred O/N. The resulting mixture was depressurized, filtered over Celite® (World Minerals Inc., Santa Barbara, Calif.), washed with ethyl acetate, concentrated under reduced pressure and the residue purified by flash chromatography (gradient, 100% ethyl acetate to 10% MeOH/90% ethyl acetate) to yield the corresponding amine F1-5 (1.15 g, 67%).

$^1$H NMR (CDCl$_3$): δ 0.99 (d, J=6.39 Hz, 6H, (CH$_3$)$_2$CH); 1.44 (s, 9H, (CH$_3$)$_3$C); 1.79 (quint., J=6.45 Hz, (CH$_3$)$_2$CH); 2.66 (t, J=7.62 Hz, 2H); 2.98 to 3.00 (m, 1H); 3.09 to 3.11 (m, 2H); 3.80 (t, J=8.21 Hz); 3.99 (dd); 5.04 to 5.06 (m); 6.82 to 6.91 (m, 2H); 7.11 to 7.18 (m, 2H).

Step 5-3. 2-{1-[2-(3-tert-Butoxycarbonylaminopropyl)-phenoxymethyl]-2-methyl-propyl-amino}-3-(3-fluorophenyl)-propionic acid benzyl ester F1

Freshly distilled (CF$_3$SO$_2$)$_2$O (29.5 μL, 175 μmol) was added to a solution of the alcohol F1-2 (45 mg, 164 μmol) in CH$_2$Cl$_2$ at 0° C. over 5 min, followed by 2,6-lutidine (22 μL, 189 μmol). The resulting solution was stirred for 10 min at 0° C., then DIPEA (32 μL, 181 μmol) added immediately followed by a solution of the amine F1-5 (55 mg, 164 μmol) in CH$_2$Cl$_2$ (1 mL) over 15 min. The resulting solution was stirred at room temperature under nitrogen O/N. Then CH$_2$Cl$_2$ was added and the organic solution washed sequentially with water, saturated aqueous NaHCO$_3$, and brine, dried over MgSO$_4$, filtered and concentrated under reduced pressure. The resulting oil was purified by flash chromatography to yield the benzyl ester F1 (40 mg, 41%).

Example 6

Standard Procedure for the Synthesis of Fragment F2

Figure 4:
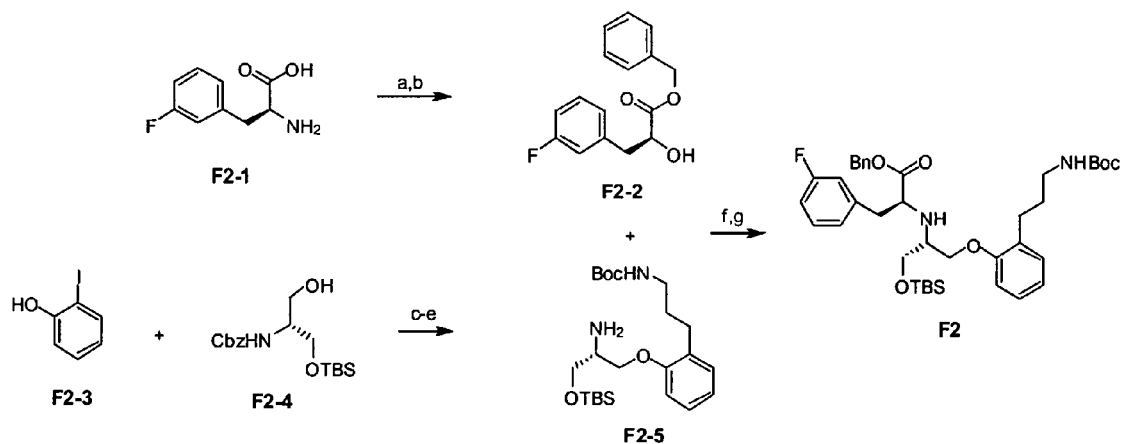
FIG. 4 shows a synthetic scheme for another representative building block of the invention.

The related fragment F2 was made following the same synthetic route as described for fragment F1 as illustrated in FIG. 4.

Example 7

Figure 5:
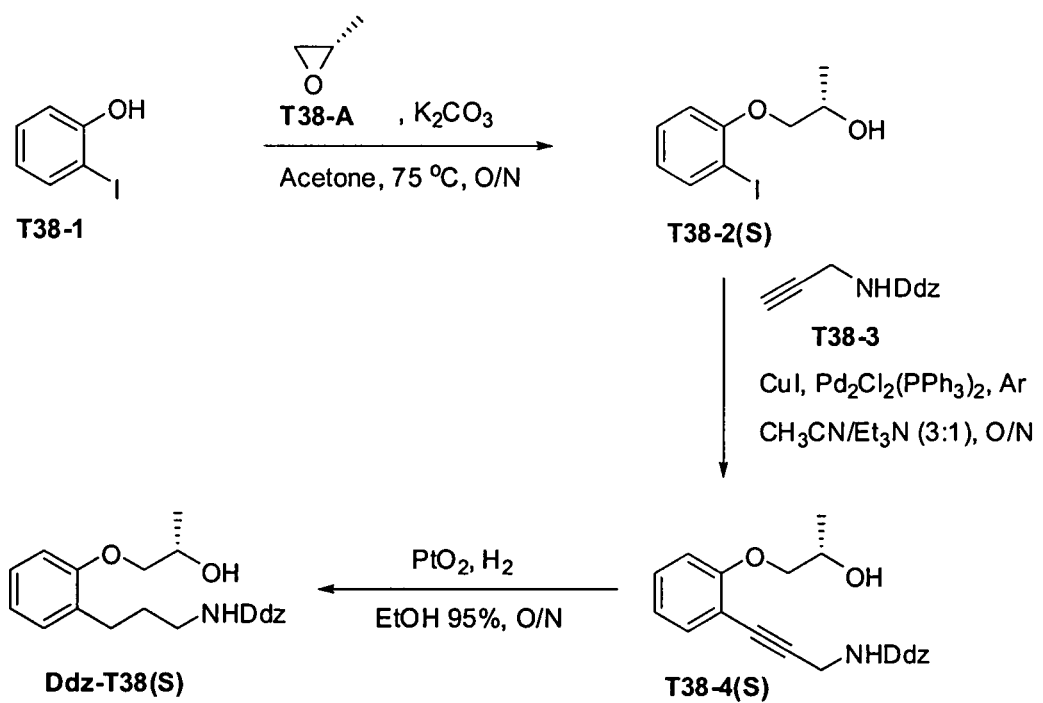
FIG. 5 shows a synthetic scheme for a representative tether building block of the invention.

Standard Procedure for the Synthesis of Protected Tether Ddz-T38(S) (FIG. 5)

Step 7-1. Iodo alcohol T38-2(S)

To a solution of 2-iodophenol (T38-1, 19.0 g, 86.2 mmol, 1.0 eq) in acetone (150 mL), potassium carbonate (13.1 g, 94.8 mmol, 1.1 eq) was added, followed by (S)-(−)-propylene oxide (T38-A, 30.1 mL, 0.431 mol, 5.0 eq). The mixture was stirred at 75° C. in a sealed high pressure flask overnight. The mixture was cooled down to room temperature, filtered and the filter rinsed twice with acetone. The combined filtrate and rinses were concentrated under reduced pressure and the resulting residue dissolved in Et$_2$O (150 mL). The organic layer was washed with 1 N NaOH (3×100 mL) and brine (2×100 mL), dried over magnesium sulfate, filtered and evaporated under reduced pressure to give 23.9 g of T38-2(S) as a yellow oil in quantitative yield. Use of (R)-(+)-propylene oxide in this step results in formation of the enantiomeric protected tether [Ddz-T38(R)] via the same procedure.

Step 7-2. Ddz-amino-alkyne [T38-4(S)]

Into a solution of T38-2(S) (23.9 g, 86.0 mmol, 1.0 eq) and Ddz-propargylamine (T38-3, 29.8 g, 107.5 mmol, 1.25 eq) in CH$_3$CN (130 mL) was bubbled argon for 10 min. Distilled (after being stirred O/N with CaH$_2$) triethylamine (45 mL) was then added to the solution and the mixture purged by bubbling with argon for 5 min. Recrystallized copper (I) iodide (572 mg, 3.0 mmol, 0.035 eq, *Organometallic in Synthesis, A Manual, Manfred Schlosser*, 2$^{nd}$ edition, 2002, p. 669.) and trans-dichlorobis(triphenylphosphine) palladium (II) (2.1 g, 3.0 mmol, 0.035 eq) were added and the reaction mixture stirred O/N under argon at room temperature. The reaction was monitored by TLC [(EtOAc/Hex, 60/40), R$_f$=0.62, UV, CMA]. The mixture was filtered through a silica gel pad and rinsed with EtOAc. The combined filtrate and rinses were concentrated under reduced pressure until dryness and the residual oil diluted with a mixture of DCM:Et$_2$O (15:85, 300 mL). The organic phase was washed sequentially with 1.0 M citrate buffer (3×150 mL), saturated NaHCO$_3$ (2×150 mL, CAUTION, pressure is generated), brine (1×150 mL), and then dried with magnesium sulfate, filtered and evaporated under reduced pressure. The crude product was purified by flash chromatography [gradient, EtOAc:Hex:Et$_3$N (30:70:0.5) to EtOAc:Hex:Et$_3$N (60:40:0.5)] to give 35.0 g of T38-4(S) as a brown syrup in quantitative yield.

Step 7-3

Ddz-Amino-alcohol [Ddz-T38(S)]. To a solution of T38-4 (S) (35.0 g, 81.9 mmol, 1.0 eq) in 95% EtOH (400 mL) under nitrogen was added platinum oxide (1.86 g, 8.2 mmol, 0.1 eq). Hydrogen was bubbled into the mixture O/N while stirring. Reaction was monitored by $^1$H NMR until completion. When the reaction was complete, nitrogen was bubbled for 10 min to remove the excess of hydrogen. The mixture was then filtered through a Celite® (World Minerals Inc., Santa Barbara, Calif.) pad and washed with 95% EtOH until no material was eluting [TLC (EtOAc/Hex, 60/40)]. The solvent was removed under reduced pressure. The product was diluted in DCM (300 mL) and MP-TMT scavenger resin (5 eq, based on amount of catalyst) was added. The mixture was stirred O/N, filtered and the resin rinsed twice with DCM. The combined filtrate and rinses were evaporated under reduced pressure to afford 34.1 g (89%) of Ddz-T38(S) as a yellow to orange oil.

$^1$H NMR (CDCl$_3$): δ 7.20-7.10, (m, 2H), 6.95-6.80 (m, 2H), 6.55 (bs, 2H), 6.35 (s, 1H), 5.18 (bt, 1H), 4.12 (m, 1H), 3.95 (m, 2H), 3.80 (s, 6H), 3.15 (bq, 2H), 2.65 (t, 2H), 1.98 (bs, 2H), 1.65 (bs, 6H), 1.25 (m, 3H).

$^{13}$C NMR (CDCl$_3$): δ 160.8, 156.6, 155.8, 149.6, 130.4, 127.5, 121.3, 111.7, 103.2, 98.4, 80.7, 73.5, 66.6, 55.5, 40.2, 30.5, 29.3, 29.1, 27.3, 19.5.

LC-MS (Grad_A4): t$_R$=8.46 min

Note that T38(S) is used to make compounds of formula I with an (R)-stereocenter. Similarly, T38(R) is used to synthesize compounds of formula I with an (S)-stereocenter as described further in Examples 10 and 11.

Additionally, protected derivatives of tethers T92 and T93 can be obtained using analogous methods to that of Example 7 starting from 3-fluoro-2-iodophenol and 6-fluoro-2-iodophenol, respectively, or the corresponding 2-bromophenols.

Example 8

Figure 6:
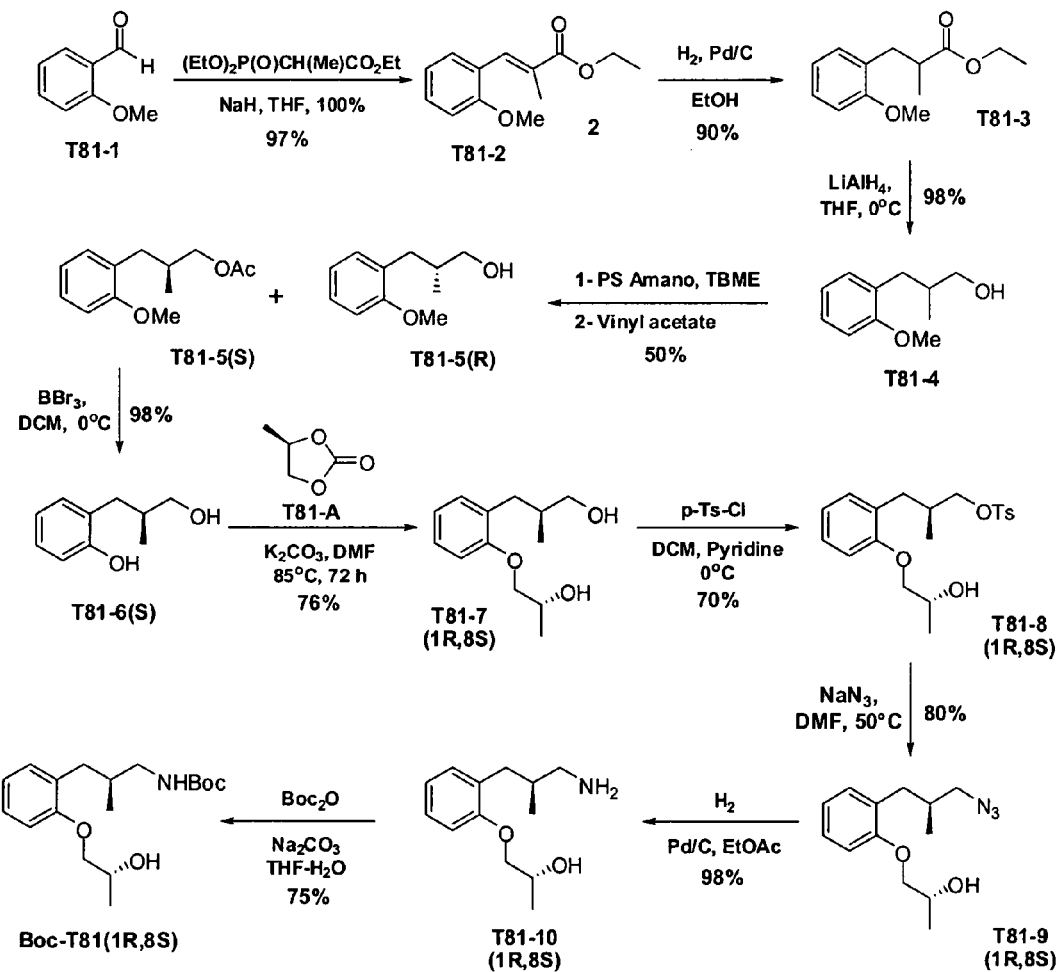
FIG. 6 shows a synthetic scheme for another representative tether building block of the invention

Standard Procedure for the Synthesis of Protected Tether Boc-T81(1R,8S) (FIG. 6)

Step 8-1. 3-(2-Methoxy-phenyl)-2-methyl-acrylic acid ethyl ester (T81-2)

To a suspension of sodium hydride (65% in oil, 26.4 g, 661 mmol, washed thoroughly with hexanes to remove oil) in THF (746 mL) at 0° C. was added $(EtO)_2P(O)CH(Me)CO_2Et$ (144 mL, 661 mmol). The mixture was stirred at room temperature for 30 min, then the solution cooled to 0° C. and aldehyde T81-1 (60.0 g, 441 mmol) slowly added. The reaction was stirred during O/N with monitoring by TLC [(ethyl acetate:hexanes, 2:7), $R_f$=0.49 (UV, CMA)]. A saturated solution of ammonium chloride was added and the aqueous phase extracted with $Et_2O$ (3×), dried over $MgSO_4$, filtered and concentrated under reduced pressure. The residue was purified by flash chromatography (ethyl acetate/hexanes, 2/8) to give T81-2 as a yellow oil (97-100% yield).

Step 8-2. 3-(2-Methoxy-phenyl)-2-methyl-propionic acid ethyl ester (T81-3)

To a solution of T81-2 (7.3 g, 23 mmol) in 95% ethanol (100 ml) was carefully added 10% Pd/C (730 mg). Hydrogen was bubbled through the solution, then the solution stirred under hydrogen atmosphere for O/N. The suspension was filtered through a pad of silica gel and washed with ethyl acetate. The combined filtrate and washes were concentrated under reduced pressure to give T81-3 which was suitable for use in the next step without any further purification (yield: 86-90%).

Step 8-3. 3-(2-Methoxy-phenyl)-2-methyl-propan-1-ol (T81-4)

To a solution of T81-3 (55.1 g, 248 mmol) in THF (1.2 L) at 0° C. was added $LiAlH_4$ (18.8 g, 496 mmol) in portions. After the addition was completed, the solution was stirred 15 min at 0° C. and monitored by TLC [(30% EtOAc, 70% hexanes), $R_f$=0.30 (UV, CMA)] until complete. An addition of water (18.8 mL) was effected very slowly (under a nitrogen flow) followed by a solution of 15% sodium hydroxide (18.8 mL), then water (56 mL). The residual salt was filtered and the filtrate concentrated under reduced pressure to give alcohol T81-4 (99%) which was used without any further purification in the next step.

Step 8-4. Acetic acid 3-(2-methoxy-phenyl)-2-methyl-propyl ester [T81-5(S)] and 3-(2-Methoxy-phenyl)-2-methyl-propan-1-ol [T81-5(R)]

Enzyme Amano PS (1.7 g) and racemic alcohol T81-4 (30.7, 0.67 mol) were mixed with TBME (292 mL) in a reaction flask containing a magnetic stirring bar with no cap. In another flask, TBME was placed in a dessicator and used to restore the volume of reaction after 24 h (due to loss by evaporation). The mixture was stirred for 24 h in a dessicator in the presence of saturated $MgCl_2$ (5-10 mL of a saturated solution of $MgCl_2$ in water was prepared and stored in the dessicator without any cap). After 24 h, the pre-equilibrated solvent was added to the reaction flask to compensate for loss by evaporation. Vinyl acetate (56 mL, 3.7 equiv) was added to the reaction flask, which was immediately sealed with a septum. The mixture was stirred at room temperature until a conversion of 42% was obtained as determined by LC-MS (aliquot starting after 2 h up to 5.5 h at which time the reaction was typically complete). The reaction was filtered through a medium flitted glass-sintered funnel. The residue was washed with hexanes and the combined filtrate and washes were concentrated under reduced pressure. The residue was purified by flash chromatography (gradient, ethyl acetate/hexanes, 10/90 to 50/50) to give the acetate T81-5(S) (18.3 g) and the alcohol T81-5(R). To determine the enantiomeric purity, a small amount of acetate T81-5(S) was hydrolyzed by stirring with $K_2CO_3$ (3 eq) in MeOH for 1 h. (For workup, water was added and MeOH evaporated under reduced pressure, then the aqueous phase extracted with $Et_2O$. The combined organic phases were dried over $MgSO_4$ and concentrated to give the alcohol in quantitative yield.) The crude alcohol was analyzed using LC-MS with a chiral HPLC column to determine the % ee.

The alcohol T81-5(R) was retreated with the Amano PS with the same procedure used for the racemic alcohol except that the reaction was permitted to proceed until a conversion of 20% as determined by LC-MS (aliquots starting at 2 h, usually reached this level after 8.5 h). Then the mixture was treated as described for T81-5(S) to give the alcohol T81-6(R) (14.1 g) and the acetate T81-5(S). (*J. Chem. Soc., Perkin Trans.* 1 2000, 367.) This alcohol can be substituted for the T81-6(S) isomer in Step 8-6 below and transformed into T81 containing an 8R-stereocenter.

Step 8-5. 3-(2-Methoxy-phenyl)-2-methyl-propan-1-ol [T81-6(S)]

To a solution of the acetate T81-5(S) (3.0 g, 13.4 mmol, 1.0 eq) in DCM (65 mL) at −30° C. was added a solution of 1 M $BBr_3$ in DCM (33.8 mL, 34 mmol, 2.5 eq). The mixture was stirred at 0° C. for 3 h, with monitoring by TLC [(30% AcOEt, 70% hexanes), $R_f$=0.30 (UV, CMA)]. Methanol (135 mL, 4× the volume of $BBr_3$) was added slowly at 0° C., followed by water. The mixture was stirred O/N. The aqueous phase was extracted with DCM (3×150 mL). The organic phase was dried over $MgSO_4$, filtrated and concentrated under reduced pressure. The residue was purified by flash chromatography (ethyl acetate/hexanes, 8/2, $R_f$=0.3) to give 2.25 g of T81-6(S) (98%).

Step 8-6. 3-[2-(2-Hydroxy-propoxy)-phenyl]-2-methyl-propan-1-ol [T81-7(1R,8S)]

To the phenol T81-6(S) (1.4 g, 8.42 mmol, 1.0 eq) in DMF (16 mL) was added potassium carbonate (1.6 g, 8.42 mmol, 1 eq), and (R)-methylcarbonate (T81-A, 0.73 mL, 8.42 mmol, 1.0 eq). The resulting mixture was stirred at 85° C. for 72 h with monitoring of the reaction by TLC [(ethyl acetate/hexanes:2/8); $R_f$=0.30, UV, CMA]. The mixture was cooled to room temperature and brine was added. The aqueous phase was extracted with ethyl acetate and the combined organic phases were extracted with brine. The organic phase was dried over $MgSO_4$ and concentrated under reduced pressure. The residue was purified by flash chromatography (ethyl acetate/hexanes, 2/8, $R_f$=0.30) to give T81-7(1R,8S) (1.45 g, 76%). Use of (S)-methylcarbonate in this reaction led to T81(1S,8S) containing a (1S)-stereocenter through the same transformations as described below for the corresponding (1R)-isomer.

Step 8-7. Toluene-4-sulfonic acid 3-[2-(2-hydroxy-propoxy)-phenyl]-2-methyl-propyl ester [T81-8(1R, 8S)]

To a solution of the alcohol T81-7(1R,8S) (2.0 g, 8.9 mmol, 1.0 eq) in pyridine:dichloromethane (1:5, 25 mL) at 0° C. was added Ts-Cl (1.90 g, 9.8 mmol, 1.1 eq) in 10 mL dichloromethane dropwise, and the resulting mixture stirred at 0° C. degree O/N with monitoring of the reaction by TLC [(ethyl acetate:hexanes, 3:7) $R_f$=0.50 (UV)]. Water was added and the aqueous phase was extracted with $CH_2Cl_2$. The combined organic phases were washed 3 times with a solution of 0.1 N HCl, then dried over $MgSO_4$ and concentrated under reduced pressure. The residue was purified by flash chromatography (ethyl acetate/hexanes, 3/7, $R_f$=0.5) to give T81-8(1R,8S) (2.29 g, 70%). A small amount of di-tosylated compound was also isolated in ~10% yield.

Step 8-8. 1-[2-(3-Azido-2-methyl-propyl)-phenoxy]-propan-2-ol [T81-9(1R,8S)]

To a solution of the tosylate T81-8(1R,8S) (2.2 g, 5.85 mmol, 1.0 eq) in DMF (25 mL) was added $NaN_3$ (1.85 g, 0.03 mol, 5 eq) and the resulting mixture was stirred at 50° C. for 24 h or until complete. The reaction was monitored by TLC [(ethyl acetate:hexanes, 3:7), $R_f$=0.35 (UV, CMA)]. Water was added and the aqueous phase was extracted with $Et_2O$. The combined organic phases were washed with brine, then dried over $MgSO_4$ and concentrated under reduced pressure. The residue was purified by flash chromatography (ethyl acetate/hexanes, 3/7) to give T81-9((1R,8S) (1.2 g, 80%).

Step 8-9. 1-[2-(3-Amino-2-methyl-propyl)-phenoxy]-propan-2-ol [T81-10 (1R,8S)]

To a solution of T81-9((1R,8S) (1.20 g, 4.8 mmol, 1.0 eq) in ethyl acetate (25 mL) was carefully added 10% Pd/C (0.12 g). Hydrogen was bubbled continuously through the solution and the resulting mixture stirred at room temperature O/N. The reaction was monitored by TLC [(ethyl acetate/hexanes; 3/7), $R_f$=baseline, UV, CMA]. The solution was filtered through a pad of Celite® (World Minerals Inc., Santa Barbara, Calif.) and rinsed with ethyl acetate. The combined filtrate and rinses were evaporated under reduced pressure to give the crude amine T81-10((1R,8S) (1.12 g, 98%).

Step 8-10. {3-[2-(2-Hydroxy-propoxy)-phenyl]-2-methyl-propyl}-carbamic acid tert-butyl ester [Boc-T81 (1R,8S)]

To a solution of T81-10(1R,8S) (1.12 g, 5.01 mmol, 1.0 eq) in $THF:H_2O$ (1:1, 20 mL) was added $K_2CO_3$ (1.43 g, 10.0 mmol, 2.0 eq) and $Boc_2O$ (3.30 g, 15.0 mmol, 3 eq). The mixture was stirred at room temperature O/N. The reaction was monitored by TLC [(ethyl acetate/hexanes, 4/6). $R_f$=0.50 (UV, ninhydrin)]. Aqueous citrate buffer was added and the mixture extracted with $Et_2O$ (3×). The combined organic phases were washed sequentially with citrate buffer, water and brine. The organic phase was dried over $MgSO_4$ and filtered. The filtrate was concentrated under reduced pressure. The residue was purified by flash chromatography (ethyl acetate/hexanes, 4/6) to give Boc-T81(1R,8S) (1.0 g, 75%).

$^1$H NMR ($CDCl_3$): δ 0.9 (d, 3H), 1.25 (d, 3H), 1.42 (s, 9H), 1.90 (m, 1H), 2.30 (m, 1H), 2.80-3.05 (m, 4H), 3.82 (m, 1H), 4.01 (m, 1H), 4.25 (m, 1H), 6.85 (m, 2H), 7.15 (m, 2H); LC-MS (Grad_A4): $t_R$=8.52 min; Mass found: 323;

$^{13}$C NMR ($CDCl_3$): δ 19.01 29.10, 35.10, 36.20, 38.10, 46.20, 62.20, 70.00, 80.10, 115.20, 120.15, 128.10, 130.00, 132.10, 158.50.

Note that T81(1R,8S) and T81(1R,8R) are used to make compounds of formula I with a (1S)-stereocenter. Similarly, T81(1S,8S) and T81(1S,8R) are used to synthesize compounds of formula I with a (1R)-stereocenter.

Example 9

FIG. 8

General Procedure for the Solution Phase Synthesis of Compounds of the Invention A.) Fragment 1 Synthesis

Step 9-1

In a round bottom flask equipped with a Dean-Stark apparatus, was suspended amino acid G-1 (0.2 mol, 1.0 eq) in toluene (1 L per 0.2 mol, solvent/wash amounts in the procedure are scaled for smaller or larger scales). p-Toluenesulfonic acid (pTSA, 1.2 eq) and benzyl alcohol (5.0 eq) were added and the mixture was stirred at reflux 16-18 h. The mixture was cooled down to room temperature and a white precipitate was formed. The precipitate was diluted with MTBE (500 mL), filtered and triturated with MTBE (3×500 mL). The solid was dried under high vacuum for 16-18 h to give the intermediate tosylate salt.

The tosylate salt was taken up in an aqueous solution of 1 M $Na_2CO_3$ (200 mL). The basic aqueous phase was extracted with EtOAc (4×150 mL) and the combined organic phases were washed with brine (1×100 mL), dried over $MgSO_4$, filtered, concentrated under reduced pressure and dried in vacuo to give the free amino-ester G-2.

As will be appreciated by those skilled in the art, alternative esters to the benzyl ester can also be employed for the procedure with modification of the deprotection protocol.

Step 9-2

To a solution of freshly free based G-2 (1.0 eq.) in DCM (90-100 mL) was added triethylamine (TEA, 1.1 eq), pyridine (3.4 eq) and Bts-Cl (2.0 eq). The reaction was stirred O/N at room temperature. The reaction mixture was diluted with DCM (100 mL), washed sequentially with aqueous citrate buffer (2×), brine (1×), dried over $MgSO_4$, filtered and concentrated under reduced pressure. The resulting residue was purified by flash chromatography to give Bts protected amino-ester G-3.

Step 9-3

Protected tether G-4 (1.5 eq.), triphenylphosphine (8.5 g, 32.4 mmol, 1.5 eq) and G-3 (1.0 eq) were dissolved in anhydrous THF (100 mL). The solution was cooled to 0° C. in an ice-water bath and diisopropylazodicarboxylate (DIAD, 1.45 eq) was added dropwise. The preformed DIAD:$PPh_3$ adduct (Example 38) could be used for this step as well. After addition, the mixture was stirred 1 h at 0° C., then warmed up slowly to room temperature and stirred for 16-18 h under nitrogen. THF was removed under reduced pressure and the crude residue was purified by flash chromatography to give alkylated amino acid ester G-5.

Note that when tether G-4 contains a hydroxy group bonded to a chiral carbon atom, inversion occurs at that center. Hence, an (S)-stereocenter in the tether leads to compounds of formula I with an (R)-stereocenter at that chiral carbon atom. Likewise, tethers with an (R)-stereocenter lead to compounds of formula I with an (S)-stereocenter at that chiral carbon atom.

Step 9-4

To a solution of G-5 (1.0 eq) in DMF (75 mL), was added solid sodium carbonate (5.0 eq), followed by 2-mercaptoethanol (5.0 eq). The mixture was stirred for 16-18 h at room temperature. Reaction was monitored by HPLC (Grad_A4). Water (150 mL) was added and the aqueous phase extracted with EtOAc (3×75 mL). The combined organic phases were washed with brine (1×100 mL), dried over $MgSO_4$, filtered and concentrated under reduced pressure. The crude residue was purified by flash chromatography to give debetsylated amino acid ester G-6. It is important to make sure no benzothiazole:mercaptoethanol adduct is left as determined by LC-MS after the reaction as this side product has been shown to inhibit the subsequent hydrogenolysis reaction.

Step 9-5

This step is described for approximately 15 mmol scale. A round bottom flask under nitrogen atmosphere, was charged with 10% Pd/C (50% wet, 10% by weight) and 95% EtOH (70 mL), followed by a solution of G-6 (15 mmol, 1.0 eq) in EtOH 95% (70 mL). The mixture was stirred under hydrogen bubbling using a gas dispersion tube for 4 hours. A precipitate formed in the mixture after 2 h. EtOAc or THF (100 mL) was added to obtain a stirring suspension. The mixture was purged with nitrogen for 10 min to remove the excess hydrogen, filtered on a Celite® (World Minerals Inc., Santa Barbara, Calif.) pad and washed with EtOAc and MeOH until TLC indicated there was no more material eluting. The solvent was evaporated under reduced pressure and the resulting solid was dried under high vacuum to give amino acid G-7.

B.) Fragment 2 Synthesis

Step 9-6

For a salt of the amino acid benzyl ester (G-8, 1 eq, described for 15 mmol scale), the solid was taken up in an aqueous solution of 1 M $Na_2CO_3$ (50 mL). The basic aqueous phase was extracted with EtOAc (4×50 mL) and the combined organic phases were washed with brine (1×600 mL), dried over $MgSO_4$, filtered, concentrated under reduced pressure and dried under high vacuum 4-6 h to give the free amino-ester G-9.

Step 9-7

G-9 (commercially available or synthesized as described in Step 9-1 or 9-6, 15.5 mmol, 1.0 eq) and the protected amino acid (G-10, 1.05 eq) were dissolved in anhydrous $THF/CH_2Cl_2$ (1:1) (80 mL). 6-Cl-HOBt (1.0 eq) and DIPEA (5.0 eq) were then added. The mixture was cooled to 0° C. in an ice-water bath and EDCI (1.1 eq) was added. The mixture was stirred 1 h at 0° C., allowed to warm to room temperature and stirred 16-18 h. Solvent was evaporated under reduced pressure and the residue was dissolved in EtOAc (100 mL). The organic phase was washed sequentially with an aqueous solution of citrate buffer (1 M, pH 3.5) (2×50 mL), $H_2O$ (1×50 mL), an aqueous solution of saturated $NaHCO_3$ (2×50 mL) and brine (1×50 mL). The organic phase was dried over $MgSO_4$, filtered, concentrated under reduced pressure and dried under high vacuum 16-18 h to give crude dipeptide.

The crude dipeptide (1.0 eq) was dissolved in a 3.3 M HCl solution in EtOAc (prepared by bubbling gaseous HCl into EtOAc at 0° C., 10 eq) and the mixture was stirred for 1 h at room temperature and a white precipitated formed. The precipitate was filtered and washed sequentially with EtOAc (1×50 mL) and MTBE (1×50 mL), then dried under high vacuum 16-18 h to give hydrochloride salt G-11.

C.) Macrocycle Synthesis

Step 9-8

To a solution of acid fragment G-7 (1.0 eq) and dipeptide hydrochloride salt G-11 (1.05 eq) in anhydrous THF/DCM (1:1) (10 mL, described for 1.50 mmol) at 0° C. was added DIPEA (5.0 eq), followed by HATU (1.05 eq). The mixture was stirred 1 h at 0° C., allowed to warm to room temperature and stirred 16-18 h under nitrogen. Solvent was removed under reduced pressure and the residue dissolved in EtOAc (50 mL). The organic phase was washed sequentially with an aqueous solution of citrate buffer (1 M, pH 3.5) (2×25 mL), an aqueous solution of saturated $NaHCO_3$ (2×25 mL) and brine (1×25 mL). The organic phase was dried over $MgSO_4$, filtered and concentrated under reduced pressure. The crude residue was purified by flash chromatography to give the desired protected alkylated tripeptide G-12.

Step 9-9

A round bottom flask under a nitrogen atmosphere was charged with 10% Pd/C (50% wet, 10% weight) and 95% EtOH 95% (5 mL, described for 1.30 mmol), followed by a solution of G-12 (1.0 eq) in 95% EtOH (8 mL). The mixture was stirred under hydrogen bubbling for 4 h. The reaction mixture turned very thick after 2-3 h. THF was added to dissolve, at least partially, the suspension. The mixture was purged with nitrogen for 5 min to remove the excess of hydrogen, filtered on a Celite® (World Minerals Inc., Santa Barbara, Calif.) pad and washed with THF until there was no further material eluting. The solvent was evaporated under reduced pressure and the resulting solid dried under high vacuum to give acid G-13.

Step 9-10

Boc protected G-13 (1.0 eq, described for 1.30 mmol) was dissolved in TFA/TES/DCM (33/3/64) (9.8 eq, approximately 3 mL). The mixture was stirred 30 min at room temperature and evaporated under reduced pressure. The residue was co-evaporated twice with THF, then dried under high vacuum for 16-18 h to give macrocyclic precursor G-14.

Step 9-11

To a solution of G-14 (1.0 eq, described for 1.30 mmol) in anhydrous THF (sufficient to form a 25 mM solution, although solutions of 10 mM concentration are also acceptable) were added DIPEA (5.0 eq) and DEPBT (1.1 eq). The mixture was stirred at room temperature 16-18 h. THF was evaporated under reduced pressure and the residue was taken up in 1 M $Na_2CO_3$ (aq):EtOAc (1:1) (50 mL). The separated basic aqueous phase was washed with brine (2×25 mL), dried over $MgSO_4$, filtered and evaporated under reduced pressure. The crude residue was purified by flash chromatography or reverse phase HPLC to give the macrocycle G-15.

Table 13 below lists the yields of this final macrocyclization step for other representative compounds of the invention that have been synthesized according to this standard procedure.

TABLE 13

Representative Yields for Step 9-11

| Compound | Macrocyclization Yield[a] | Concentration |
|---|---|---|
| 513 | 73% | 25 mM |
| 554 | 75% | 25 mM |
| 555 | 78% | 25 mM |
| 557 | 76% | 25 mM |
| 558 | 72% | 25 mM |
| 559 | 83% | 10 mM |
| 560 | 73% | 10 mM |
| 561 | 55% | 10 mM |
| 562 | 87% | 10 mM |

[a]Yield determined after silica gel purification, based on linear precursor prior Boc deprotection.

Example 10

Figure 9:
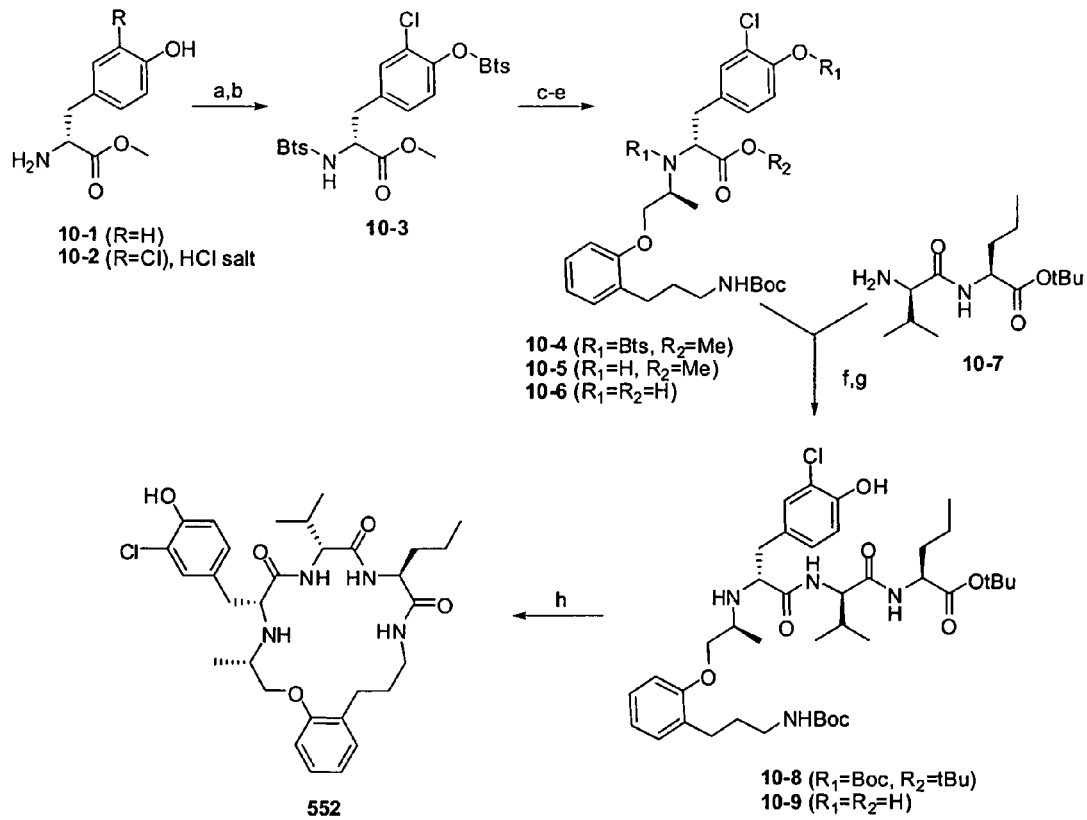
FIG. 9 shows a synthetic scheme for a representative compound of the present invention.

Standard Procedure for the Synthesis of Compound 552 (FIG. 9)

Step 10-1. Chlorination of H-(D)Tyr-OMe

To a solution of H-(D)Tyr-OMe (free base, 10-1, 0.11 mol, 21.7 g) in glacial acetic acid (550 mL) at 5° C. was added $SO_2Cl_2$ (12.1 mL, 0.15 mmol, 1.35 eq) dropwise. After 1 h stirring, $Et_2O$ was added and the product precipitated. It was filtered and washed with $Et_2O$, to give 20.8 g (85.4%) of 10-2.

LC-MS (UV, CLND, ELSD): 98.2/98.4/99.4; $t_R$=3.39 min, $(M+H)^+$229.

Step 10-2. Double Bts Protection

To a solution of 10-2, HCl salt in DCM (50 mL) was added pyridine (5.8 mL, 68 mmol, 6.8 eq) and $Et_3N$ (3.0 mL, 22 mmol, 2.2 eq), followed by solid Bts-Cl (9.3 g, 40 mmol, 4 eq). The mixture was then stirred for 16 h at rt. It was diluted with DCM (100 mL), washed sequentially with citrate buffer (2×50 mL), saturated aqueous sodium bicarbonate (2×50 mL), brine once then dried on $MgSO_4$ and concentrated. The product was purified by flash chromatography (gradient, EtOAc:hexanes 30:70 to 50:50) to give 10-3 as an off-white solid (5.3 g, 85%). Alternatively, the product can be isolated in quantitative yield by trituration with 1.0 M HCl/EtOAc.

$^1$H NMR ($CDCl_3$): consistent with structure

LC-MS (UV, CLND, ELSD): 94.2/95.2/100; $t_R$=8.88 min, $(M+H)^+$624

Step 10-3. Fukuyama-Mitsunobu

To a solution of 10-3 (3.2 g, 5.1 mmol), Boc-T38(R) (2.2 g, 7.2 mmol, 1.4 eq), $PPh_3$ (1.9 g, 7.2 mmol, 1.4 eq) in THF (25 mL) at 0° C. under $N_2$, was added DIAD (1.5 mL, 7.2 mmol, 1.4 eq) dropwise. After the addition, the mixture was stirred at rt for 16 h then concentrated under reduced pressure. The residue was purified by flash chromatography (gradient, EtOAc:hexanes, 30:70 to 45:55) to give 10-4 as a yellow oil that solidified on standing (5.7 g, >100%). This material can be used directly in the next step. Alternatively, the $PPh_3$ and DIAD can be reduced to 1.1 eq initially, then an additional 0.3-0.4 eq of each added later if required to drive the reaction to completion.

LC-MS (UV, CLND, ELSD): 91/80/100; $t_R$=14.53 min, $(M+H)^+$229 Step 10-4. Debetsylation. To a solution of 10-4 (5.2 g) in DMF (50 mL) was added sodium carbonate (3.3 g, 31 mmol, 5 eq) and 2-mercaptoethanol (2.2 mL, 31 mmol, 5 eq). The mixture was then stirred for 16 h under $N_2$, then DMF was evaporated and the mixture was diluted with water (200 mL) and pH was adjusted to 8. The aqueous layer was extracted with EtOAc (3×100 mL). The combined organic layers were washed with brine, then dried with $MgSO_4$ and concentrated under reduced pressure. The product was purified by flash chromatography (EtOAc:hexanes, gradient, 40:60 to 70:30) to give 10-5 as a yellow oil, 4.98 g. LC/MS indicated that this material contained a significant quantity of an adduct of benzothiazole:mercaptoethanol (84% by UV). For higher reaction concentrations, the reaction can also be performed in $THF/H_2O$ (1:2) as solvent with LiOH as base.

Step 10-5. Ester Hydrolysis

To a solution of the crude 10-5 (4.98 g, contaminated with benzothiazolemercaptoethanol adduct) in a 1:1 mixture of THF:water (40 mL total), was added 2.6 g of $LiOH.H_2O$ (62 mmol). The mixture was stirred for 16 h at rt, then THF was removed under reduced pressure. To the mixture was added 200 mL water and the pH adjusted to 6. A white precipitate formed, which was filtered off and washed with cold water (2×40 mL), then cold MTBE (2×40 mL) and triturated with iPrOH:heptane (1:2). An off-white solid, 10-6, was obtained (1.94 g, 75% for the last three steps). The product can also be recrystallized in 95% EtOH using heptane to induce solid formation.

LC-MS (UV, CLND, ELSD): 65/98/100 (16% benzothiazole adduct remains, $t_R$=5.05 min): $t_R$=6.48 min, $(M+H)^+$507.

Step 10-6. Fragment Coupling

To a mixture of 10-6 (1.94 g, 3.8 mmol, 1.0 eq) and 10-7 (synthesized as described in Step 10-9, 1.24 g, 4.6 mmol, 1.2 eq) in DMF (20 mL) were added HATU (1.75 g, 4.6 mmol, 1.2 eq) and DIPEA (4.0 ml, 23 mmol, 5 eq.). The mixture was stirred for 16 h at rt under $N_2$, then the solvent evaporated under reduced pressure. The residue was taken up in water (20 mL), the pH adjusted to 8-9 and the product extracted with EtOAc (2×20 mL) and DCM (2×20 mL). THF was added to the combined organic layers to dissolve the suspended solids, and the mixture was dried on $MgSO_4$ and concentrated under reduced pressure. The product was purified by flash chromatography (gradient, EtOAc:hexanes, 40:60 to 60:40) to give a 10-8 as a yellowish oil (1.5 g, 52%). Repeated reactions provided a crude yield of as high as 73.6%.

LC-MS (UV, CLND, ELSD): 90.7/100/98.7; $t_R$=11.33 min; $(M+H)^+$761.

Step 10-7. Deprotections

To 10-8 (1.5 g, 2.0 mmol) was added a mixture of TFA (70 mL), DCM (30 mL) and $Et_3SiH$ (3 mL). The mixture was stirred at rt for 2 h, then concentrated under reduced pressure. It was evaporated twice with DCM, then dried in vacuo. The crude residue, 10-9, was azeotroped with THF (2×) prior to macrocyclization in Step X-8.

Step 10-8. Macrocyclization

To the above crude 10-9 in THF (100 mL) was added DEPBT (1.2 g, 4.0 mmol, 2 eq) and DIPEA (4.2 mL, 24 mmol, 6 eq) and the mixture stirred at rt under $N_2$ for 16-86 h.

THF was removed and the product purified by flash chromatography (100% EtOAc) to give compound 552 as a white foam (0.80 g, 68.3% for two steps). Similar yields (70.9%) and purity (89.3/91.1/100, UV, CLND, ELSD) were obtained by modifying the above procedure to replace the flash chromatography with passage through a silica gel pad.

LC-MS (UV, CLND, ELSD): 92.9/100/98.6; $t_R$=5.84 min; $(M+H)^+$586.

Step 10-9. Hydrochloride Salt Formation

Compound 552 was dissolved in acetonitrile (60 mg·mL) and 1.5 eq. 0.5 M HCl (aq) added to immediately form a solid precipitate. The solid was collected by filtration and washed with acetonitrile. The resulting HCl salt of compound 552 can be recrystallized one or more times from 95% EtOH using heptane to induce solid formation.

Step 10-10. Dipeptide Hydrogenolysis

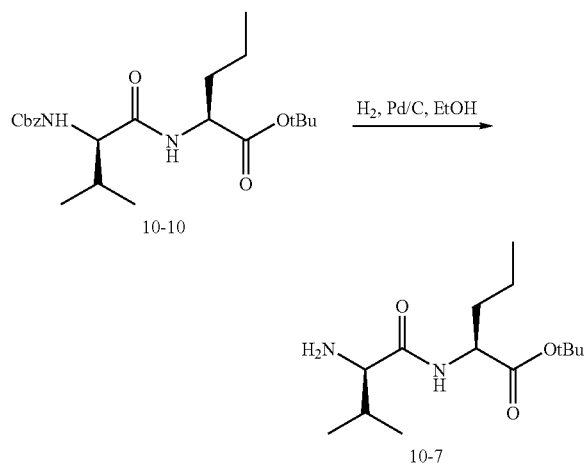

A mixture of dipeptide 10-10 (formed via standard methods from Cbz-Val-OH and H-Nva-OtBu, 2.4 g, 6.0 mmol) and 10% Pd/C (50% wet, 0.5 g) in 95% EtOH (150 mL) was shaken under 30 psi hydrogen in a Parr apparatus. After 6 h, TLC indicated the reaction is over. The mixture was filtered on a well packed Celite® (World Minerals Inc., Santa Barbara, Calif.) plug and washed with ethanol, then the combined filtrate and washings concentrated under reduced pressure to provide 10-7 sufficiently pure for us in Step 10-6 above.

$^1$H NMR: consistent with structure
LC-MS: $t_R$=5.86 min; $(M+H)^+$272.

Example 11

Figure 10:
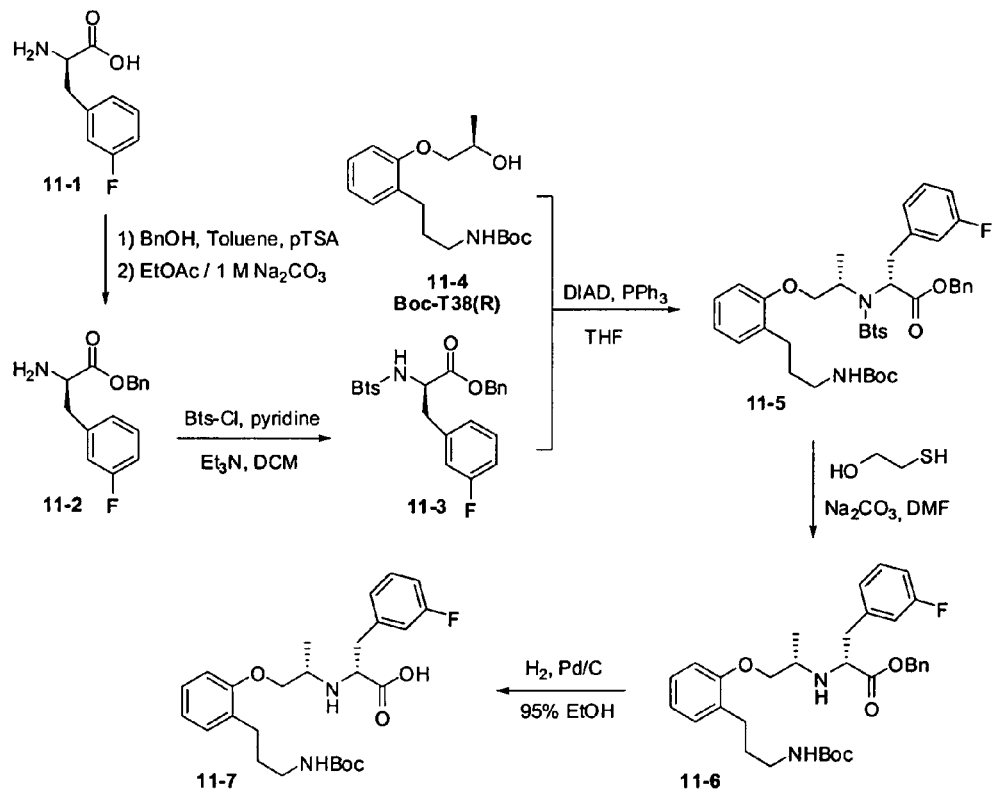
FIG. 10 shows a synthetic scheme for another representative compound of the present invention.
Figure 10:
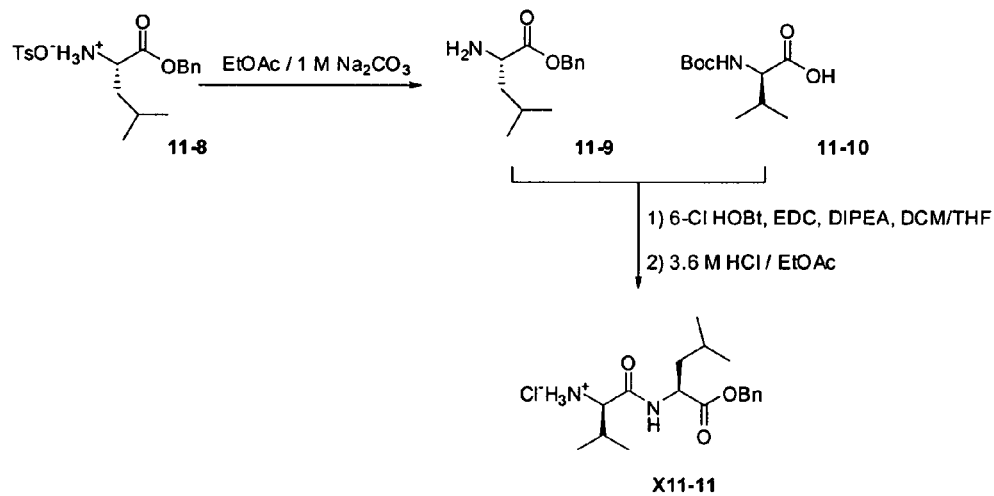
Figure 10:
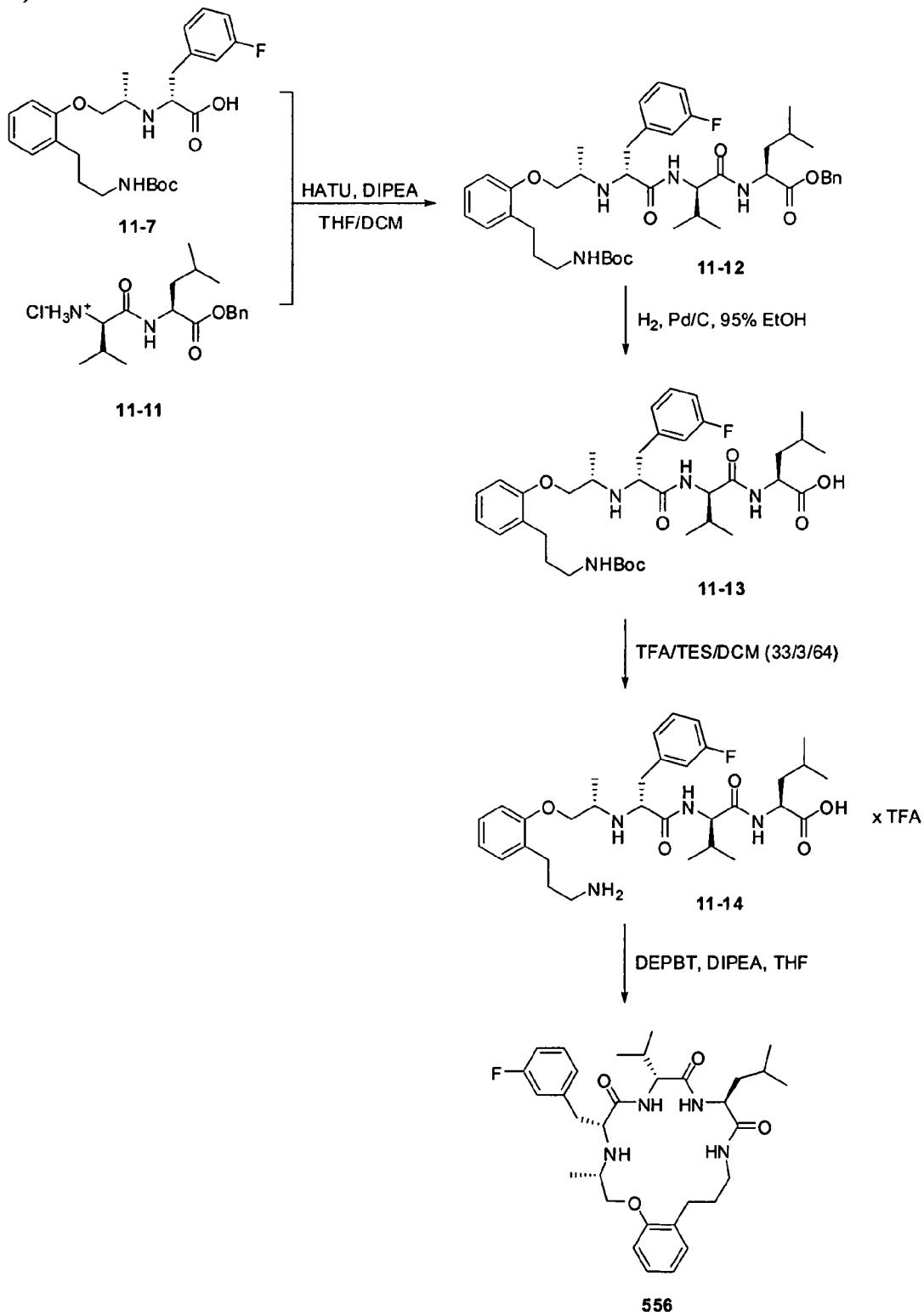

Standard Procedure for the Synthesis of Representative Compound 556 (FIG. 10)

A. AA$_1$-Tether Fragment Synthesis

Step 11-1

In a round bottom flask equipped with a Dean-Stark apparatus, was suspended H-(D)Phe(3F)-OH (11-1, 35.6 g, 194 mmol, 1.0 eq) in toluene (1 L). para-Toluenesulfonic acid (44.3 g, 233 mmol, 1.2 eq), benzyl alcohol (101 mL, 970 mmol, 5.0 eq) were added and the mixture was stirred at reflux 16-18 hours. The mixture was cooled down to room temperature and a white precipitate formed. The precipitate was diluted with MTBE (500 mL), filtered and triturated with MTBE (3×500 mL). The solid was dried under high vacuum for 16-18 h to give the tosylate salt as a white solid (85.1 g, 98.6%).

The tosylate salt (85.1 g) was taken up in an aqueous solution of 1 M Na$_2$CO$_3$ (210 mL). The basic aqueous phase was extracted with EtOAc (4×150 mL), then the combined organic phases were washed with brine (1×100 mL), dried over MgSO$_4$, filtered, concentrated under reduced pressure and dried under high vacuum to give the free amino-ester 11-2 as a clear oil (49.5 g, 95%).

Step 11-2

To a solution of freshly free based 11-2 (49.5 g, 181 mmol, 1.0 eq) in DCM (90 mL) was added triethylamine (27.8 mL, 616 mmol, 1.1 eq), pyridine (49.8 mL, 616 mmol, 3.4 eq) and Bts-Cl (84.7 g, 363 mmol, 2.0 eq). The reaction was stirred O/N at room temperature during which time the solution turned orange. The reaction mixture was diluted with DCM (100 mL), washed sequentially with citrate buffer (2×) and brine (1×), dried over MgSO$_4$, filtered and concentrated under reduced pressure. The residual oil was purified by flash chromatography [gradient, hexanes:EtOAc (8:2) to hexanes:EtOAc (7:3)] to give Bts protected amino-ester 11-3 as a yellowish solid (63.4 g, 74.4%).

TLC [hexanes:EtOAc (1:1)]: $R_f$=0.30 (UV, CMA).

Step 11-3

Boc-T38(R) tether (11-4, 10.0 g, 32.4 mmol, 1.5 eq), triphenylphosphine (8.5 g, 32.4 mmol, 1.5 eq) and Bts-(D)Phe (3F)-OBn (11-3, 10.2 g, 21.6 mmol, 1.0 eq) were dissolved in anhydrous THF (108 mL). The solution was cooled to 0° C. in an ice-water bath and diisopropylazodicarboxylate (DIAD, 6.2 mL, 31.3 mmol, 1.45 eq) was added dropwise. After addition, the mixture was stirred 1 h at 0° C., then warmed up slowly to room temperature and stirred for 16-18 h under nitrogen. THF was removed under reduced pressure and the crude residue was purified by flash chromatography [gradient, hexanes/EtOAc (9:1) to hexanes/EtOAc (75:25)] to give alkylated amino acid ester 11-5 as a pale yellow solid (15.1 g, 91%).

TLC [hexanes:EtOAc (1:1)]: $R_f$=0.67 (UV, CMA).

Step 11-4

To a solution of alkylated amino acid 11-5 (14.0 g, 18.4 mmol, 1.0 eq) in DMF (74 mL), was added sodium carbonate (9.8 g, 92.0 mmol, 5.0 eq), followed by 2-mercaptoethanol (6.5 mL, 92.0 mmol, 5.0 eq). The mixture was stirred for 16-18 h at room temperature. Reaction was monitored by HPLC [(Grad_A4): 9.69 min (product), 15.37 min (starting material)]. Water (150 mL) was added and the aqueous phase extracted with EtOAc (3×75 mL). The combined organic phases were washed with brine (1×100 mL), dried over MgSO$_4$, filtered and concentrated under reduced pressure. The crude residue was purified by dry pack silica gel chromatography [hexanes:EtOAc (8:2)] to give debetsylated amino acid ester 11-6 as a yellow oil (7.95 g, 76%). It is very important to make sure no benzothiazole:mercaptoethanol adduct is left by LC-MS after the reaction. This side product has been known to inhibit the subsequent hydrogenolysis reaction.

Step 11-5

A round bottom flask under nitrogen atmosphere was charged with 10% Pd/C (50% wet, 785 mg, 10% by weight) and 95% EtOH (70 mL), followed by a solution of amino acid ester 11-6 (7.85 g, 13.9 mmol, 1.0 eq) in 95% EtOH (70 mL). The mixture was stirred under hydrogen bubbling using a gas dispersion tube for 4 h. A precipitate formed after 2 h. EtOAc (100 mL) was added to obtain a stirring suspension. The reaction mixture was purged with nitrogen for 10 min to remove the excess of hydrogen, filtered on a Celite® (World Minerals Inc., Santa Barbara, Calif.) pad and washed with EtOAc and MeOH until there was no further material eluting. The solvent was evaporated under reduced pressure and the resulting solid dried under high vacuum to give amino acid 11-7 as a white solid (6.2 g, 94%).

TLC [hexanes/EtOAc (1:1)]: $R_f$=baseline (UV, CMA);
LC-MS (Grad_A4): 7.04 min.

B. $AA_2$-$AA_3$ Dipeptide Synthesis

Step 11-6

Commercially available H-Leu-OBn tosylate salt (11-8, 6.1 g) was taken up in an aqueous solution of 1 M $Na_2CO_3$ (50 mL). The basic aqueous phase was extracted with EtOAc (4×50 mL) and the combined organic phases were washed with brine (1×580 mL), dried over $MgSO_4$, filtered, concentrated under reduced pressure and dried under vacuum 4-6 h to give the free amino-ester 11-9 as a pale yellow oil (3.44 g, 100%).

Step 11-7

Freshly free based H-Leu-OBn (11-9, 3.44 g, 15.5 mmol, 1.0 eq) and Boc-(D)Val-OH (11-10, 3.54 g, 16.3 mmol, 1.05 eq) were dissolved in anhydrous THF:$CH_2Cl_2$ (1:1, 81 mL). 6-Cl-HOBt (2.63 g, 15.5 mmol, 1.0 eq) and DIPEA (14.2 mL, 81.5 mmol, 5.0 eq) were added. The mixture was cooled to 0° C. in an ice-water bath and EDC (3.28 g, 17.1 mmol, 1.1 eq) was added. The mixture was stirred 1 hour at 0° C., allowed to warm to room temperature and stirred 16-18 h. Solvent was evaporated under vacuum and the residue was dissolved in EtOAc (100 mL). The organic phase was washed sequentially with an aqueous solution of citrate buffer (1 M, pH 3.5) (2×50 mL), $H_2O$ (1×50 mL), an aqueous solution of saturated $NaHCO_3$ (2×50 mL) and brine (1×50 mL). The organic phase was dried over $MgSO_4$, filtered, concentrated under reduced pressure and dried under high vacuum 16-18 h to give crude dipeptide as a pale yellow solid (6.6 g, >100% crude).

TLC [hexanes/EtOAc (1:1)]: $R_f$=0.40 (UV, CMA).

The crude dipeptide (6.6 g, 15.7 mmol, 1.0 eq) was dissolved in a 3.3M HCl solution in EtOAc (prepared by bubbling gaseous HCl in EtOAc at 0° C., 43.6 mL, 157 mmol, 10 eq). The mixture was stirred for 1 h at room temperature and a white precipitate formed. The precipitate was filtered and washed with EtOAc (1×50 mL) and MTBE (1×50 mL), then dried under vacuum 16-18 h to give hydrochloride salt 11-11 as a white solid (4.38 g, 79% for 2 steps).

TLC [hexanes:EtOAc (1:1)]: $R_f$=baseline (UV, ninhydrin);
LC-MS (Grad_A4): 6.59 min.

C.) Macrocycle Synthesis

Step 11-8

To a solution of 11-7 (750 mg, 1.58 mmol, 1.0 eq) and 11-11 (591 g, 1.66 mmol, 1.05 eq) in anhydrous THF:DCM (1:1, 10.5 mL) at 0° C. was added DIPEA (1.4 mL, 7.9 mmol, 5.0 eq), followed by HATU (631 mg, 1.66 mmol, 1.05 eq). The mixture was stirred 1 h at 0° C., allowed to warm to room temperature and stirred 16-18 h under nitrogen. Solvent was removed under reduced pressure and the residue was dissolved in EtOAc (50 mL). The organic phase was washed with an aqueous solution of citrate buffer (1 M, pH 3.5, 2×25 mL), an aqueous solution of saturated $NaHCO_3$ (2×25 mL) and brine (1×25 mL). The organic phase was dried over $MgSO_4$, filtered, then concentrated under reduced pressure. The crude residue was purified by flash chromatography [gradient, hexanes:EtOAc (75:25) to hexanes:EtOAc (6:4)] to give the desired protected alkylated tripeptide 11-12 as a pale yellow gummy solid (988 mg, 81%).

TLC [hexanes/EtOAc (1:1)]: $R_f$=0.43 (UV, CMA).

Step 11-9

A round bottom flask under nitrogen atmosphere, was charged with Pd/C 10% (50% wet, 208 mg, 10% by weight) and 95% EtOH (5 mL), followed by a solution of benzyl ester X-12 (1.04 g, 1.34 mmol, 1.0 eq) in 95% EtOH (8.4 mL). The mixture was stirred under hydrogen bubbling for 4 h. The reaction mixture turned very thick after 2-3 h and THF was added to dissolve the suspension. The mixture was purged with nitrogen for 5 min to remove the excess of hydrogen, filtered on a Celite® (World Minerals Inc., Santa Barbara, Calif.) pad and washed with THF until there was no further material eluting. The solvent was evaporated under reduced pressure and the resulting solid was dried under high vacuum to give acid 11-13 as a white solid (911 mg, 100%).

TLC: [hexanes/EtOAc (1:1)]: $R_f$=baseline (UV, CMA).

Step 11-10

Boc protected alkylated tripeptide 11-13 (911 mg, 1.33 mmol, 1.0 eq) was dissolve in a TFA/TES/DCM (33/3/64, 3.0 mL, 12.9 mmol, 9.8 eq). The mixture was stirred 30 min at room temperature and evaporated under reduced pressure. The oily residue was co-evaporated twice with THF, then dried under high vacuum for 16-18 h to give macrocyclic precursor 11-14 as a pale yellow gummy solid (1.27 g, >100%).

TLC: [EtOAc:MeOH (9:1)]: $R_f$=baseline (UV, ninhydrin).

Step 11-11

To a solution of macrocyclic precursor 11-14 [1.27 g, 1.33 mmol (based on quantity obtained after hydrogenolysis), 1.0 eq) in anhydrous THF (53.6 mL, for a 25 mM solution) were added DIPEA (1.17 mL, 6.79 mmol, 5.0 eq) and DEPBT (440 mg, 1.47 mmol, 1.1 eq). The mixture was stirred at room temperature 16-18 h. THF was evaporated under reduced pressure and the residue was taken up in 1 M $Na_2CO_3$:EtOAc (1:1, 50 mL). The separated basic aqueous phase was washed with brine (2×25 mL), dried over $MgSO_4$, filtered and evaporated under reduced pressure. The crude residue was purified by flash chromatography [gradient, 100% EtOAc to EtOAc:MeOH (98:2)] to give macrocycle 556 as a pale yellow solid (617 mg, 81%).

TLC [EtOAc/MeOH (9:1)]: $R_f$=0.45 (UV, CMA);
LC/MS (Grad_B4): 10.88 min.

Example 12

Standard Procedure for the Synthesis of Imidazolinyl and Dihydropyrimidinyl Macrocycles

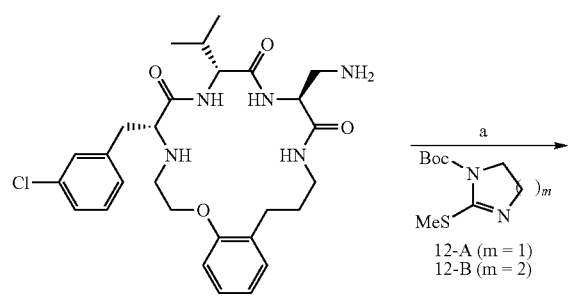

12-1
a. 12-A or 12-B, Et$_3$N, THF, 70° C.

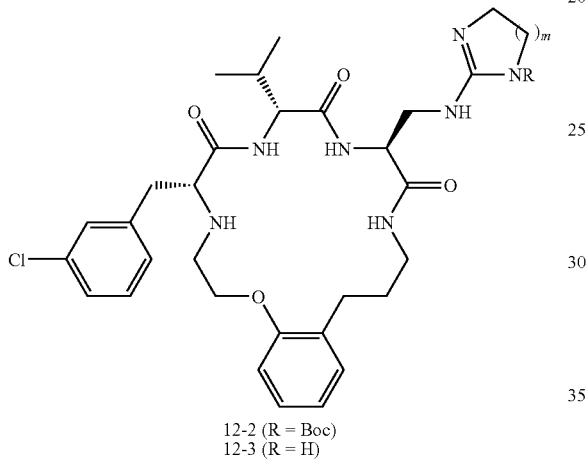

12-2 (R = Boc)
12-3 (R = H)

The synthesis is based upon that in the literature for introduction of this functionality (St Laurent, D. R.; et al. *Bioorg. Med. Chem.* 1995, 3, 1145). To a solution of primary amine macrocycle 12-1 (0.030 mmol) in 15 mL anhydrous THF, was added the thioether reagent 12-A or 12-B (0.30 mmol, 10 eq, 65 mg) followed by Et$_3$N (0.60 mmol, 20 eq, 0.083 mL). The mixture was stirred at reflux under nitrogen for 16 h, then evaporated to dryness under reduced pressure. LC-MS analysis indicated in both cases a mixture of Boc-protected (12-2) and Boc-deprotected (12-3) macrocyclic products. The Boc-deprotected product was isolated from the mixture by MS-triggered reverse phase HPLC. Alternatively, the mixture could be treated with HCl in EtOAc to cleave the Boc group prior to the purification. The general procedure was applied for the representative macrocycles 519 (12-3, m=1) and 521 (12-3, m=2).

Example 13

Standard Procedure for the Synthesis of Guanidinyl Macrocycles

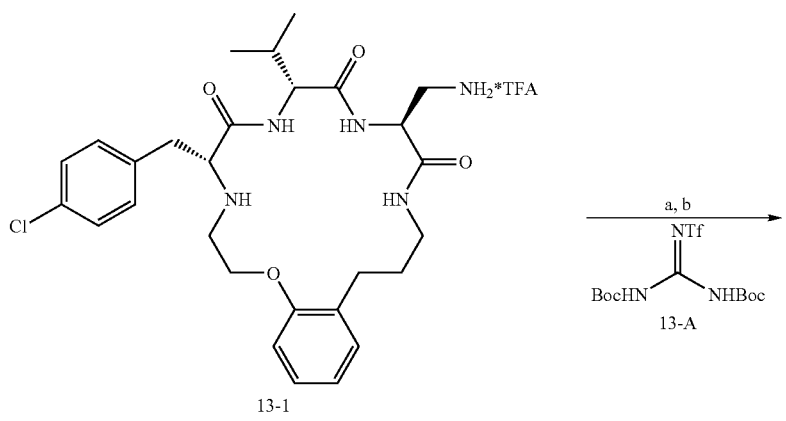

13-1
a. 13-A, Et$_3$N, DCM;
b. TFA, Et$_3$SiH, DCM

-continued

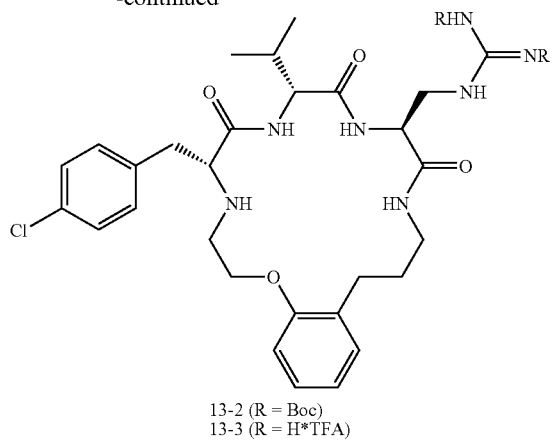

13-2 (R = Boc)
13-3 (R = H*TFA)

To a solution of the fully deprotected macrocycle 13-1 (7.0 mg, 12.9 μmol, 1.0 eq) in anhydrous THF (1.5 mL) was added Et₃N (18 μL, 129 μmol, 10 eq) followed by guanidylation reagent 13-A (10.1 mg, 25.8 μmol, 2.0 eq). (Fechtinger, K.; Zapf, C.; Sings, H. L.; Goodman, M. *J. Org. Chem.* 1998, 63, 3804.) The mixture was stirred O/N at room temperature under nitrogen atmosphere. The solvent was evaporated under reduced pressure and the crude residue purified by flash chromatography [gradient, MeOH/DCM (1:99) to (5:95)] to provide 13-2. After evaporation of the desired fractions, a solution of TFA/Et₃SiH/DCM (50/3/47, 2 mL) was added to the doubly Boc protected macrocycle product 13-2 in a 20 mL vial. The mixture was stirred for 2 h at room temperature, then concentrated under reduced pressure to give the desired guanidine analog 13-3 as its TFA salt. The crude product was purified by reverse phase HPLC.

TLC [MeOH:DCM (1:9)]: $R_f$=0.57 (UV, CMA).

Example 14

Standard Procedure for the Synthesis of Cyanoguanidinyl Macrocycles

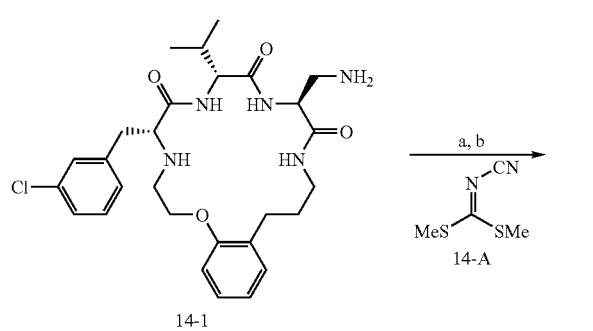

14-1 a. 14-A, Et₃N, EtOH 50° C.;
b. NH₃, MeOH 55° C.

-continued

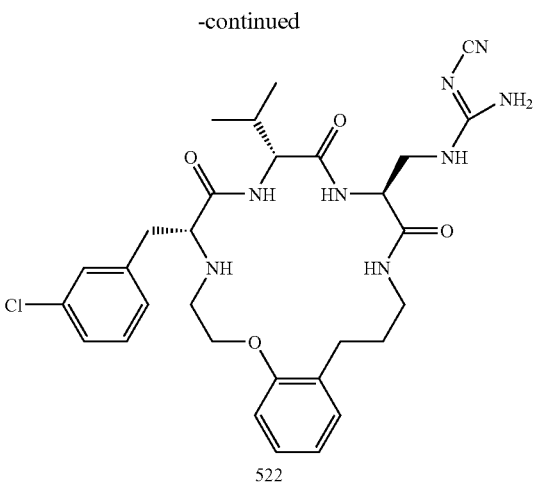

522

The general procedure is exemplified for the representative macrocycle 522. To a solution of macrocycle 14-1 (0.01 mmol) in EtOH (3 mL) was added triethylamine (0.1 mmol, 10 eq) and the reagent 14-A. The mixture was stirred at 55° C. for 16 h, then concentrated under reduced pressure. The product was purified using the ISCO CombiFlash® (Teledyne Isco, Inc., Lincoln, Nebr., USA), then directly subjected to the next step. The intermediate thioether was dissolved in 7 N NH₃ in MeOH, then stirred at 55° C. for 16 h in a pressure bottle. The solvent was evaporated and the residue subjected to preparative HPLC to provide the cyanoguanidine macrocycle 522.

Example 15

Figure 11:
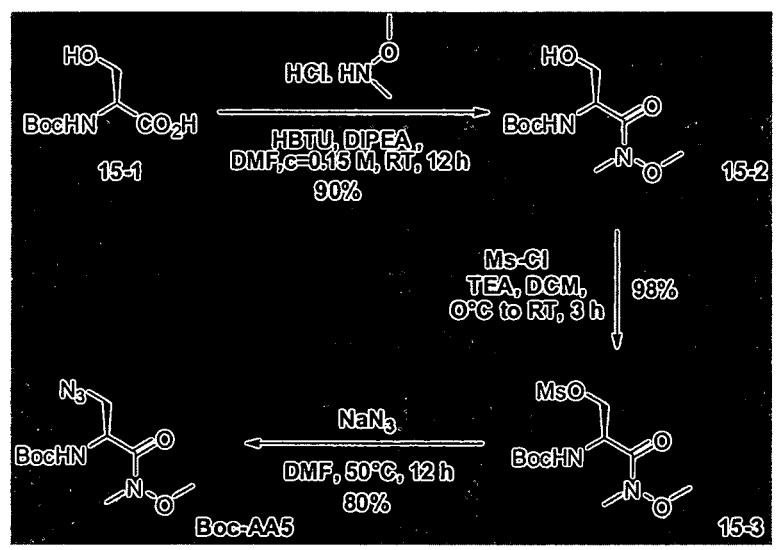
FIG. 11 shows a synthetic scheme for another representative amino acid building block of the invention.

Standard Procedure for the Synthesis of Boc-AA5
(FIG. 11)

Step 15-1

(Panda, G.; Rao, N. V. *Synlett* 2004, 714.) To a stirred suspension of Boc-L-Ser-OH (15-1, 5.0 g, 24.5 mmol, 1.0 eq) in 160 mL of anhydrous DMF at room temperature was added N,N-diisopropylethylamine (DIPEA, 4.25 mL, 24.5 mmol, 1.0 eq). To the mixture was added HBTU (9.30 g, 24.5 mmol, 1.0 eq) and the reaction stirred vigorously at room temperature for 5-10 min, then cooled in an ice-water bath and N,O-dimethyl hydroxylamine HCl salt (2.65 g, 27 mmol, 1.1 eq) added followed by N,N-diisopropylethylamine (4.70 mL, 27 mmol, 1.1 eq). The mixture was stirred for 1 h, then the ice bath removed and the reaction stirred O/N at room temperature. The reaction mixture was cooled to 0° C. and saturated aqueous NaHCO₃ solution (200 mL) was added slowly. The reaction mixture was extracted with ethyl acetate (4×200 mL). The combined organic extracts were washed with brine, dried over sodium sulfate, filtered, and concentrated under reduced pressure. The crude residue was purified by flash chromatography (100% EtOAc) to afford 15-2 as a colorless solid (5.50 g, 90%).

TLC (100% EtOAc): $R_f$=0.40 (ninhydrin).

Step 15-2

To a mixture of the alcohol 15-2 (5.0 g, 20 mmol, 1 eq) and triethylamine (5.60 mL, 40.3 mmol, 2 eq) in 100 mL of anhydrous dichloromethane under $N_2$, was added freshly distilled methanesulfonyl chloride (2.35 mL, 30 mmol, 1.5 eq) dropwise over 5 min. The reaction was allowed to warm to room temperature and stirred for 3 h. The mixture was washed sequentially with cold water, 1 M citrate buffer, saturated aqueous sodium bicarbonate, and brine. The organic layer was dried over magnesium sulfate and concentrated under reduced pressure to provide 15-3 (98% combined yield), sufficient for use in the following step. This compound should be prepared and used in the same day.

Step 15-3

To a solution of 15-3 (5.0 g, 15.3 mmol, 1 eq) in 60 ml of anhydrous DMF was added sodium azide (3.0 g, 46 mmol, 3 eq) under an argon atmosphere and the mixture stirred at 50° C. for 12 h. (CAUTION! Such quantities of $NaN_3$ should be handled carefully.). The reaction mixture was cooled to 0° C. and water (100 mL) added very slowly. The reaction mixture was extracted with ethyl acetate (3×100 mL). The combined organic extracts were washed with brine (2×200 mL), dried over sodium sulfate, filtered, and concentrated under reduced pressure. The oily residue was purified by flash chromatography (hexanes:EtOAc, 1:1), to afford Boc-AA5 as a colorless solid (3.35 g, 80%).

TLC [hexanes:EtOAc (1:1)]: $R_f$=0.5 (ninhydrin);

$^1$H NMR (CDCl$_3$): δ 1.42 (s, 9H), 3.21 (s, 3H), 3.45-3.55 (m, 2H), 3.75 (s, 3H), 4.80 (m, 1H), 5.50 (br s, 1H);

LC-MS: $t_R$=5.66 min; [M+H]⁺: 275.

Example 16

Standard Procedure for Boc Protection of Macrocycles

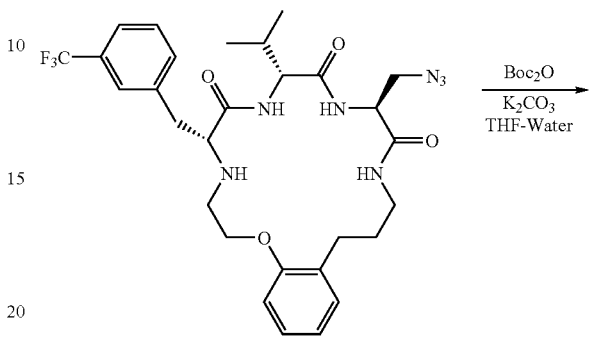

537

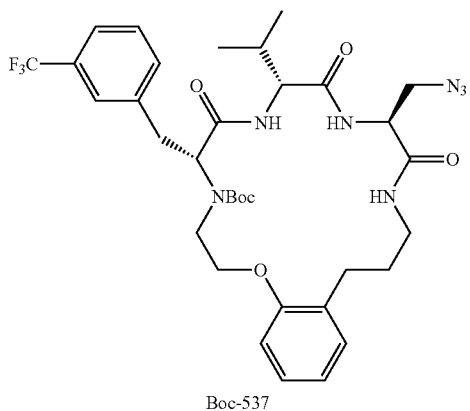

Boc-537

To a solution of 537 (1 g, 1.66 mmol, 1 eq) in THF:Water (1:1, 10 mL) at room temperature was added Boc$_2$O (1.08 g, 4.97 mmol, 1 eq) and K$_2$CO$_3$ (0.352 g, 3.33 mmol, 2 eq). The mixture was stirred at room temperature for 72 h. The solution was extracted with ethyl acetate, then the organic layers washed with brine, dried over magnesium sulfate and concentrated to dryness under reduced pressure. The resulting residue was purified by flash column chromatography (ethyl acetate:hexanes, 1:1) to give the protected macrocycle Boc-537 (75% yield).

Example 17

Standard Procedure for the Formation of Amine Macrocycles from Azido Macrocycles

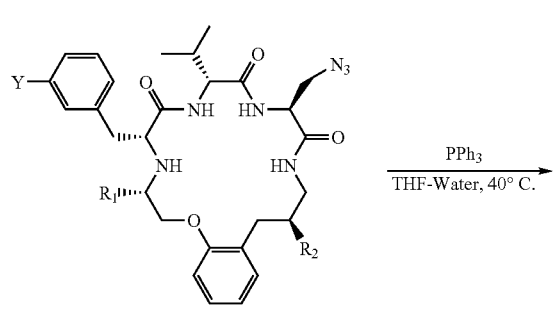

537 (Y = CF$_3$, R$_1$ = H, R$_2$ = H)
538 (Y = F, R$_1$ = Me, R$_2$ = H)
545 (Y = F, R$_1$ = Me, R$_2$ = Me)

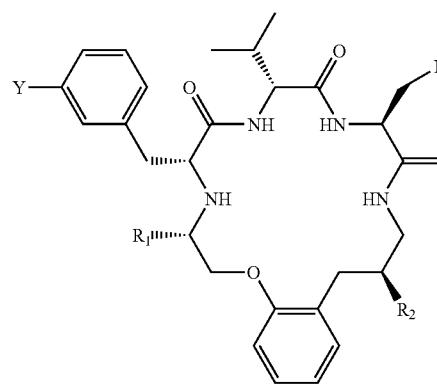

17-2 (Y = CF$_3$, R$_1$ = H, R$_2$ = H)
17-13 (Y = F, R$_1$ = Me, R$_2$ = H)
17-20 (Y = F, R$_1$ = Me, R$_2$ = Me)

To a solution of macrocycle (537, synthesized via the General Procedure of Example 9, 1.0 g, 1.65 mmol, 1 eq) in THF (10 mL) at room temperature was added triphenylphosphine (0.440 g, 1.65 mmol, 1 eq), and 1 ml of water. The mixture was stirred at 40° C. for overnight reaction. The reaction mixture was concentrated to dryness under reduced pressure and the aqueous phase was extracted with ethyl acetate (3 times), dried over MgSO$_4$, filtered and concentrated. The residue was purified by flash column chromatography on silica gels (ethyl acetate:methanol, 9:1) to give 17-2 (90% yield).

Similarly, this procedure applied to compound 538 (also synthesized via the General Procedure of Example 9, 0.940 g, 1.65 mmol, 1 eq) gave 17-13 (90% yield), and applied to compound 545 (also synthesized via the General Procedure of Example 9, 0.960 g, 1.65 mmol, 1 eq) gave 17-20 (90% yield).

Such amino macrocycles can also be synthesized by assembly with appropriately protected Dap derivatives using Example 9 or the solid phase procedure illustrated in FIG. 7.

Example 18

Standard Procedure for the Synthesis of Morpholine-Containing Macrocycles

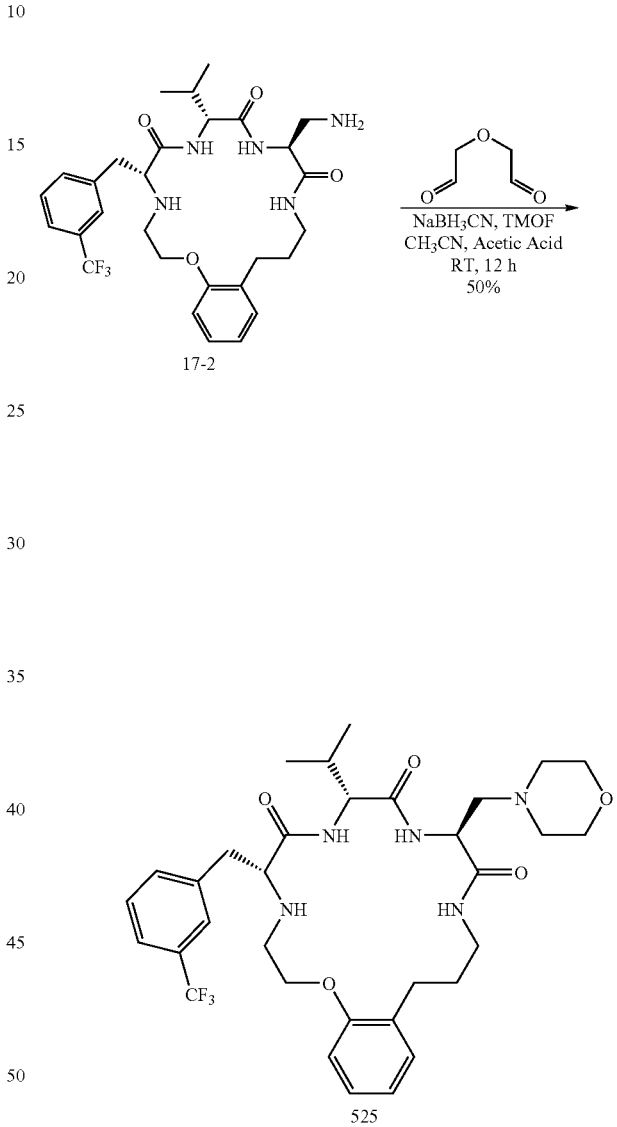

The procedure is exemplified for the representative macrocycle 525. To a solution of macrocycle 17-2 (50 mg, 86.5 μmol, 1 eq) in acetonitrile/trimethylorthoformate (TMOF, 2 mL/0.5 mL) at room temperature was added glutaraldehde (35 μl, 86.5 μmol, 1 eq), NaBH$_3$CN (8.10 mg, 0.13 mmol, 1 eq) and 1 drop of acetic acid. The mixture was stirred at room temperature O/N. The solution was cooled to 0° C. and 1 mL of a solution of NaOH (25%) was slowed added. The reaction was stirred during 5 min. The aqueous phase was extracted with ethyl acetate (3x), then the combined organic phases washed with brine, dried over MgSO$_4$, filtered and concentrated under reduced pressure. The residue was purified by flash chromatography (100% EtOAc to give 525 (50% yield).

Compound 534 was synthesized from 17-13 using the standard procedure of Example 18 in 50% yield.

Example 19

Standard Procedure for the Synthesis of Pyrrole-Containing Macrocycles

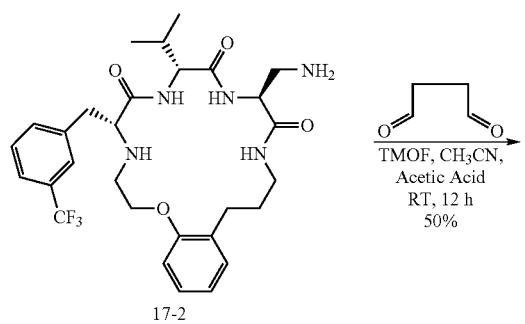

17-2

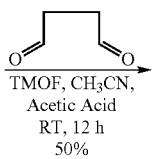

TMOF, CH$_3$CN,
Acetic Acid
RT, 12 h
50%

19-1

To a solution of macrocycle 17-2 (50 mg, 86.5 µmol, 1 eq) in acetonitrile/TMOF (2 mL/0.5 mL) at room temperature was added butane 1,4-dialdehyde (7.5 mg, 86.5 µmol, 1 eq), and 1 drop of acetic acid. The mixture was stirred at room temperature O/N. The solution was cooled to 0° C. and 1 mL of a solution of 25% NaOH was slowed added. The reaction was stirred for 5 min, then the aqueous phase extracted with ethyl acetate (3×). The combined organic phases were washed with brine, dried over MgSO$_4$, filtered and concentrated under reduced pressure. The resulting residue was purified by flash column chromatography (100% EtOAc) to give macrocycle 19-1 (50% yield).

Compound 540 was synthesized from 17-13 using the standard procedure of Example 19 in 50% overall yield for the three step sequence.

Example 20

Standard Procedure for the Synthesis of Pyrrolidine-Containing Macrocycles

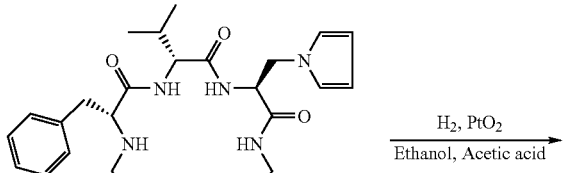

19-1

H$_2$, PtO$_2$
Ethanol, Acetic acid

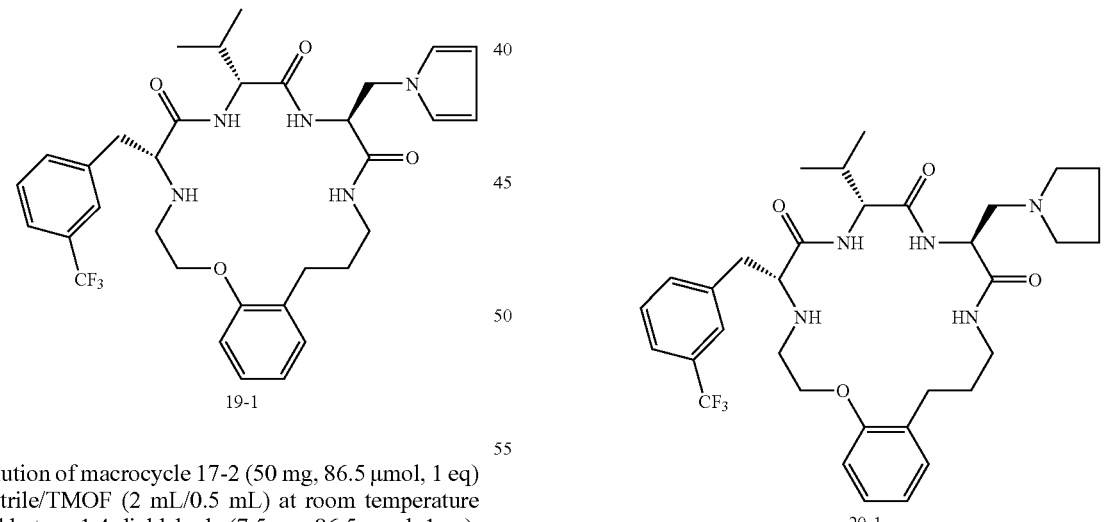

20-1

To a solution of macrocycle 19-1 (50 mg, 86.5 µmol, 1 eq) in 95% ethanol (2 mL) at room temperature was added PtO$_2$ (10 mg, 20% weight), and 1 drop of acetic acid. The mixture was stirred at room temperature under a hydrogen atmosphere using a balloon O/N. The PtO$_2$ was filtered through Celite® (World Minerals Inc., Santa Barbara, Calif.) and washed with ethanol. All solvents were removed under reduced pressure. The resulting residue was purified by HPLC to give 20-1 (98% yield).

Example 21

Standard Procedure for the Synthesis of 5-Methyl-Triazole-Containing Macrocycles

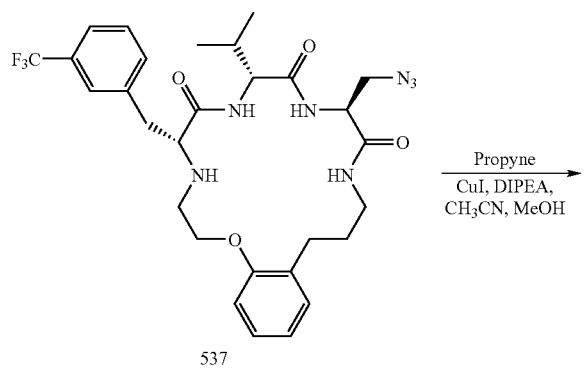

537

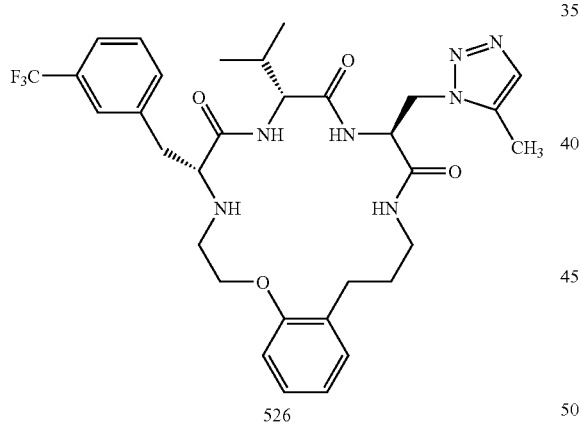

526

The procedure is exemplified for the representative macrocycle 526 and is based upon the literature procedure for this functional group (Rostovstev, V.; Green, L. K.; Fokin, V. V.; Sharpless, K. B. *Angew. Chem. Int. Ed. Engl.* 2002, 41, 2596 and references cited). To a solution of macrocycle 537 (100 mg, 0.165 mmol, 1 eq), CuI (3.4 mg, 0.0165 mmol, 0.1 eq) and DIPEA (30 µL, 0.165 mmol, 1 eq) in acetonitrile/methanol (2 mL/0.5 mL) at room temperature. The reaction was cooled to −78° C. and an excess of propylene gas was bubbled (over 10 eq) into the solution and the flask sealed. The mixture was stirred at room temperature O/N. The reaction was cooled to 0° C., propylene was released slowly, and Cu was filtered through Celite® (World Minerals Inc., Santa Barbara, Calif.) and washed with acetonitrile. All solvents were removed under reduced pressure. The resulting residue was purified by flash chromatography (ethyl acetate:methanol, 95:05) to give 526 (76% yield).

Example 22

Standard Procedure for the Synthesis of 4,5-Dimethyl-Triazole-Containing Macrocycles

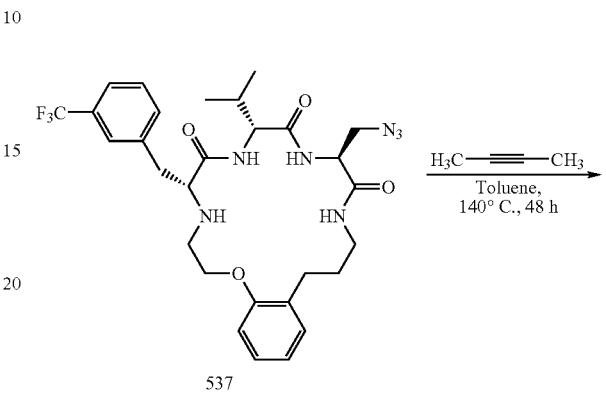

537

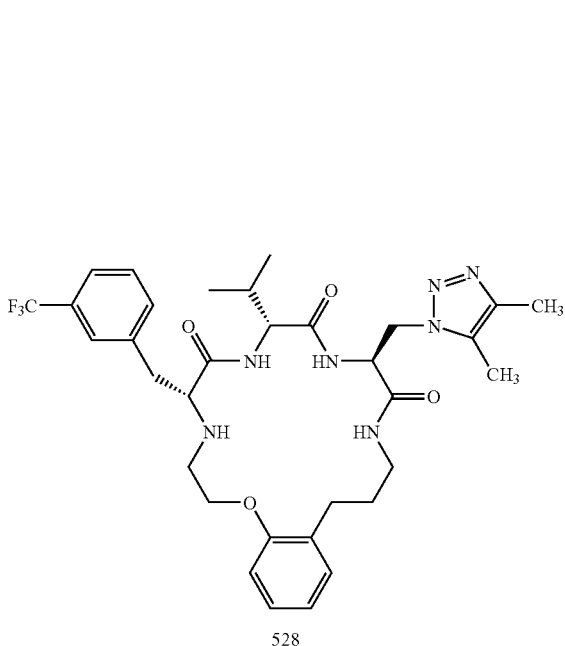

528

The procedure is exemplified for the representative macrocycle 528. To a solution of 537 (100 mg, 0.165 mmol, 1 eq) in toluene (1 mL) was added 2-butyne (3 mL, excess) at room temperature and the flask sealed. The mixture was stirred at 140° C. for 48 h. The reaction was cooled to 0° C., 2-butyne was released slowly and all solvents removed under reduced pressure. The residue was purified by purified by flash chromatography (100% ethyl acetate) to give 528 (65% yield).

Example 23

Standard Procedure for the Synthesis of 5-Methyl-Tetrazole-Containing Macrocycles

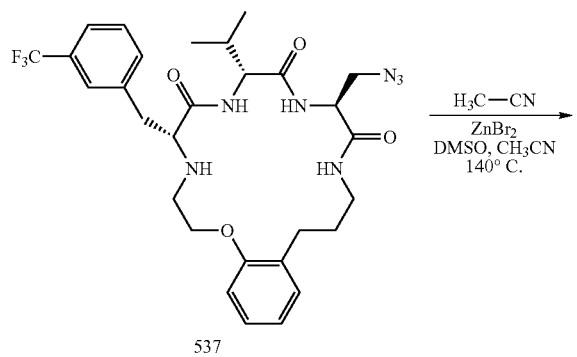

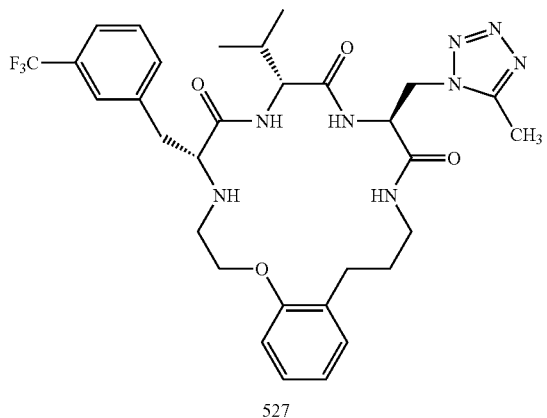

The procedure is exemplified for the representative macrocycle 527. To a solution of 537 (100 mg, 0.165 mmol, 1 eq) in DMSO (1 mL) was added ZnBr$_2$ (37 mg, 0.165 mmol, 1 eq), acetonitrile (5 mL, excess) at room temperature. The mixture was stirred at 140° C. for 48 h. The reaction was cooled to room temperature, then solvents were removed under reduced pressure. The resulting residue was purified by purified by flash chromatography on silica gels (100% ethyl acetate) to give 527 (35% yield).

Example 24

Standard Procedure for the Synthesis of 4-Aminomethyl-Triazole-Containing Macrocycles

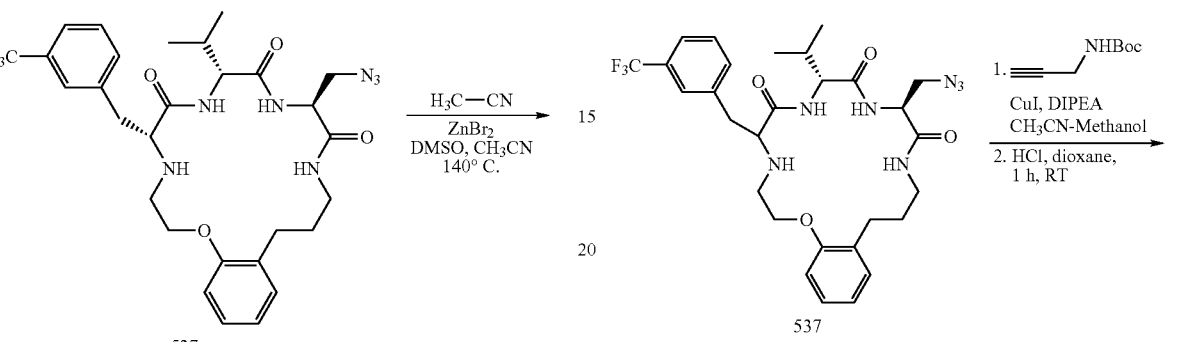

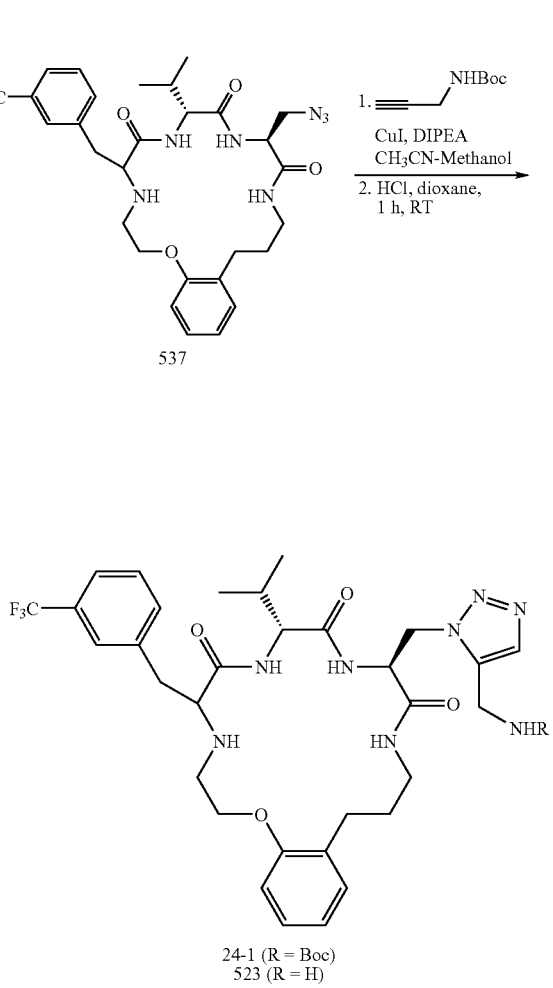

The procedure is exemplified for the representative macrocycle 523. To a solution of 537 (100 mg, 0.165 mmol, 1 eq) were added Boc-propargylamine (28 mg, 0.184 mmol, 1.1 eq), DIPEA (30 μL, 0.165 mmol, 1 eq), and CuI (3.4 mg, 0.0165 mmol, 0.1 eq) in acetonitrile/methanol (2 mL/0.5 mL) was stirred at room temperature O/N. The solvents were removed under reduced pressure and the resulting residue purified by purified by flash chromatography (ethyl acetate:methanol, 95:05) to give 24-1 (80% yield).

24-1 was treated with 2 mL of HCl in dioxane (4 N, 0.79 mmol, 20 eq) and the mixture stirred at room temperature for 1 h. The reaction mixture was concentrated to dryness under reduced pressure to give 523 (98% yield).

Example 25

Standard Procedure for the Synthesis of Monomethylamino-Containing Macrocycles

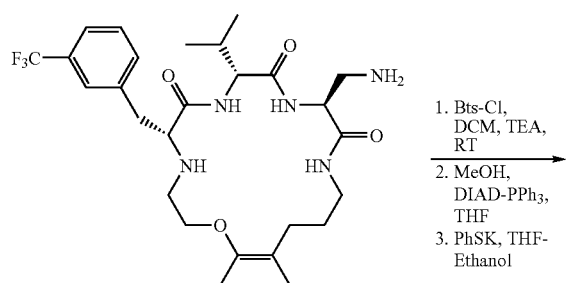

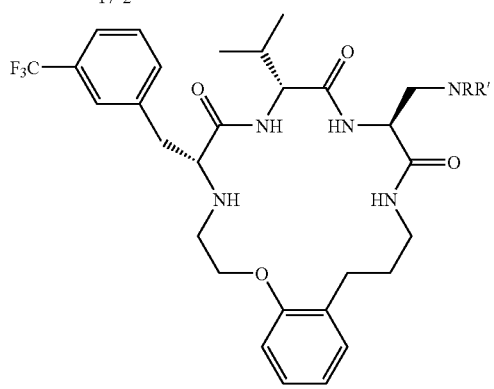

25-1 (R = Bts, R' = H)
25-2 (R = Bts, R' = Me)
25-3 (R = H, R' = Me)

Step 25-1

To a solution of 17-2 (1.0 g, 1.73 mmol, 1 eq) in DCM (10 mL) at room temperature was added Bts-Cl (0.41 g, 1.73 mmol, 1 eq), and triethylamine (0.175 g, 1.73 mmol, 1 eq). The mixture was stirred at room temperature O/N. The reaction mixture was washed with 0.1 N HCl, dried over magnesium sulfate and concentrated to dryness under reduced pressure. The resulting residue was purified by flash chromatography (EtOAc:hexanes, 1:1) to give 25-1 (95% yield).

Step 25-2

To a solution of 25-1 (50 mg, 64.5 μmmol, 1 eq) in THF (10 mL) at room temperature was added methanol (26 μL, 0.645 mmol, 10 eq), the pre-formed triphenylphosphine-DIAD adduct (synthesized as described in Example 38, 32 mg, 0.071 mmol, 1.1 eq). The mixture was stirred at room temperature O/N. The reaction mixture was concentrated to dryness under reduced pressure. The residue was purified by flash chromatography (ethyl acetate:hexanes, 1:1) to give 25-2 (98% yield).

Step 25-3. 25-2

(50 mg) was dissolved in ethanol:THF (1:1, 2 mL) at room temperature, treated with thiophenol resin (1 g) and agitated on an orbital shaker for 2 h. The resin was filtered off and washed several times with ethanol:THF. The filtrate and washings were removed under reduced pressure and the crude residue subjected to HPLC purification to give 25-3 (50% yield).

Compound 546 was synthesized from 17-20 using the standard procedure of Example 25 in ~44% overall yield for the three step sequence.

Compound 548 was synthesized from 17-13 using the standard procedure of Example 25 in 40% overall yield for the three step sequence.

Monomethylamino-containing macrocycles are also synthesized using building block Boc-AA4 in solid phase methods as illustrated in FIG. 7 or in solution phase procedures as described in Example 9.

Example 26

Standard Procedure for the Synthesis of Pyrimidine-Containing Macrocycles

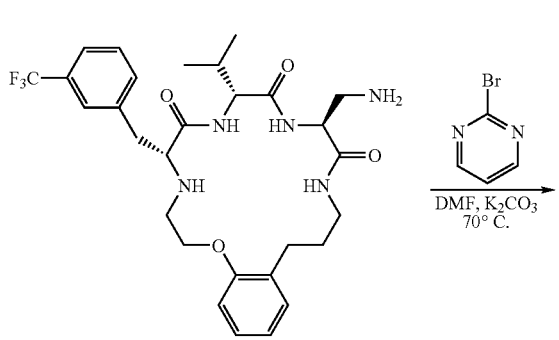

17-2

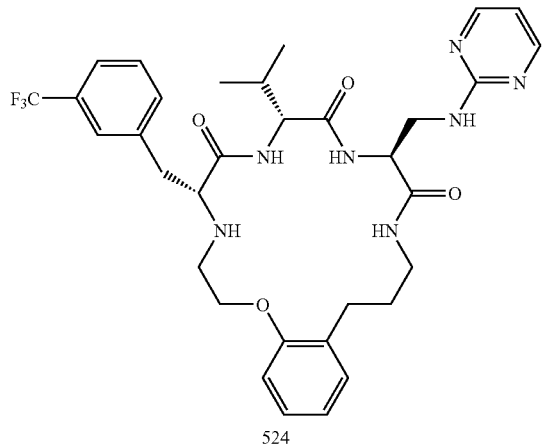

524

The procedure is exemplified for the representative macrocycle 524. To a solution of 17-2 (0.10 g, 0.173 mmol, 1 eq) in DMF (1.7 mL) at room temperature was added 2-bromopyrimidine (0.136 g, 0.865 mmol, 5 eq), and K$_2$CO$_3$ (60 mg, 0.432 mmol, 2.5 eq). The mixture was stirred at 70° C., O/N, then cooled to RT. The reaction mixture was diluted with 10 mL of ethyl acetate, washed with 0.1 N HCl and brine, then dried over magnesium sulfate and concentrated to dryness under reduced pressure. The resulting residue was purified by flash chromatography (ethyl acetate:hexanes, 1:1) to give 524 (96% yield).

Compound 535 was synthesized from 17-13 using the standard procedure of Example 26 in 96% yield.

Compound 550 was synthesized from X-13 using the standard procedure of Example 26 in 80% yield.

Example 27

Figure 12:
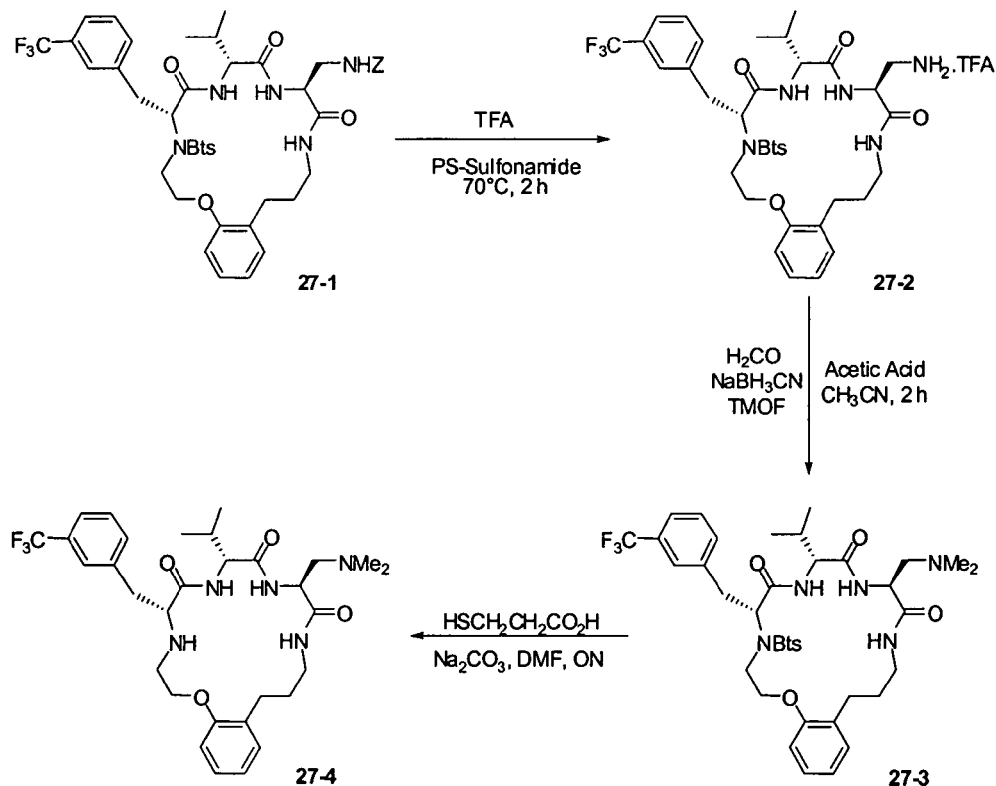
FIG. 12 shows a synthetic scheme for representative compounds of the present invention.
Figure 12:
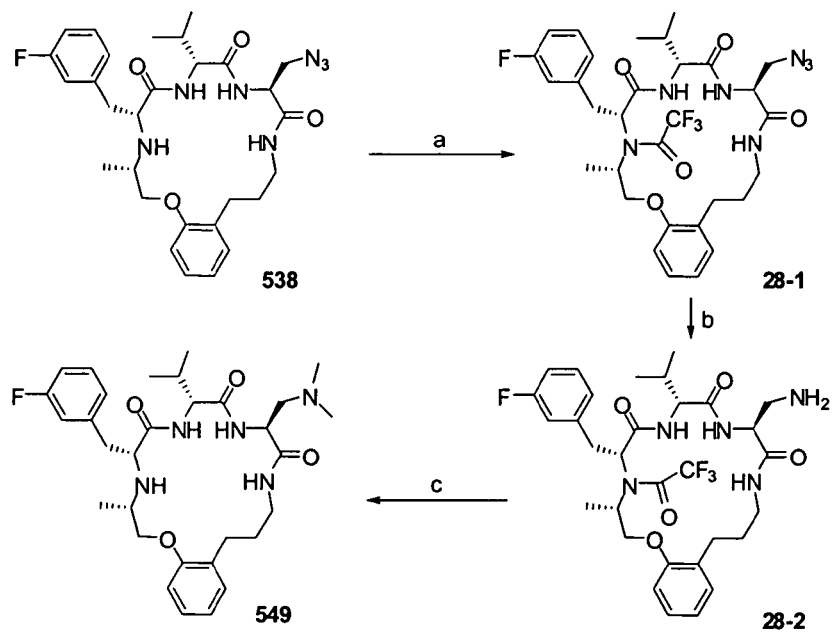
Figure 13:
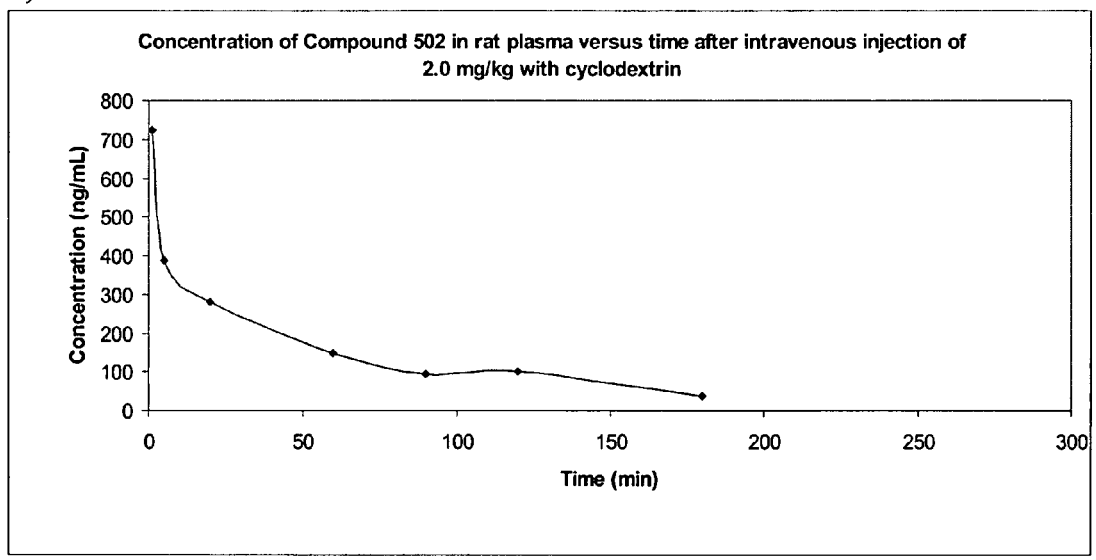
FIG. 13 presents graphs depicting pharmacokinetic parameters for exemplary compounds of the present invention, specifically after intravenous administration of 2.0 mg/kg compound 502 with cyclodextrin (panel A), after subcutaneous injection of 2.0 mg/kg compound 502 without cyclodextrin (panel B), after intravenous administration of 1.9 mg/kg compound 552 with cyclodextrin (panel C), after subcutaneous administration of 2.0 mg/kg compound 552 without cyclodextrin (panel D), after oral administration of 8.0 mg/kg compound 552 with cyclodextrin (panel E), after intravenous administration of 2.0 mg/kg compound 563 with cyclodextrin (panel F), and after oral administration of 7.7 mg/kg compound 563 with cyclodextrin (panel G).
Figure 13:
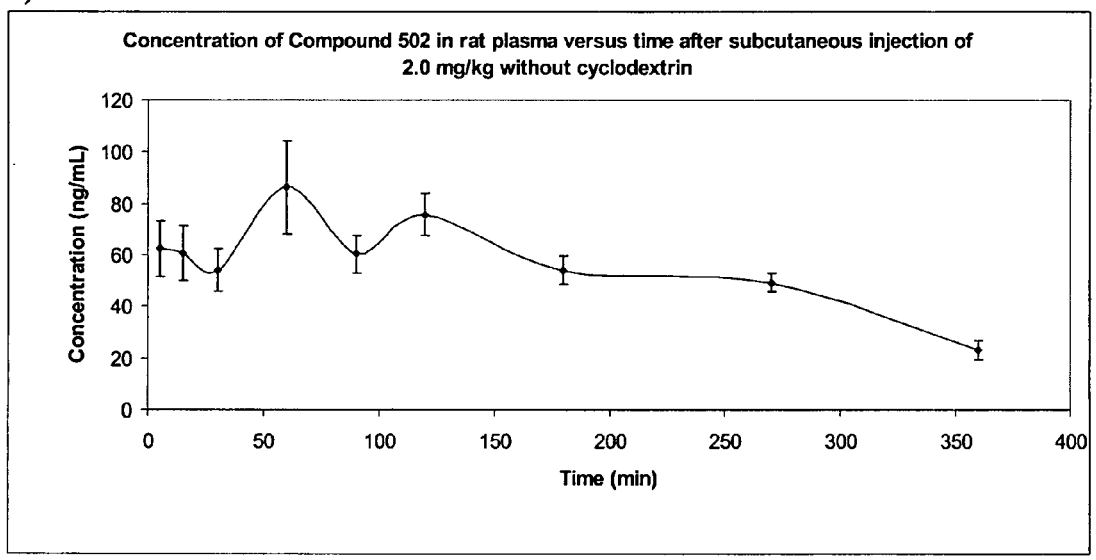
Figure 13:
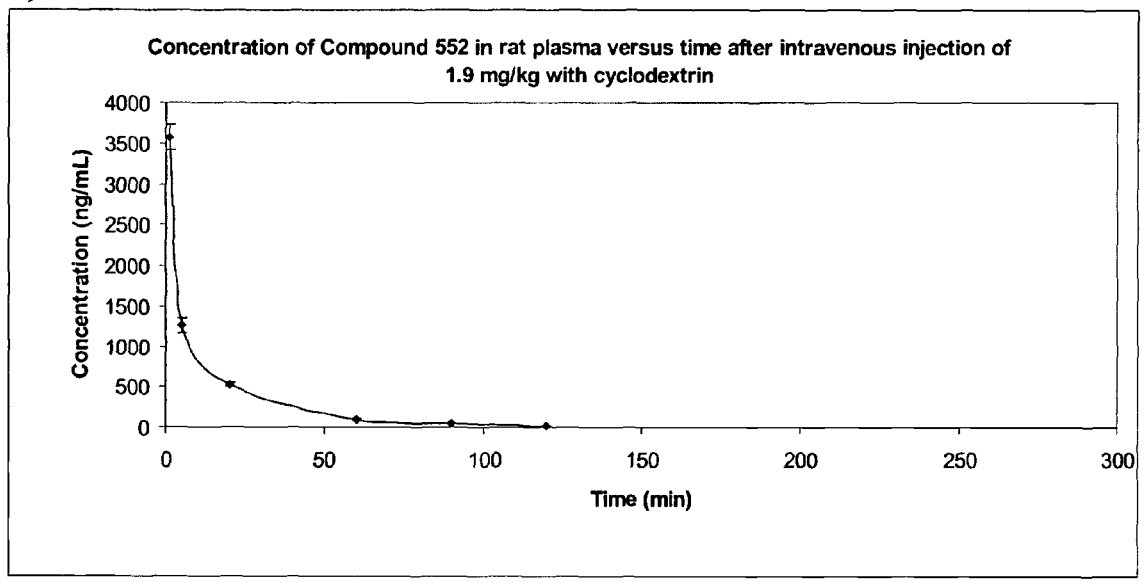
Figure 13:
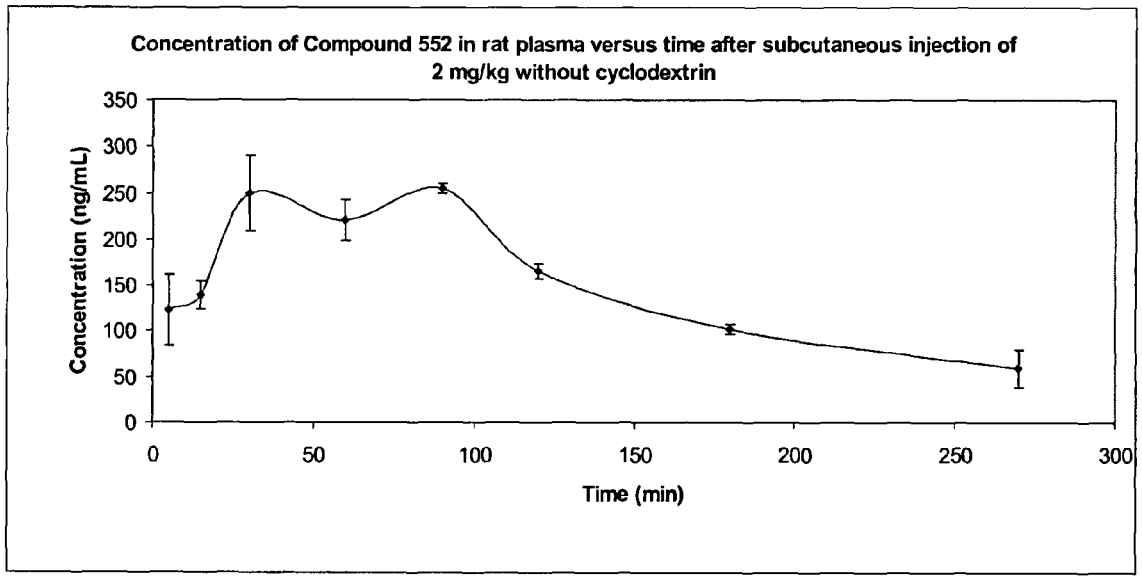
Figure 13:
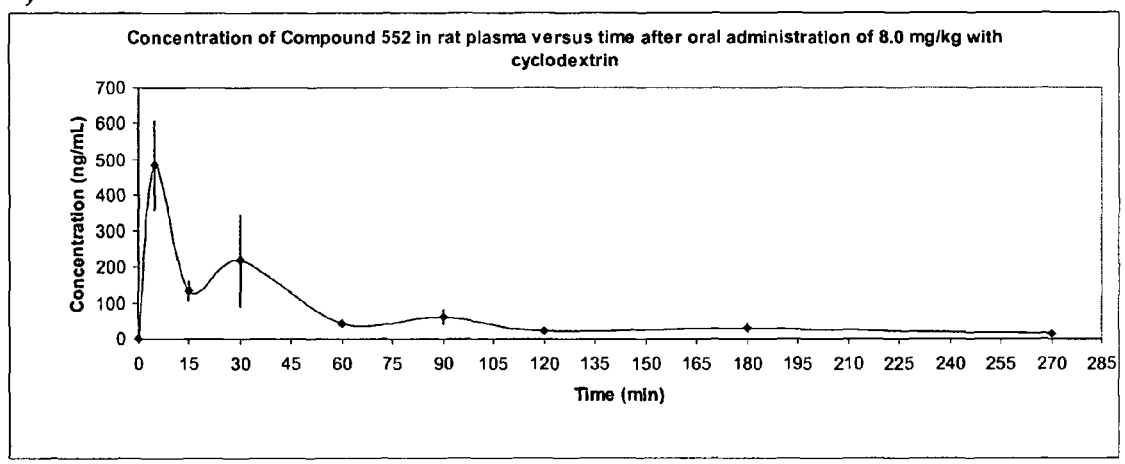
Figure 13:
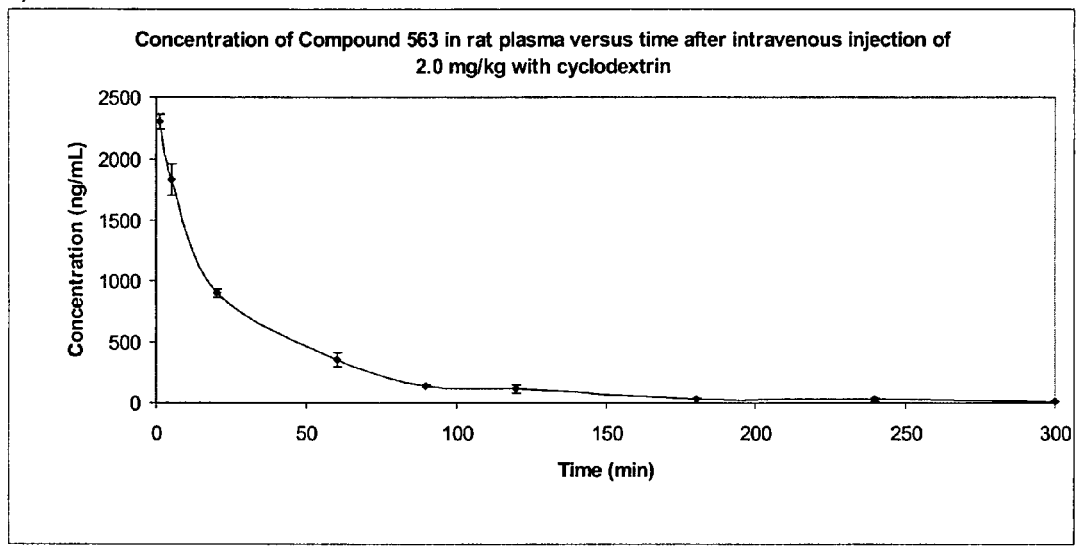
Figure 13:
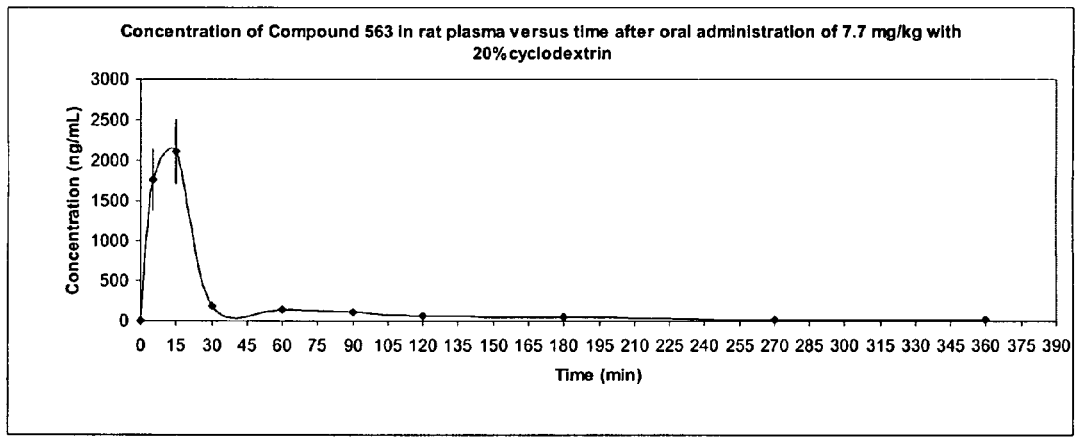

Standard Procedure for the Synthesis of Dimethylamino-Containing Macrocycles (FIG. 12A)

Step 27-1

To a solution of 27-1 (synthesized from the corresponding macrocycle containing a free secondary amine and a protected primary amine by treatment with Bts-Cl similarly to as described in Step 11-2 followed by deprotection of the Boc under standard conditions, 3.3 g, 3.63 mmol, 1 eq) in TFA (50 mL, 0.653 mol, 180 eq) at room temperature was added polystyrene (PS) sulfonamide resin (Argonaut Technologies, now part of Biotage AB, Uppsala, Sweden, 1.1 mmol/g 16.8 g, 18.2 mmol, 5 eq). The mixture was stirred at 70° C. for 2 h. The resin was filtered off and washed with TFA and DCM several times. The filtrate and washings were removed under reduced pressure. The resulting residue was purified by flash chromatography (100% ethyl acetate) to give 27-2 (70% yield).

Step 27-2

To a solution of 27-2 (1.2 g, 1.55 mmol, 1 eq) in acetonitrile/TMOF (6 mL/2 mL) at room temperature was added formaldehyde (0.426 ml, 15.5 mmol, 10 eq), NaBH$_3$CN (97 mg, 15.5 mmol, 10 eq) and 1 drop of acetic acid. The reaction was stirred at room temperature for 2 h. The solution was cooled to 0° C., then 1 mL of a solution of 25% NaOH slowly added and the reaction stirred for 5 min. The aqueous phase was extracted with ethyl acetate (3×), washed with brine, dried over MgSO$_4$, filtered and concentrated under reduced pressure. The resulting residue was purified by flash chromatography (ethyl acetate:methanol, 95:5) to give 27-3 (75% yield).

Step 27-3

To a solution of 27-3 (1.33 g, 1.66 mmol, 1 eq) in DMF (10 mL) at room temperature was added mercaptopropanoic acid (0.9 g, 8.30 mmol, 5 eq), and K$_2$CO$_3$ (1.15 g, 8.30 mmol, 5 eq). The mixture was stirred at room temperature for 12 h. The reaction mixture was diluted with ethyl acetate and water, then extracted with ethyl acetate. The combined organic layers were washed with brine, dried over magnesium sulfate and concentrated to dryness under reduced pressure. The resulting residue was purified by flash chromatography (ethyl acetate:methanol, 9:1) to give 27-4 (80% yield).

Example 28

Additional Standard Procedure for the Synthesis of Dimethylamino-Containing Macrocycles (FIG. 12B)

Step 28-1

To a solution of 538 (0.200 g, 0.352 mmol, 1 eq) in DCM (2 mL) at room temperature were added trifluoroacetic anhydride (TFAA, 122 µL, 0.882 mmol, 2.5 eq) and triethylamine (TEA, 250 µL, 1.76 mmol, 5 eq). The reaction was stirred at 0° C. for 1 h. The mixture was then diluted with 10 mL of dichloromethane and washed with 0.1 N HCl and brine, dried over magnesium sulfate and concentrated to dryness under reduced pressure. The residue was purified by flash chromatography (ethyl acetate:hexanes, 1:1) to give 28-1 (35% yield)

Step 28-2

To a solution of 28-1 (66 mg, 0.0994 mmol, 1 eq) in ethyl acetate (5 mL) at room temperature was added Pd/C (15 mg, 20% by weight), and 1 drop of acetic acid. The mixture was stirred at room temperature under a hydrogen atmosphere using a balloon O/N. The Pd/C was filtered through Celite® (World Minerals Inc., Santa Barbara, Calif.) and washed with ethyl acetate. The filtrate and washings were removed under reduced pressure to provide 28-2.

Step 28-3

The crude 28-2 was dissolved in acetonitrile/TMOF (6 mL/2 mL) at room temperature and formaldehyde (22 µL, 0.0995 mmol, 3 eq), NaBH$_3$CN (6.15 mg, 0.0298 mmol, 2 eq) and 1 drop of acetic acid were added. The mixture was stirred at room temperature for 2 h. The solution was cooled to 0° C. and 1 mL of a solution of 25% NaOH was slowly added and the mixture stirred for 5 min. The aqueous phase was extracted with ethyl acetate (3×), washed with brine, dried over MgSO$_4$, filtered and concentrated under reduced pressure. The residue was directly dissolved in methanol (5 mL) at room temperature, K$_2$CO$_3$ (15 mg) added and the mixture stirred at room temperature for 1 h. The solution was cooled to 0° C. and 1 mL of a solution of 0.1 N HCl was slowly added and the mixture stirred for 5 min. The aqueous phase was extracted with ethyl acetate (3×), washed with brine, dried over MgSO$_4$, filtered and concentrated under reduced pressure. The crude residue was subjected to HPLC purification to give 549 (<5 mg).

Example 29

Standard Procedure for Deprotection of Compounds of the Invention Containing AA1

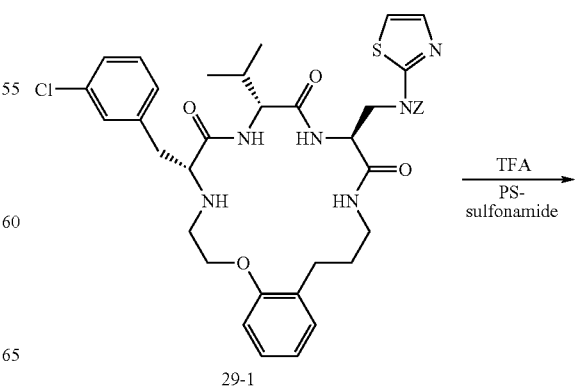

29-1

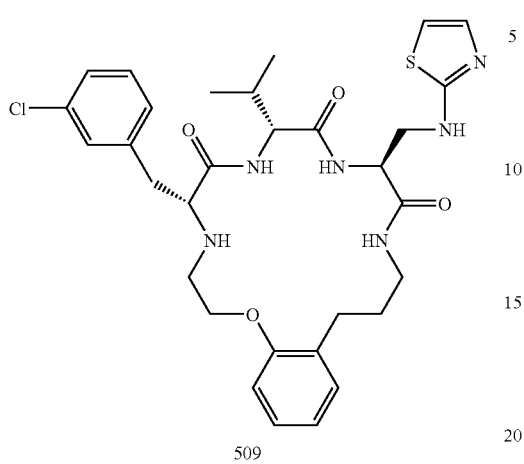

509

To a solution of 29-1 (36 mg, 1 eq) in TFA (10 mL, 180 eq) at room temperature was added polystyrene (PS) sulfonamide resin (Argonaut Technologies, now part of Biotage AB, Uppsala, Sweden, 1.1 mmol/g, 0.5 g, 5 eq). The mixture was stirred at 70° C. for 2 h. The resin was filtered off and washed with TFA and DCM several times. The filtrate and washings were removed under reduced pressure. The resulting residue was purified by flash chromatography (100% ethyl acetate) to give 509 (50%).

Example 30

Standard Procedure for the Synthesis of Side-Chain Sulfonamides

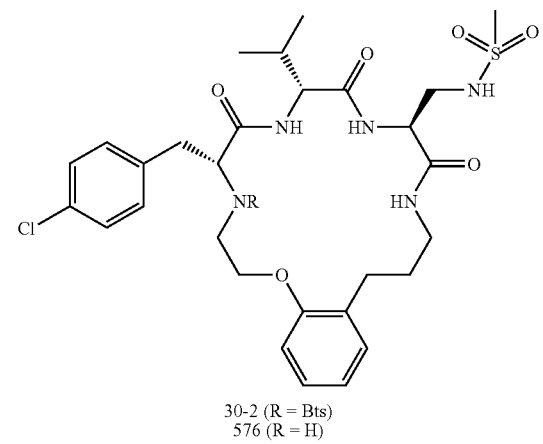

30-2 (R = Bts)
576 (R = H)

a. MsCl, Et₃N, DMAP, DCM; b. PS-C₆H₅S⁻K⁺, THF/95% EtOH

The procedure is exemplified for the synthesis of compound 576. To a solution of the Bts protected macrocycle 30-1 (50 mg, 67.6 µmol, 1.0 eq) in anhydrous DCM (4 mL) was added Et₃N (188 µL, 1.35 mmol, 20 eq) followed by DMAP (1.6 mg, 13.5 µmol, 0.2 eq). The mixture was cooled to 0° C. in an ice-water bath and MsCl (105 µL, 1.35 mmol, 20 eq.) added. The mixture was stirred for 1 h at 0° C., warmed to room temperature and stirred O/N under nitrogen atmosphere. The solvent was evaporated under reduced pressure and the Bts protecting group was removed from 30-2 using polymer bound thiophenol (1 g of freshly prepared resin) in a solution of THF 95% EtOH (1:1) for 2 h. Filtration and evaporation of the solvents under reduced pressure gave crude 576 which was purified by reverse phase HPLC.

TLC [MeOH:DCM (5:95)]: R$_f$=0.24 (UV, CMA).

Example 31

Standard Procedure for the Synthesis of Side-Chain Carboxamides

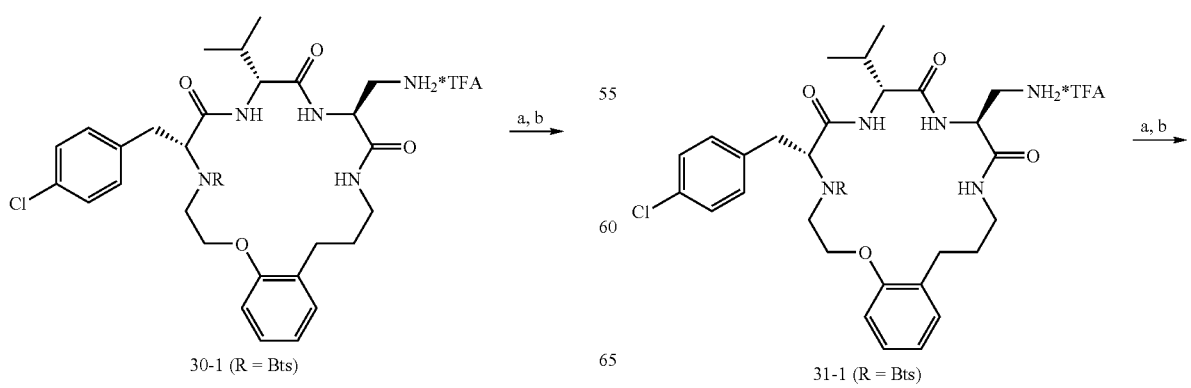

30-1 (R = Bts)

31-1 (R = Bts)

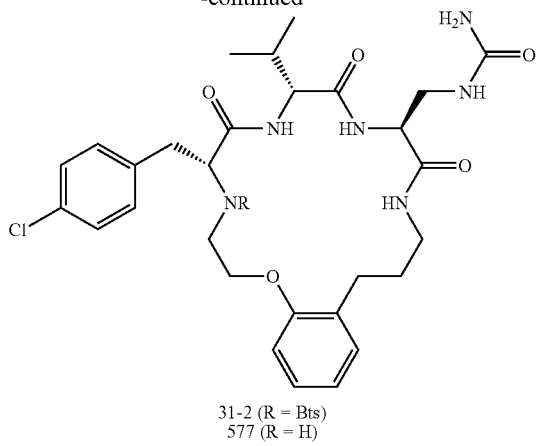

31-2 (R = Bts)
577 (R = H)

a. TMS isocyanate, Et₃N, DMAP, DCM; b. PS-C₆H₅S⁻K⁺, THF/95% EtOH

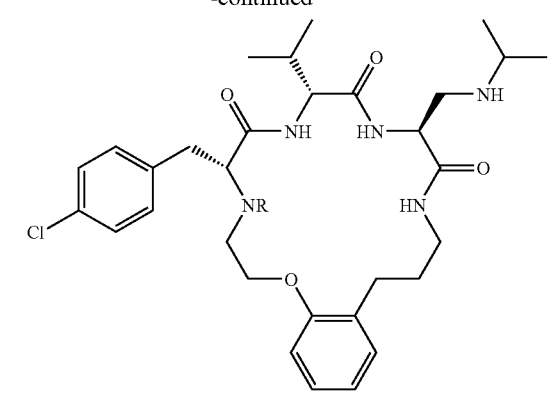

32-2 (R = Bts)
581 (R = H)

a. Acetone, NaBH₃CN, AcOH, TMOF/MeCN; b. PS-C₆H₅S⁻K⁺, THF/95% EtOH

The procedure is exemplified for the synthesis of compound 577. To a solution of the Bts protected macrocycle 31-1 (synthesized from the corresponding macrocycle containing a free secondary amine and a protected primary amine by treatment with Bts-Cl similarly to as described in Step 11-2 followed by deprotection of the Boc under standard conditions, 40 mg, 54.0 µmol, 1.0 eq) in anhydrous DCM (3.5 mL) was added Et₃N (150 µL, 1.08 mmol, 20 eq) followed by DMAP (1.3 mg, 10.8 µmol, 0.2 eq). The mixture cooled to 0° C. in an ice-water bath and TMS isocyanate (143 µL, 1.08 mmol, 20 eq) then added. The mixture was stirred for 1 h at 0° C., warmed to room temperature and stirred O/N under nitrogen atmosphere. The reaction was monitored by HPLC-MS. The solvent was evaporated under reduced pressure and the crude residue purified by flash chromatography [gradient, DCM to MeOH:DCM (1:9)]. After evaporation of the combined product-containing fractions, the Bts protecting group was removed from 31-2 using polymer bound thiophenol (1 g of freshly prepared resin) in a solution of THF 95% EtOH (1:1) for 2 h. Filtration and evaporation of the solvents under reduced pressure gave crude 577 which was purified by reverse phase HPLC.

The procedure is exemplified by the synthesis of the representative compound 581. To a solution of 32-1 (60 mg, 81.1 µmol, 1.0 eq) in TMOF:MeCN (1:1, 5 mL) was added acetone (148 µL, 2.02 mmol, 25 eq) followed by NaBH₃CN (126 mg, 2.02 mmol, 25 eq) and glacial acetic acid (11.6 µL, 202.8 umol, 2.5 eq). The mixture was stirred at room temperature O/N under a nitrogen atmosphere. A solution of sodium hydroxide (1 M) was then added until pH 10-12 and the resulting aqueous phase extracted with DCM (3×). The combined organic phases were washed once with brine, dried over MgSO₄, filtered and evaporated under reduced pressure to give crude 32-2 which was purified by reverse phase HPLC. Removal of the Bts group was achieved as described for Example 31.

Use of other aliphatic aldehydes and ketones in place of acetone in this procedure leads to other analogous alkylated amine products.

Example 32

Standard Procedure for the Synthesis of Side-Chain Alkylamines

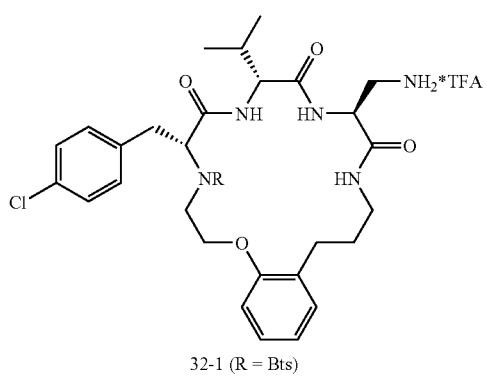

32-1 (R = Bts)

Example 33

Standard Procedure for the Synthesis of Amidinyl-Containing Macrocycles

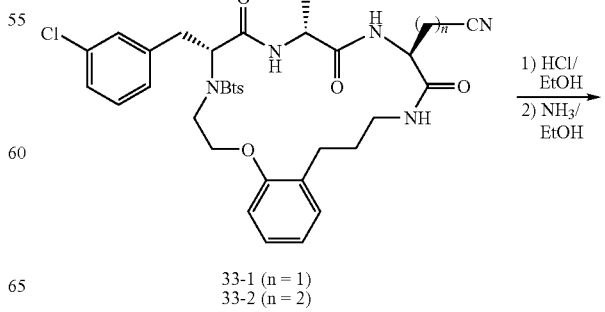

33-1 (n = 1)
33-2 (n = 2)

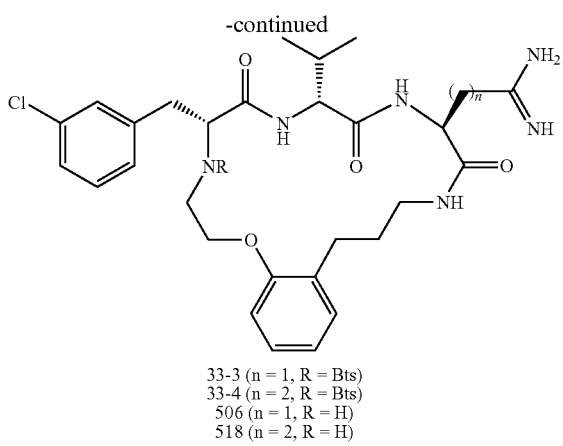

33-3 (n = 1, R = Bts)
33-4 (n = 2, R = Bts)
506 (n = 1, R = H)
518 (n = 2, R = H)

The procedure is exemplified by the synthesis of the representative compound 506 and is also applicable for representative compound 518 starting from 33-2. Nitrile 33-1 (obtained from solid phase synthesis with appropriate amino acid building blocks according to the procedure outlined in FIG. 7, 218 mg crude) was dissolved in a solution of 1.25 M HCl in EtOH (25 mL) at 0° C. and gaseous HCl was bubbled into the solution for 30 min. The mixture was then stirred at room temperature for 2 h. The solution was evaporated under reduced pressure, then dried under high vacuum. The crude residue was dissolved in a solution of 2 M ammonia in ethanol (25 mL) and the mixture stirred at room temperature O/N. The solution was evaporated under reduced pressure and purified by reverse phase HPLC to give 33-3 (17.4 mg). Removal of the Bts group was achieved as described for Example 31.

Example 34

Figure 14:
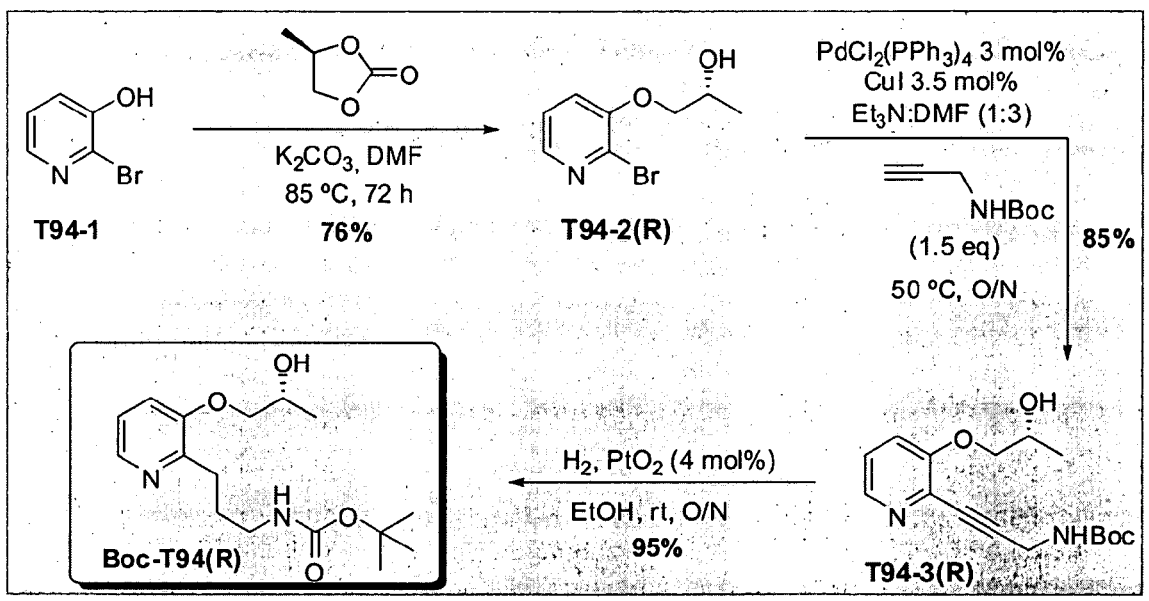
FIG. 14 shows a synthetic scheme for a representative tether building block of the invention.

Standard Procedure for the Synthesis of Tether Boc-T94(R) (FIG. 14)

Step 34-1. 3-(2-(R) Hydroxyethyl-1-oxy)-2-bromopyridine [T94-2(R)]

2-Bromo-3-pyridinol T94-1, 2.0 g, 12 mmol, 1 eq) was dissolved in DMF (anhydrous, 50 mL) at room temperature under an atmosphere of nitrogen. Potassium carbonate (1.6 g, 12 mmol, 1 eq) and (R)-methyl carbonate (1 mL, 12 mmol, 1 eq) was added and the mixture stirred vigorously for 15 min. The reaction was then heated to 85° C. using an oil-bath for 72 h. To the mixture was added 100 mL of water and the aqueous layer extracted with ethyl acetate (5×100 mL). The combined organic layers were washed with brine (200 mL) and dried over MgSO$_4$. The organic layer was concentrated under reduced pressure. The resulting residue was subjected to flash chromatography (100% ethyl acetate) to obtain T94-2(R) as a pale-yellow oil (2.12 g, 76%).

TLC (100% ethyl acetate): R$_f$: 0.55 (UV, CMA)

Step 34-2. 3-(2-(R) Hydroxyethyl-1-oxy)-2-(1-tert-butoxycarbonylamino-prop-2-yn-3-yl)pyridine [T94-3(R)]. T94-2(R)

(1 g, 4.3 mmol, 1 eq) and Boc-propargylamine derivative (1.1 g, 6.46 mmol, 1.5 eq) were dissolved in Et$_3$N (distilled over CaH$_2$):DMF (1:3, 15 mL) and the reaction mixture was degassed by bubbling argon through the solution. trans-Dichloro-bis(triphenylphosphine)palladium(II) (91 mg, 3 mol %, 0.13 mmol) and freshly recrystallized copper(I) iodide (28.5 mg, 0.15 mmol, 3.5 mol %) were added and the mixture was warmed to 50° C. and stirred O/N. The solvent was removed under reduced pressure (oil pump vacuum) and the resulting residue purified by flash chromatography (100% ethyl acetate) to obtain T94-3(R) as a pale brown solid (1.12 g, 85%).

TLC (100% ethyl acetate): R$_f$: 0.33 (UV, CMA)

Step 34-3. 3-(2-(R)Hydroxyethyl-1-oxy)-2-(1-tert-butoxycarbonylaminoprop-3-yl)pyridine [Boc-T94(R)]

The acetylenic compound T94-3(R) (5.0 g, 16 mmol) was dissolved in EtOH (80 mL), then PtO$_2$ (4 mol %, 150 mg) was added and the mixture stirred under a hydrogen atmosphere (a balloon full of hydrogen gas was used) O/N. After this period of time, the reaction mixture was filtered through a pad of Celite® (World Minerals Inc., Santa Barbara, Calif.), washed with THF, then the combined filtrate and washings were concentrated under reduced pressure to afford a relatively pure (by $^1$H NMR), but still colored, sample of Boc-T94(R) in a quantitative yield. Further purification can be achieved by subjecting this material to flash chromatography (100% ethyl acetate). The product Boc-T94(R) has the same R$_f$ as the starting material and hence, $^1$H NMR is the best way to distinguish them. TLC (100% ethyl acetate): R$_f$: 0.33 (UV, CMA)

$^1$H NMR (CDCl$_3$): δ 1.30 (d, 3H), 1.4 (s, 9H), 1.90 (m, 2H), 2.80 (m, 2H), 3.15 (m, 2H), 3.80-3.90 (m, 2H), 4.150 (m, 1H), 5.01 (m, 1H), 7.10 (m, 2H), 8.01 (sb, 1H).

$^{13}$C NMR (CDCl$_3$): δ 19.69, 28.62, 29.77, 40.25, 66.07, 73.62, 76.90, 77.32, 79.18, 118.21, 122.19, 128.80, 132.49, 140.74, 151.63, 153.08, 156.41.

LC-MS (Condition Grad_A4): t$_R$=4.71 min; [M+H]$^+$411.

Note that T94(R) is used to make compounds of formula I with an (S)-stereocenter. Similarly, T94(S) is used to synthesize compounds of formula I with an (R)-stereocenter.

Example 35

Figure 15:
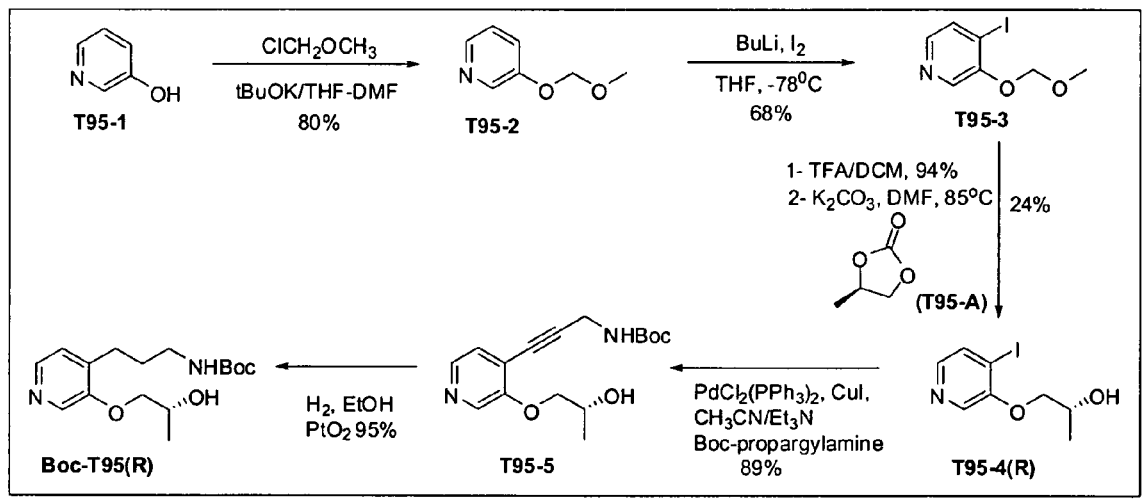
FIG. 15 shows a synthetic scheme for another representative tether building block of the invention.

Standard Procedure for the Synthesis of Tether Boc-T95(R) (FIG. 15)

The sequence was based upon reaction methodology reported in the literature. (Lin, N. *Bioorg. Med. Chem. Lett* 1998, 8, 249-254; Swindell, C. *Heterocycles* 1986, 24, 3373-3377; Shimano, Masanao, *Tetrahedron Lett.* 1998, 39, 4363-4366; Snieckus, V. *J. Org. Chem.* 1985, 50, 5436-5438.)

Step 35-1

A solution of 3-hydroxypyridine (T95-1, 14.0 g, 0.147 mmol) in THF/DMF (315 mL/315 mL) was cooled to 0° C., then potassium tert-butoxide (24.7 g, 221 mmol) added in small portions. The mixture was stirred for 5 min, then MOM-Cl (13.0 mL, 162 mmol) added dropwise over 10 min. A saturated aqueous solution of ammonium chloride was added and the THF removed under reduced pressure. The aqueous phase was then extracted with Et$_2$O (3×). The combined organic phases were dried over MgSO$_4$, filtered and concentrated under reduced pressure. The crude T95-2 (orange oil) was used as obtained in the next step.

Step 35-2

A solution of T95-2 (6.0 g, 43 mmol) and TMEDA (7.8 mL, 52 mmol) in THF (175 mL) was cooled to −78° C. and agitated with a mechanical stirrer. nBuLi (1.56 M in hexane, 31.4 mL, 49 mmol) was added dropwise. A sticky orange thick syrup was formed and dissolved over time. The solution was stirred for 1 h then $I_2$ (14.2 g, 56 mmol) was added and the solution stirred another 1 h at −78° C. then warmed up to rt O/N. Water was added to the reaction and the THF removed under reduced pressure. The aqueous phase was extracted with $Et_2O$ (3×). The organic phases were combined, dried over $MgSO_4$, filtered and concentrated under reduced pressure. The resulting residue was purified by flash chromatography (gradient, 8/2 EtOAc/Hex to 6/4 EtOAc/Hex) to give 7.0 g (68%) of T95-3 as a yellowish solid.

Step 35-3

To a solution of T95-3 (6.5 g, 24.6 mmol) in DCM (49 mL) at rt was added TFA (49 mL). The mixture was stirred for 2 h at rt. The solvent was removed under reduced pressure and re-treated with the same reagents under the same conditions for an additional hour. The reaction was monitored by $^1$H NMR spectroscopy on a worked-up reaction aliquot. A saturated aqueous solution of sodium bicarbonate was added and the aqueous phase extracted with EtOAc (3×). The combined organic phases were dried over $MgSO_4$, filtered and concentrated under reduced pressure to give 5.1 g (94%) of T95-4 as a yellowish solid, which was used as such for the following step.

Step 35-4

To a solution of 3-hydroxy-4-iodopyridine (5.09 g, 23.0 mmol) in DMF (95 mL) were added (R)-propylene carbonate (T95-A, 2.35 g, 23.0 mmol)) and potassium carbonate (3.18 g, 23.0 mmol). The solution was stirred at 85° C. for 72 h. Water was added and the aqueous phase extracted with EtOAc (3×). The combined organic phases were washed with brine (1×) and water (1×), dried over $MgSO_4$, filtered and concentrated under reduced pressure. The resulting residue was purified by flash chromatography (100% EtOAc) to give 1.4 g (24%) of T95-4(R).

Step 35-5

A solution of iodide T95-4(R) (1.27 g, 4.56 mmol) and Boc-propargylamine (1.06 g, 6.83 mmol) in $CH_3CN$/TEA (13.2 mL/5.4 mL) was degassed for 5 min with argon, then $Pd(Cl)_2(PPh_3)_2$ (95 mg) and CuI (25 mg) were added. The solution was heated at 50° C., O/N. The solvent was removed under reduced pressure and the resulting residue was purified by flash chromatography (100% EtOAc) to give 1.23 g (89%) of T95-5(R).

Step 35-6

To a solution of T95-5(R) (935 mg, 3.05 mmol) in 95% EtOH (20 mL) was added $PtO_2$ (28 mg, 0.122 mmol). The solution was saturated with hydrogen ($H_2$ gas bubbled into the reaction mixture for 2 h), then stirred O/N under a hydrogen atmosphere. The mixture was filtered through Celite® (World Minerals Inc., Santa Barbara, Calif.), washed several times with EtOAc, then MeOH. The filtrate was concentrated under reduced pressure and the residue thus obtained was suitable for use in the construction of macrocyclic compounds of the present invention without any further purification (see Example 37).

LC-MS (Grad B4): $t_R$=4.83 min

Note that T95(R) is used to make compounds of formula I with an (S)-stereocenter as described further in Example 37. Similarly, T95(S) is used to synthesize compounds of formula I with an (R)-stereocenter.

Example 36

Figure 16:
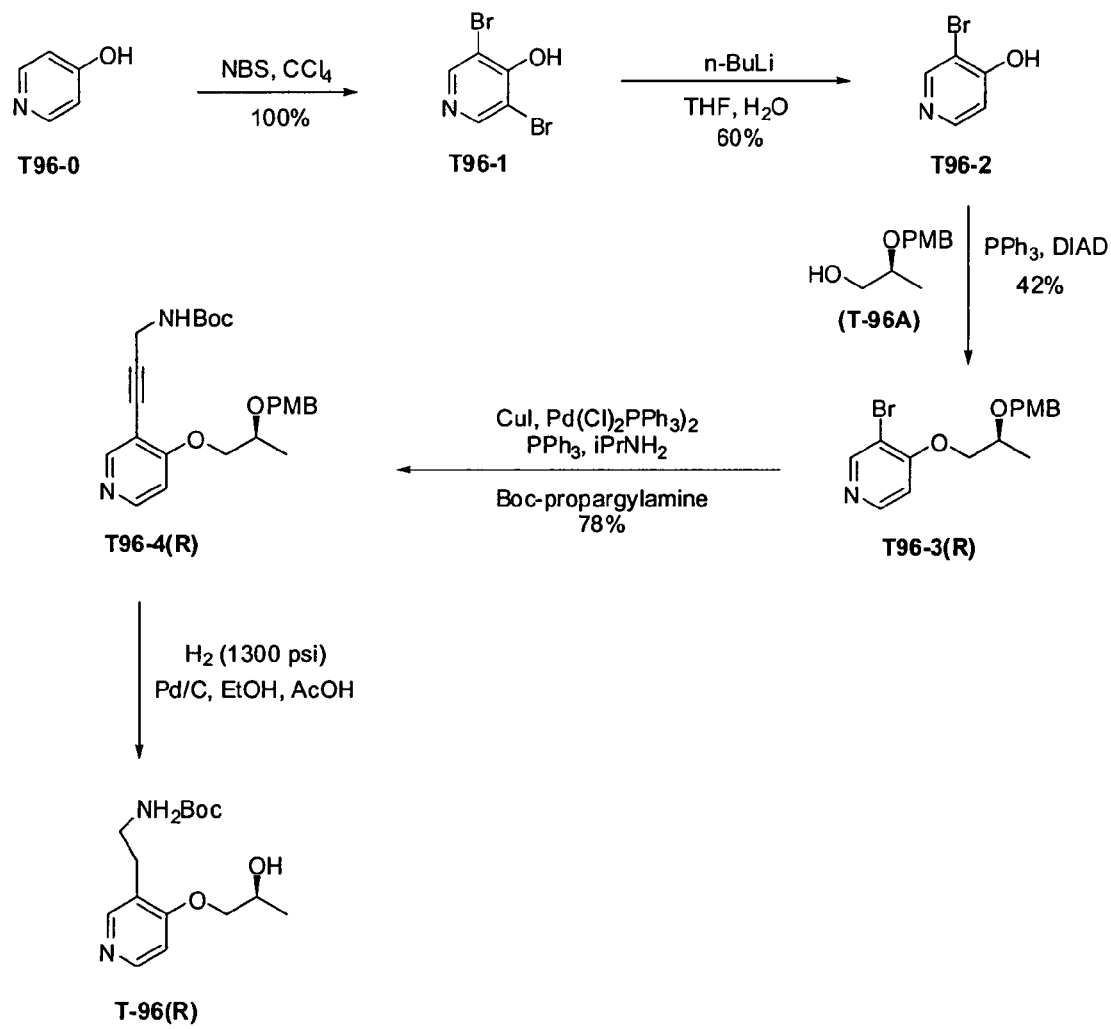
FIG. 16 shows a synthetic scheme for another representative tether building block of the invention.

Standard Procedure for the Synthesis of Tether Boc-T96(R) (FIG. 16)

The sequence was based upon reaction methodology reported in the literature. (Meana, A. *Synlett* 2003, 1678-1682; Canibano, V. *Synthesis* 2001, 2175-2179.) Step 36-1. To a solution of 4-hydroxypyridine (T96-1, 7.0 g, 74 mmol) in $CCl_4$ (360 mL) at rt was added NBS (26.2 g, 0.147 mol). The solution was stirred for 24 h in the dark (covered with aluminum foil). The mixture was concentrated under reduced pressure and the resulting residue triturated with MeOH, then with acetone to give 18.9 g (100%) of T96-2.

Step 36-2

To a solution of T96-2 (8.0 g, 31.3 mmol) in THF (307 mL) at −90° C. was added slowly a solution of n-BuLi (1.15 M in hexanes, 71 mL). The mixture was stirred for 40 min, then water (10 eq) was added and the mixture warmed to room temperature. The solvent was removed under reduced pressure and the resulting residue purified by flash chromatography (acetone:MeOH, 10:1) to give 3.22 g (60%) of T 96-3.

Step 36-3. T 96-3

(3.22 g, 18.4 mmol), $PPh_3$ (4.82 g, 18.4 mmol) and the mono-PMB ether of (R)-glycerol (T96-A, synthesized from the corresponding diol using standard methods, 1.8 g, 9.2 mmol) were dissolved in THF (14 mL). The mixture was cooled to 0° C., then DIAD (3.5 mL, 17.9 mmol) added dropwise maintaining the temperature at 0° C. The solution was stirred at 0° C. for 1 h, then at rt O/N. The mixture was concentrated under reduced pressure and the residue purified by flash chromatography (50/50 EtOAc/Hex) to yield T96-4 (R) (42%).

Step 36-4

To a solution of T96-4(R) (1.25 g, 3.56 mmol) in DIPEA (20 mL) was added Boc-propargylamine and the mixture degassed with argon for 10 min. Triphenylphosphine (121 mg), CuI (29 mg) and $Pd(Cl)_2PPH_3$ (160 mg) were then added. The solution was stirred at 70° C., O/N. The reaction mixture was concentrated under reduced pressure and the resulting residue purified by flash chromatography (gradient, 40% to 90% EtOAc/Hexane) to give 1.3 g (80%) of T96-5(R).

Step 36-5

Pd/C (10%, 50% wet, 628 mg) was added to a solution of T96-5(R) (900 mg) and AcOH (1.5 eq) in 95% EtOH (20 mL). The solution was saturated with $H_2$ at 1300 psi. The mixture was filtered through Celite® (World Minerals Inc., Santa Barbara, Calif.) and washed several times with EtOAc, then with MeOH. The combined filtrate and washings were concentrated under reduced pressure and the crude Boc-T96(R) obtained was used in the synthesis of macrocyclic compounds of the invention without any further purification.

¹H NMR (CDCl₃): δ 1.4 (d, CH3), 1.5 (s, Boc), 1.8 (t, CH2), 2.6 (t, CH2), 3.15 (t, CH2), 4.0 (m, 2×CH), 4.3 (m, 1H), 4.98 (1H, NH), 6.8 (d, 1H aromatic), 8.3 (d, 1H), 8.4 (s, 1H aromatic).

Note that T96(R) is used to make compounds of formula I with an (S)-stereocenter. Similarly, T96(S) is used to synthesize compounds of formula I with an (R)-stereocenter.

Example 37

Figure 17:
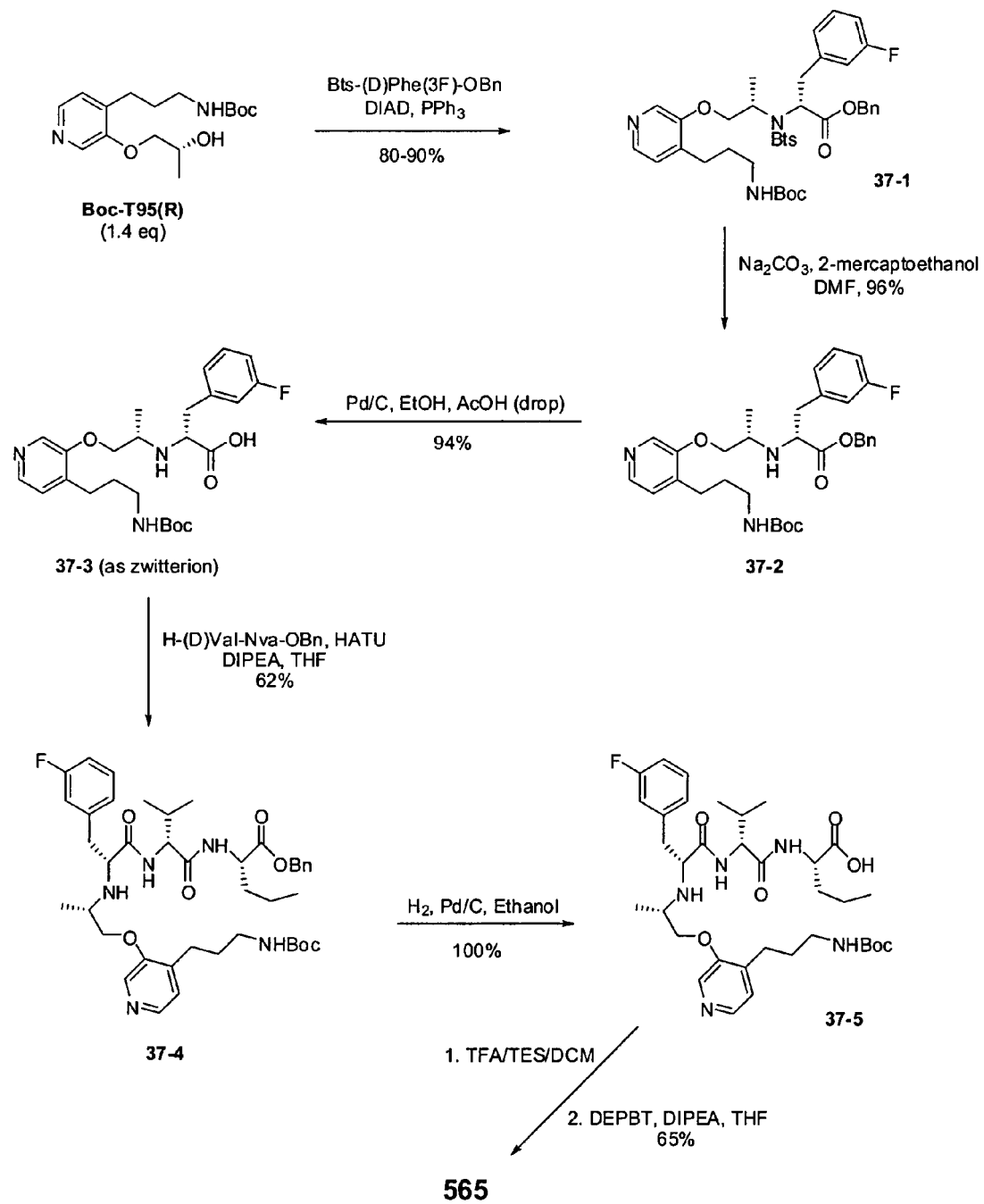
FIG. 17 shows a synthetic scheme for a representative compound of the present invention.

Standard Procedure for the Synthesis of Compound 565 (FIG. 17)

Step 37-1. Boc-T95(R)

(901 mg, 2.90 mmol), triphenylphosphine (762 mg, 2.90 mmol) and Bts-(D)Phe(3F)-OBn (976 mg, 2.07 mmol) were dissolved in anhydrous THF (10 mL). The solution was cooled to 0° C. in an ice-water bath and diisopropylazodicarboxylate (DIAD, 551 µL) was added dropwise. Once the addition was completed, the mixture was stirred for 1 h at 0° C., then warmed up slowly to room temperature and stirred for an additional 16-18 h under nitrogen. The THF was removed under reduced pressure and the crude residue obtained purified by flash chromatography (gradient, 50/50 EtOAc/Hexane to 80/20 EtOAc/Hex) to give 858 mg of 37-1. Yield for this step is typically 80-90%.

Step 37-2

To a solution of alkylated amino acid 37-1 (778 mg, 1.02 mmol) in DMF (6 mL) was added sodium carbonate (519 mg, 5 eq), followed by 2-mercaptoethanol (346 µL, 5 eq). The mixture was stirred for 16-18 hours at room temperature. Water was added and the aqueous phase was extracted with EtOAc (3×). The combined organic phases were washed with brine (1×), dried over MgSO₄, filtered and concentrated under reduced pressure. The crude residue was purified by flash chromatography (gradient 6/3 EtOAc/Hexane to 100% EtOAc) to give 552 mg of 37-2 (96%).

Step 37-3

Pd/C (10%, 50% wet, 628 mg) was carefully added to a solution of 37-2 (502 mg, 0.888 mmol) and AcOH (2 drops) in 95% EtOH (6 mL). The solution was saturated with hydrogen (H₂ gas bubbled into the reaction mixture for 2 h), then stirred O/N under H₂ atmosphere. The mixture was filtered through Celite® (World Minerals Inc., Santa Barbara, Calif.) and washed several times with EtOAc, then with MeOH. The filtrate was concentrated under reduced pressure and the crude 37-3 (94%) thus obtained was used in the next step without any further purification.

Step 37-4

To a solution of the amino acid zwitterion 37-3 (293 mg, 0.617 mmol) and H-D-Val-Nva-OBn hydrochloride salt (422 mg, 1.23 mmol) in anhydrous THF (3.0 mL) at 0° C. was added DIPEA (1.1 mL, 6.17 mmol), followed by HATU (469 mg, 1.23 mmol). The mixture was stirred for 16-18 h under nitrogen. The solvent was removed under reduced pressure and the resulting residue dissolved in EtOAc. The organic phase was washed sequentially with an aqueous solution of citrate buffer (1 M, pH 3.5, 2×), a saturated aqueous of sodium bicarbonate (2×) and brine (2×). The organic phase was dried over MgSO₄, filtered and concentrated under reduced pressure. The residue thus obtained was purified by flash chromatography (80/20 EtOAc/Hex) to give 290 mg of 37-4 (62%).

Step 37-5

Pd/C (10%, 50% wet, 28 mg) was added to a solution of 37-4 (284 mg, 0.373 mmol) in 95% EtOH (4 mL). The solution was saturated with hydrogen (H₂ gas bubbled into the reaction mixture for 2 h), then stirred O/N under a H₂ atmosphere. The mixture was filtered through Celite® (World Minerals Inc., Santa Barbara, Calif.) and washed several times with EtOAc, then with MeOH. The filtrate was concentrated under reduced pressure and the crude 37-5 obtained, 256 mg (100%), was used in the next step without any further purification.

Step 37-6

Boc protected alkylated tripeptide 37-5 (256 mg) was dissolved in a TFA/TES/DCM (33/3/64, 17 mL) mixture. The reaction was stirred 1 h at room temperature, then concentrated under reduced pressure. The resulting oily residue was co-evaporated with DCM (3×), then THF (3×) and dried under reduced pressure to give macrocyclic precursor 37-6.

Step 37-7

To a solution of 37-6 (0.380 mmol) in anhydrous THF (33 mL) were added DIPEA (330 µL, 5 eq) and DEPBT (136 mg, 1.2 eq). The mixture was stirred at room temperature 16-18 h. THF was evaporated under reduced pressure, the residue taken up in EtOAc and washed with brine (2×). The organic solution was dried over MgSO₄, filtered and concentrated under reduced pressure. The crude residue obtained was purified by flash chromatography (95/5 DCM/MeOH) to give the macrocycle 565 (65%).

LC/MS (Grad_B4): $t_R$=5.26 min.

Example 38

Synthesis of PPh₃-DIAD Adduct

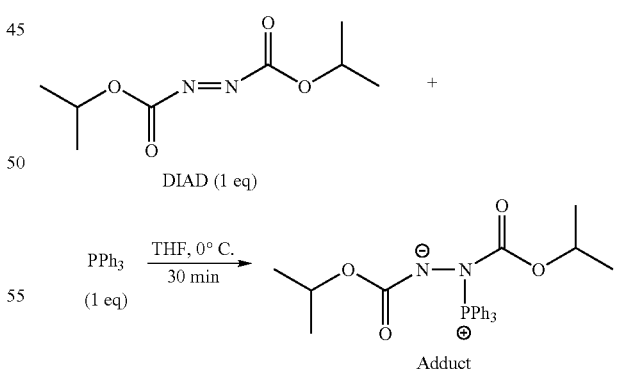

Diisopropyl azodicarboxylate (DIAD, 1 eq) is added dropwise to a well-stirred solution of triphenylphosphine (1 eq) in THF (0.4 M) at 0° C. under nitrogen. After completion of the addition, the mixture is stirred at 0° C. for an additional 30 min. The white solid obtained is collected by filtration (use medium sized fitted filters) and washed with cold anhydrous THF until the washes are colorless. Finally, the white precipitate is washed once with anhydrous Et₂O. The adduct is then dried well in vacuo, and stored under nitrogen. (It is important to store this reagent under anhydrous conditions!) The adduct can be used in place of the separately added reagents in Mitsunobu-type reactions.

Example 39

Preparation of Representative Formulations of Compounds of the Invention

Formulations designed to enhance the solubility of drugs often result in both increasing oral bioavailability and clinical efficacy. The most popular approaches incorporate the active lipophilic component into inert lipid vehicles (Christopher J. H. Porter & al. Lipid and lipid-based formulation; optimizing the oral delivery of lipophilic drugs. *Nat. Rev. Drug. Disc.* 2007, 6, 231-246; Aungst, B. J. Novel formulation strategies for improving oral bioavailability of drugs with poor membrane permeation or presystemic metabolism. *J. Pharm. Sci.* 1993, 82, 979-987), such as oils (Burcham, D. L.; Maurin, M. B.; Hausner, E. A.; Huang, S. M. Improved oral bioavailability of the hypocholesterolemic DMP 565 in dogs following oral dosing in oil and glycol solutions. *Biopharm. Drug Dispos.* 1997, 18, 737-742), surfactant dispersions (Serajuddin, A. T. M.; Sheen, P.-C.; Mufson, D.; Bernstein, D. F.; Augustine, M. A. Effect of vehicle amphiphilicity on the dissolution and bioavailability of a poorly water-soluble drug from solid dispersion. *J. Pharm. Sci.* 1988, 77, 414-417), self-emulsifying formulations, (Charman, S. A.; Charman, W. N.; Rogge, M. C.; Wilson, T. D.; Dutko, F. J.; Pouton, C. W. Self-emulsifying drug delivery systems: formulation and biopharmaceutical evaluation of an investigational lipophilic compound. *Pharm. Res.* 1992, 9, 87-93; Craig, D. Q. M.; Lievens, H. S. R.; Pitt, K. G.; Storey, D. E. An investigation into the physicochemical properties of self-emulsifying systems using low frequency dielectric spectroscopy, surface tension measurements and particle size analysis. *Int. J. Pharm.* 1993, 96, 147-155; Shah, N. H.; Carvajal, M. T.; Patel, C. I.; Infeld, M. H.; Malick, A. W. Self-emulsifying drug delivery systems (SEDDS) with polyglycolysed glycerides for improving in vitro dissolution and oral absorption of lipophilic drugs. *Int. J. Pharm.* 1994, 106, 15-23) and emulsions (Palin, K. J.; Phillips, A. J.; Ning, A. The oral absorption of cefoxitin from oil and emulsion vehicles in rats. *Int. J. Pharm.* 1986, 33, 99-104; Kararli, T. T.; Needham, T. E.; Grifæn, M.; Schoenhard, G.; Ferro, L. J.; Alcorn, L. Oral delivery of a renin inhibitor compound using emulsion formulations. *Pharm. Res.* 1992, 9, 888-893).

The pharmacokinetic parameters of representative formulations are determined through established methods known to those skilled-in the art as previously referenced in Method 3-I. Results with representative formulations for a representative compound of the present invention are shown below.

TABLE 14

| | Oral Bioavailability in Rat of Representative Formulations of Compound 552 | | | |
|---|---|---|---|---|
| Vehicle | 5% HP-β-CD in water | 5% HP-β-CD in water | Cremophor EL/ Lysorbate 80/Soybean oil | Oleic Acid/ Labrafil |
| Dosing Route | IV | oral | oral | oral |
| n (rats) | 3 | 3 | 3 | 3 |
| Dose (mg/kg) | 2 | 8 | 8 | 8 |
| Dose volume (mL/kg) | 4 | 16 | 1 | 1 |
| Dosing solution concentration (mg/mL) | 0.5 | 0.5 | 8 | 8 |
| $t_{1/2}$ (min) | 45 ± 13 | — | — | — |
| $C_{max}$ (ng/mL) | 1719 ± 299 | 369 ± 97 | 229 ± 162 | 143 ± 77 |
| $T_{max}$ (min) | 5 | 5/15 | 15/30 | 30/60 |
| Clearance (mL/min/kg) | 55 ± 10 | — | — | — |
| $AUC_{inf}$ (ng · min/mL) | 36977 ± 6980 | 15291 ± 6811 | 23806 ± 2141 | 21412 ± 10039 |
| F (%) (individual results) | — | 6, 15, 9 | 18, 15, 16 | 7, 21, 15 |
| F (%) (average) | — | 10 ± 5 | 16 ± 1 | 14 ± 7 |

CD = cyclodextrin

The foregoing is illustrative of the present invention, and is not to be construed as limiting thereof. The invention is defined by the following claims, with equivalents of the claims to be included therein.

What is claimed is:

1. A compound having the following structure:

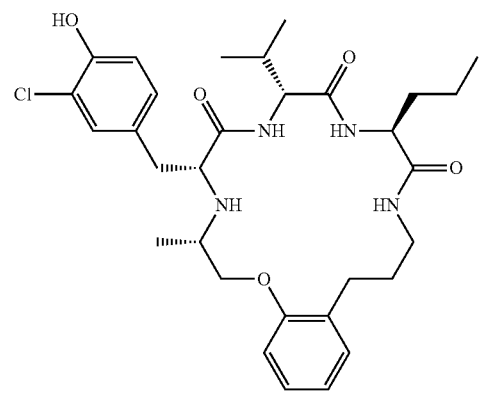

552 and pharmaceutical salts thereof, or an optical isomer, enantiomer, diastereomer, racemate or stereochemical mixture thereof.

2. A pharmaceutical composition comprising:
(a) a compound of claim 1; and
(b) a pharmaceutically acceptable carrier, excipient or diluent.

3. A method of suppressing gastrointestinal motility comprising administering to a subject suffering from one or more disorders caused by gastrointestinal hypermotility or hypermotilinemia an effective amount of a compound of claim 1.

4. The method of claim 3, wherein the compound is administered orally.

5. The method of claim 3, wherein the compound is administered parenterally.

6. The method of claim 3, wherein the subject is a mammal.

7. The method of claim 3, wherein the subject is a human.

8. The method of claim 3, wherein the compound is co-administered with an additional agent useful for suppressing gastrointestinal motility.

9. The method of claim 3, wherein the gastrointestinal disorder is selected from diarrhea, cancer treatment-related diarrhea, cancer-induced diarrhea, chemotherapy-induced diarrhea, radiation enteritis, radiation-induced diarrhea, stress-induced diarrhea, chronic diarrhea, AIDS-related diarrhea, *C. difficile* associated diarrhea, traveller's diarrhea, diarrhea induced by graph versus host disease, dyspepsia, irritable bowel syndrome, chemotherapy-induced nausea and vomiting (emesis) and post-operative nausea and vomiting and functional gastrointestinal disorders.

* * * * *

UNITED STATES PATENT AND TRADEMARK OFFICE
CERTIFICATE OF CORRECTION

Page 1 of 1

PATENT NO. : 9,133,235 B2
APPLICATION NO. : 12/440802
DATED : September 15, 2015
INVENTOR(S) : Marsault et al.

It is certified that error appears in the above-identified patent and that said Letters Patent is hereby corrected as shown below:

In the Claims:
Column 117, Claim 9, Lines 22-23: Please correct "and vomiting and functional gastrointestinal disorders."
    to read -- and vomiting. --

Signed and Sealed this
Sixteenth Day of August, 2016

Michelle K. Lee
*Director of the United States Patent and Trademark Office*